US009636410B2

(12) United States Patent
Brito et al.

(10) Patent No.: US 9,636,410 B2
(45) Date of Patent: May 2, 2017

(54) CATIONIC OIL-IN-WATER EMULSIONS

(75) Inventors: Luis Brito, Concord, MA (US);
Michelle Chan, Florence, MA (US);
Andrew Geall, Littleton, MA (US);
Derek O'Hagan, Winchester, MA (US);
Manmohan Singh, Cary, NC (US)

(73) Assignee: GLAXOSMITHKLINE
BIOLOGICALS SA (BE)

( * ) Notice: Subject to any disclaimer, the term of this patent is extended or adjusted under 35 U.S.C. 154(b) by 0 days.

(21) Appl. No.: 14/130,886

(22) PCT Filed: Jul. 6, 2012

(86) PCT No.: PCT/US2012/045845
§ 371 (c)(1),
(2), (4) Date: Apr. 14, 2014

(87) PCT Pub. No.: WO2013/006837
PCT Pub. Date: Jan. 10, 2013

(65) Prior Publication Data
US 2014/0220083 A1 Aug. 7, 2014

Related U.S. Application Data

(60) Provisional application No. 61/505,109, filed on Jul. 6, 2011, provisional application No. 61/545,936, filed on Oct. 11, 2011, provisional application No. 61/585,641, filed on Jan. 11, 2012.

(51) Int. Cl.
A61K 47/48 (2006.01)
A61K 9/107 (2006.01)
A61K 47/06 (2006.01)
A61K 47/24 (2006.01)
A61K 39/12 (2006.01)
A61K 39/39 (2006.01)
A61K 39/00 (2006.01)

(52) U.S. Cl.
CPC ...... *A61K 47/48046* (2013.01); *A61K 9/1075* (2013.01); *A61K 39/12* (2013.01); *A61K 39/39* (2013.01); *A61K 47/06* (2013.01); *A61K 47/24* (2013.01); *A61K 2039/5256* (2013.01); *A61K 2039/53* (2013.01); *A61K 2039/55555* (2013.01); *A61K 2039/55566* (2013.01); *C12N 2710/16134* (2013.01); *C12N 2710/16734* (2013.01); *C12N 2760/18534* (2013.01); *C12N 2770/36134* (2013.01); *C12N 2770/36143* (2013.01)

(58) Field of Classification Search
CPC ........ A61K 39/12; A61K 39/39; A61K 47/06; A61K 47/24; A61K 47/48046; A61K 2039/5256; A61K 2039/55555
USPC .......................... 424/193.1, 196.11, 400, 450
See application file for complete search history.

(56) References Cited

U.S. PATENT DOCUMENTS

| | | |
|---|---|---|
| 3,906,092 A | 9/1975 | Hilleman et al. |
| 5,264,618 A | 11/1993 | Felgner et al. |
| 5,384,133 A | 1/1995 | Boyes et al. |
| 5,670,152 A | 9/1997 | Weiner et al. |
| 5,712,257 A | 1/1998 | Carter |
| 5,739,118 A | 4/1998 | Carrano et al. |
| 5,795,587 A | 8/1998 | Gao et al. |
| 5,906,980 A | 5/1999 | Carter |
| 6,040,295 A | 3/2000 | Rolland et al. |
| 6,086,901 A | 7/2000 | O'Hagan et al. |
| 6,150,087 A | 11/2000 | Chien |
| 6,171,586 B1 | 1/2001 | Lam et al. |
| 6,218,371 B1 | 4/2001 | Krieg et al. |
| 6,239,116 B1 | 5/2001 | Krieg et al. |
| 6,299,884 B1 | 10/2001 | Van Nest et al. |
| 6,306,405 B1 | 10/2001 | O'Hagan et al. |
| 6,451,325 B1 | 9/2002 | Van Nest et al. |
| 6,458,370 B1 | 10/2002 | O'Hagan et al. |
| 6,610,321 B2 | 8/2003 | Huang et al. |
| 6,855,492 B2 | 2/2005 | O'Hagan et al. |
| 6,861,410 B1 | 3/2005 | Ott et al. |
| 6,884,435 B1 | 4/2005 | O'Hagan et al. |
| 6,890,554 B2 | 5/2005 | Jessee et al. |
| 7,303,881 B2 | 12/2007 | Huang et al. |
| 7,314,627 B2 | 1/2008 | Haynes et al. |
| 7,550,145 B2 | 6/2009 | O'Hagan et al. |

(Continued)

FOREIGN PATENT DOCUMENTS

EP 00/50006 A2 8/2000
EP 1723972 A1 11/2006
(Continued)

OTHER PUBLICATIONS

Ott, G., et al., "A cationic sub-micron emulsion (MF59/DOTAP) is an effective delivery system for DNA vaccines", J. Control Release, 79(1-3): 1-5 (2002).
Yi, S.W.,et al, "A cationic lipid emulsion/DNA complex as a physically stable and serum-resistant gene delivery system", Pharm. Res. 17(3): 314-320 (2000).
Kim, T.W., et al., "Optimization of Lipid Composition in Cationic Emulsion as In Vitro and In Vivo Transfection Agents", Pharm. Res. 18(1): 54-60 (2001).
Chung, H., et al. "Oil components modulate physical characteristics and function of the natural oil emulsions as drug or gene delivery system", J. Control Release, 71(3) 339-350 (2001).
(Continued)

Primary Examiner — Janet Epps-Smith
(74) Attorney, Agent, or Firm — Joseph J. Schuller; Rebecca Stephens

(57) ABSTRACT

This invention generally relates to cationic oil-in-water emulsions that contain high concentrations of cationic lipids and have a defined oil:lipid ratio. The cationic lipid can interact with the negatively charged molecule thereby anchoring the molecule to the emulsion particles. The cationic emulsions described herein are useful for delivering negatively charged molecules, such as nucleic acid molecules to cells, and for formulating nucleic acid-based vaccines.

13 Claims, 4 Drawing Sheets

(56) References Cited

U.S. PATENT DOCUMENTS

| | | | |
|---|---|---|---|
| 7,641,911 B2 | 1/2010 | Ott et al. | |
| 7,749,520 B2 | 7/2010 | Davidsen et al. | |
| 7,790,696 B2 | 9/2010 | Gregoriadis | |
| 9,295,646 B2 | 3/2016 | Brito et al. | |
| 2003/0170273 A1* | 9/2003 | O'Hagan | A61K 39/39 424/225.1 |
| 2006/0084617 A1* | 4/2006 | Satishchandran | A61K 9/1075 514/44 R |
| 2009/0017057 A1 | 1/2009 | Chen et al. | |
| 2011/0110972 A1 | 5/2011 | Vasievich et al. | |
| 2012/0156251 A1* | 6/2012 | Brito et al. | 424/400 |
| 2013/0195968 A1 | 8/2013 | Geall et al. | |

FOREIGN PATENT DOCUMENTS

| | | |
|---|---|---|
| WO | WO 90/14837 A1 | 12/1990 |
| WO | WO 96/22765 A1 | 8/1996 |
| WO | WO 97/11682 A2 | 4/1997 |
| WO | 98/33487 A1 | 8/1998 |
| WO | WO 99/02132 A2 | 1/1999 |
| WO | 99/30737 A1 | 6/1999 |
| WO | 00/06123 A1 | 2/2000 |
| WO | 00/15768 A1 | 3/2000 |
| WO | WO 00/50006 A2 | 8/2000 |
| WO | 0067787 A2 | 11/2000 |
| WO | 01/36599 A1 | 5/2001 |
| WO | 02/26209 A2 | 4/2002 |
| WO | WO 03/028656 A2 | 4/2003 |
| WO | WO 2004/053056 A2 | 6/2004 |
| WO | 2007/001423 A2 | 1/2007 |
| WO | 2007/121947 A1 | 11/2007 |
| WO | 2008/029276 A2 | 3/2008 |
| WO | WO 2008/116078 A2 | 9/2008 |
| WO | WO 2009/129227 A1 | 10/2009 |
| WO | WO 2010/009277 A2 | 1/2010 |
| WO | WO 2011/005799 A2 | 1/2011 |
| WO | WO 2012/006380 A2 | 1/2012 |
| WO | WO 2013/006834 A1 | 1/2013 |

OTHER PUBLICATIONS

Choi et al, "Low toxicity of cationic lipid-based emulsion for gene transfer", Biomaterials 25(27):5893-5903 (2004).
Min et al, "Improved gene expression pattern using Epstein-Barr virus (EBV)-based plasmid and cationic emulsion", Biomaterials 26: 1063-1070 (2005).
Kim, et al., "Polycations enhance emulsion-mediated in vitro and in vivo transfection", Int. J. Pharrn. 295(1-2): 35-45 (2005).
Kim, et al., "Airway gene transfer using cationic emulsion as a mucosal gene carrier", J. Gene Med, 7(6): 749-758 (2005).
Hagigit, et al., "The influence of cationic lipid type on in-vitro release kinetic profiles of antisense oligonucleotide from cationic nanoemulsions" Eur J Pharm Biopharm, 70( 1): 248-259 (2008).
Ying, "Cancer therapy using a self-replicating RNA vaccine", Nat. Med. 5: 823-827 (1999).
Hoerr, "In vivo application of RNA leads to induction of specific cytotoxic T lymphocytes and antibodies", Eur. J. Immunol. 30: 1-7 (2000).
Montana, "Employment of Cationic Solid-Lipid Nanoparticles as RNA Carriers", Bioconjugate Chem. 18: 302-308 (2007).
Brgles et al., "Liposome fusogenicity and entrapment efficiency of antigen determine the Th1/Th2 bias of antigen-specific immune response", Vaccine 27: 5435-5442 (2009).
Vajdy, et al., "Mucosal adjuvants and delivery systems for protein-, DNA- and RNA-based vaccines", Immunol. Cell Biol. 82(6): 617-627 (2004).
Shi et al., "TLR4 links innate immunity and fatty acid-induced insulin resistance", J. Clin. Invest. 116: 3015-3025 (2006).
Martinon et al., "Induction of virus-specific cytotoxic T lymphocytes in vivo by liposome-entrapped mRNA", Eur. J. Immunol. 23: 1719-1722 (1993).

Hung, et al., "Physicochemical characterization and gene transfection efficiency of lipid emulsions with various co-emulsifiers" Int. J. Pharm. 289(1-2): 197-208 (2005).
Moret et al., "Stability of PEI—DNA and DOTAP—DNA complexes: effect of alkaline pH, heparin and serum", J. Controlled Release 76:169-181 (2001).
Kang, et al., "Delivery of interleukin-18 gene to lung cancer cells using cationic emulsion", J. Drug Target 17(I): 19-28 (2009).
Kwon, et al., "In vivo time-dependent gene expression of cationic lipid-based emulsion as a stable and biocompatible non-viral gene carrier", J. Control Release 128(1): 89-97 (2008).
Min, et al., "Improved gene expression pattern using Epstein-Barr virus (EBV)-based plasmid and cationic emulsion", Biomaterials 26(9): 1063-1070 (2005).
Nam, et al., "Lipid-based emulsion system as non-viral gene carriers", Arch. Pharm. Res. 32(5): 639-646 (2009).
Yoo, et al., "In vivo gene therapy of type 1 diabetic mellitus using a cationic emulsion containing an Epstein Barr Virus (EBY) based plasmid vector", J. Control Release 112(1): 139-144 (2006).
Muhlen et al., "Solid Lipid Nanoparticles (SLN) for Controled Drug Delivery—Drug Release and Release Mechanism", Eur. J. of Pharmaceutics and Biopharmaceutics 45:149-155 (1998).
Tabatt et al., "Effect of Cationic Lipid and Matrix Lipid Composition on Solid Lipid Nanoparticle-mediated Gene Transfer", Eur. J. Pharmaceut. Biopharmaceut. 57:155-162 (2004).
Malone et al., "Catonic liposome-mediated RNA transfection", Proc. Natl. Acad. Sci. USA 86:16 6077-6081 (1989).
Perrie, Y., et al., "Liposome-mediated DNA vaccination: the effect of vesicle composition", Vaccine 19:3301-3310 (2001).
Walker, C., et al., "Cationic lipids direct a viral glycoprotein into the class I major histocompatibility complex antigen-presentation pathway", Proc. Natl. Acad. Sci. USA 89:7915-7918 (1992).
Dow, S.W., et al., "Lipid-DNA Complexes Induce Potent Activiation of Innate Immune Responses and Antitumor Activity When Administered Intravenously", J. Immunol. 163:1552-1561 (1999).
Bramson, J.L., et al., "Activation of host antitumoral respones by cationic lipid/DNA complexes", Cancer Gene Therapy 7(3):353-359 (2000).
Yew, N.S., et al., "Toxicity of Cationic Lipid-DNA Complexes", Adv. in Genetics 53: 189-214 (2005).
Simberg, D., et al., "DOTAP (and Other Cationic Lipids): Chemistry, Biophysics, and Transfection", Crit. Rev. in Therapeu. Drug Carrier Systems 21(4):257-317 (2004).
Geall, A. et al., "Nonviral delivery of self-amplifying RNA vaccines", Proc. Natl. Acad. Sci. 109(36): 14604-14609 (2012).
Jeffs, L. et al., "A scalable extrusion-free method for efficient liposomal encapsulation of plasmid DNA", Pharm. Res. 22(3): 362-372 (2005).
Heyes, J. et al."Catonic lipid saturation influences intracellular delivery of encapsulated nucleic acids", J. Controlled Rel. 07(2): 267-287 (2005).
Weide, B., et al. "Plasmid DNA- and messenger RNA-based anti-cancer vaccination", Immunol. Letters 115(1): 33-42 (2008).
Semple, C., et al. "Rational design of cationic lipids for siRNA delivery", Nat. Biotech. 28(2): 172-176 (2010).
Pascolo, "Vaccination with messenger RNA (mRNA)", Handbook of Experimental Pharmacology, 183: 221-233 (2008).
Pascolo, "Vaccination with Messenger RNA", Meth. Mol. Med., 23-40 (2006).
Montana, G. et al. "Cloning, expression, and localization of a new member of a Paracentrotus lividus cell surface multigene family", Mol. Reprod. Develop. 44(1) 36-43 (1996).
Brito et al., A Cationic Nanoemulsion for Delivery of Next-Generation RNA Vaccines, The American Society of Gene & Cell Therapy 1-12 (2014).
Cella et al., Maturation, Activation, and Protection of Dendritic Cells Induced by Double-Stranded RNA, J. Exp. Med. 189(5): 821-829 (1999).
Dupuis et al., Dendritic Cells Internalize Vaccine Adjuvant After Intramuscular Injection, Cellular Immunology 186: 18-27 (1998).
Elbashir et al., Duplexes of 21-Nucleotide RNAs Mediate RNA Interference in Cultured Mammalian Cells, Nature 411(6836):494-498 (2001).

(56) References Cited

OTHER PUBLICATIONS

Even-Chen et al., DOTAP Cationic Liposomes Prefer Relaxed Over Supercoiled Plasmids, Biochemica et Biophysic. Acta 1509:176-188 (2000).
Fire et al., RNA-Triggered Gene Silencing, Trends in Genetics 15:358-363 (1999).
Fox, Squalene Emulsions for Parenteral Vaccine and Drug Delivery, Molecules 14:2386-3312 (2009).
Gregoriadis et al., Liposome-Mediated DNA Vaccination, FEBS Letters 402:107-110 (1997).
Guy, The Perfect Mix: Recent Progress in Adjuvant Research, Nature Reviews Microbiology 5(7):505-517 (2007).
htttps://en.wikipedia.orldwiki/Phosphate_buffered_saline, entitled Phosphate Buffered Saline, Author unknown, published by Wikipedia, San Francisco, CA, accessed Jun. 24, 2015, 2 pages.
Le Bon et al., Type I Interferons Potently Enhance Humoral Immunity and can Promote Isotype Switching by Stimulating Dendritic Cells in Vivo, Immunity 14:461-470 (2001).
Lee et al., Novel Molecular Approaches to Cystic Fibrosis Gene Therapy, The Biochemical Journal 387(Pt. 1):1-15 :2005).
Liu et al., Effect ofNon-ionic Surfactants on the Formation of DNA/Emulsion Complexes and Emulsion-Mediated Gene Transfer, Pharmaceutical Research 13(11):1642-1646 (1996).
Majde, Viral Double-Stranded RNA, Cytokines, and the Flu, J. Interferon and Cytokine Research 20:259-272 (2000).
McCluskie et al., CpG DNA is an Effective Oral Adjuvant to Protein Antigens in Mice, Vaccine 19:950-957 (2001).
Moss et al., Human Immunodeficiency Virus (HIV)-Specific Immune Responses are Generated with the Simultaneous Vaccination of gp 120-Depleted Whole-Killed HIV-1 Immunogen with Cytosine-Phosphorothioate-Guanine Dinucleotide Immunostimulatory Sequence of DNA, J. Hum. Virol. 4:39-43 (2001).
Moss et al., In Vitro Immune Function After Vaccination with an Inactivated gp 120 Depleted HIV-1 Antigen with Immunostimulatory Oligonucleotides, Vaccine 18: 1081-1087 (2000).
O'Hagan et al., Microparticles in MF59, a Potent Adjuvant Combination for a Recombinant Protein Vaccine Against HIV-1, Vaccine 18:1793-1801 (2000).

O'Hagan et al., Synergistic Adjuvant Activity of Immunostmulatory DNA Oil/Water Emulsions for Immunization with HIV p55 Gag Antigen, Vaccine 20:3389-3398 (2002).
O'Hagen et al., Induction of Potent Immune Responses by Cationic Microparticles with Adsorbed Human Immunodeficiency Virus DNA Vaccines, J. Virology 75(19):9037-9043 (Oct. 2001).
Opawale et al., Influence of Interfacial Rheological Properties of Mixed Emulsifier Films on the Stability of Water-in-oil-in-water Emulsions, Journal of Pharmacy and Pharmacology 50(9):965-973 (1998).
Ott et al., MF59—Design and Evaluation of a Safe and Potent Adjuvant for Human Vaccines, in Vaccine Design: The Subunit and Adjuvant Approach (Powell, M.F. And Newman, M.J., eds.) Plenum Press, New York, 1995, pp. 277-296.
Parkin et al., An Overview of the Immune System, The Lancet 357:1777-1789 (2001).
Pizza et al., Identification of Vaccine Candidates Against Serogroup B Meningococcus by Whole-Genome Sequencing, Science 287:1816-1820 (Mar. 10, 2000).
Singh et al., Advances in Vaccine Adjuvants, Nature Biotechnol. 17(11):1075-1081 (1999).
Singh et al., Cationic Microparticles: a Potent Delivery System of DNA Vaccines, PNAS 97(2):811-816 (2000).
Tamilvanan et al., Manufacturing Techniques and Excipients Used During the Formulation of Oil-in-water Type Nanosized Emulsions for Medical Applications, J. Of Excipients and Food Chemistry, 1(1):11-29.
Tamilvanan et al., Stability Assessment of Injectable Castor Oil-Based Nano-Sized Emulsion Containing Cationic Droplets Stabilized by Poloxamer-Chitosan Emulsifer Films, AAPS PharmSciTechnology 11(2):904-909.
Tazulakhova et al., Russian Experience in Screening, Analysis, and Clinical Application of Novel interferon nducers, J. Interferon and Cytokine Research 21:65-73 (2001).
Woo et al., A cationic lipid emulsion /DNA complex as physically stable and serum-resistant gene delivery system, 3harmaceutical Research , vol. 17, No. 3, Mar. 1, 2000, pp. 314-320.
Benita et al., Submicron Emulsions as Colloidal Drug Carriers for Intravenous Administration: Comprehensive Physicochemical Characterization, J Pharmaceutical Sciences, vol. 82, No. 11 (1993).

\* cited by examiner

SEQUENCE LISTING

```
<160> NUMBER OF SEQ ID NOS: 28

<210> SEQ ID NO 1
<211> LENGTH: 12463
<212> TYPE: DNA
<213> ORGANISM: Respiratory syncytial virus

<400> SEQUENCE: 1
ataggcggcg catgagagaa gcccagacca attacctacc caaaatggag aaagttcacg    60
ttgacatcga ggaagacagc ccattcctca gagctttgca gcggagcttc ccgcagtttg   120
aggtagaagc caagcaggtc actgataatg accatgctaa tgccagagcg ttttcgcatc   180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactaa gctgaagaaa aactgtaagg   360
aaataactga taaggaattg gacaagaaaa tgaaggagct cgccgccgtc atgagcgacc   420
ctgacctgga aactgagact atgtgcctcc acgacgacga gtcgtgtcgc tacgaagggc   480
aagtcgctgt ttaccaggat gtatacgcgg ttgacgacc gacaagtctc tatcaccaag   540
ccaataaggg agttagagtc gcctactgga taggctttga caccacccct tttatgttta   600
agaacttggc tggagcatat ccatcatact ctaccaactg ggccgacgaa accgtgttaa   660
cggctcgtaa cataggccta tgcagctctg acgttatgga gcggtcacgt agagggatgt   720
ccattcttag aaagaagtat ttgaaaccat ccaacaatgt tctattctct gttggctcga   780
ccatctacca cgagaagagg gacttactga ggagctggca cctgccgtct gtatttcact   840
tacgtggcaa gcaaaattac acatgtcggt gtgagactat agttagttgc gacgggtacg   900
tcgttaaaag aatagctatc agtccaggcc tgtatgggaa gccttcaggc tatgctgcta   960
```

-continued

```
cgatgcaccg cgagggattc ttgtgctgca aagtgacaga cacattgaac ggggagaggg      1020 tctctttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctgggccg gctcagtgga gacacctcgt ggcttgataa     1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg tttttttaac atgatgtgcc     2520
tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga aataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag tacctggga atttcactgc cacgatagag gagtggcaag    3000
cagagcatga tgccatcatg aggcacatct ggagagacc ggaccctacc gacgtcttcc    3060
agaataaggc aaacgtgtgt tgggccaagg cttttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
```

```
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg ccagcgaaa    3840 gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag acaacctgg cggaggggtg tgcggagcgc    4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttaccag gcggccaagg    4680 atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga ccgatcatc atcgaagagg    5160 aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggaggagct agcgtgacca   5340 gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccgc    5520 caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
```

```
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaagaagaa ttactacgca agaaattaca gttaaatccc acacctgcta    5880
acagaagcag ataccagtcc aggaaggtgg agaaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca agctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct ctttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgacgcc    7560
accatggaac tgctgatcct gaaggccaac gccatcacca ccatcctgac cgccgtgacc    7620
ttctgcttcg ccagcggcca gaacatcacc gaggaattct accagagcac ctgcagcgcc    7680
gtgagcaagg gctacctgag cgccctgcgg accggctggt acaccagcgt gatcaccatc    7740
gagctgtcca acatcaaaga aaacaagtgc aacggcaccg acgccaaggt gaaactgatc    7800
aagcaggaac tggacaagta caagaacgcc gtgaccgagc tgcagctgct gatgcagagc    7860
acccccgcca ccaacaaccg ggccagaaga gagctgcccc ggttcatgaa ctacacctg    7920
aacaacgcca agaaaaccaa cgtgaccctg agcaagaagc ggaagcggcg gttcctgggc    7980
ttcctgctgg gcgtgggcag cgccatcgcc agcggggtgg ccgtgtccaa ggtgctgcac    8040
ctggaaggcg aggtgaacaa gatcaagtcc gccctgctgt ccaccaacaa ggccgtggtg    8100
```

```
tccctgagca acggcgtgag cgtgctgacc agcaaggtgc tggatctgaa gaactacatc    8160
gacaagcagc tgctgcccat cgtgaacaag cagagctgca gcatcagcaa catcgagacc    8220
gtgatcgagt tccagcagaa gaacaaccgg ctgctggaaa tcacccggga gttcagcgtg    8280
aacgccggcg tgaccacccc cgtgagcacc tacatgctga ccaacagcga gctgctgtcc    8340
ctgatcaatg acatgcccat caccaacgac cagaaaaagc tgatgagcaa caacgtgcag    8400
atcgtgcggc agcagagcta ctccatcatg agcatcatca agaagaggt gctggcctac    8460 gtggtgcagc tgcccctgta cggcgtgatc gacacccct gctggaagct gcacaccagc    8520
cccctgtgca ccaccaacac caaagagggc agcaacatct gcctgacccg gaccgaccgg    8580
ggctggtact gcgacaacgc cggcagcgtg agcttcttcc cccaagccga gcctgcaag    8640 gtgcagagca accgggtgtt ctgcgacacc atgaacagcc tgacctgcc ctccgaggtg    8700 aacctgtgca acgtggacat cttcaacccc aagtacgact gcaagatcat gacctccaag    8760
accgacgtga gcagctccgt gatcacctcc ctgggcgcca tcgtgagctg ctacggcaag    8820
accaagtgca ccgccagcaa caagaaccgg ggcatcatca agacccttcag caacggctgc    8880 gactacgtga gcaacaaggg cgtggacacc gtgagcgtgg gcaacacact gtactacgtg    8940
aataagcagg aaggcaagag cctgtacgtg aagggcgagc ccatcatcaa cttctacgac    9000
cccctggtgt tccccagcga cgagttcgac gccagcatca gccaggtcaa cgagaagatc    9060
aaccagagcc tggccttcat ccggaagagc gacgagctgc tgcacaatgt gaatgccggc    9120
aagagcacca ccaatatcat gatcaccaca atcatcatcg tgatcattgt gatcctgctg    9180
tctctgattg ccgtgggcct gctgctgtac tgcaaggccc gcagcacccc tgtgaccctg    9240
tccaaggacc agctgtccgg catcaacaat atcgccttct ccaactgaag tctagacggc    9300
gcgcccaccc agcggccgca tacagcagca attggcaagc tgcttacata gaactcgcgg    9360
cgattggcat gccgccttaa aattttattt ttatttttct tttctttttcc gaatcggatt    9420 ttgttttttaa tatttcaaaa aaaaaaaaaa aaaaaaaaa aaaaaaaaa agggtcggca    9480 tggcatctcc acctcctcgc ggtccgacct gggcatccga aggaggacgc acgtccactc    9540
ggatggctaa gggagagcca cgtttaaacc agctccaatt cgccctatag tgagtcgtat    9600
tacgcgcgct cactggccgt cgttttacaa cgtcgtgact gggaaaaccc tggcgttacc    9660
caacttaatc gccttgcagc acatcccct ttcgccagct ggcgtaatag cgaagaggcc    9720
cgcaccgatc gcccttccca acagttgcgc agcctgaatg gcgaatggga cgcgccctgt    9780
agcggcgcat taagcgcggc gggtgtggtg gttacgcgca gcgtgaccgc tacacttgcc    9840
agcgccctag cgcccgctcc tttcgctttc ttcccttcct ttctcgccac gttcgccggc    9900
tttccccgtc aagctctaaa tcgggggctc cctttagggt tccgatttag tgctttacgg    9960
cacctcgacc ccaaaaaact tgattagggt gatggttcac gtagtgggcc atcgccctga   10020
tagacggttt ttcgcccttt gacgttggag tccacgttct ttaatagtgg actcttgttc   10080
caaactggaa caacactcaa ccctatctcg gtctattctt ttgatttata agggattttg   10140
ccgatttcgg cctattggtt aaaaaatgag ctgatttaac aaaaatttaa cgcgaatttt   10200
aacaaaatat taacgcttac aatttaggtg cacttttcg gggaaatgtg cgcggaaccc   10260
ctatttgttt atttttctaa atacattcaa atatgtatcc gctcatgaga caataaccct   10320
gataaatgct tcaataatat tgaaaaagga agagtatgag tattcaacat ttccgtgtcg   10380
cccttattcc cttttttgcg gcattttgcc ttcctgtttt tgctcaccca gaaacgctgg   10440
```

```
tgaaagtaaa agatgctgaa gatcagttgg gtgcacgagt gggttacatc gaactggatc    10500
tcaacagcgg taagatcctt gagagttttc gccccgaaga acgttttcca atgatgagca    10560
cttttaaagt tctgctatgt ggcgcggtat tatcccgtat tgacgccggg caagagcaac    10620
tcggtcgccg catacactat tctcagaatg acttggttga gtactcacca gtcacagaaa    10680
agcatcttac ggatggcatg acagtaagag aattatgcag tgctgccata accatgagtg    10740
ataacactgc ggccaactta cttctgacaa cgatcggagg accgaaggag ctaaccgctt    10800
ttttgcacaa catgggggat catgtaactc gccttgatcg ttgggaaccg gagctgaatg    10860
aagccatacc aaacgacgag cgtgacacca cgatgcctgt agcaatggca acaacgttgc    10920
gcaaactatt aactggcgaa ctacttactc tagcttcccg gcaacaatta atagactgga    10980
tggaggcgga taaagttgca ggaccacttc tgcgctcggc ccttccggct ggctggttta    11040
ttgctgataa atctggagcc ggtgagcgtg gtctcgcgg tatcattgca gcactggggc    11100
cagatggtaa gccctcccgt atcgtagtta tctacacgac ggggagtcag gcaactatgg    11160
atgaacgaaa tagacagatc gctgagatag gtgcctcact gattaagcat tggtaactgt    11220
cagaccaagt ttactcatat atactttaga ttgatttaaa acttcatttt taatttaaaa    11280
ggatctaggt gaagatcctt tttgataatc tcatgaccaa aatcccttaa cgtgagtttt    11340
cgttccactg agcgtcagac cccgtagaaa agatcaaagg atcttcttga tccttttt    11400 ttctgcgcgt aatctgctgc ttgcaaacaa aaaaaccacc gctaccagcg gtggtttgtt    11460
tgccggatca agagctacca actctttttc cgaaggtaac tggcttcagc agagcgcaga    11520
taccaaatac tgttcttcta gtgtagccgt agttaggcca ccacttcaag aactctgtag    11580
caccgcctac atacctcgct ctgctaatcc tgttaccagt ggctgctgcc agtggcgata    11640
agtcgtgtct taccgggttg gactcaagac gatagttacc ggataaggcg cagcggtcgg    11700
gctgaacggg gggttcgtgc acacagccca gcttggagcg aacgacctac accgaactga    11760
gatacctaca gcgtgagcta tgagaaagcg ccacgcttcc cgaagggaga aaggcggaca    11820
ggtatccggt aagcggcagg gtcggaacag gagagcgcac gagggagctt ccagggggaa    11880
acgcctggta tctttatagt cctgtcgggt ttcgccacct ctgacttgag cgtcgatttt    11940
tgtgatgctc gtcaggggg cggagcctat ggaaaaacgc cagcaacgcg gccttttac    12000 ggttcctggc cttttgctgg ccttttgctc acatgttctt tcctgcgtta tcccctgatt    12060
ctgtggataa ccgtattacc gcctttgagt gagctgatac cgctcgccgc agccgaacga    12120
ccgagcgcag cgagtcagtg agcgaggaag cggaagagcg cccaatacgc aaaccgcctc    12180
tccccgcgcg ttggccgatt cattaatgca gctggcacga caggtttccc gactggaaag    12240
cgggcagtga gcgcaacgca attaatgtga gttagctcac tcattaggca ccccaggctt    12300
tacactttat gctcccggct cgtatgttgt gtggaattgt gagcggataa caatttcaca    12360
caggaaacag ctatgaccat gattacgcca agcgcgcaat taaccctcac taaagggaac    12420
aaaagctggg taccgggccc acgcgtaata cgactcacta tag    12463

<210> SEQ ID NO 2
<211> LENGTH: 12436
<212> TYPE: DNA
<213> ORGANISM: Respiratory syncytial virus

<400> SEQUENCE: 2
ataggcggcg catgagagaa gcccagacca attacctacc caaaatggag aaagttcacg      60
ttgacatcga ggaagacagc ccattcctca gagctttgca gcggagcttc ccgcagtttg     120
```

-continued

```
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg acaagaaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020 tctctttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaagggctg acgtcaatg    2340 ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
```

```
ctaaaaaggc agtgctctgc ggggatccca aacagtgcgg ttttttttaac atgatgtgcc    2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg ccaccgaag    4080 gagtgattat aaatgctgct aacagcaaag gacaacctgg cggagggtg tgcggagcgc    4140 tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gttcaccag gcggccaagg    4680 atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
```

```
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggaggagct agcgtgacca    5340 gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttacccg tcacgcactc     5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaatca gtaaggcaaa     5760 cggtgctatc cgaagtggtg ttggagagga ccgaattgga gatttcgtat gccccgcgcc    5820
tcgaccaaga aaagaagaa ttactacgca agaaattaca gttaaatccc acctgcta      5880 acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca agctgcgca gctttccaaa gaaacactcc tatttggaac     6240
ccacaatacg atcggcagtg ccttcagcga tccagaacac gctccagaac gtcctggcag    6300
ctgccacaaa agaaattgc aatgtcacgc aaatgagaga attgcccgta ttggattcgg     6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
```

-continued

```
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgacgcc    7560
accatggaac tgctgatcct gaaggccaac gccatcacca ccatcctgac cgccgtgacc    7620
ttctgcttcg ccagcggcca gaacatcacc gaggaattct accagagcac ctgcagcgcc    7680
gtgagcaagg gctacctgag cgccctgcgg accggctggt acaccagcgt gatcaccatc    7740
gagctgtcca acatcaaaga aaacaagtgc aacggcaccg acgccaaggt gaaactgatc    7800
aagcaggaac tggacaagta caagaacgcc gtgaccgagc tgcagctgct gatgcagagc    7860
accccgcca ccaacaaccg ggccagaaga gagctgcccc ggttcatgaa ctacaccctg    7920
aacaacgcca agaaaaccaa cgtgaccctg agcaagaagc ggaagcggcg gagcgccatc    7980
gccagcgggg tggccgtgtc caaggtgctg cacctggaag gcgaggtgaa caagatcaag    8040
tccgccctgc tgtccaccaa caaggccgtg gtgtccctga gcaacggcgt gagcgtgctg    8100
accagcaagg tgctggatct gaagaactac atcgacaagc agctgctgcc catcgtgaac    8160
aagcagagct gcagcatcag caacatcgag accgtgatcg agttccagca gaagaacaac    8220
cggctgctgg aaatcacccg ggagttcagc gtgaacgccg gcgtgaccac cccgtgagc    8280
acctacatgc tgaccaacag cgagctgctg tccctgatca atgacatgcc catcaccaac    8340
gaccagaaaa agctgatgag caacaacgtg cagatcgtgc ggcagcagag ctactccatc    8400
atgagcatca tcaaagaaga ggtgctggcc tacgtggtgc agctgcccct gtacggcgtg    8460
atcgacaccc cctgctggaa gctgcacacc agccccctgt gcaccaccaa caccaaagag    8520
ggcagcaaca tctgcctgac ccggaccgac cggggctggt actgcgacaa cgccggcagc    8580
gtgagcttct cccccaagc cgagacctgc aaggtgcaga gcaaccgggt gttctgcgac    8640
accatgaaca gcctgaccct gccctccgag gtgaacctgt gcaacgtgga catcttcaac    8700
cccaagtacg actgcaagat catgaccctcc aagaccgacg tgagcagctc cgtgatcacc    8760
tccctgggcg ccatcgtgag ctgctacggc aagaccaagt gcaccgccag caacaagaac    8820
cggggcatca tcaagacctt cagcaacggc tgcgactacg tgagcaacaa gggcgtggac    8880
accgtgagcg tgggcaacac actgtactac gtgaataagc aggaaggcaa gagcctgtac    8940
gtgaagggcg agcccatcat caacttctac gacccctgg tgttccccag cgacgagttc    9000
gacgccagca tcagccaggt caacgagaag atcaaccaga gcctggcctt catccggaag    9060
agcgacgagc tgctgcacaa tgtgaatgcc ggcaagagca ccaccaatat catgatcacc    9120
acaatcatca tcgtgatcat tgtgatcctg ctgtctctga ttgccgtggg cctgctgctg    9180
tactgcaagg cccgcagcac ccctgtgacc ctgtccaagg accagctgtc cggcatcaac    9240
aatatcgcct ctccaactg aagtctagac ggcgcgccca cccagcggcc gcatacagca    9300
gcaattggca agctgcttac atagaactcg cggcgattgg catgccgcct taaaatttttt   9360
atttttatttt tcttttcttt tccgaatcgg attttgtttt taatatttca aaaaaaaaa    9420
aaaaaaaaaa aaaaaaaaaa aaagggtcg gcatggcatc tccacctcct cgcggtccga    9480
cctgggcatc cgaaggagga cgcacgtcca ctcggatggc taaggagag ccacgtttaa     9540
accagctcca attcgcccta tagtgagtcg tattacgcgc gctcactggc cgtcgtttta    9600
```

```
caacgtcgtg actgggaaaa ccctggcgtt acccaactta atcgccttgc agcacatccc   9660
cctttcgcca gctggcgtaa tagcgaagag gcccgcaccg atcgcccttc ccaacagttg   9720
cgcagcctga atggcgaatg ggacgcgccc tgtagcggcg cattaagcgc ggcgggtgtg   9780
gtggttacgc gcagcgtgac cgctacactt gccagcgccc tagcgcccgc tcctttcgct   9840
ttcttccctt cctttctcgc cacgttcgcc ggctttcccc gtcaagctct aaatcggggg   9900
ctccctttag ggttccgatt tagtgcttta cggcacctcg accccaaaaa acttgattag   9960
ggtgatggtt cacgtagtgg gccatcgccc tgatagacgg ttttttcgccc tttgacgttg  10020
gagtccacgt tctttaatag tggactcttg ttccaaactg gaacaacact caaccctatc  10080
tcggtctatt cttttgattt ataagggatt ttgccgattt cggcctattg gttaaaaaat  10140
gagctgattt aacaaaaatt taacgcgaat tttaacaaaa tattaacgct tacaatttag  10200
gtggcacttt tcggggaaat gtgcgcggaa cccctatttg tttatttttc taaatacatt  10260
caaatatgta tccgctcatg agacaataac cctgataaat gcttcaataa tattgaaaaa  10320
ggaagagtat gagtattcaa catttccgtg tcgcccttat tccctttttt gcggcatttt  10380
gccttcctgt ttttgctcac ccagaaacgc tggtgaaagt aaaagatgct gaagatcagt  10440
tgggtgcacg agtgggttac atcgaactgg atctcaacag cggtaagatc cttgagagtt  10500
ttcgccccga agaacgtttt ccaatgatga gcacttttaa agttctgcta tgtggcgcgg  10560
tattatcccg tattgacgcc gggcaagagc aactcggtcg ccgcatacac tattctcaga  10620
atgacttggt tgagtactca ccagtcacag aaaagcatct tacgatggc atgcagtaa   10680
gagaattatg cagtgctgcc ataaccatga gtgataacac tgcggccaac ttacttctga  10740
caacgatcgg aggaccgaag gagctaaccg cttttttgca acatggggg gatcatgtaa  10800
ctcgccttga tcgttgggaa ccggagctga atgaagccat accaaacgac gagcgtgaca  10860
ccacgatgcc tgtagcaatg gcaacaacgt tgcgcaaact attaactggc gaactactta  10920
ctctagcttc ccggcaacaa ttaatagact ggatggaggc ggataaagtt gcaggaccac  10980
ttctgcgctc ggcccttccg gctggctggt ttattgctga taaatctgga gccggtgagc  11040
gtgggtctcg cggtatcatt gcagcactgg ggccagatgg taagccctcc cgtatcgtag  11100
ttatctacac gacggggagt caggcaacta tggatgaacg aaatagacag atcgctgaga  11160
taggtgcctc actgattaag cattggtaac tgtcagacca agtttactca tatatacttt  11220
agattgattt aaaacttcat ttttaattta aaaggatcta ggtgaagatc ctttttgata  11280
atctcatgac caaaatccct taacgtgagt tttcgttcca ctgagcgtca gaccccgtag  11340
aaaagatcaa aggatcttct tgagatcctt ttttctgcg cgtaatctgc tgcttgcaaa  11400
caaaaaaacc accgctacca gcggtggttt gtttgccgga tcaagagcta ccaactcttt  11460
ttccgaaggt aactggcttc agcagagcgc agataccaaa tactgttctt ctagtgtagc  11520
cgtagttagg ccaccacttc aagaactctg tagcaccgcc tacatacctc gctctgctaa  11580
tcctgttacc agtggctgct gccagtggcg ataagtcgtg tcttaccggg ttggactcaa  11640
gacgatagtt accggataag gcgcagcggt cgggctgaac ggggggttcg tgcacacagc  11700
ccagcttgga gcgaacgacc tacaccgaac tgagatacct acagcgtgag ctatgagaaa  11760
gcgccacgct tcccgaaggg agaaaggcgg acaggtatcc ggtaagcggc agggtcggaa  11820
caggagagcg cacgagggag cttccagggg gaaacgcctg gtatctttat agtcctgtcg  11880
ggtttcgcca cctctgactt gagcgtcgat ttttgtgatg ctcgtcaggg gggcggagcc  11940
```

-continued

| | |
|---|---|
| tatggaaaaa cgccagcaac gcggccttttt tacggttcct ggccttttgc tggccttttg | 12000 |
| ctcacatgtt ctttcctgcg ttatcccctg attctgtgga taaccgtatt accgcctttg | 12060 |
| agtgagctga taccgctcgc cgcagccgaa cgaccgagcg cagcgagtca gtgagcgagg | 12120 |
| aagcggaaga gcgcccaata cgcaaaccgc ctctccccgc gcgttggccg attcattaat | 12180 |
| gcagctggca cgacaggttt cccgactgga aagcgggcag tgagcgcaac gcaattaatg | 12240 |
| tgagttagct cactcattag gcaccccagg ctttacactt tatgctcccg gctcgtatgt | 12300 |
| tgtgtggaat tgtgagcgga taacaatttc acacaggaaa cagctatgac catgattacg | 12360 |
| ccaagcgcgc aattaaccct cactaaaggg aacaaaagct gggtaccggg cccacgcgta | 12420 |
| atacgactca ctatag | 12436 |

<210> SEQ ID NO 3
<211> LENGTH: 11702
<212> TYPE: DNA
<213> ORGANISM: Respiratory syncytial virus

<400> SEQUENCE: 3

| | |
|---|---|
| gcagtcacca aaaagatct agtggtgagc gccaagaaag aaaactgtgc agaaattata | 60 |
| agggacgtca agaaaatgaa agggctggac gtcaatgcca gaactgtgga ctcagtgctc | 120 |
| ttgaatggat gcaaacaccc cgtagagacc ctgtatattg acgaagcttt tgcttgtcat | 180 |
| gcaggtactc tcagagcgct catagccatt ataagaccta aaaaggcagt gctctgcggg | 240 |
| gatcccaaac agtgcggttt ttttaacatg atgtgcctga agtgcatttt taaccacgag | 300 |
| atttgcacac aagtcttcca caaaagcatc tctcgccgtt gcactaaatc tgtgacttcg | 360 |
| gtcgtctcaa ccttgttttta cgacaaaaaa atgagaacga cgaatccgaa agagactaag | 420 |
| attgtgattg acactaccgg cagtaccaaa cctaagcagg acgatctcat tctcacttgt | 480 |
| ttcagagggt gggtgaagca gttgcaaata gattacaaag caacgaaat aatgacggca | 540 |
| gctgcctctc aagggctgac ccgtaaaggt gtgtatgccg ttcggtacaa ggtgaatgaa | 600 |
| aatcctctgt acgcacccac ctcagaacat gtgaacgtcc tactgacccg cacggaggac | 660 |
| cgcatcgtgt ggaaaacact agccggcgac ccatggataa aaacactgac tgccaagtac | 720 |
| cctgggaatt tcactgccac gatagaggag tggcaagcag agcatgatgc catcatgagg | 780 |
| cacatcttgg agagaccgga ccctaccgac gtcttccaga ataaggcaaa cgtgtgttgg | 840 |
| gccaaggctt tagtgccggt gctgaagacc gctggcatag acatgaccac tgaacaatgg | 900 |
| aacactgtgg attattttga aacggacaaa gctcactcag cagagatagt attgaaccaa | 960 |
| ctatgcgtga ggttctttgg actcgatctg gactccggtc tattttctgc acccactgtt | 1020 |
| ccgttatcca ttaggaataa tcactgggat aactccccgt cgcctaacat gtacgggctg | 1080 |
| aataaagaag tggtccgtca gctctctcgc aggtacccac aactgcctcg gcagttgcc | 1140 |
| actggaagag tctatgacat gaacactggt acactgcgca attatgatcc gcgcataaac | 1200 |
| ctagtacctg taaacagaag actgcctcat gctttagtcc tccaccataa tgaacaccca | 1260 |
| cagagtgact tttcttcatt cgtcagcaaa ttgaagggca aactgtcct ggtggtcggg | 1320 |
| gaaaagttgt ccgtcccagg caaaatggtt gactggttgt cagaccggcc tgaggctacc | 1380 |
| ttcagagctc ggctggattt aggcatccca ggtgatgtgc ccaaatatga cataatatt | 1440 |
| gttaatgtga ggaccccata taaataccat cactatcagc agtgtgaaga ccatgccatt | 1500 |
| aagcttgcag tgttgaccaa gaaagcttgt ctgcatctga atcccggcgg aacctgtgtc | 1560 |
| agcataggtt atggttacgc tgacagggcc agcgaaagca tcattggtgc tatagcgcgg | 1620 |

```
cagttcaagt tttcccgggt atgcaaaccg aaatcctcac ttgaagagac ggaagttctg    1680
tttgtattca ttgggtacga tcgcaaggcc cgtacgcaca atccttacaa gctttcatca    1740
accttgacca acatttatac aggttccaga ctccacgaag ccggatgtgc accctcatat    1800
catgtggtgc gagggatat tgccacggcc accgaaggac tgattataaa tgctgctaac    1860
agcaaaggac aacctggcgg aggggtgtgc ggagcgctgt ataagaaatt cccggaaagc    1920
ttcgatttac agccgatcga agtaggaaaa gcgcgactgg tcaaaggtgc agctaaacat    1980
atcattcatg ccgtaggacc aaacttcaac aaagtttcgg aggttgaagg tgacaaacag    2040
ttggcagagg cttatgagtc catcgctaag attgtcaacg ataacaatta caagtcagta    2100
gcgattccac tgttgtccac cggcatcttt tccgggaaca agatcgact aacccaatca    2160 ttgaaccatt tgctgacagc tttagacacc actgatgcag atgtagccat atactgcagg    2220
gacaagaaat gggaaatgac tctcaaggaa gcagtggcta ggagagaagc agtggaggag    2280
atatgcatat ccgacgactc ttcagtgaca gaacctgatg cagagctggt gagggtgcat    2340
ccgaagagtt ctttggctgg aaggaagggc tacagcacaa gcgatggcaa aactttctca    2400
tatttggaag ggaccaagtt tcaccaggcg gccaaggata tagcagaaat taatgccatg    2460
tggcccgttg caacggaggc caatgagcag gtatgcatgt atatcctcgg agaaagcatg    2520
agcagtatta ggtcgaaatg ccccgtcgaa gagtcggaag cctccacacc acctagcacg    2580
ctgccttgct tgtgcatcca tgccatgact ccagaaagag tacagcgcct aaaagcctca    2640
cgtccagaac aaattactgt gtgctcatcc tttccattgc cgaagtatag aatcactggt    2700
gtgcagaaga tccaatgctc ccagcctata ttgttctcac cgaaagtgcc tgcgtatatt    2760
catccaagga agtatctcgt ggaaacacca ccggtagacg agactccgga gccatcggca    2820
gagaaccaat ccacagaggg gacacctgaa caaccaccac ttataaccga ggatgagacc    2880
aggactagaa cgcctgagcc gatcatcatc gaagaggaag aagaggatag cataagtttg    2940
ctgtcagatg gcccgacccca ccaggtgctg caagtcgagg cagacattca cgggccgccc    3000
tctgtatcta gctcatcctg gtccattcct catgcatccg actttgatgt ggacagttta    3060
tccatacttg acaccctgga gggagctagc gtgaccagcg gggcaacgtc agccgagact    3120
aactcttact tcgcaaagag tatggagttt ctggcgcgac cggtgcctgc gcctcgaaca    3180
gtattcagga accctccaca tcccgctccg cgcacaagaa caccgtcact tgcacccagc    3240
agggcctgct cgagaaccag cctagttttcc accccgccag gcgtgaatag ggtgatcact    3300
agagaggagc tcgaggcgct tacccccgtca cgcactccta gcaggtcggt ctcgagaacc    3360
agcctggtct ccaacccgcc aggcgtaaat agggtgatta caagagagga gtttgaggcg    3420
ttcgtagcac aacaacaatg acggtttgat gcgggtgcat acatcttttc ctccgacacc    3480
ggtcaagggc atttacaaca aaaatcagta aggcaaacgg tgctatccga agtggtgttg    3540
gagaggaccg aattggagat ttcgtatgcc ccgcgcctcg accaagaaaa agaagaatta    3600
ctacgcaaga aattacagtt aaatcccaca cctgctaaca gaagcagata ccagtccagg    3660
aaggtggaga acatgaaagc cataacagct agacgtattc tgcaaggcct agggcattat    3720
ttgaaggcag aaggaaaagt ggagtgctac cgaaccctgc atcctgttcc tttgtattca    3780
tctagtgtga accgtgcctt ttcaagcccc aaggtcgcag tggaagcctg taacgccatg    3840
ttgaaagaga actttccgac tgtggcttct tactgtatta ttccagagta cgatgcctat    3900
ttggacatgg ttgacggagc ttcatgctgc ttagacactg ccagttttttg ccctgcaaag    3960
```

```
ctgcgcagct tttccaaagaa acactcctat ttggaaccca caatacgatc ggcagtgcct    4020
tcagcgatcc agaacacgct ccagaacgtc ctggcagctg ccacaaaaag aaattgcaat    4080
gtcacgcaaa tgagagaatt gcccgtattg gattcggcgg cctttaatgt ggaatgcttc    4140
aagaaatatg cgtgtaataa tgaatattgg gaaacgttta agaaaaaccc catcaggctt    4200
actgaagaaa acgtggtaaa ttacattacc aaattaaaag gaccaaaagc tgctgctctt    4260
tttgcgaaga cacataattt gaatatgttg caggacatac caatggacag gtttgtaatg    4320
gacttaaaga gagacgtgaa agtgactcca ggaacaaaac atactgaaga acggcccaag    4380
gtacaggtga tccaggctgc cgatccgcta gcaacagcgt atctgtgcgg aatccaccga    4440
gagctggtta ggagattaaa tgcggtcctg cttccgaaca ttcatacact gtttgatatg    4500
tcggctgaag actttgacgc tattatagcc gagcacttcc agcctgggga ttgtgttctg    4560
gaaactgaca tcgcgtcgtt tgataaaagt gaggacgacg ccatggctct gaccgcgtta    4620
atgattctgg aagacttagg tgtggacgca gagctgttga cgctgattga ggcggctttc    4680
ggcgaaattt catcaataca tttgcccact aaaactaaat ttaaattcgg agccatgatg    4740
aaatctggaa tgttcctcac actgtttgtg aacacagtca ttaacattgt aatcgcaagc    4800
agagtgttga gagaacggct aaccggatca ccatgtgcag cattcattgg agatgacaat    4860
atcgtgaaag gagtcaaatc ggacaaatta atggcagaca ggtgcgccac ctggttgaat    4920
atggaagtca agattataga tgctgtggtg ggcgagaaag cgccttattt ctgtggaggg    4980
tttattttgt gtgactccgt gaccggcaca gcgtgccgtg tggcagaccc cctaaaaagg    5040
ctgtttaagc ttggcaaacc tctggcagca gacgatgaac atgatgatga caggagaagg    5100
gcattgcatg aagagtcaac acgctggaac cgagtgggta ttctttcaga gctgtgcaag    5160
gcagtagaat caaggtatga accgtagga acttccatca tagttatggc catgactact    5220
ctagctagca gtgttaaatc attcagctac ctgagagggg cccctataac tctctacggc    5280
taacctgaat ggactacgac atagtctagt cgacgccacc atggaactgc tgatcctgaa    5340
ggccaacgcc atcaccacca tcctgaccgc cgtgaccttc tgcttcgcca gcggccagaa    5400
catcaccgag gaattctacc agagcacctg cagcgccgtg agcaagggct acctgagcgc    5460
cctgcggacc ggctggtaca ccagcgtgat caccatcgag ctgtccaaca tcaaagaaaa    5520
caagtgcaac ggcaccgacg ccaaggtgaa actgatcaag caggaactgg acaagtacaa    5580
gaacgccgtg accgagctgc agctgctgat gcagagcacc cccgccacca acaaccgggc    5640
cagaagagag ctgccccggt tcatgaacta caccctgaac aacgccaaga aaaccaacgt    5700
gaccctgagc aagaagcgga gcggcggag cgccatcgcc agcggggtgg ccgtgtccaa    5760
ggtgctgcac ctggaaggcg aggtgaacaa gatcaagtcc gccctgctgt ccaccaacaa    5820
ggccgtggtg tccctgagca acggcgtgag cgtgctgacc agcaaggtgc tggatctgaa    5880
gaactacatc gacaagcagc tgctgcccat cgtgaacaag cagagctgca gcatcagcaa    5940
catcgagacc gtgatcgagt tccagcagaa gaacaaccgg ctgctggaaa tcacccggga    6000
gttcagcgtg aacgccggcg tgaccacccc cgtgagcacc tacatgctga ccaacagcga    6060
gctgctgtcc ctgatcaatg acatgcccat caccaacgac cagaaaaagc tgatgagcaa    6120
caacgtgcag atcgtgcggc agcagagcta ctccatcatg agcatcatca agaagaggt    6180
gctggcctac gtggtgcagc tgcccctgta cggcgtgatc gacacccct gctggaagct    6240
gcacaccagc ccccctgtgca ccaccaacac caaagagggc agcaacatct gcctgacccg    6300
gaccgaccgg ggctggtact gcgacaacgc cggcagcgtg agcttcttcc cccaagccga    6360
```

```
gacctgcaag gtgcagagca accgggtgtt ctgcgacacc atgaacagcc tgaccctgcc   6420
ctccgaggtg aacctgtgca acgtggacat cttcaacccc aagtacgact gcaagatcat   6480
gacctccaag accgacgtga gcagctccgt gatcacctcc ctgggcgcca tcgtgagctg   6540
ctacggcaag accaagtgca ccgccagcaa caagaaccgg ggcatcatca agaccttcag   6600
caacggctgc gactacgtga gcaacaaggg cgtggacacc gtgagcgtgg caacacact   6660
gtactacgtg aataagcagg aaggcaagag cctgtacgtg aagggcgagc ccatcatcaa   6720
cttctacgac cccctggtgt tccccagcga cgagttcgac gccagcatca gccaggtcaa   6780
cgagaagatc aaccagagcc tggccttcat ccggaagtcc gacgagctgc tgcacaatgt   6840
gaatgccggc aagagcacca ccaatatcat gatcaccaca atcatcatcg tgatcattgt   6900
gatcctgctg tctctgattg ccgtgggcct gctgctgtac tgcaaggccc gcagcacccc   6960
tgtgaccctg tccaaggacc agctgtccgg catcaacaat atcgccttct ccaactgaag   7020
tctagacggc gcgccaccc agcggccgca tacagcagca attggcaagc tgcttacata   7080
gaactcgcgg cgattggcat gccgccttaa aatttttatt ttatttttct tttcttttcc   7140
gaatcggatt ttgttttaa tatttcaaaa aaaaaaaaaa aaaaaaaaaa aaaaaaaaaa   7200
aaaaagaag agcgtttaaa cacgtgatat ctggcctcat gggccttcct ttcactgccc   7260
gctttccagt cgggaaacct gtcgtgccag ctgcattaac atggtcatag ctgtttcctt   7320
gcgtattggg cgctctccgc ttcctcgctc actgactcgc tgcgctcggt cgttcgggta   7380
aagcctgggt gcctaatga gcaaaaggcc agcaaaaggc caggaaccgt aaaaaggccg   7440
cgttgctggc gttttccat aggctccgcc ccctgacga gcatcacaaa aatcgacgct   7500
caagtcagag gtggcgaaac ccgacaggac tataaagata ccaggcgttt ccccctggaa   7560
gctccctcgt gcgctctcct gttccgaccc tgccgcttac cggatacctg tccgcctttc   7620
tcccttcggg aagcgtggcg ctttctcata gctcacgctg taggtatctc agttcggtgt   7680
aggtcgttcg ctccaagctg gctgtgtgc acgaaccccc cgttcagccc gaccgctgcg   7740
ccttatccgg taactatcgt cttgagtcca acccggtaag acacgactta tcgccactgg   7800
cagcagccac tggtaacagg attagcagag cgaggtatgt aggcggtgct acagagttct   7860
tgaagtggtg gcctaactac ggctacacta agaacagt atttggtatc tgcgctctgc   7920
tgaagccagt taccttcgga aaagagttg gtagctcttg atccggcaaa caaccaccg   7980
ctggtagcgg tggtttttt gtttgcaagc agcagattac gcgcagaaaa aaggatctc   8040
aagaagatcc tttgatcttt tctacggggt ctgacgctca gtggaacgaa actcacgtt   8100
aagggatttt ggtcatgaat acacggtgcc tgactgcgtt agcaatttaa ctgtgataaa   8160
ctaccgcatt aaagcttatc gatgataagc tgtcaaacat gagaattctt agaaaactc   8220
atcgagcatc aaatgaaact gcaatttatt catatcagga ttatcaatac catattttg   8280
aaaaagccgt ttctgtaatg aaggagaaaa ctcaccgagg cagttccata ggatggcaag   8340
atcctggtat cggtctgcga ttccgactcg tccaacatca atacaaccta ttaatttccc   8400
ctcgtcaaaa ataaggttat caagtgagaa atcaccatga gtgacgactg aatccggtga   8460
gaatggcaaa agcttatgca tttctttcca gacttgttca acaggccagc cattacgctc   8520
gtcatcaaaa tcactcgcat caaccaaacc gttattcatt cgtgattgcg cctgagcgag   8580
acgaaatacg cgatcgctgt taaaaggaca attacaaaca ggaatcgaat gcaaccggcg   8640
caggaacact gccagcgcat caacaatatt ttcacctgaa tcaggatatt cttctaatac   8700
```

```
ctggaatgct gttttcccgg ggatcgcagt ggtgagtaac catgcatcat caggagtacg   8760
gataaaatgc ttgatggtcg gaagaggcat aaattccgtc agccagttta gtctgaccat   8820
ctcatctgta acatcattgg caacgctacc tttgccatgt ttcagaaaca actctggcgc   8880
atcgggcttc ccatacaatc gatagattgt cgcacctgat tgcccgacat tatcgcgagc   8940
ccatttatac ccatataaat cagcatccat gttggaattt aatcgcggcc tcgagcaaga   9000
cgtttcccgt tgaatatggc tcataacacc ccttgtatta ctgtttatgt aagcagacag   9060
ttttattgtt catgagcgga tacatatttg aatgtattta gaaaaataaa caaataggggg   9120
ttccgcgcac atttcccccga aaagtgccac ctaaattgta agcgttaata ttttgttaaa   9180
attgcgtta aatttttgtt aaatcagctc attttttaac caataggccg aaatcggcaa   9240
aatcccttat aaatcaaaag aatagaccga tagggttg agtggccgct acagggcgct   9300
cccattcgcc attcaggctg cgcaactgtt gggaagggcg tttcggtgcg ggcctcttcg   9360
ctattacgcc agctggcgaa agggggatgt gctgcaaggc gattaagttg gtaacgcca   9420
gggttttccc agtcacacgc gtaatacgac tcactataga taggcggcgc atgagagaag   9480
cccagaccaa ttacctaccc aaaatggaga aagttcacgt tgacatcgag gaagacagcc   9540
cattcctcag agctttgcag cggagcttcc cgcagtttga ggtagaagcc aagcaggtca   9600
ctgataatga ccatgctaat gccagagcgt tttcgcatct ggcttcaaaa ctgatcgaaa   9660
cggaggtgga cccatccgac acgatccttg acattggaag tgcgcccgcc cgcagaatgt   9720
attctaagca caagtatcat tgtatctgtc cgatgagatg tgcggaagat ccggacagat   9780
tgtataagta tgcaactaag ctgaagaaaa actgtaagga ataactgat aaggaattgg   9840
acaagaaaat gaaggagctc gccgccgtca tgagcgaccc tgacctggaa actgagacta   9900
tgtgcctcca cgacgacgag tcgtgtcgct acgaagggca agtcgctgtt taccaggatg   9960
tatacgcggt tgacggaccg acaagtctct atcaccaagc caataaggga gttagagtcg  10020
cctactggat aggcttttgac accacccctt ttatgtttaa gaacttggct ggagcatatc  10080
catcatactc taccaactgg gccgacgaaa ccgtgttaac ggctcgtaac ataggcctat  10140
gcagctctga cgttatggag cggtcacgta gagggatgtc cattcttaga aagaagtatt  10200
tgaaaccatc caacaatgtt ctattctctg ttggctcgac catctaccac gagaagaggg  10260
acttactgag gagctggcac ctgccgtctg tatttcactt acgtggcaag caaaattaca  10320
catgtcggtg tgagactata gttagttgcg acgggtacgt cgttaaaaga atagctatca  10380
gtccaggcct gtatgggaag ccttcaggct atgctgctac gatgcaccgc gagggattct  10440
tgtgctgcaa agtgacagac acattgaacg gggagagggt ctctttttcc cgtgtgcacgt  10500
atgtgccagc tacattgtgt gaccaaatga ctggcatact ggcaacgat gtcagtgcgg  10560
acgacgcgca aaaactgctg gttgggctca accagcgtat agtcgtcaac ggtcgcaccc  10620
agagaaacac caataccatg aaaaattacc ttttgcccgt agtggccag gcatttgcta  10680
ggtgggcaaa ggaatataag gaagatcaag aagatgaaag gccactagga ctacgagata  10740
gacagttagt catggggtgt tgtgggctt ttagaaggca caagataaca tctatttata  10800
agcgcccgga tacccaaacc atcatcaaag tgaacagcga tttccactca ttcgtgctgc  10860
ccaggatagg cagtaacaca ttggagatcg ggctgagaac aagaatcagg aaaatgttag  10920
aggagcacaa ggagccgtca cctctcatta ccgccgagga cgtacaagaa gctaagtgcg  10980
cagccgatga ggctaaggag gtgcgtgaag ccgaggagtt gcgcgcagct ctaccacctt  11040
tggcagctga tgttgaggag cccactctgg aagccgatgt agacttgatg ttacaagagg  11100
```

```
ctggggccgg ctcagtggag acacctcgtg gcttgataaa ggttaccagc tacgatggcg    11160
aggacaagat cggctcttac gctgtgcttt ctccgcaggc tgtactcaag agtgaaaaat    11220
tatcttgcat ccaccctctc gctgaacaag tcatagtgat aacacactct ggccgaaaag    11280
ggcgttatgc cgtggaacca taccatggta agtagtggg gccagaggga catgcaatac     11340
ccgtccagga ctttcaagct ctgagtgaaa gtgccaccat tgtgtacaac gaacgtgagt    11400
tcgtaaacag gtacctgcac catattgcca cacatggagg agcgctgaac actgatgaag    11460
aatattacaa aactgtcaag cccagcgagc acgacggcga atacctgtac gacatcgaca    11520
ggaaacagtg cgtcaagaaa gaactagtca ctgggctagg gctcacaggc gagctggtgg    11580
atcctcccct ccatgaattc gcctacgaga gtctgagaac acgaccagcc gctccttacc    11640
aagtaccaac catagggggtg tatggcgtgc caggatcagg caagtctggc atcattaaaa   11700
gc                                                                   11702
```

<210> SEQ ID NO 4
<211> LENGTH: 15271
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgaagagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cattgaac ggggagaggg       1020 tctcttttcc cgtgtgcacg tatgtgccag ctacattgtg tgaccaaatg actggcatac     1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg     1200
tagtggccca ggcatttgct aggtgggcaa aggaatataa ggaagatcaa gaagatgaaa    1260
ggccactagg actacgagat agacagttag tcatgggggtg ttgttgggct tttagaaggc    1320
```

```
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccataggggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc gggatcccca acagtgcgg ttttttaac atgatgtgcc    2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg cttttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcaccacct gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
```

```
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg ccaccgaag     4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga atgggaaat  gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccacccccgc    5520
caggcgtgaa tagggtgatc actagagagg agctcgaggc gcttacccg  tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag gcatttaca  acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tccttttgtat tcatctagtg tgaaccgtgc cttttcaagc cccaaggtcg    6060
```

```
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgttttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta gcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgaggcct ggcctgccct cctacctgat catcctggcc gtgtgcctgt tcagccacct    7620
gctgtccagc agatacggcg ccgaggccgt gagcgagccc ctggacaagg ctttccacct    7680
gctgctgaac acctacggca gacccatccg gtttctgcgg gagaacacca cccagtgcac    7740
ctacaacagc agcctgcgga acagcaccgt cgtgagagag aacgccatca gcttcaactt    7800
tttccagagc tacaaccagt actacgtgtt ccacatgccc agatgcctgt tgccggccc    7860 tctggccgag cagttcctga ccaggtgga cctgaccgag acactggaaa gataccagca    7920
gcggctgaat acctacgccc tggtgtccaa ggacctggcc agctaccggt cctttagcca    7980
gcagctcaag gctcaggata gcctcggcga gcagcctacc accgtgcccc ctcccatcga    8040
cctgagcatc cccacgtgt ggatgcctcc ccagaccacc cctcacggct ggaccgagag    8100
ccacaccacc tccggcctgc acagacccca cttcaaccag acctgcatcc tgttcgacgg    8160
ccacgacctg ctgtttagca ccgtgacccc ctgcctgcac cagggcttct acctgatcga    8220
cgagctgaga tacgtgaaga tcaccctgac cgaggatttc ttcgtggtca ccgtgtccat    8280
cgacgacgac acccccatgc tgctgatctt cggccacctg cccagagtgc tgttcaaggc    8340
cccctaccag cgggacaact tcatcctgcg gcagaccgag aagcacgagc tgctggtgct    8400
ggtcaagaag gaccagctga accggcactc ctacctgaag gaccccgact tctggacgc    8460
```

```
cgccctggac ttcaactacc tggacctgag cgccctgctg agaaacagct tccacagata   8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga ccccccctag aaccaccctg ctgctgtacc ccacagccgt   8760
ggatctggcc aagagggccc tgtggacccc aaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaaact gcgctttctg tcagtctgcc ctgctggaat acgacgatac   9540
ccagggcgtg atcaacatca tgtacatgca cgacagcgac gacgtgctgt cgccctgga   9600
cccctacaac gaggtggtgg tgtccagccc ccggacccac tacctgatgc tgctgaagaa   9660
cggcaccgtg ctggaagtga ccgacgtggt ggtggacgcc accgacagca gactgctgat   9720
gatgagcgtg tacgccctga cgccatcat cggcatctac ctgctgtacc ggatgctgaa   9780
aacctgctga taatctagag gccctataa ctctctacgg ctaacctgaa tggactacga   9840
catagtctag tccgccaaga tgtgcagaag gcccgactgc ggcttcagct tcagccctgg   9900
acccgtgatc ctgctgtggt gctgcctgct gctgccatc gtgtcctctg ccgccgtgtc   9960
tgtggcccct acagccgccg agaaggtgcc agccgagtgc cccgagctga ccagaagatg  10020
cctgctgggc gaggtgttcg agggcgacaa gtacgagagc tggctgcggc ccctggtcaa  10080
cgtgaccggc agagatggcc ccctgagcca gctgatccgg tacagacccg tgaccccga  10140
ggccgccaat agcgtgctgc tggacgaggc cttcctggat accctggccc tgctgtacaa  10200
caaccccgac cagctgagag ccctgctgac cctgctgtcc agcgacaccg ccccagatg  10260
gatgaccgtg atgcggggct acagcgagtg tggagatggc agccctgccg tgtacacctg  10320
cgtggacgac ctgtgcagag gctacgacct gaccagactg agctacggcc ggtccatctt  10380
cacagagcac gtgctgggct tcgagctggt gccccccagc ctgttcaacg tggtggtggc  10440
catccggaac gaggccacca gaaccaacag agccgtgcgg ctgcctgtgt ctacagccgc  10500
tgcacctgag ggcatcacac tgttctacgg cctgtacaac gccgtgaaag agttctgcct  10560
ccggcaccag ctggatcccc ccctgctgag acacctggaa aagtactacg ccggcctgcc  10620
cccagagctg aagcagacca gagtgaacct gcccgcccac agcagatatg ccctcaggc  10680
cgtggacgcc agatgataac gccggcggcc cctataactc tctacggcta acctgaatgg  10740
actacgacat agtctagtcc gccaagatga gccccaagga cctgacccc ttcctgacaa  10800
```

-continued

```
ccctgtggct gctcctgggc catagcagag tgcctagagt gcgggccgag gaatgctgcg    10860
agttcatcaa cgtgaaccac ccccccgagc ggtgctacga cttcaagatg tgcaaccggt    10920
tcaccgtggc cctgagatgc cccgacggcg aagtgtgcta cagccccgag aaaaccgccg    10980
agatccgggg catcgtgacc accatgaccc acagcctgac ccggcaggtg gtgcacaaca    11040
agctgaccag ctgcaactac aaccccctgt acctggaagc cgacggccgg atcagatgcg    11100
gcaaagtgaa cgacaaggcc cagtacctgc tgggagccgc cggaagcgtg ccctaccggt    11160
ggatcaacct ggaatacgac aagatcaccc ggatcgtggg cctggaccag tacctggaaa    11220
gcgtgaagaa gcacaagcgg ctggacgtgt gcagagccaa gatgggctac atgctgcagc    11280
tgttgaattt tgaccttctt aagcttgcgg agacgtcga gtccaacccc gggcccatgc    11340
tgcggctgct gctgagacac cacttccact gcctgctgct gtgtgccgtg tgggccaccc    11400
cttgtctggc cagcccttgg agcaccctga ccgccaacca gaaccctagc ccccttggt    11460
ccaagctgac ctacagcaag ccccacgacg ccgccacctt ctactgcccc tttctgtacc    11520
ccagccctcc cagaagcccc ctgcagttca gcggcttcca gagagtgtcc accggccctg    11580
agtgccggaa cgagacactg tacctgctgt acaaccggga gggccagaca ctggtggagc    11640
ggagcagcac ctgggtgaaa aaagtgatct ggtatctgag cggccggaac cagaccatcc    11700
tgcagcggat gcccagaacc gccagcaagc ccagcgacgg caacgtgcag atcagcgtgg    11760
aggacgccaa aatcttcggc gcccacatgg tgcccaagca gaccaagctg ctgagattcg    11820
tggtcaacga cggcaccaga tatcagatgt gcgtgatgaa gctggaaagc tgggcccacg    11880
tgttccggga ctactccgtg agcttccagg tccggctgac cttcaccgag gccaacaacc    11940
agacctacac cttctgcacc caccccaacc tgatcgtgct gctgaacttc gacctgctga    12000
agctggccgg cgacgtggag agcaacccg gcccccatat gcggctgtgc agagtgtggc    12060
tgtccgtgtg cctgtgtgcc gtggtgctgg ccagtgcca gagagagaca gccgagaaga    12120
acgactacta ccgggtgccc cactactggg atgcctgcag cagagccctg cccgaccaga    12180
cccggtacaa atacgtggag cagctcgtgg acctgaccct gaactaccac tacgacgcca    12240
gccacgcct ggacaacttc gacgtgctga agcggatcaa cgtgaccgag gtgtccctgc    12300
tgatcagcga cttccggcgg cagaacagaa gaggcggcac caacaagcgg accaccttca    12360
acgccgctgg ctctctggcc cctcacgcca gatccctgga attcagcgtg cggctgttcg    12420
ccaactgata acgttgcatc ctgcaggata cagcagcaat tggcaagctg cttacataga    12480
actcgcggcg attggcatgc cgccttaaaa tttttatttt attttttcttt tcttttccga    12540
atcggatttt gttttttaata tttcaaaaaa aaaaaaaaaa aaaaaaaaaa aaaaaaaag    12600
ggtcggcatg gcatctccac ctcctcgcgg tccgacctgg gcatccgaag gaggacgcac    12660
gtccactcgg atggctaagg gagagccacg tttaaacgct agagcaagac gtttcccgtt    12720
gaatatggct cataacaccc cttgtattac tgtttatgta agcagacagt tttattgttc    12780
atgatgatat atttttatct tgtgcaatgt aacatcagag attttgagac acaacgtggc    12840
tttgttgaat aaatcgaact tttgctgagt tgaaggatca gatcacgcat cttcccgaca    12900
acgcagaccg ttccgtggca aagcaaaagt tcaaaatcac caactggtcc acctacaaca    12960
aagctctcat caaccgtggc tccctcactt tctggctgga tgatggggcg attcaggcct    13020
ggtatgagtc agcaacacct tcttcacgag gcagacctca gcgctagcgg agtgtatact    13080
ggcttactat gttggcactg atgagggtgt cagtgaagtg cttcatgtgg caggagaaaa    13140
aaggctgcac cggtgcgtca gcagaatatg tgatacagga tatattccgc ttcctcgctc    13200
```

```
actgactcgc tacgctcggt cgttcgactg cggcgagcgg aaatggctta cgaacggggc   13260
ggagatttcc tggaagatgc caggaagata cttaacaggg aagtgagagg gccgcggcaa   13320
agccgttttt ccataggctc cgcccccctg acaagcatca cgaaatctga cgctcaaatc   13380
agtggtggcg aaacccgaca ggactataaa gataccaggc gtttcccctg gcggctccct   13440
cgtgcgctct cctgttcctg cctttcggtt taccggtgtc attccgctgt tatggccgcg   13500
tttgtctcat tccacgcctg acactcagtt ccgggtaggc agttcgctcc aagctggact   13560
gtatgcacga accccccgtt cagtccgacc gctgcgcctt atccggtaac tatcgtcttg   13620
agtccaaccc ggaaagacat gcaaaagcac cactggcagc agccactggt aattgattta   13680
gaggagttag tcttgaagtc atgcgccggt taaggctaaa ctgaaaggac aagttttggt   13740
gactgcgctc ctccaagcca gttacctcgg ttcaaagagt tggtagctca gagaaccttc   13800
gaaaaaccgc cctgcaaggc ggttttttcg ttttcagagc aagagattac gcgcagacca   13860
aaacgatctc aagaagatca tcttattaag gggtctgacg ctcagtggaa cgaaaactca   13920
cgttaaggga ttttggtcat gagattatca aaaaggatct tcacctagat ccttttaaat   13980
taaaaatgaa gttttaaatc aatctaaagt atatatgagt aaacttggtc tgacagttat   14040
tagaaaaatt catccagcag acgataaaac gcaatacgct ggctatccgg tgccgcaatg   14100
ccatacagca ccagaaaacg atccgcccat tcgccgccca gttcttccgc aatatcacgg   14160
gtggccagcg caatatcctg ataacgatcc gccacgccca gacggccgca atcaataaag   14220
ccgctaaaac ggccatttc caccataatg ttcggcaggc acgcatcacc atgggtcacc   14280
accagatctt cgccatccgg catgctcgct ttcagacgcg caaacagctc tgccggtgcc   14340
aggccctgat gttcttcatc cagatcatcc tgatccacca ggcccgcttc catacgggta   14400
cgcgcacgtt caatacgatg tttcgcctga tgatcaaacg gacaggtcgc cgggtccagg   14460
gtatgcagac gacgcatggc atccgccata atgctcactt tttctgccgg cgccagatgg   14520
ctagacagca gatcctgacc cggcacttcg cccagcagca gccaatcacg gcccgcttcg   14580
gtcaccacat ccagcaccgc cgcacacgga acaccggtgg tggccagcca gctcagacgc   14640
gccgcttcat cctgcagctc gttcagcgca ccgctcagat cggttttcac aaacagcacc   14700
ggacgaccct gcgcgctcag acgaaacacc gccgcatcag agcagccaat ggtctgctgc   14760
gcccaatcat agccaaacag acgttccacc cacgctgccg ggctacccgc atgcaggcca   14820
tcctgttcaa tcatactctt ccttttcaa tattattgaa gcatttatca gggttattgt   14880
ctcatgagcg gatacatatt tgaatgtatt tagaaaaata aacaaatagg ggttccgcgc   14940
acatttcccc gaaaagtgcc acctaaattg taagcgttaa tattttgtta aaattcgcgt   15000 taaattttg ttaaatcagc tcattttta accaataggc cgaaatcggc aaaatccctt   15060
ataaatcaaa agaatagacc gagatagggt tgagtggccg ctacagggcg ctcccattcg   15120
ccattcaggc tgcgcaactg ttgggaaggg cgtttcggtg cgggcctctt cgctattacg   15180
ccagctggcg aaagggggat gtgctgcaag gcgattaagt tgggtaacgc cagggttttc   15240
ccagtcacac gcgtaatacg actcactata g                                 15271
```

<210> SEQ ID NO 5
<211> LENGTH: 16405
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 5

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg dacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt ccgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccacctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gccagcgag cacgacggcg    2040
aatacctgta cgacatcgac aggaaacagt gcgtcaagaa agaactagtc actgggctag    2100
ggctcacagg cgagctggtg gatcctccct ccatgaatt cgcctacgag agtctgagaa    2160
cacgaccagc cgctccttac caagtaccaa ccataggggt gtatgcgtg ccaggatcag    2220
gcaagtctgg catcattaaa agcgcagtca ccaaaaaaga tctagtggtg agcgccaaga    2280
```

```
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca aacagtgcgg ttttttttaac atgatgtgcc   2520 tgaaagtgca ttttaaccac gagatttgca cacaagtctt ccacaaaagc atctctcgcc    2580
gttgcactaa atctgtgact tcggtcgtct caaccttgtt ttacgacaaa aaatgagaa     2640 cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct ggagagacc ggaccctacc gacgtcttcc     3060
agaataaggc aaacgtgtgt gggccaagg ctttagtgcc ggtgctgaag accgctggca     3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgcttag    3480 tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataaaatac catcactatc    3720 agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga atgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
```

```
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcagaaac cagcctagtt tccaccccgc    5520
caggcgtgaa tagggtgatc actagagagg agctcgaggc gcttaccccg tcacgcactc    5580
ctagcaggtc ggtctcgaga accagcctgg tctccaaccc gccaggcgta ataggtgtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaacttttc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
```

```
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgaggcct ggcctgccct cctacctgat catcctggcc gtgtgcctgt tcagccacct    7620
gctgtccagc agatacggcg ccgaggccgt gagcgagccc ctggacaagg ctttccacct    7680
gctgctgaac acctacggca gacccatccg gtttctgcgg gagaacacca cccagtgcac    7740
ctacaacagc agcctgcgga acagcaccgt cgtgagagag aacgccatca gcttcaactt    7800
tttccagagc tacaaccagt actacgtgtt ccacatgccc agatgcctgt ttgccggccc    7860
tctggccgag cagttcctga accaggtgga cctgaccgag acactggaaa gataccagca    7920
gcggctgaat acctacgccc tggtgtccaa ggacctggcc agctaccggt cctttagcca    7980
gcagctcaag gctcaggata gcctcggcga gcagcctacc accgtgcccc ctcccatcga    8040
cctgagcatc ccccacgtgt ggatgcctcc ccagaccacc cctcacggct ggaccgagag    8100
ccacaccacc tccggcctgc acagaccccca cttcaaccag acctgcatcc tgttcgacgg    8160
ccacgacctg ctgtttagca ccgtgacccc ctgcctgcac cagggcttct acctgatcga    8220
cgagctgaga tacgtgaaga tcaccctgac cgaggatttc ttcgtggtca ccgtgtccat    8280
cgacgacgac acccccatgc tgctgatctt cggccacctg cccagagtgc tgttcaaggc    8340
cccctaccag cgggacaact tcatcctgcg gcagaccgag aagcacgagc tgctggtgct    8400
ggtcaagaag gaccagctga accggcactc ctacctgaag gaccccgact tcctggacgc    8460
cgccctggac ttcaactacc tggacctgag cgccctgctg agaaacagct ccacagata    8520 cgccgtggac gtgctgaagt ccggacggtg ccagatgctc gatcggcgga ccgtggagat    8580
ggccttcgcc tatgccctcg ccctgttcgc cgctgccaga caggaagagg ctggcgccca    8640
ggtgtcagtg cccagagccc tggatagaca ggccgccctg ctgcagatcc aggaattcat    8700
gatcacctgc ctgagccaga ccccccctag aaccaccctg ctgctgtacc ccacagccgt    8760
ggatctggcc aagagggccc tgtggacccc caaccagatc accgacatca aagcctcgt    8820 gcggctcgtg tacatcctga gcaagcagaa ccagcagcac ctgatccccc agtgggccct    8880
gagacagatc gccgacttcg ccctgaagct gcacaagacc catctggcca gctttctgag    8940
cgccttcgcc aggcaggaac tgtacctgat gggcagcctg gtccacagca tgctggtgca    9000
taccaccgag cggcgggaga tcttcatcgt ggagacaggc ctgtgtagcc tggccgagct    9060
gtcccacttt acccagctgc tggcccacc tcaccacgag tacctgagcg acctgtacac    9120
cccctgcagc agcagcggca gacgggacca cagcctggaa cggctgacca gactgttccc    9180
cgatgccacc gtgcctgcta cagtgcctgc cgccctgtcc atcctgtcca ccatgcagcc    9240
cagcacctcg gaaaccttcc ccgacctgtt ctgcctgccc ctgggcgaga gctttagcgc    9300
cctgaccgtg tccgagcacg tgtcctacat cgtgaccaat cagtacctga tcaagggcat    9360
```

```
cagctacccc gtgtccacca cagtcgtggg ccagagcctg atcatcaccc agaccgacag    9420
ccagaccaag tgcgagctga cccggaacat gcacaccaca cacagcatca ccgtggccct    9480
gaacatcagc ctggaaaact gcgctttctg tcagtctgcc ctgctggaat acgacgatac    9540
ccagggcgtg atcaacatca tgtacatgca cgacagcgac gacgtgctgt tcgccctgga    9600
cccctacaac gaggtggtgg tgtccagccc ccggacccac tacctgatgc tgctgaagaa    9660
cggcaccgtg ctggaagtga ccgacgtggt ggtggacgcc accgacagca gactgctgat    9720
gatgagcgtg tacgccctga cgccatcat cggcatctac ctgctgtacc ggatgctgaa    9780
aacctgctga taatctagag gcccctataa ctctctacgg ctaacctgaa tggactacga    9840
catagtctag tccgccaaga tgtgcagaag gcccgactgc ggcttcagct tcagccctgg    9900
acccgtgatc ctgctgtggt gctgcctgct gctgcctatc gtgtcctctg ccgccgtgtc    9960
tgtggcccct acagccgccg agaaggtgcc agccgagtgc cccgagctga ccagaagatg   10020
cctgctgggc gaggtgttcg agggcgacaa gtacgagagc tggctgcggc ccctggtcaa   10080
cgtgaccggc agagatggcc ccctgagcca gctgatccgg tacagacccg tgaccccga    10140 ggccgccaat agcgtgctgc tggacgaggc cttcctggat accctggccc tgctgtacaa   10200
caaccccgac cagctgagag ccctgctgac cctgctgtcc agcgacaccg ccccagatg    10260 gatgaccgtg atgcggggct acagcgagtg tggagatggc agccctgccg tgtacacctg   10320
cgtggacgac ctgtgcagag gctacgacct gaccagactg agctacgcc ggtccatctt    10380 cacagagcac gtgctgggct tcgagctggt gccccccagc ctgttcaacg tggtggtggc   10440
catccggaac gaggccacca gaaccaacag agccgtgcgg ctgcctgtgt ctacagccgc   10500
tgcacctgag ggcatcacac tgttctacgg cctgtacaac gccgtgaaag agttctgcct   10560
ccggcaccag ctggatcccc ccctgctgag acacctggac aagtactacg ccggcctgcc   10620
cccagagctg aagcagacca gagtgaacct gcccgcccac agcagatatg ccctcaggc    10680 cgtggacgcc agatgataac gccggcggcc cctataactc tctacggcta acctgaatgg   10740
actacgacat agtctagtcc gccaagatga gccccaagga cctgaccccc ttcctgacaa   10800 ccctgtgget getcctgggc catagcagag tgcctagagt gcgggccgag gaatgctgcg    10860
agttcatcaa cgtgaaccac ccccccgagc ggtgctacga cttcaagatg tgcaaccggt   10920
tcaccgtggc cctgagatgc cccgacgcg aagtgtgcta cagccccgag aaaaccgccg    10980
agatccgggg catcgtgacc accatgacccc acagcctgac ccggcaggtg gtgcacaaca   11040
agctgaccag ctgcaactac aaccccctgt acctggaagc cgacggcagg atcagatgcg   11100
gcaaagtgaa cgacaaggcc cagtacctgc tgggagccgc cggaagcgtg ccctaccggt   11160
ggatcaacct ggaatacgac aagatcaccc ggatcgtggg cctggaccag tacctggaaa   11220
gcgtgaagaa gcacaagcgg ctggacgtgt gcagagccaa gatgggctac atgctgcagt   11280
gataaggcgc gccaacgtta ctggccgaag ccgcttggaa taaggccggt gtgcgtttgt    11340
ctatatgtta ttttccacca tattgccgtc ttttggcaat gtgagggccc ggaaacctgg   11400
ccctgtcttc ttgacgagca ttcctagggg tctttcccct ctcgccaaag gaatgcaagg   11460
tctgttgaat gtcgtgaagg aagcagttcc tctggaagct tcttgaagac aaacaacgtc   11520
tgtagcgacc ctttgcaggc agcggaaccc cccacctggc gacaggtgcc tctgcggcca    11580
aaagccacgt gtataagata cacctgcaaa ggcggcacaa ccccagtgcc acgttgtgag   11640
ttggatagtt gtggaaagag tcaaatggct ctcctcaagc gtattcaaca aggggctgaa   11700
ggatgcccag aaggtacccc attgtatggg atctgatctg gggcctcggt gcacatgctt   11760
```

```
tacatgtgtt tagtcgaggt taaaaaaacg tctaggcccc ccgaaccacg gggacgtggt   11820
tttcctttga aaaacacgat aatatgctgc ggctgctgct gagacaccac ttccactgcc   11880
tgctgctgtg tgccgtgtgg gccacccctt gtctggccag cccttggagc accctgaccg   11940
ccaaccagaa ccctagcccc ccttggtcca agctgaccta cagcaagccc cacgacgccc   12000
ccaccttcta ctgccccttt ctgtacccca gccctcccag aagcccctg cagttcagcg    12060 gcttccagag agtgtccacc ggccctgagt gccggaacga gacactgtac ctgctgtaca   12120
accgggaggg ccagacactg gtggagcgga gcagcacctg ggtgaaaaaa gtgatctggt   12180
atctgagcgg ccggaaccag accatcctgc agcggatgcc cagaaccgcc agcaagccca   12240
gcgacggcaa cgtgcagatc agcgtggagg acgccaaaat cttcggagcc cacatggtgc   12300
ccaagcagac caagctgctg agattcgtgg tcaacgacgg caccagatat cagatgtgcg   12360
tgatgaagct ggaaagctgg gcccacgtgt tccgggacta ctccgtgagc ttccaggtcc   12420
ggctgacctt caccgaggcc aacaaccaga cctacacctt ctgcacccac cccaacctga   12480
tcgtgtgata agtacctttg tacgcctgtt ttatacccccc tccctgattt gcaacttaga  12540
agcaacgcaa accagatcaa tagtaggtgt gacataccag tcgcatcttg atcaagcact   12600
tctgtatccc cggaccgagt atcaatagac tgtgcacacg gttgaaggag aaaacgtccg   12660
ttacccggct aactacttcg agaagcctag taacgccatt gaagttgcag agtgtttcgc   12720
tcagcactcc ccccgtgtag atcaggtcga tgagtcaccg cattcccccac gggcgaccgt   12780 ggcggtggct gcgttggcgg cctgcctatg gggtaaccca taggacgctc taatacggac   12840
atggcgtgaa gagtctattg agctagttag tagtcctccg gcccctgaat gcggctaatc   12900
ctaactgcgg agcacatacc cttaatccaa agggcagtgt gtcgtaacgg gcaactctgc   12960
agcggaaccg actactttgg gtgtccgtgt ttctttttat tcttgtattg gctgcttatg   13020
gtgacaatta aagaattgtt accatatagc tattggattg gccatccagt gtcaaacaga   13080
gctattgtat atctctttgt tggattcaca cctctcactc ttgaaacgtt acacaccctc   13140
aattacatta tactgctgaa cacgaagcgc atatgcggct gtgcagagtg tggctgtccg   13200
tgtgcctgtg tgccgtggtg ctgggccagt gccagagaga gacagccgag aagaacgact   13260
actaccgggt gccccactac tgggatgcct gcagcagagc cctgcccgac cagacccggt   13320
acaaatacgt ggagcagctc gtggacctga ccctgaacta ccactacgac gccagccacg   13380
gcctggacaa cttcgacgtg ctgaagcgga tcaacgtgac cgaggtgtcc ctgctgatca   13440
gcgacttccg gcggcagaac agaagaggcg gcaccaacaa gcggaccacc ttcaacgccg   13500
ctggctctct ggcccctcac gccagatccc tggaattcag cgtgcggctg ttcgccaact   13560
gataacgttg catcctgcag gatacagcag caattggcaa gctgcttaca tagaactcgc   13620
ggcgattggc atgccgcctt aaaattttta tttattttt cttttctttt ccgaatcgga    13680
ttttgttttt aatatttcaa aaaaaaaaa aaaaaaaa aaaaaaaaa aagggtcgg        13740 catggcatct ccacctcctc gcggtccgac ctgggcatcc gaaggaggac gcacgtccac   13800
tcggatggct aagggagagc cacgtttaaa cgctagagca agacgtttcc cgttgaatat   13860
ggctcataac accccttgta ttactgttta tgtaagcaga cagttttatt gttcatgatg   13920
atatattttt atcttgtgca atgtaacatc agagattttg agacacaacg tggctttgtt   13980
gaataaatcg aacttttgct gagttgaagg atcagatcac gcatcttccc gacaacgcag   14040
accgttccgt ggcaaagcaa aagttcaaaa tcaccaactg gtccacctac aacaaagctc   14100
```

```
tcatcaaccg tggctccctc actttctggc tggatgatgg ggcgattcag gcctggtatg   14160
agtcagcaac accttcttca cgaggcagac ctcagcgcta gcggagtgta tactggctta   14220
ctatgttggc actgatgagg gtgtcagtga agtgcttcat gtggcaggag aaaaaaggct   14280
gcaccggtgc gtcagcagaa tatgtgatac aggatatatt ccgcttcctc gctcactgac   14340
tcgctacgct cggtcgttcg actgcggcga gcggaaatgg cttacgaacg gggcggagat   14400
ttcctggaag atgccaggaa gatacttaac agggaagtga gagggccgcg gcaaagccgt   14460
ttttccatag gctccgcccc cctgacaagc atcacgaaat ctgacgctca aatcagtggt   14520
ggcgaaaccc gacaggacta taaagatacc aggcgtttcc cctggcggct ccctcgtgcg   14580
ctctcctgtt cctgcctttc ggtttaccgg tgtcattccg ctgttatggc cgcgtttgtc   14640
tcattccacg cctgacactc agttccgggt aggcagttcg ctccaagctg gactgtatgc   14700
acgaaccccc cgttcagtcc gaccgctgcg ccttatccgg taactatcgt cttgagtcca   14760
acccggaaag acatgcaaaa gcaccactgg cagcagccac tggtaattga tttagaggag   14820
ttagtcttga agtcatgcgc cggttaaggc taaactgaaa ggacaagttt tggtgactgc   14880
gctcctccaa gccagttacc tcggttcaaa gagttggtag ctcagagaac cttcgaaaaa   14940 ccgcctgca aggcggtttt tcgttttca gagcaagaga ttacgcgcag accaaaacga   15000
tctcaagaag atcatcttat taagggtct gacgctcagt ggaacgaaaa ctcacgttaa   15060 gggatttgg tcatgagatt atcaaaaagg atcttcacct agatccttt aaattaaaa   15120 tgaagtttta aatcaatcta agtatatat gagtaaactt ggtctgacag ttattagaaa   15180
aattcatcca gcagacgata aaacgcaata cgctggctat ccggtgccgc aatgccatac   15240
agcaccagaa aacgatccgc ccattcgccg cccagttctt ccgcaatatc acgggtggcc   15300
agcgcaatat cctgataacg atccgccacg cccagacggc cgcaatcaat aaagccgcta   15360
aaacggccat tttccaccat aatgttcggc aggcacgcat caccatgggt caccaccaga   15420
tcttcgccat ccggcatgct cgcttcaga gcgcaaaca gctctgccgg tgccaggccc   15480
tgatgttctt catccagatc atcctgatcc accaggcccg cttccatacg ggtacgcgca   15540
cgttcaatac gatgtttcgc ctgatgatca aacggacagg tcgccgggtc cagggtatgc   15600
agacgacgca tggcatccgc cataatgctc acttttctg ccggcgccag atggctagac   15660
agcagatcct gacccggcac ttcgcccagc agcagccaat cacggcccgc ttcggtcacc   15720
acatccagca ccgccgcaca cggaacaccg gtggtggcca gccagctcag acgcgccgct   15780
tcatcctgca gctcgttcag cgcaccgctc agatcggttt tcacaaacag caccggacga   15840
ccctgcgcgc tcagacgaaa caccgccgca tcagagcagc caatggtctg ctgcgcccaa   15900
tcatagccaa acagacgttc cacccacgct gccgggctac ccgcatgcag gccatcctgt   15960
tcaatcatac tcttcctttt tcaatattat tgaagcattt atcagggtta ttgtctcatg   16020
agcggataca tatttgaatg tatttagaaa aataaacaaa tagggggttcc gcgcacattt   16080 ccccgaaaag tgccacctaa attgtaagcg ttaatatttt gttaaaattc gcgttaaatt   16140
tttgttaaat cagctcattt tttaaccaat aggccgaaat cggcaaaatc ccttataaat   16200
caaaagaata gaccgagata gggttgagtg gccgctacag ggcgctccca ttcgccattc   16260
aggctgcgca actgttggga agggcgtttc ggtgcgggcc tcttcgctat tacgccagct   16320
ggcgaaaggg ggatgtgctg caaggcgatt aagttgggta acgccagggt tttcccagtc   16380
acacgcgtaa tacgactcac tatag                                        16405
```

<210> SEQ ID NO 6
<211> LENGTH: 13102
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

| | | | | | |
|---|---|---|---|---|---|
| ataggcggcg | catgagagaa | gcccagacca | attacctacc | caaaatggag | aaagttcacg | 60 |
| ttgacatcga | ggaagacagc | ccattcctca | gagctttgca | gcggagcttc | ccgcagtttg | 120 |
| aggtagaagc | caagcaggtc | actgataatg | accatgctaa | tgccagagcg | ttttcgcatc | 180 |
| tggcttcaaa | actgatcgaa | acggaggtgg | acccatccga | cacgatcctt | gacattggaa | 240 |
| gtgcgcccgc | ccgcagaatg | tattctaagc | acaagtatca | ttgtatctgt | ccgatgagat | 300 |
| gtgcggaaga | tccggacaga | ttgtataagt | atgcaactaa | gctgaagaaa | aactgtaagg | 360 |
| aaataactga | taaggaattg | acaagaaaa | tgaaggagct | cgccgccgtc | atgagcgacc | 420 |
| ctgacctgga | aactgagact | atgtgcctcc | acgacgacga | gtcgtgtcgc | tacgaagggc | 480 |
| aagtcgctgt | ttaccaggat | gtatacgcgg | ttgacggacc | gacaagtctc | tatcaccaag | 540 |
| ccaataaggg | agttagagtc | gcctactgga | taggctttga | caccacccct | tttatgttta | 600 |
| agaacttggc | tggagcatat | ccatcatact | ctaccaactg | ggccgacgaa | accgtgttaa | 660 |
| cggctcgtaa | cataggccta | tgcagctctg | acgttatgga | gcggtcacgt | agagggatgt | 720 |
| ccattcttag | aaagaagtat | ttgaaaccat | ccaacaatgt | tctattctct | gttggctcga | 780 |
| ccatctacca | cgagaagagg | gacttactga | ggagctggca | cctgccgtct | gtatttcact | 840 |
| tacgtggcaa | gcaaaattac | acatgtcggt | gtgagactat | agttagttgc | gacgggtacg | 900 |
| tcgttaaaag | aatagctatc | agtccaggcc | tgtatgggaa | gccttcaggc | tatgctgcta | 960 |
| cgatgcaccg | cgagggattc | ttgtgctgca | aagtgacaga | cattgaac | ggggagaggg | 1020 |
| tctctttttcc | cgtgtgcacg | tatgtgccag | ctacattgtg | tgaccaaatg | actggcatac | 1080 |
| tggcaacaga | tgtcagtgcg | gacgacgcgc | aaaaactgct | ggttgggctc | aaccagcgta | 1140 |
| tagtcgtcaa | cggtcgcacc | cagagaaaca | ccaataccat | gaaaaattac | cttttgcccg | 1200 |
| tagtggccca | ggcatttgct | aggtgggcaa | aggaatataa | ggaagatcaa | gaagatgaaa | 1260 |
| ggccactagg | actacgagat | agacagttag | tcatggggtg | ttgttgggct | tttagaaggc | 1320 |
| acaagataac | atctatttat | aagcgcccgg | atacccaaac | catcatcaaa | gtgaacagcg | 1380 |
| atttccactc | attcgtgctg | cccaggatag | gcagtaacac | attggagatc | gggctgaaaa | 1440 |
| caagaatcag | gaaaatgtta | gaggagcaca | aggagccgtc | acctctcatt | accgccgagg | 1500 |
| acgtacaaga | agctaagtgc | gcagccgatg | aggctaagga | ggtgcgtgaa | gccgaggagt | 1560 |
| tgcgcgcagc | tctaccacct | ttggcagctg | atgttgagga | gcccactctg | gaagccgatg | 1620 |
| tcgacttgat | gttacaagag | gctggggccg | gctcagtgga | gacacctgt | ggcttgataa | 1680 |
| aggttaccag | ctacgatggc | gaggacaaga | tcggctctta | cgctgtgctt | tctccgcagg | 1740 |
| ctgtactcaa | gagtgaaaaa | ttatcttgca | tccaccctct | cgctgaacaa | gtcatagtga | 1800 |
| taacacactc | tggccgaaaa | gggcgttatg | ccgtggaacc | ataccatggt | aaagtagtgg | 1860 |
| tgccagaggg | acatgcaata | cccgtccagg | actttcaagc | tctgagtgaa | agtgccacca | 1920 |
| ttgtgtacaa | cgaacgtgag | ttcgtaaaca | ggtacctgca | ccatattgcc | acacatggag | 1980 |
| gagcgctgaa | cactgatgaa | gaatattaca | aaactgtcaa | gcccagcgag | cacgacggcg | 2040 |

-continued

```
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag     2220
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg     2340 ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca aacagtgcgg ttttttttaac atgatgtgcc   2520 tgaaagtgca ttttaaccac gagatttgca cacaagtctt ccacaaaagc atctctcgcc    2580
gttgcactaa atctgtgact tcggtcgtct caaccttgtt ttacgacaaa aaatgagaa     2640 cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct ggagagacc ggaccctacc gacgtcttcc     3060
agaataaggc aaacgtgtgt gggccaagg ctttagtgcc ggtgctgaag accgctggca     3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg ccaccgaag    4080 gagtgattat aaatgctgct aacagcaaag acaacctgg cggagggtg tgcggagcgc      4140 tgtataagaa attcccggaa agcttcgatt tacagccgat cgaagtagga aaagcgcgac    4200
tggtcaaagg tgcagctaaa catatcattc atgccgtagg accaaacttc aacaaagttt    4260 cggagggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
```

```
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgc caaaacttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga ccgatcatc atcgaagagg     5160 aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttaccccg tcacgcactc    5580
ctagcaggtc ggtctcgaga accagcctgg tctccaaccc gccaggcgta aataggtga     5640 ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa agaaattgc aatgtcacgc aaatgagaga attgcccgta ttggattcgg     6360
cggcctttaa tgtggaatgc ttcaagaaat atgcgtgtaa taatgaatat gggaaacgt     6420 ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
```

```
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg aatgttcct cacactgttt gtgaacacag    7020
tcattaacat tgtaatcgca agcagagtgt tgagagaacg gctaaccgga tcaccatgtg   7080
cagcattcat tggagatgac aatatcgtga aggagtcaa atcggacaaa ttaatggcag    7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac acatagtct agtccgccaa     7560
gatgaggcct ggcctgccct cctacctgat catcctggcc gtgtgcctgt tcagccacct   7620
gctgtccagc agatacggcg ccgaggccgt gagcgagccc ctggacaagg cttttccacct  7680
gctgctgaac acctacggca gacccatccg gtttctgcgg gagaacacca cccagtgcac   7740
ctacaacagc agcctgcgga acagcaccgt cgtgagagag aacgccatca gcttcaactt   7800
tttccagagc tacaaccagt actacgtgtt ccacatgccc agatgcctgt tgccggccc    7860
tctggccgag cagttcctga accaggtgga cctgaccgag acactggaaa gataccagca   7920
gcggctgaat acctacgccc tggtgtccaa ggacctggcc agctaccggt cctttagcca   7980
gcagctcaag gctcaggata gcctcggcga gcagcctacc accgtgcccc ctcccatcga   8040
cctgagcatc ccccacgtgt ggatgcctcc ccagaccacc cctcacggct ggaccgagag   8100
ccacaccacc tccggcctgc acagacccca cttcaaccag acctgcatcc tgttcgacgg   8160
ccacgacctg ctgtttagca ccgtgacccc ctgcctgcac cagggcttct acctgatcga   8220
cgagctgaga tacgtgaaga tcaccctgac cgaggatttc ttcgtggtca ccgtgtccat   8280
cgacgacgac accccccatgc tgctgatctt cggccacctg cccagagtgc tgttcaaggc   8340
cccctaccag cgggacaact tcatcctgcg gcagaccgag aagcacgagc tgctggtgct   8400
ggtcaagaag gaccagctga accggcactc ctacctgaag gaccccgact tcctggacgc   8460
cgccctggac ttcaactacc tggacctgag cgccctgctg agaaacagct ccacagata    8520
cgccgtggac gtgctgaagt ccggacggtg ccagatgctc gatcggcgga ccgtggagat   8580
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga ccccccctag aaccaccctg ctgctgtacc ccacagccgt   8760
ggatctggcc aagagggccc tgtggacccc caaccagatc accgacatca aagcctcgt    8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggccccacc tcaccacgag tacctgagcg acctgtacac   9120
cccctgcagc agcagcggca cgacgggacca cagcctggaa cggctgacca gactgttccc   9180
```

```
cgatgccacc gtgcctgcta cagtgcctgc cgccctgtcc atcctgtcca ccatgcagcc    9240
cagcaccctg gaaaccttcc ccgacctgtt ctgcctgccc ctgggcgaga gctttagcgc    9300
cctgaccgtg tccgagcacg tgtcctacat cgtgaccaat cagtacctga tcaagggcat    9360
cagctacccc gtgtccacca cagtcgtggg ccagagcctg atcatcaccc agaccgacag    9420
ccagaccaag tgcgagctga cccggaacat gcacaccaca cacagcatca ccgtggccct    9480
gaacatcagc ctggaaaact gcgctttctg tcagtctgcc ctgctggaat acgacgatac    9540
ccagggcgtg atcaacatca tgtacatgca cgacagcgac gacgtgctgt cgccctgga    9600 cccctacaac gaggtggtgg tgtccagccc ccggacccac tacctgatgc tgctgaagaa    9660
cggcaccgtg ctggaagtga ccgacgtggt ggtggacgcc accgactgat aatctagagg    9720
cccctataac tctctacggc taacctgaat ggactacgac atagtctagt ccgccaagat    9780
gtgcagaagg cccgactgcg gcttcagctt cagccctgga cccgtgatcc tgctgtggtg    9840
ctgcctgctg ctgcctatcg tgtcctctgc cgccgtgtct gtggcccta cagccgccga    9900 gaaggtgcca gccgagtgcc ccgagctgac cagaagatgc ctgctgggcg aggtgttcga    9960
gggcgacaag tacgagagct ggctgcggcc cctggtcaac gtgaccggca gagatggccc    10020
cctgagccag ctgatccggt acagacccgt gaccccgag gccgccaata gcgtgctgct    10080
ggacgaggcc ttcctggata ccctggccct gctgtacaac aaccccgacc agctgagagc    10140
cctgctgacc ctgctgtcca cgacaccgc ccccagatgg atgaccgtga tgcggggcta    10200
cagcgagtgt ggagatggca gccctgccgt gtacacctgc gtggacgacc tgtgcagagg    10260
ctacgacctg accagactga gctacggccg gtccatcttc acagagcacg tgctgggctt    10320
cgagctggtg ccccccagcc tgttcaacgt ggtggtggcc atccggaacg aggccaccag    10380
aaccaacaga gccgtgcggc tgcctgtgtc tacagccgct gcacctgagg gcatcacact    10440
gttctacggc ctgtacaacg ccgtgaaaga gttctgcctc cggcaccagc tggatccccc    10500
cctgctgaga cacctggaca agtactacgc cggcctgccc ccagagctga agcagaccag    10560
agtgaacctg cccgcccaca gcagatatgg ccctcaggcc gtggacgcca gatgataagc    10620
ggccgcatac agcagcaatt ggcaagctgc ttacatagaa ctcgcggcga ttggcatgcc    10680
gccttaaaat tttatttta tttttcttt cttttccgaa tcggattttg tttttaatat    10740 ttcaaaaaa aaaaaaaaa aaaaaaaaa aaaaaaagg gtcggcatgg catctccacc    10800
tcctcgcggt ccgacctggg catccgaagg aggacgcacg tccactcgga tggctaaggg    10860
agagccacgt ttaaacacgt gatatctggc ctcatgggcc ttccttcac tgcccgcttt    10920 ccagtcggga aacctgtcgt gccagctgca ttaacatggt catagctgtt ccttgcgta    10980 ttgggcgctc tccgcttcct cgctcactga ctcgctgcgc tcggtcgttc gggtaaagcc    11040
tggggtgcct aatgagcaaa aggccagcaa aaggccagga accgtaaaaa ggccgcgttg    11100
ctggcgtttt tccataggct ccgcccccct gacgagcatc acaaaaatcg acgctcaagt    11160
cagaggtggc gaaacccgac aggactataa agataccagg cgtttccccc tggaagctcc    11220
ctcgtgcgct ctcctgttcc gaccctgccg cttaccggat acctgtccgc ctttctccct    11280
tcgggaagcg tggcgctttc tcatagctca cgctgtaggt atctcagttc ggtgtaggtc    11340
gttcgctcca agctgggctg tgtgcacgaa ccccccgttc agcccgaccg ctgcgcctta    11400
tccggtaact atcgtcttga gtccaacccg gtaagacacg acttatcgcc actggcagca    11460
gccactggta acaggattag cagagcgagg tatgtaggcg gtgctacaga gttcttgaag    11520
```

```
tggtggccta actacggcta cactagaaga acagtatttg gtatctgcgc tctgctgaag    11580
ccagttacct tcggaaaaag agttggtagc tcttgatccg gcaaacaaac caccgctggt    11640
agcggtggtt ttttttgtttg caagcagcag attacgcgca gaaaaaaagg atctcaagaa   11700
gatcctttga tcttttctac ggggtctgac gctcagtgga acgaaaactc acgttaaggg    11760
attttggtca tgagattatc aaaaaggatc ttcacctaga tccttttaaa ttaaaaatga    11820
agttttaaat caatctaaag tatatatgag taaacttggt ctgacagtta ttagaaaaat    11880
tcatccagca gacgataaaa cgcaatacgc tggctatccg gtgccgcaat gccatacagc    11940
accagaaaac gatccgccca ttcgccgccc agttcttccg caatatcacg gtggccagc     12000
gcaatatcct gataacgatc cgccacgccc agacggccgc aatcaataaa gccgctaaaa    12060
cggccatttt ccaccataat gttcggcagg cacgcatcac catgggtcac caccagatct    12120
tcgccatccg gcatgctcgc tttcagacgc gcaaacagct ctgccggtgc caggccctga    12180
tgttcttcat ccagatcatc ctgatccacc aggcccgctt ccatacgggt acgcgcacgt    12240
tcaatacgat gtttcgcctg atgatcaaac ggacaggtcg ccgggtccag ggtatgcaga    12300
cgacgcatgg catccgccat aatgctcact ttttctgccg gcgccagatg gctagacagc    12360
agatcctgac ccggcacttc gcccagcagc agccaatcac ggcccgcttc ggtcaccaca    12420
tccagcaccg ccgcacacgg aacaccggtg gtggccagcc agctcagacg gccgcttca    12480
tcctgcagct cgttcagcgc accgctcaga tcggttttca caaacagcac cggacgaccc    12540
tgcgcgctca gacgaaacac cgccgcatca gagcagccaa tggtctgctg cgcccaatca    12600
tagccaaaca gacgttccac ccacgctgcc gggctaccg catgcaggcc atcctgttca    12660
atcatactct tcctttttca atattattga agcatttatc agggttattg tctcatgagc    12720
ggatacatat ttgaatgtat ttagaaaaat aaacaaatag gggttccgcg cacatttccc    12780
cgaaaagtgc cacctaaatt gtaagcgtta atattttgtt aaaattcgcg ttaaattttt    12840
gttaaatcag ctcattttt aaccaatagg ccgaaatcgg caaaatccct tataaatcaa    12900
aagaatagac cgagataggg ttgagtggcc gctacagggc gctcccattc gccattcagg    12960
ctgcgcaact gttgggaagg gcgtttcggt gcgggcctct tcgctattac gccagctggc    13020
gaaaggggga tgtgctgcaa ggcgattaag ttgggtaacg ccagggtttt cccagtcaca    13080
cgcgtaatac gactcactat ag                                              13102
```

<210> SEQ ID NO 7
<211> LENGTH: 13087
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa actgtaaggg     360
aaataactga taaggaattg gacaagaaaa tgaaggagct cgccgccgtc atgagcgacc     420
```

| | |
|---|---|
| ctgacctgga aactgagact atgtgcctcc acgacgacga gtcgtgtcgc tacgaagggc | 480 |
| aagtcgctgt ttaccaggat gtatacgcgg ttgacggacc gacaagtctc tatcaccaag | 540 |
| ccaataaggg agttagagtc gcctactgga taggctttga caccacccct tttatgttta | 600 |
| agaacttggc tggagcatat ccatcatact ctaccaactg ggccgacgaa accgtgttaa | 660 |
| cggctcgtaa cataggccta tgcagctctg acgttatgga gcggtcacgt agagggatgt | 720 |
| ccattcttag aaagaagtat ttgaaaccat ccaacaatgt tctattctct gttggctcga | 780 |
| ccatctacca cgagaagagg gacttactga ggagctggca cctgccgtct gtatttcact | 840 |
| tacgtggcaa gcaaaattac acatgtcggt gtgagactat agttagttgc gacgggtacg | 900 |
| tcgttaaaag aatagctatc agtccaggcc tgtatgggaa gccttcaggc tatgctgcta | 960 |
| cgatgcaccg cgagggattc ttgtgctgca aagtgacaga cacattgaac ggggagaggg | 1020 |
| tctcttttcc cgtgtgcacg tatgtgccag ctacattgtg tgaccaaatg actggcatac | 1080 |
| tggcaacaga tgtcagtgcg gacgacgcgc aaaaactgct ggttgggctc aaccagcgta | 1140 |
| tagtcgtcaa cggtcgcacc cagagaaaca ccaataccat gaaaaattac cttttgcccg | 1200 |
| tagtggccca ggcatttgct aggtgggcaa aggaatataa ggaagatcaa gaagatgaaa | 1260 |
| ggccactagg actacgagat agacagttag tcatggggtg ttgttgggct tttagaaggc | 1320 |
| acaagataac atctatttat aagcgcccgg atacccaaac catcatcaaa gtgaacagcg | 1380 |
| atttccactc attcgtgctg cccaggatag gcagtaacac attggagatc gggctgagaa | 1440 |
| caagaatcag gaaaatgtta gaggagcaca aggagccgtc acctctcatt accgccgagg | 1500 |
| acgtacaaga agctaagtgc gcagccgatg aggctaagga ggtgcgtgaa gccgaggagt | 1560 |
| tgcgcgcagc tctaccacct ttggcagctg atgttgagga gcccactctg gaagccgatg | 1620 |
| tcgacttgat gttacaagag gctggggccg gctcagtgga gacacctcgt ggcttgataa | 1680 |
| aggttaccag ctacgatggc gaggacaaga tcggctctta cgctgtgctt tctccgcagg | 1740 |
| ctgtactcaa gagtgaaaaa ttatcttgca tccaccctct cgctgaacaa gtcatagtga | 1800 |
| taacacactc tggccgaaaa gggcgttatg ccgtggaacc ataccatggt aaagtagtgg | 1860 |
| tgccagaggg acatgcaata cccgtccagg actttcaagc tctgagtgaa agtgccacca | 1920 |
| ttgtgtacaa cgaacgtgag ttcgtaaaca ggtacctgca ccatattgcc acacatggag | 1980 |
| gagcgctgaa cactgatgaa gaatattaca aaactgtcaa gcccagcgag cacgacggcg | 2040 |
| aatacctgta cgacatcgac aggaaacagt gcgtcaagaa agaactagtc actgggctag | 2100 |
| ggctcacagg cgagctggtg gatcctcccT tccatgaatt cgcctacgag agtctgagaa | 2160 |
| cacgaccagc cgctccttac caagtaccaa ccatagggGt gtatgGcgtg ccaggatcag | 2220 |
| gcaagtctgg catcattaaa agcgcagtca ccaaaaaaga tctagtggtg agcgccaaga | 2280 |
| aagaaaactg tgcagaaatt ataagggacg tcaagaaaat gaaagggctg gacgtcaatg | 2340 |
| ccagaactgt ggactcagtg ctcttgaatg gatgcaaaca ccccgtagag accctgtata | 2400 |
| ttgacgaagc ttttgcttgt catgcaggta ctctcagagc gctcatagcc attataagac | 2460 |
| ctaaaaaggc agtgctctgc ggggatccca aacagtgcgg tttttttaac atgatgtgcc | 2520 |
| tgaaagtgca ttttaaccac gagatttgca cacaagtctt ccacaaaagc atctctcgcc | 2580 |
| gttgcactaa atctgtgact tcggtcgtct caaccttgtt ttacgacaaa aaaatgagaa | 2640 |
| cgacgaatcc gaaagagact aagattgtga ttgacactac cggcagtacc aaacctaagc | 2700 |
| aggacgatct cattctcact tgtttcagag ggtgggtgaa gcagttgcaa atagattaca | 2760 |

-continued

| | |
|---|---|
| aaggcaacga aataatgacg gcagctgcct ctcaagggct gacccgtaaa ggtgtgtatg | 2820 |
| ccgttcggta caaggtgaat gaaaatcctc tgtacgcacc cacctcagaa catgtgaacg | 2880 |
| tcctactgac ccgcacggag gaccgcatcg tgtggaaaac actagccggc gacccatgga | 2940 |
| taaaaacact gactgccaag taccctggga atttcactgc cacgatagag gagtggcaag | 3000 |
| cagagcatga tgccatcatg aggcacatct ggagagacc ggaccctacc gacgtcttcc | 3060 |
| agaataaggc aaacgtgtgt tgggccaagg ctttagtgcc ggtgctgaag accgctggca | 3120 |
| tagacatgac cactgaacaa tggaacactg tggattattt tgaaacggac aaagctcact | 3180 |
| cagcagagat agtattgaac caactatgcg tgaggttctt tggactcgat ctggactccg | 3240 |
| gtctattttc tgcacccact gttccgttat ccattaggaa taatcactgg gataactccc | 3300 |
| cgtcgcctaa catgtacggg ctgaataaag aagtggtccg tcagctctct cgcaggtacc | 3360 |
| cacaactgcc tcgggcagtt gccactggaa gagtctatga catgaacact ggtacactgc | 3420 |
| gcaattatga tccgcgcata aacctagtac ctgtaaacag aagactgcct catgctttag | 3480 |
| tcctccacca taatgaacac ccacagagtg acttttcttc attcgtcagc aaattgaagg | 3540 |
| gcagaactgt cctggtggtc ggggaaaagt tgtccgtccc aggcaaaatg gttgactggt | 3600 |
| tgtcagaccg gcctgaggct accttcagag ctcggctgga tttaggcatc ccaggtgatg | 3660 |
| tgcccaaata tgacataata tttgttaatg tgaggacccc atataaatac catcactatc | 3720 |
| agcagtgtga agaccatgcc attaagctta gcatgttgac caagaaagct tgtctgcatc | 3780 |
| tgaatcccgg cggaacctgt gtcagcatag gttatggtta cgctgacagg gccagcgaaa | 3840 |
| gcatcattgg tgctatagcg cggcagttca agttttcccg ggtatgcaaa ccgaaatcct | 3900 |
| cacttgaaga gacggaagtt ctgtttgtat tcattgggta cgatcgcaag gcccgtacgc | 3960 |
| acaatccttc aagctttca tcaaccttga ccaacattta tacaggttcc agactccacg | 4020 |
| aagccggatg tgcaccctca tatcatgtgg tgcgagggga tattgccacg gccaccgaag | 4080 |
| gagtgattat aaatgctgct aacagcaaag gacaacctgg cggagggggtg tgcggagcgc | 4140 |
| tgtataagaa attcccggaa agcttcgatt tacagccgat cgaagtagga aaagcgcgac | 4200 |
| tggtcaaagg tgcagctaaa catatcattc atgccgtagg accaaacttc aacaaagttt | 4260 |
| cggaggttga aggtgacaaa cagttggcag aggcttatga gtccatcgct aagattgtca | 4320 |
| acgataacaa ttacaagtca gtagcgattc cactgttgtc caccggcatc ttttccggga | 4380 |
| acaaagatcg actaaccaa tcattgaacc atttgctgac agctttagac accactgatg | 4440 |
| cagatgtagc catatactgc agggacaaga aatgggaaat gactctcaag gaagcagtgg | 4500 |
| ctaggagaga agcagtggag gagatatgca tatccgacga ctcttcagtg acagaacctg | 4560 |
| atgcagagct ggtgagggtg catccgaaga gttctttggc tggaaggaag ggctacagca | 4620 |
| caagcgatgg caaaactttc tcatatttgg aagggaccaa gtttcaccag gcggccaagg | 4680 |
| atatagcaga aattaatgcc atgtggcccg ttgcaacgga ggccaatgag caggtatgca | 4740 |
| tgtatatcct cggagaaagc atgagcagta ttaggtcgaa atgccccgtc gaagagtcgg | 4800 |
| aagcctccac accacctagc acgctgcctt gcttgtgcat ccatgccatg actccagaaa | 4860 |
| gagtacagcg cctaaaagcc tcacgtccag aacaaattac tgtgtgctca tcctttccat | 4920 |
| tgccgaagta tagaatcact ggtgtgcaga agatccaatg ctcccagcct atattgttct | 4980 |
| caccgaaagt gcctgcgtat attcatccaa ggaagtatct cgtggaaaca ccaccggtag | 5040 |
| acgagactcc ggagccatcg gcagagaacc aatccacaga ggggacacct gaacaaccac | 5100 |
| cacttataac cgaggatgag accaggacta gaacgcctga gccgatcatc atcgaagagg | 5160 |

```
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca agctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggttttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aggagtcaa atcggacaaa ttaatgcag   7140 acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
```

-continued

```
gggcccctat aactctctac ggctaacctg aatggactac acatagtct agtccgccaa      7560 gatgaggcct ggcctgccct cctacctgat catcctggcc gtgtgcctgt tcagccacct      7620
gctgtccagc agatacggcg ccgaggccgt gagcgagccc ctggacaagg ctttccacct      7680
gctgctgaac acctacggca gacccatccg gtttctgcgg gagaacacca cccagtgcac      7740
ctacaacagc agcctgcgga acagcaccgt cgtgagagag aacgccatca gcttcaactt      7800
tttccagagc tacaaccagt actacgtgtt ccacatgccc agatgcctgt ttgccggccc      7860
tctggccgag cagttcctga accaggtgga cctgaccgag acactggaaa gataccagca      7920
gcggctgaat acctacgccc tggtgtccaa ggacctggcc agctaccggt cctttagcca      7980
gcagctcaag gctcaggata gcctcggcga gcagcctacc accgtgcccc ctcccatcga      8040
cctgagcatc ccccacgtgt ggatgcctcc ccagaccacc cctcacggct ggaccgagag      8100
ccacaccacc tccggcctgc acagacccca cttcaaccag acctgcatcc tgttcgacgg      8160
ccacgacctg ctgtttagca ccgtgacccc ctgcctgcac cagggcttct acctgatcga      8220
cgagctgaga tacgtgaaga tcaccctgac cgaggatttc ttcgtggtca ccgtgtccat      8280
cgacgacgac accccccatgc tgctgatctt cggccacctg cccagagtgc tgttcaaggc      8340
cccctaccag cgggacaact tcatcctgcg gcagaccgag aagcacgagc tgctggtgct      8400
ggtcaagaag gaccagctga accggcactc ctacctgaag gaccccgact tcctggacgc      8460
cgccctggac ttcaactacc tggacctgag cgccctgctg agaaacagct ccacagata      8520 cgccgtggac gtgctgaagt ccggacggtg ccagatgctc gatcggcgga ccgtggagat      8580
ggccttcgcc tatgccctcg ccctgttcgc cgctgccaga caggaagagg ctggcgccca      8640
ggtgtcagtg cccagagccc tggatagaca ggccgccctg ctgcagatcc aggaattcat      8700
gatcacctgc ctgagccaga cccccctag aaccaccctg ctgctgtacc ccacagccgt      8760
ggatctggcc aagagggccc tgtggacccc caaccagatc accgacatca aagcctcgt      8820 gcggctcgtg tacatcctga gcaagcagaa ccagcagcac ctgatccccc agtgggccct      8880
gagacagatc gccgacttcg ccctgaagct gcacaagacc catctggcca gctttctgag      8940
cgccttcgcc aggcaggaac tgtacctgat gggcagcctg gtccacagca tgctggtgca      9000
taccaccgag cggcgggaga tcttcatcgt ggagacaggc ctgtgtagcc tggccgagct      9060
gtcccacttt acccagctgc tggcccaccc tcaccgagc tacctgagcg acctgtacac      9120
cccctgcagc agcagcggca gacgggacca cagcctggaa cggctgacca gactgttccc      9180
cgatgccacc gtgcctgcta cagtgcctgc cgccctgtcc atcctgtcca ccatgcagcc      9240
cagcaccctg gaaaccttcc ccgacctgtt ctgcctgccc ctgggcgaga ctttagcgc      9300 cctgaccgtg tccgagcacg tgtcctacat cgtgaccaat cagtacctga tcaagggcat      9360
cagctacccc gtgtccacca cagtcgtggg ccagagcctg atcatcaccc agaccgacag      9420
ccagaccaag tgcgagctga cccggaacat gcacaccaca cacagcatca ccgtggccct      9480
gaacatcagc ctggaaaact gcgctttctg tcagtctgcc ctgctggaat acgacgatac      9540
ccagggcgtg atcaacatca tgtacatgca cgacagcgac gacgtgctgt cgccctgga      9600 ccctacaac gaggtggtgg tgtccagccc ccggacccac tacctgatgc tgctgaagaa      9660
cggcaccgtg ctggaagtga ccgacgtggt ggtggacgcc accgacctgt tgaatttga      9720 ccttcttaag cttgcgggag acgtcgagtc caacccgggg ccatgtgca gaaggcccga      9780 ctgcggcttc agcttcagcc ctggaccgt gatcctgctg tggtgctgcc tgctgctgcc      9840
tatcgtgtcc tctgccgccg tgtctgtggc ccctacagcc gccgagaagg tgccagccga      9900
```

-continued

```
gtgccccgag ctgaccagaa gatgcctgct gggcgaggtg ttcgagggcg acaagtacga      9960
gagctggctg cggcccctgg tcaacgtgac cggcagagat ggcccctga gccagctgat     10020 ccggtacaga cccgtgaccc ccgaggccgc caatagcgtg ctgctggacg aggccttcct     10080
ggataccctg gccctgctgt acaacaaccc cgaccagctg agagccctgc tgaccctgct     10140
gtccagcgac accgccccca gatggatgac cgtgatgcgg ggctacagcg agtgtggaga     10200
tggcagccct gccgtgtaca cctgcgtgga cgacctgtgc agaggctacg acctgaccag     10260
actgagctac ggccggtcca tcttcacaga gcacgtgctg ggcttcgagc tggtgccccc     10320
cagcctgttc aacgtggtgg tggccatccg gaacgaggcc accagaacca acagagccgt     10380
gcggctgcct gtgtctacag ccgctgcacc tgagggcatc acactgttct acggcctgta     10440
caacgccgtg aaagagttct gcctccggca ccagctggat cccccctgc tgagacacct     10500 ggacaagtac tacgccggcc tgcccccaga gctgaagcag accagagtga acctgcccgc     10560
ccacagcaga tatggccctc aggccgtgga cgccagatga taagcggccg catacagcag     10620
caattggcaa gctgcttaca tagaactcgc ggcgattggc atgccgcctt aaaattttta     10680
ttttattttt cttttctttt ccgaatcgga ttttgttttt aatatttcaa aaaaaaaaa     10740 aaaaaaaaa aaaaaaaaa aaagggtcgg catggcatct ccacctcctc gcggtccgac     10800
ctgggcatcc gaaggaggac gcacgtccac tcggatggct aagggagagc cacgtttaaa     10860
cacgtgatat ctggcctcat gggccttcct ttcactgccc gctttccagt cgggaaacct     10920
gtcgtgccag ctgcattaac atggtcatag ctgtttcctt gcgtattggg cgctctccgc     10980
ttcctcgctc actgactcgc tgcgctcggt cgttcgggta aagcctgggg tgcctaatga     11040
gcaaaaggcc agcaaaaggc caggaaccgt aaaaaggccg cgttgctggc gttttttccat    11100 aggctccgcc cccctgacga gcatcacaaa aatcgacgct caagtcagag gtggcgaaac     11160
ccgacaggac tataaagata ccaggcgttt cccctggaa gctccctcgt gcgctctcct     11220
gttccgaccc tgccgcttac cggatacctg tccgcctttc tcccttcggg aagcgtggcg     11280
ctttctcata gctcacgctg taggtatctc agttcggtgt aggtcgttcg ctccaagctg     11340
ggctgtgtgc acgaaccccc cgttcagccc gaccgctgcg ccttatccgg taactatcgt     11400
cttgagtcca acccggtaag acacgactta tcgccactgg cagcagccac tggtaacagg     11460
attagcagag cgaggtatgt aggcggtgct acagagttct tgaagtggtg gcctaactac     11520
ggctacacta agaagaacagt atttggtatc tgcgctctgc tgaagccagt taccttcgga     11580
aaaagagttg gtagctcttg atccggcaaa caaaccaccg ctggtagcgg tggtttttt     11640 gtttgcaagc agcagattac gcgcagaaaa aaaggatctc aagaagatcc tttgatcttt     11700
tctacggggt ctgacgctca gtggaacgaa aactcacgtt aagggatttt ggtcatgaga     11760
ttatcaaaaa ggatcttcac ctagatcctt ttaaattaaa aatgaagttt taaatcaatc     11820
taaagtatat atgagtaaac ttggtctgac agttattaga aaaattcatc cagcagacga     11880
taaaacgcaa tacgctggct atccggtgcc gcaatgccat acagcaccag aaaacgatcc     11940
gcccattcgc cgcccagttc ttccgcaata tcacgggtgg ccagcgcaat atcctgataa     12000
cgatccgcca cgcccagacg gccgcaatca ataaagccgc taaaacgcc attttccacc     12060 ataatgttcg gcaggcacgc atcaccatgg gtcaccacca gatcttcgcc atccggcatg     12120
ctcgctttca gacgcgcaaa cagctctgcc ggtgccaggc cctgatgttc ttcatccaga     12180
tcatcctgat ccaccaggcc cgcttccata cgggtacgcg cacgttcaat acgatgtttc     12240
```

```
gcctgatgat caaacggaca ggtcgccggg tccagggtat gcagacgacg catggcatcc    12300
gccataatgc tcactttttc tgccggcgcc agatggctag acagcagatc ctgacccggc    12360
acttcgccca gcagcagcca atcacggccc gcttcggtca ccacatccag caccgccgca    12420
cacggaacac cggtggtggc cagccagctc agacgcgccg cttcatcctg cagctcgttc    12480
agcgcaccgc tcagatcggt tttcacaaac agcaccggac gaccctgcgc gctcagacga    12540
aacaccgccg catcagagca gccaatggtc tgctgcgccc aatcatagcc aaacagacgt    12600
tccacccacg ctgccgggct acccgcatgc aggccatcct gttcaatcat actcttcctt    12660
tttcaatatt attgaagcat ttatcagggt tattgtctca tgagcggata catatttgaa    12720
tgtatttaga aaataaaca aataggggtt ccgcgcacat ttccccgaaa agtgccacct    12780
aaattgtaag cgttaatatt ttgttaaaat tcgcgttaaa ttttttgttaa atcagctcat    12840 tttttaacca ataggccgaa atcggcaaaa tcccttataa atcaaaagaa tagaccgaga    12900
tagggttgag tggccgctac agggcgctcc cattcgccat tcaggctgcg caactgttgg    12960
gaagggcgtt tcggtgcggg cctcttcgct attacgccag ctggcgaaag ggggatgtgc    13020
tgcaaggcga ttaagttggg taacgccagg gttttcccag tcacacgcgt aatacgactc    13080
actatag                                                              13087

<210> SEQ ID NO 8
<211> LENGTH: 13788
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
ataggcggcg catgagagaa gcccagacca attacctacc caaaatggag aaagttcacg      60
ttgacatcga ggaagacagc ccattcctca gagctttgca gcggagcttc cgcagtttg     120 aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactact agttagttgc gacgggtacg     900
tcgttaaaag aatagctatc agtccaggcc tgtatgggaa gccttcaggc tatgctgcta     960
cgatgcaccg cgaggattc ttgtgctgca aagtgacaga cattgaac ggggagaggg     1020 tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
```

```
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca acagtgcgg ttttttttaac atgatgtgcc   2520 tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct ggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
```

```
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg ccagcgaaa    3840 gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggagggggtg tgcggagcgc    4140 tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tccttttccat    4920 tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccacccccgc    5520
caggcgtgaa tagggtgatc actagagagg agctcgaggc gcttacccg tcacgcactc    5580 ctagcaggtc ggtctcgaga accagcctgg tctccaaccc gccaggcgta atagggtga    5640 ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
```

```
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca agctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggttttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaccgta ggaacttcca    7440 tcatagttat ggccatgact actctagcta gcagtgttaa atcattcagc tacctgagag    7500
gggcccctat aactctctac ggctaacctg aatggactac gacatagtct agtccgccaa    7560
gatgaggcct ggcctgccct cctacctgat catcctggcc gtgtgcctgt tcagccacct    7620
gctgtccagc agatacggcg ccgaggccgt gagcgagccc ctggacaagg ctttccacct    7680
gctgctgaac acctacggca gacccatccg gtttctgcgg gagaacacca cccagtgcac    7740
ctacaacagc agcctgcgga acagcaccgt cgtgagagag aacgccatca gcttcaactt    7800
tttccagagc tacaaccagt actacgtgtt ccacatgccc agatgcctgt tgccggccc    7860 tctggccgag cagttcctga accaggtgga cctgaccgag acactggaaa gataccagca    7920
gcggctgaat acctacgccc tggtgtccaa ggacctggcc agctaccggt cctttagcca    7980
gcagctcaag gctcaggata gcctcggcga gcagcctacc accgtgcccc ctcccatcga    8040
cctgagcatc ccccacgtgt ggatgcctcc ccagaccacc cctcacggct ggaccgagag    8100
ccacaccacc tccggcctgc acagacccca cttcaaccag acctgcatcc tgttcgacgg    8160
ccacgacctg ctgtttagca ccgtgacccc ctgcctgcac cagggcttct acctgatcga    8220
```

```
cgagctgaga tacgtgaaga tcaccctgac cgaggatttc ttcgtggtca ccgtgtccat    8280
cgacgacgac accccatgc tgctgatctt cggccacctg cccagagtgc tgttcaaggc    8340
cccctaccag cgggacaact tcatcctgcg gcagaccgag aagcacgagc tgctggtgct    8400
ggtcaagaag gaccagctga accggcactc ctacctgaag acccccgact tcctggacgc    8460
cgccctggac ttcaactacc tggacctgag cgccctgctg agaaacagct ccacagata    8520 cgccgtggac gtgctgaagt ccggacggtg ccagatgctc gatcggcgga ccgtggagat    8580
ggccttcgcc tatgccctcg ccctgttcgc cgctgccaga caggaagagg ctggcgccca    8640
ggtgtcagtg cccagagccc tggatagaca ggccgccctg ctgcagatcc aggaattcat    8700
gatcacctgc ctgagccaga ccccccctag aaccaccctg ctgctgtacc ccacagccgt    8760
ggatctggcc aagagggccc tgtggacccc aaccagatc accgacatca caagcctcgt    8820
gcggctcgtg tacatcctga gcaagcagaa ccagcagcac ctgatccccc agtgggccct    8880
gagacagatc gccgacttcg ccctgaagct gcacaagacc catctggcca gctttctgag    8940
cgccttcgcc aggcaggaac tgtacctgat gggcagcctg gtccacagca tgctggtgca    9000
taccaccgag cggcgggaga tcttcatcgt ggagacaggc ctgtgtagcc tggccgagct    9060
gtcccacttt acccagctgc tggccccacc tcaccacgag tacctgagcg acctgtacac    9120
cccctgcagc agcagcggca gacgggacca cagcctggaa cggctgacca gactgttccc    9180
cgatgccacc gtgcctgcta cagtgcctgc cgccctgtcc atcctgtcca ccatgcagcc    9240
cagcaccctg gaaaaccttcc ccgacctgtt ctgcctgccc ctgggcgaga gctttagcgc    9300
cctgaccgtg tccgagcacg tgtcctacat cgtgaccaat cagtacctga tcaagggcat    9360
cagctacccc gtgtccacca cagtcgtggg ccagagcctg atcatcaccc agaccgacag    9420
ccagaccaag tgcgagctga cccggaacat gcacaccaca cacagcatca ccgtggccct    9480
gaacatcagc ctggaaaact gcgctttctg tcagtctgcc ctgctggaat cgacgatac    9540 ccagggcgtg atcaacatca tgtacatgca cgacagcgac gacgtgctgt cgccctgga    9600 ccccctacaac gaggtggtgg tgtccagccc ccggacccac tacctgatgc tgctgaagaa    9660
cggcaccgtg ctggaagtga ccgacgtggt ggtggacgcc accgactgat aatctagatt    9720
aaaacagctg tgggttgttc ccacccacag ggcccactgg gcgctagcac tctgatttta    9780
cgaaatcctt gtgcgcctgt tttatatccc ttccctaatt cgaaacgtag aagcaatgcg    9840
caccactgat caatagtagg cgtaacgcgc cagttacgtc atgatcaagc atatctgttc    9900
ccccggactg agtatcaata gactgcttac gcggttgaag gagaaaacgt tcgttatccg    9960
gctaactact tcgagaagcc cagtaacacc atggaagctg cagggtgttt cgctcagcac   10020 ttccccgtg tagatcaggt cgatgagcca ctgcaatccc cacaggtgac tgtggcagtg   10080
gctgcgttgg cggcctgcct atggggagac ccataggacg ctctaatgtg gacatggtgc   10140
gaagagccta ttgagctagt tagtagtcct ccggccctg aatgcggcta atcctaactg   10200
cggagcacat gccttcaacc cagagggtag tgtgtcgtaa tgggcaactc tgcagcggaa   10260
ccgactactt tgggtgtccg tgtttctttt tattcttata ttggctgctt atggtgacaa   10320
ttacagaatt gttaccatat agctattgga ttggccatcc ggtgtgtaat agagctgtta   10380
tatacctatt tgttggcttt gtaccactaa ctttaaaatc tataactacc ctcaacttta   10440
tattaaccct caatacagtt gaacatgtgc agaaggcccg actgcggctt cagcttcagc   10500 cctgacccg tgatcctgct gtggtgctgc ctgctgctgc ctatcgtgtc ctctgccgcc   10560
gtgtctgtgg cccctacagc cgccgagaag gtgccagccg agtgccccga gctgaccaga   10620
```

```
agatgcctgc tgggcgaggt gttcgagggc gacaagtacg agagctggct gcggccctg    10680
gtcaacgtga ccggcagaga tggcccctg agccagctga tccggtacag acccgtgacc    10740
cccgaggccg ccaatagcgt gctgctggac gaggccttcc tggataccct ggccctgctg   10800
tacaacaacc ccgaccagct gagagccctg ctgaccctgc tgtccagcga caccgccccc   10860
agatggatga ccgtgatgcg gggctacagc gagtgtggag atggcagccc tgccgtgtac   10920
acctgcgtgg acgacctgtg cagaggctac gacctgacca gactgagcta cggccggtcc   10980
atcttcacag agcacgtgct gggcttcgag ctggtgcccc ccagcctgtt caacgtggtg   11040
gtggccatcc ggaacgaggc caccagaacc aacagagccg tgcggctgcc tgtgtctaca   11100
gccgctgcac ctgagggcat cacactgttc tacggcctgt acaacgccgt gaaagagttc   11160
tgcctccggc accagctgga tccccccctg ctgagacacc tggacaagta ctacgccggc   11220
ctgcccccag agctgaagca gaccagagtg aacctgcccg cccacagcag atatggccct   11280
caggccgtgg acgccagatg ataagcggcc gcatacagca gcaattggca agctgcttac   11340
atagaactcg cggcgattgg catgccgcct taaaatttt atttttatttt tcttttcttt   11400
tccgaatcgg attttgtttt taatatttca aaaaaaaaa aaaaaaaaa aaaaaaaaa      11460
aaaagggtcg gcatggcatc tccacctcct cgcggtccga cctgggcatc cgaaggagga   11520
cgcacgtcca ctcggatggc taagggagag ccacgtttaa acacgtgata tctgcctca   11580
tgggccttcc tttcactgcc cgcttttcag tcgggaaacc tgtcgtgcca gctgcattaa   11640
catggtcata gctgtttcct tgcgtattgg gcgctctccg cttcctcgct cactgactcg   11700
ctgcgctcgg tcgttcgggt aaagcctggg gtgcctaatg agcaaaaggc cagcaaaagg   11760
ccaggaaccg taaaaaggcc gcgttgctgg cgttttttcca taggctccgc ccccctgacg   11820
agcatcacaa aaatcgacgc tcaagtcaga ggtggcgaaa cccgacagga ctataaagat   11880
accaggcgtt ccccctgga agctcccctcg tgcgctctcc tgttccgacc ctgccgctta   11940
ccggatacct gtccgccttt ctcccttcgg gaagcgtggc gctttctcat agctcacgct   12000
gtaggtatct cagttcggtg taggtcgttc gctccaagct gggctgtgtg cacgaacccc   12060
ccgttcagcc cgaccgctgc gccttatccg gtaactatcg tcttgagtcc aacccggtaa   12120
gacacgactt atcgccactg gcagcagcca ctggtaacag gattagcaga gcgaggtatg   12180
taggcggtgc tacagagttc ttgaagtggt ggcctaacta cggctacact agaagaacag   12240
tatttggtat ctgcgctctg ctgaagccag ttaccttcgg aaaaagagtt ggtagctctt   12300
gatccggcaa acaaaccacc gctggtagcg gtggtttttt tgtttgcaag cagcagatta   12360
cgcgcagaaa aaaaggatct caagaagatc ctttgatctt ttctacgggg tctgacgctc   12420
agtggaacga aaactcacgt taagggattt tggtcatgag attatcaaaa aggatcttca   12480
cctagatcct tttaaattaa aaatgaagtt ttaaatcaat ctaaagtata tatgagtaaa   12540
cttggtctga cagttattag aaaaattcat ccagcagacg ataaaacgca atacgctggc   12600
tatccggtgc cgcaatgcca tacagcacca gaaaacgatc cgcccattcg ccgcccagtt   12660
cttccgcaat atcacgggtg ccagcgcaa tatcctgata acgatccgcc acgcccagac   12720
ggccgcaatc aataaagccg ctaaaacggc cattttccac cataatgttc ggcaggcacg   12780
catcaccatg ggtcaccacc agatcttcgc catccggcat gctcgctttc agacgcgcaa   12840
acagctctgc cggtgccagg ccctgatgtt cttcatccag atcatcctga tccaccaggc   12900
ccgcttccat acgggtacgc gcacgttcaa tacgatgttt cgcctgatga tcaaacggac   12960
```

```
aggtcgccgg gtccagggta tgcagacgac gcatggcatc cgccataatg ctcactttt    13020 ctgccggcgc cagatggcta gacagcagat cctgacccgg cacttcgccc agcagcagcc    13080
aatcacggcc cgcttcggtc accacatcca gcaccgccgc acacggaaca ccggtggtgg    13140
ccagccagct cagacgcgcc gcttcatcct gcagctcgtt cagcgcaccg ctcagatcgg    13200 tttcacaaa cagcaccgga cgaccctgcg cgctcagacg aaacaccgcc gcatcagagc    13260
agccaatggt ctgctgcgcc caatcatagc caaacagacg ttccacccac gctgccgggc    13320
tacccgcatg caggccatcc tgttcaatca tactcttcct ttttcaatat tattgaagca    13380
tttatcaggg ttattgtctc atgagcggat acatatttga atgtatttag aaaaataaac    13440
aaataggggt tccgcgcaca tttccccgaa aagtgccacc taaattgtaa gcgttaatat    13500
tttgttaaaa ttcgcgttaa attttgtta aatcagctca ttttttaacc aataggccga    13560
aatcggcaaa atcccttata atcaaaaga atagaccgag atagggttga gtggccgcta    13620
cagggcgctc ccattcgcca ttcaggctgc gcaactgttg ggaagggcgt tcggtgcgg    13680 gcctcttcgc tattacgcca gctggcgaaa ggggatgtg ctgcaaggcg attaagttgg    13740
gtaacgccag ggttttccca gtcacacgcg taatacgact cactatag              13788

<210> SEQ ID NO 9
<211> LENGTH: 13788
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
ataggcggcg catgagagaa gcccagacca attacctacc caaaatggag aaagttcacg       60
ttgacatcga ggaagacagc ccattcctca gagctttgca gcggagcttc ccgcagtttg      120
aggtagaagc caagcaggtc actgataatg accatgctaa tgccagagcg ttttcgcatc      180
tggcttcaaa actgatcgaa acggaggtgg acccatccga cacgatcctt gacattggaa      240
gtgcgcccgc ccgcagaatg tattctaagc acaagtatca ttgtatctgt ccgatgagat      300
gtgcggaaga tccggacaga ttgtataagt atgcaactaa gctgaagaaa aactgtaagg      360
aaataactga taaggaattg acaagaaaa tgaaggagct cgccgccgtc atgagcgacc      420
ctgacctgga aactgagact atgtgcctcc acgacgacga gtcgtgtcgc tacgaagggc      480
aagtcgctgt ttaccaggat gtatacgcgg ttgacggacc gacaagtctc tatcaccaag      540
ccaataaggg agttagagtc gcctactgga taggctttga caccaccct tttatgttta      600 agaacttggc tggagcatat ccatcatact ctaccaactg gccgacgaa accgtgttaa      660 cggctcgtaa cataggccta tgcagctctg acgttatgga gcggtcacgt agagggatgt      720
ccattcttag aaagaagtat ttgaaaccat ccaacaatgt tctattctct gttggctcga      780
ccatctacca cgagaagagg gacttactga ggagctggca cctgccgtct gtatttcact      840
tacgtggcaa gcaaaattac acatgtcggt gtgagactat agttagttgc gacgggtacg      900
tcgttaaaag aatagctatc agtccaggcc tgtatgggaa gccttcaggc tatgctgcta      960
cgatgcaccg cgagggattc ttgtgctgca aagtgacaga cacattgaac ggggagaggg     1020
tctcttttcc cgtgtgcacg tatgtgccag ctacattgtg tgaccaaatg actggcatac     1080
tggcaacaga tgtcagtgcg gacgacgcgc aaaaactgct ggttgggctc aaccagcgta     1140
tagtcgtcaa cggtcgcacc cagagaaaca ccaataccat gaaaaattac cttttgcccg     1200
```

```
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg    2340 ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg tttttttaac atgatgtgcc    2520
tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct ggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
```

```
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgc caaaacttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tccttttccat    4920 tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacacccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccgc     5520 caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
```

```
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgtgcaga aggcccgact gcggcttcag cttcagccct ggaccgtgga tcctgctgtg    7620
gtgctgcctc ctgctgccta tcgtgtcctc tgccgccgtg tctgtggccc ctacagccgc    7680
cgagaaggtg ccagccgagt gccccgagct gaccagaaga tgcctgctgg gcgaggtgtt    7740
cgagggcgac aagtacgaga gctggctgcg gcccctggtc aacgtgaccg gcagagatgg    7800 cccccctgagc cagctgatcc ggtacagacc cgtgacccc gaggccgcca atagcgtgct    7860
gctggacgag gccttcctgg ataccctggc cctgctgtac aacaacccg accagctgag    7920 agccctgctg acccctgctgt ccagcgacac cgcccccaga tggatgaccg tgatgcgggg    7980
ctacagcgag tgtggagatg gcagcccctgc cgtgtacacc tgcgtggacg acctgtgcag    8040
aggctacgac ctgaccagac tgagctacgg ccggtccatc ttcacagagc acgtgctggg    8100
cttcgagctg gtgccccca gcctgttcaa cgtggtggtg gccatccgga acgaggccac    8160
cagaaccaac agagccgtgc ggctgcctgt gtctacagcc gctgcacctg agggcatcac    8220
actgttctac ggcctgtaca acgccgtgaa agagttctgc ctccggcacc agctggatcc    8280
```

```
ccccctgctg agacacctgg acaagtacta cgccggcctg cccccagagc tgaagcagac      8340
cagagtgaac ctgcccgccc acagcagata tggccctcag gccgtggacg ccagatgata      8400
atctagatta aaacagctgt gggttgttcc cacccacagg gcccactggg cgctagcact      8460
ctgattttac gaaatccttg tgcgcctgtt ttatatccct tccctaattc gaaacgtaga      8520
agcaatgcgc accactgatc aatagtaggc gtaacgcgcc agttacgtca tgatcaagca      8580
tatctgttcc cccggactga gtatcaatag actgcttacg cggttgaagg agaaaacgtt      8640
cgttatccgg ctaactactt cgagaagccc agtaacacca tggaagctgc agggtgtttc      8700
gctcagcact tccccgtgt agatcaggtc gatgagccac tgcaatcccc acaggtgact       8760
gtggcagtgg ctgcgttggc ggcctgccta tggggagacc cataggacgc tctaatgtgg      8820
acatggtgcg aagagcctat tgagctagtt agtagtcctc cggcccctga atgcggctaa      8880
tcctaactgc ggagcacatg ccttcaaccc agagggtagt gtgtcgtaat gggcaactct      8940
gcagcggaac cgactacttt gggtgtccgt gtttcttttt attcttatat tggctgctta      9000
tggtgacaat tacagaattg ttaccatata gctattggat tggccatccg gtgtgtaata      9060
gagctgttat atacctattt gttggctttg taccactaac tttaaaatct ataactaccc      9120
tcaactttat ataaccctc aatacagttg aacatgaggc ctggcctgcc ctcctacctg      9180
atcatcctgg ccgtgtgcct gttcagccac ctgctgtcca gcagatacgg cgccgaggcc      9240
gtgagcgagc ccctggacaa ggctttccac ctgctgctga cacctacgg cagacccatc       9300 cggtttctgc gggagaacac cacccagtgc acctacaaca gcagcctgcg gaacagcacc      9360
gtcgtgagag agaacgccat cagcttcaac ттттттccaga gctacaacca gtactacgtg      9420

ttccacatgc ccagatgcct gtttgccggc cctctggccg agcagttcct gaaccaggtg      9480
gacctgaccg agacactgga agataccag cagcggctga atacctacgc cctggtgtcc       9540
aaggacctgg ccagctaccg gtcctttagc cagcagctca aggctcagga tagcctcggc      9600
gagcagccta ccaccgtgcc ccctcccatc gacctgagca tccccacgt gtggatgcct       9660 ccccagacca cccctcacgg ctggaccgag agccacacca cctccggcct gcacagaccc      9720
cacttcaacc agacctgcat cctgttcgac ggccacgacc tgctgtttag caccgtgacc      9780
ccctgcctgc accagggctt ctacctgatc gacgagctga gatacgtgaa gatcaccctg      9840
accgaggatt tcttcgtggt caccgtgtcc atcgacgacg acacccccat gctgctgatc      9900

ttcggccacc tgcccagagt gctgttcaag gccccctacc agcgggacaa cttcatcctg       9960
cggcagaccg agaagcacga gctgctggtg ctggtcaaga aggaccagct gaaccggcac      10020

tcctacctga aggaccccga cttcctggac gccgccctgg acttcaacta cctggacctg      10080
agcgccctgc tgagaaacag cttccacaga tacgccgtgg acgtgctgaa gtccggacgg      10140

tgccagatgc tcgatcggcg gaccgtggag atggccttcg cctatgccct cgccctgttc      10200
gccgctgcca gacaggaaga ggctggcgcc caggtgtcag tgcccagagc cctggataga      10260
caggccgccc tgctgcagat ccaggaattc atgatcacct gctgagccca gaccccccct      10320
agaaccaccc tgctgctgta ccccacagcc gtggatctgg ccaagagggc cctgtggacc      10380
cccaaccaga tcaccgacat cacaagcctc gtgcggctcg tgtacatcct gagcaagcag      10440
aaccagcagc acctgatccc ccagtgggcc ctgagacaga tcgccgactt cgccctgaag      10500
ctgcacaaga cccatctggc cagctttctg agcgccttcg ccaggcagga actgtacctg      10560

atgggcagcc tggtccacag catgctggtg cataccaccg agcggcggga gatcttcatc      10620
gtggagacag gcctgtgtag cctggccgag ctgtcccact ttacccagct gctgggcccac      10680
```

```
cctcaccacg agtacctgag cgacctgtac accccctgca gcagcagcgg cagacgggac   10740
cacagcctgg aacggctgac cagactgttc cccgatgcca ccgtgcctgc tacagtgcct   10800
gccgccctgt ccatcctgtc caccatgcag cccagcaccc tggaaaacctt ccccgacctg   10860
ttctgcctgc ccctgggcga gagctttagc gccctgaccg tgtccagca cgtgtcctac   10920
atcgtgacca atcagtacct gatcaagggc atcagctacc ccgtgtccac cacagtcgtg   10980
ggccagagcc tgatcatcac ccagaccgac agccagacca agtgcgagct gacccggaac   11040
atgcacacca cacacagcat caccgtggcc ctgaacatca gcctggaaaa ctgcgctttc   11100
tgtcagtctg ccctgctgga atacgacgat acccagggcg tgatcaacat catgtacatg   11160
cacgacagcg acgacgtgct gttcgccctg gaccectaca cgaggtggt ggtgtccagc   11220
ccccggaccc actacctgat gctgctgaag aacggcaccg tgctggaagt gaccgacgtg   11280
gtggtggacg ccaccgactg ataagcggcc gcatacagca gcaattggca agctgcttac   11340
atagaactcg cggcgattgg catgccgcct taaaattttt attttatttt tcttttcttt   11400
tccgaatcgg attttgtttt taatatttca aaaaaaaaa aaaaaaaaaa aaaaaaaaaa   11460
aaaagggtcg gcatggcatc tccacctcct cgcggtccga cctgggcatc cgaaggagga   11520
cgcacgtcca ctcggatggc taagggagag ccacgtttaa acacgtgata tctggcctca   11580
tgggccttcc tttcactgcc cgcttccag tcgggaaacc tgtcgtgcca gctgcattaa   11640
catggtcata gctgtttcct tgcgtattgg gcgctctccg cttcctcgct cactgactcg   11700
ctgcgctcgg tcgttcgggt aaagcctggg gtgcctaatg agcaaaaggc cagcaaaagg   11760
ccaggaaccg taaaaaggcc gcgttgctgg cgttttttcca taggctccgc cccctgacg   11820
agcatcacaa aaatcgacgc tcaagtcaga ggtggcgaaa cccgacagga ctataaagat   11880
accaggcgtt tccccctgga agctccctcg tgcgctctcc tgttccgacc ctgccgctta   11940
ccggatacct gtccgccttt ctcccttcgg gaagcgtggc gctttctcat agctcacgct   12000
gtaggtatct cagttcggtg taggtcgttc gctccaagct gggctgtgtg cacgaacccc   12060
ccgttcagcc cgaccgctgc gccttatccg gtaactatcg tcttgagtcc aacccggtaa   12120
gacacgactt atcgccactg gcagcagcca ctggtaacag gattagcaga gcgaggtatg   12180
taggcggtgc tacagagttc ttgaagtggt ggcctaacta cggctacact agaagaacag   12240
tatttggtat ctgcgctctg ctgaagccag ttaccttcgg aaaaagagtt ggtagctctt   12300
gatccggcaa acaaaccacc gctggtagcg gtggtttttt tgtttgcaag cagcagatta   12360
cgcgcagaaa aaaaggatct caagaagatc ctttgatctt ttctacgggg tctgacgctc   12420
agtggaacga aaactcacgt taagggattt tggtcatgag attatcaaaa aggatcttca   12480
cctagatcct tttaaattaa aaatgaagtt ttaaatcaat ctaaagtata tatgagtaaa   12540
cttggtctga cagttattag aaaaattcat ccagcagacg ataaaacgca atacgctggc   12600
tatccggtgc cgcaatgcca tacagcacca gaaaacgatc cgcccattcg ccgcccagtt   12660
cttccgcaat atcacgggtg ccagcgcaa tatcctgata acgatccgcc acgcccagac   12720
ggccgcaatc aataaagccg ctaaaacggc catttccac cataatgttc ggcaggcacg   12780
catcaccatg ggtcaccacc agatcttcgc catccggcat gctcgctttc agacgcgcaa   12840
acagctctgc cggtgccagg ccctgatgtt cttcatccag atcatcctga tccaccaggc   12900
ccgcttccat acgggtacgc gcacgttcaa tacgatgttt cgcctgatga tcaaacggac   12960
aggtcgccgg gtccagggta tgcagacgac gcatggcatc cgccataatg ctcacttttt   13020
```

```
ctgccggcgc cagatggcta gacagcagat cctgacccgg cacttcgccc agcagcagcc    13080
aatcacggcc cgcttcggtc accacatcca gcaccgccgc acacggaaca ccggtggtgg    13140
ccagccagct cagacgcgcc gcttcatcct gcagctcgtt cagcgcaccg ctcagatcgg    13200
ttttcacaaa cagcaccgga cgaccctgcg cgctcagacg aaacaccgcc gcatcagagc    13260
agccaatggt ctgctgcgcc caatcatagc caaacagacg ttccacccac gctgccgggc    13320
tacccgcatg caggccatcc tgttcaatca tactcttcct ttttcaatat tattgaagca    13380
tttatcaggg ttattgtctc atgagcggat acatatttga atgtatttag aaaaataaac    13440 aaatagggt tccgcgcaca tttccccgaa aagtgccacc taaattgtaa gcgttaatat    13500
tttgttaaaa ttcgcgttaa attttgtta aatcagctca tttttaacc aataggccga    13560 aatcggcaaa atcccttata aatcaaaaga atagaccgag atagggttga gtggccgcta    13620
cagggcgctc ccattcgcca ttcaggctgc gcaactgttg ggaagggcgt tcggtgcgg    13680 gcctcttcgc tattacgcca gctggcgaaa gggggatgtg ctgcaaggcg attaagttgg    13740
gtaacgccag ggttttccca gtcacacgcg taatacgact cactatag                 13788
```

<210> SEQ ID NO 10
<211> LENGTH: 14202
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg acaagaaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cattgaac ggggagaggg        1020 tctctttcc cgtgtgcacg tatgtgccag ctacattgtg tgaccaaatg actggcatac       1080 tgcaacaga tgtcagtgcg gacgacgcgc aaaaactgct ggttgggctc aaccagcgta       1140
tagtcgtcaa cggtcgcacc cagagaaaca ccaataccat gaaaaattac cttttgccg       1200 tagtggccca ggcatttgct aggtgggcaa aggaatataa ggaagatcaa gaagatgaaa      1260
```

```
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccataggggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttttaac atgatgtgcc     2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga aataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
```

```
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga agtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt ccacccccgc   5520
caggcgtgaa tagggtgatc actagagagg agctcgaggc gcttacccg tcacgcactc   5580 ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca caaaaatca gtaaggcaaa   5760 cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
```

```
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gcttttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggttttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gctattccag aagtagtgag gaggcttttt tggaggccta ggcttttgca aaaagcttgt   7620
atatccattt tcggatctga tcaagagaca ggatgaggat cgtttcgcat gattgaataa   7680
gatggattgc acgtaggttc tccggccgct gggtggaga ggctattcgg ctatgactgg   7740
gcacaactga caatcggctg ctctgatgcc gccgtgatcc ggttgtcagc gcaggggcgc   7800
ccggttcttt ttgtcaagac cgacctgtcc ggtgccctga tgaactgaa ggacgaggca   7860 gcgcggctat cgtggctggc cacgacgggc gttccttgcg cagtctagac tggcgcgcca   7920
aacctgcagg ttaaacagc tgtgggttgt tcccacccac agggcccact gggcgctagc   7980
actctgattt tacgaaatcc ttgtgcgcct gttttatatc ccttccctaa ttcgaaacgt   8040
agaagcaatg cgcaccactg atcaatagta ggcgtaacgc gccagttacg tcatgatcaa   8100
gcatatctgt tcccccggac tgagtatcaa tagactgctt acgcggttga aggagaaaac   8160
gttcgttatc cggctaacta cttcgagaag cccagtaaca ccatggaagc tgcagggtgt   8220
ttcgctcagc acttccccccg tgtagatcag gtcgatgagc cactgcaatc cccacaggtg   8280
actgtggcag tggctgcgtt ggcggcctgc ctatggggag acccatagga cgctctaatg   8340
```

```
tggacatggt gcgaagagcc tattgagcta gttagtagtc ctccggcccc tgaatgcggc   8400
taatcctaac tgcggagcac atgccttcaa cccagagggt agtgtgtcgt aatgggcaac   8460
tctgcagcgg aaccgactac tttgggtgtc cgtgtttctt tttattctta tattggctgc   8520
ttatggtgac aattacagaa ttgttaccat atagctattg gattggccat ccggtgtgta   8580
atagagctgt tatataccta tttgttggct ttgtaccact aactttaaaa tctataacta   8640
ccctcaactt tatattaacc ctcaatacag ttgaacatga ggcctggcct gccctcctac   8700
ctgatcatcc tggccgtgtg cctgttcagc cacctgctgt ccagcagata cggcgccgag   8760
gccgtgagcg agcccctgga caaggctttc cacctgctgc tgaacaccta cggcagaccc   8820
atccggtttc tgcgggagaa caccacccag tgcacctaca acagcagcct gcggaacagc   8880
accgtcgtga gagagaacgc catcagcttc aacttttttcc agagctacaa ccagtactac   8940
gtgttccaca tgcccagatg cctgtttgcc ggccctctgg ccgagcagtt cctgaaccag   9000
gtggacctga ccgagacact ggaaagatac cagcagcggc tgaataccta cgccctggtg   9060
tccaaggacc tggccagcta ccggtccttt agccagcagc tcaaggctca ggatagcctc   9120
ggcgagcagc ctaccaccgt gcccccctccc atcgacctga gcatcccccca cgtgtggatg   9180 cctccccaga ccacccctca cggctggacc gagagccaca ccacctccgg cctgcacaga   9240
ccccacttca accagacctg catcctgttc gacggccacg acctgctgtt tagcaccgtg   9300
accccctgcc tgcaccaggg cttctacctg atcgacgagc tgagatacgt gaagatcacc   9360
ctgaccgagg atttcttcgt ggtcaccgtg tccatcgacg acgacacccc catgctgctg   9420
atcttcggcc acctgcccag agtgctgttc aaggcccccct accagcggga caacttcatc   9480
ctgcggcaga ccgagaagca cgagctgctg gtgctggtca agaaggacca gctgaaccgg   9540
cactcctacc tgaaggaccc cgacttcctg gacgccgccc tggacttcaa ctacctggac   9600
ctgagcgccc tgctgagaaa cagcttccac agatacgccg tggacgtgct gaagtccgga   9660
cggtgccaga tgctcgatcg gcggaccgtg gagatggcct tcgcctatgc cctcgccctg   9720
ttcgccgctg ccagacagga agaggctggc gcccaggtgt cagtgcccag agccctggat   9780
agacaggccg ccctgctgca gatccaggaa ttcatgatca cctgcctgag ccagacccccc   9840 cctagaacca ccctgctgct gtaccccaca gccgtggatc tggccaagag ggccctgtgg   9900
acccccaacc agatcaccga catcacaagc ctcgtgcggc tcgtgtacat cctgagcaag   9960
cagaaccagc agcacctgat cccccagtgg gccctgagac agatcgccga cttcgccctg  10020
aagctgcaca gacccatct ggccagcttt ctgagcgcct tcgccaggca ggaactgtac  10080
ctgatgggca gcctggtcca cagcatgctg gtgcatacca ccgagcggcg ggagatcttc  10140
atcgtggaga caggcctgtg tagcctggcc gagctgtccc actttaccca gctgctggcc  10200 cacccctcacc acgagtacct gagcgacctg tacacccccct gcagcagcag cggcagacgg  10260
gaccacagcc tggaacggct gaccagactg ttccccgatg ccaccgtgcc tgctacagtg  10320
cctgccgccc tgtccatcct gtccaccatg cagcccagca cctggaaaac cttcccccgac  10380 ctgttctgcc tgcccctggg cgagagcttt agcgccctga ccgtgtccga gcacgtgtcc  10440
tacatcgtga ccaatcagta cctgatcaag ggcatcagct acccccgtgtc cacccacgtc  10500 gtgggccaga gcctgatcat cacccagacc gacagccaga ccaagtgcga gctgacccgg  10560
aacatgcaca ccacacacag catcaccgtg gccctgaaca tcagcctgga aaactgcgct  10620
ttctgtcagt ctgcccctgct ggaatacgac gatacccagg gcgtgatcaa catcatgtac  10680
atgcacgaca gcgacgacgt gctgttcgcc ctggacccct acaacgaggt ggtggtgtcc  10740
```

```
agcccccgga cccactacct gatgctgctg aagaacggca ccgtgctgga agtgaccgac   10800
gtggtggtgg acgccaccga cctgttgaat tttgaccttc ttaagcttgc gggagacgtc   10860
gagtccaacc ccgggcccat gtgcagaagg cccgactgcg gcttcagctt cagccctgga   10920
cccgtgatcc tgctgtggtg ctgcctgctg ctgcctatcg tgtcctctgc cgccgtgtct   10980 gtggcccta cagccgccga gaaggtgcca gccgagtgcc ccgagctgac cagaagatgc   11040
ctgctgggcg aggtgttcga gggcgacaag tacgagagct ggctgcggcc cctggtcaac   11100
gtgaccggca gagatggccc cctgagccag ctgatccggt acagacccgt gaccccgag    11160 gccgccaata gcgtgctgct ggacgaggcc ttcctggata ccctggccct gctgtacaac   11220
aaccccgacc agctgagagc cctgctgacc ctgctgtcca gcgacaccgc cccagatgg    11280 atgaccgtga tgcgggggcta cagcgagtgt ggagatggca gccctgccgt gtacacctgc   11340
gtggacgacc tgtgcagagg ctacgacctg accagactga gctacggccg gtccatcttc   11400
acagagcacg tgctgggctt cgagctggtg cccccagcc tgttcaacgt ggtggtggcc    11460
atccggaacg aggccaccag aaccaacaga gccgtgcggc tgcctgtgtc tacagccgct   11520
gcacctgagg gcatcacact gttctacggc ctgtacaacg ccgtgaaaga gttctgcctc   11580
cggcaccagc tggatccccc cctgctgaga cacctggaca agtactacgc cggcctgccc   11640
ccagagctga agcagaccag agtgaacctg cccgcccaca gcagatatgg ccctcaggcc   11700
gtggacgcca atgataagc ggccgcatac agcagcaatt ggcaagctgc ttacatagaa    11760
ctcgcggcga ttggcatgcc gccttaaaat ttttatttta tttttctttt cttttccgaa   11820
tcggattttg ttttaatat ttcaaaaaaa aaaaaaaaa aaaaaaaaa aaaaaaaagg      11880 gtcggcatgg catctccacc tcctcgcggt ccgacctggg catccgaagg aggacgcacg   11940
tccactcgga tggctaaggg agagccacgt ttaaacacgt gatatctggc ctcatgggcc   12000
ttcctttcac tgcccgcttt ccagtcggga aacctgtcgt gccagctgca ttaacatggt   12060
catagctgtt tccttgcgta ttgggcgctc tccgcttcct cgctcactga ctcgctgcgc   12120
tcggtcgttc gggtaaagcc tggggtgcct aatgagcaaa aggccagcaa aaggccagga   12180
accgtaaaaa ggccgcgttg ctggcgtttt tccataggct ccgcccccct gacgagcatc   12240
acaaaaatcg acgctcaagt cagaggtggc gaaacccgac aggactataa agataccagg   12300
cgtttccccc tggaagctcc ctcgtgcgct ctcctgttcc gaccctgccg cttaccggat   12360
acctgtccgc ctttctccct tcgggaagcg tggcgctttc tcatagctca cgctgtaggt   12420
atctcagttc ggtgtaggtc gttcgctcca agctgggctg tgtgcacgaa ccccccgttc   12480
agcccgaccg ctgcgcctta tccggtaact atcgtcttga gtccaacccg gtaagacacg   12540
acttatcgcc actggcagca gccactggta acaggattag cagagcgagg tatgtaggcg   12600
gtgctacaga gttcttgaag tggtggccta actacggcta cactagaaga acagtatttg   12660
gtatctgcgc tctgctgaag ccagttacct tcggaaaaag agttggtagc tcttgatccg   12720
gcaaacaaac caccgctggt agcggtggtt tttttgtttg caagcagcag attacgcgca   12780
gaaaaaaagg atctcaagaa gatcctttga tcttttctac ggggtctgac gctcagtgga   12840
acgaaaactc acgttaaggg attttggtca tgagattatc aaaaaggatc ttcacctaga   12900
tccttttaaa ttaaaaatga agttttaaat caatctaaag tatatatgag taaacttggt   12960
ctgacagtta ttagaaaaat tcatccagca gacgataaaa cgcaatacgc tggctatccg   13020
gtgccgcaat gccatacagc accagaaaac gatccgccca ttcgccgccc agttcttccg   13080
```

| | |
|---|---:|
| caatatcacg ggtggccagc gcaatatcct gataacgatc cgccacgccc agacggccgc | 13140 |
| aatcaataaa gccgctaaaa cggccatttt ccaccataat gttcggcagg cacgcatcac | 13200 |
| catgggtcac caccagatct tcgccatccg gcatgctcgc tttcagacgc gcaaacagct | 13260 |
| ctgccggtgc caggccctga tgttcttcat ccagatcatc ctgatccacc aggcccgctt | 13320 |
| ccatacgggt acgcgcacgt tcaatacgat gtttcgcctg atgatcaaac ggacaggtcg | 13380 |
| ccgggtccag ggtatgcaga cgacgcatgg catccgccat aatgctcact ttttctgccg | 13440 |
| gcgccagatg gctagacagc agatcctgac ccggcacttc gcccagcagc agccaatcac | 13500 |
| ggcccgcttc ggtcaccaca tccagcaccg ccgcacacgg aacaccggtg gtggccagcc | 13560 |
| agctcagacg cgccgcttca tcctgcagct cgttcagcgc accgctcaga tcggttttca | 13620 |
| caaacagcac cggacgaccc tgcgcgctca gacgaaacac cgccgcatca gagcagccaa | 13680 |
| tggtctgctg cgcccaatca tagccaaaca gacgttccac ccacgctgcc gggctacccg | 13740 |
| catgcaggcc atcctgttca atcatactct tccttttca atattattga agcatttatc | 13800 |
| agggttattg tctcatgagc ggatacatat ttgaatgtat ttagaaaaat aaacaaatag | 13860 |
| gggttccgcg cacatttccc cgaaaagtgc cacctaaatt gtaagcgtta atattttgtt | 13920 |
| aaaattcgcg ttaaattttt gttaaatcag ctcattttt aaccaatagg ccgaaatcgg | 13980 |
| caaaatccct tataaatcaa agaatagac cgagataggg ttgagtggcc gctacagggc | 14040 |
| gctcccattc gccattcagg ctgcgcaact gttgggaagg gcgtttcggt gcgggcctct | 14100 |
| tcgctattac gccagctggc gaaaggggga tgtgctgcaa ggcgattaag ttgggtaacg | 14160 |
| ccagggtttt cccagtcaca cgcgtaatac gactcactat ag | 14202 |

<210> SEQ ID NO 11
<211> LENGTH: 14721
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 11

| | |
|---|---:|
| ataggcggcg catgagagaa gcccagacca attacctacc caaaatggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |
| gtgcggaaga tccggacaga ttgtataagt atgcaactaa gctgaagaaa aactgtaagg | 360 |
| aaataactga taaggaattg gacaagaaaa tgaaggagct cgccgccgtc atgagcgacc | 420 |
| ctgacctgga aactgagact atgtgcctcc acgacgacga gtcgtgtcgc tacgaagggc | 480 |
| aagtcgctgt ttaccaggat gtatacgcgg ttgacggacc gacaagtctc tatcaccaag | 540 |
| ccaataaggg agttagagtc gcctactgga taggctttga caccaccct tttatgttta | 600 |
| agaacttggc tggagcatat ccatcatact ctaccaactg ggcgacgaa accgtgttaa | 660 |
| cggctcgtaa cataggccta tgcagctctg acgttatgga gcggtcacgt agagggatgt | 720 |
| ccattcttag aaagaagtat ttgaaaccat ccaacaatgt tctattctct gttggctcga | 780 |
| ccatctacca cgagaagagg gacttactga ggagctggca cctgccgtct gtatttcact | 840 |
| tacgtggcaa gcaaaattac acatgtcggt gtgagactat agttagttgc gacgggtacg | 900 |

```
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt ctccgcaggg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg acgtcaatg    2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatcccA aacagtgcgg ttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa    2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag tacccgggga atttcactgc cacgatagag gagtggcaag   3000
cagagcatga tgccatcatg aggcacatct ggagagaccc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
```

```
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaacttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tccttttccat    4920 tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctc tacttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccgc    5520 caggcgtgaa tagggtgatc actagagagg agctcgaggc gcttacccg tcacgcactc    5580 ctagcaggtc ggtctcgaga accagcctgg tctccaaccc gccaggcgta aataggg tga    5640
```

```
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat gggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta gcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
ggcccctat aactctctac ggctaacctg aatggactac gacatagtct agtccgccaa    7560
gctattccag aagtagtgag gaggcttttt tggaggccta ggcttttgca aaaagcttgt    7620
atatccattt tcggatctga tcaagagaca ggatgaggat cgtttcgcat gattgaataa    7680
gatggattgc acgtaggttc tccggccgct tgggtggaga ggctattcgg ctatgactgg    7740
gcacaactga caatcggctg ctctgatgcc gccgtgatcc ggttgtcagc gcaggggcgc    7800
ccggttcttt ttgtcaagac cgacctgtcc ggtgccctga atgaactgaa ggacgaggca    7860
gcgcggctat cgtggctggc cacgacgggc gttccttgcg cagtctagac tggcgcgcca    7920
aacctgcagg ttaaaacagc tgtgggttgt tcccacccac agggcccact gggcgctagc    7980
```

```
actctgattt  tacgaaatcc  ttgtgcgcct  gttttatatc  ccttccctaa  ttcgaaacgt    8040
agaagcaatg  cgcaccactg  atcaatagta  ggcgtaacgc  gccagttacg  tcatgatcaa    8100
gcatatctgt  tcccccggac  tgagtatcaa  tagactgctt  acgcggttga  aggagaaaac    8160
gttcgttatc  cggctaacta  cttcgagaag  cccagtaaca  ccatggaagc  tgcagggtgt    8220
ttcgctcagc  acttcccccg  tgtagatcag  gtcgatgagc  cactgcaatc  cccacaggtg    8280
actgtggcag  tggctgcgtt  ggcggcctgc  ctatggggag  acccatagga  cgctctaatg    8340
tggacatggt  gcgaagagcc  tattgagcta  gttagtagtc  ctccggcccc  tgaatgcggc    8400
taatcctaac  tgcggagcac  atgccttcaa  cccagagggt  agtgtgtcgt  aatgggcaac    8460
tctgcagcgg  aaccgactac  tttgggtgtc  cgtgtttctt  tttattctta  tattggctgc    8520
ttatggtgac  aattacagaa  ttgttaccat  atagctattg  gattggccat  ccggtgtgta    8580
atagagctgt  tatataccta  tttgttggct  ttgtaccact  aactttaaaa  tctataacta    8640
ccctcaactt  tatattaacc  ctcaatacag  ttgaacatga  ggcctggcct  gccctcctac    8700
ctgatcatcc  tggccgtgtg  cctgttcagc  cacctgctgt  ccagcagata  cggcgccgag    8760
gccgtgagcg  agcccctgga  caaggctttc  cacctgctgc  tgaacaccta  cggcagaccc    8820
atccggtttc  tgcgggagaa  caccacccag  tgcacctaca  acagcagcct  gcggaacagc    8880
accgtcgtga  gagaaacgc   catcagcttc  aacttttcc   agagctacaa  ccagtactac    8940
gtgttccaca  tgcccagatg  cctgtttgcc  ggccctctgg  ccgagcagtt  cctgaaccag    9000
gtggacctga  ccgagacact  ggaaagatac  cagcagcggc  tgaataccta  cgccctggtg    9060
tccaaggacc  tggccagcta  ccggtccttt  agccagcagc  tcaaggctca  ggatagcctc    9120
ggcgagcagc  ctaccaccgt  gcccctccc   atcgacctga  gcatccccca  cgtgtggatg    9180
cctccccaga  ccacccctca  cggctggacc  gagagccaca  ccacctccgg  cctgcacaga    9240
ccccacttca  accagacctg  catcctgttc  gacggccacg  acctgctgtt  tagcaccgtg    9300
accccctgcc  tgcaccaggg  cttctacctg  atcgacgagc  tgagatacgt  gaagatcacc    9360
ctgaccgagg  atttcttcgt  ggtcaccgtg  tccatcgacg  acgacacccc  catgctgctg    9420
atcttcggcc  acctgcccag  agtgctgttc  aaggcccct   accagcggga  caacttcatc    9480
ctgcggcaga  ccgagaagca  cgagctgctg  gtgctggtca  agaaggacca  gctgaaccgg    9540
cactcctacc  tgaaggaccc  cgacttcctg  gacgccgccc  tggacttcaa  ctacctggac    9600
ctgagcgccc  tgctgagaaa  cagcttccac  agatacgccg  tggacgtgct  gaagtccgga    9660
cggtgccaga  tgctcgatcg  gcggaccgtg  gagatggcct  tcgcctatgc  cctcgccctg    9720
ttcgccgctg  ccagacagga  agaggctggc  gcccaggtgt  cagtgcccag  agccctggat    9780
agacaggccg  ccctgctgca  gatccaggaa  ttcatgatca  cctgcctgag  ccagaccccc    9840
cctagaacca  ccctgctgct  gtaccccaca  gccgtggatc  tggccaagag  ggccctgtgg    9900 accccccaacc  agatcaccga  catcacaagc  ctcgtgcggc  tcgtgtacat  cctgagcaag    9960
cagaaccagc  agcacctgat  cccccagtgg  gccctgagac  agatcgccga  cttcgccctg    10020
aagctgcaca  agacccatct  ggccagcttt  ctgagcgcct  tcgccaggca  ggaactgtac    10080
ctgatgggca  gcctggtcca  cagcatgctg  gtgcatacca  ccgagcggcg  ggagatcttc    10140
atcgtggaga  caggcctgtg  tagcctggcc  gagctgtccc  actttaccca  gctgctggcc    10200
caccctcacc  acgagtacct  gagcgacctg  tacacccccct gcagcagcag  cggcagacgg    10260
gaccacagcc  tggaacggct  gaccagactg  ttccccgatg  ccaccgtgcc  tgctacagtg    10320
cctgccgccc  tgtccatcct  gtccaccatg  cagcccagca  ccctggaaac  cttccccgac    10380
```

```
ctgttctgcc tgcccctggg cgagagcttt agcgccctga ccgtgtccga gcacgtgtcc   10440
tacatcgtga ccaatcagta cctgatcaag ggcatcagct accccgtgtc caccacagtc   10500
gtgggccaga gcctgatcat cacccagacc gacagccaga ccaagtgcga gctgacccgg   10560
aacatgcaca ccacacacag catcaccgtg ccctgaaca tcagcctgga aaactgcgct   10620
ttctgtcagt ctgccctgct ggaatacgac gatacccagg gcgtgatcaa catcatgtac   10680
atgcacgaca gcgacgacgt gctgttcgcc ctggacccct acaacgaggt ggtggtgtcc   10740
agcccccgga cccactacct gatgctgctg aagaacggca ccgtgctgga agtgaccgac   10800
gtggtggtgg acgccaccga ctgataacgc cggcgccccc ccctaacgtt actggccgaa   10860
gccgcttgga ataaggccgg tgtgcgtttg tctatatgtt attttccacc atattgccgt   10920
cttttggcaa tgtgagggcc cggaaacctg gccctgtctt cttgacgagc attcctaggg   10980
gtctttcccc tctcgccaaa ggaatgcaag gtctgttgaa tgtcgtgaag gaagcagttc   11040
ctctggaagc ttcttgaaga caaacaacgt ctgtagcgac cctttgcagg cagcggaacc   11100
ccccacctgg cgacaggtgc ctctgcggcc aaaagccacg tgtataagat acacctgcaa   11160
aggcggcaca ccccagtgc cacgttgtga gttggatagt tgtggaaaga gtcaaatggc   11220
tctcctcaag cgtattcaac aaggggctga aggatgccca gaaggtaccc cattgtatgg   11280
gatctgatct ggggcctcgg tgcacatgct ttacatgtgt ttagtcgagg ttaaaaaaac   11340
gtctaggccc cccgaaccac ggggacgtgg ttttcctttg aaaaacacga taataatatg   11400
tgcagaaggc ccgactgcgg cttcagcttc agccctggac ccgtgatcct gctgtggtgc   11460
tgcctgctgc tgcctatcgt gtcctctgcc gccgtgtctg tggcccctac agccgccgag   11520
aaggtgccag ccgagtgccc cgagctgacc agaagatgcc tgctgggcga ggtgttcgag   11580
ggcgacaagt acgagagctg gctgcggccc ctggtcaacg tgaccggcag agatggcccc   11640
ctgagccagc tgatccggta cagacccgtg accccgagg ccgccaatag cgtgctgctg   11700
gacgaggcct tcctggatac cctggccctg ctgtacaaca ccccgacca gctgagagcc   11760
ctgctgaccc tgctgtccag cgacaccgcc cccagatgga tgaccgtgat gcggggctac   11820
agcgagtgtg gagatggcag ccctgccgtg tacacctgcg tggacgacct gtgcagaggc   11880
tacgacctga ccagactgag ctacggccgg tccatcttca cagagcacgt gctgggcttc   11940
gagctggtgc cccccagcct gttcaacgtg gtggtggcca tccggaacga ggccaccaga   12000
accaacagag ccgtgcggct gcctgtgtct acagccgctg cacctgaggg catcacactg   12060
ttctacggcc tgtacaacgc cgtgaaagag ttctgcctcc ggcaccagct ggatcccccc   12120
ctgctgagac acctggacaa gtactacgcc ggcctgcccc cagagctgaa gcagaccaga   12180
gtgaacctgc ccgccacag cagatatggc cctcaggccg tggacgccag atgataagcg   12240
gccgcataca gcagcaattg gcaagctgct tacatagaac tcgcggcgat tggcatgccg   12300
ccttaaaatt tttattttat ttttcttttc ttttccgaat cggattttgt ttttaatatt   12360
tcaaaaaaaa aaaaaaaaaa aaaaaaaaaa aaaaaaggg tcggcatggc atctccacct   12420
cctcgcggtc cgacctgggc atccgaagga ggacgcacgt ccactcggat ggctaaggga   12480
gagccacgtt taaacacgtg atatctggcc tcatgggcct tcctttcact gcccgctttc   12540
cagtcgggaa acctgtcgtg ccagctgcat taacatggtc atagctgttt ccttgcgtat   12600
tgggcgctct ccgcttcctc gctcactgac tcgctgcgct cggtcgttcg ggtaaagcct   12660
ggggtgccta atgagcaaaa ggccagcaaa aggccaggaa ccgtaaaaag gccgcgttgc   12720
```

```
tggcgttttt ccataggctc cgccccctg acgagcatca caaaaatcga cgctcaagtc   12780
agaggtggcg aaacccgaca ggactataaa gataccaggc gtttcccct ggaagctccc    12840
tcgtgcgctc tcctgttccg accctgccgc ttaccggata cctgtccgcc tttctccctt   12900
cgggaagcgt ggcgctttct catagctcac gctgtaggta tctcagttcg gtgtaggtcg   12960
ttcgctccaa gctgggctgt gtgcacgaac ccccgttca gcccgaccgc tgcgccttat    13020
ccggtaacta tcgtcttgag tccaacccgg taagacacga cttatcgcca ctggcagcag   13080
ccactggtaa caggattagc agagcgaggt atgtaggcgg tgctacagag ttcttgaagt   13140
ggtggcctaa ctacggctac actagaagaa cagtatttgg tatctgcgct ctgctgaagc   13200
cagttacctt cggaaaaaga gttggtagct cttgatccgg caaacaaacc accgctggta   13260
gcggtggttt ttttgtttgc aagcagcaga ttacgcgcag aaaaaaagga tctcaagaag   13320
atcctttgat cttttctacg gggtctgacg ctcagtggaa cgaaaactca cgttaaggga   13380
ttttggtcat gagattatca aaaggatct tcacctagat cctttaaat taaaaatgaa     13440
gttttaaatc aatctaaagt atatatgagt aaacttggtc tgacagttat tagaaaaatt   13500
catccagcag acgataaaac gcaatacgct ggctatccgg tgccgcaatg ccatacagca   13560
ccagaaaacg atccgcccat cgcgcgccca gttcttccgc aatatcacgg gtggccagcg   13620
caatatcctg ataacgatcc gccacgccca gacggccgca atcaataaag ccgctaaaac   13680
ggccattttc caccataatg ttcggcaggc acgcatcacc atgggtcacc accagatctt   13740
cgccatccgg catgctcgct ttcagacgcg caaacagctc tgccggtgcc aggccctgat   13800
gttcttcatc cagatcatcc tgatccacca ggcccgcttc catacgggta cgcgcacgtt   13860
caatacgatg tttcgcctga tgatcaaacg gacaggtcgc cgggtccagg gtatgcagac   13920
gacgcatggc atccgccata atgctcactt tttctgccgg cgccagatgg ctagacagca   13980
gatcctgacc cggcacttcg cccagcagca gccaatcacg gcccgcttcg gtcaccacat   14040
ccagcaccgc cgcacacgga acaccggtgg tggccagcca gctcagacgc gccgcttcat   14100
cctgcagctc gttcagcgca ccgctcagat cggttttcac aaacagcacc ggacgaccct   14160
gcgcgctcag acgaaacacc gccgcatcag agcagccaat ggtctgctgc gcccaatcat   14220
agccaaacag acgttccacc cacgctgccg ggctacccgc atgcaggcca tcctgttcaa   14280
tcatactctt cctttttcaa tattattgaa gcatttatca gggttattgt ctcatgagcg   14340
gatacatatt tgaatgtatt tagaaaaata acaaataggg gttccgcgc acatttcccc    14400
gaaaagtgcc acctaaattg taagcgttaa tattttgtta aaattcgcgt taaattttg    14460
ttaaatcagc tcatttttta accaataggc cgaaatcggc aaaatccctt ataaatcaaa   14520
agaatagacc gagatagggt tgagtggccg ctacagggcg ctcccattcg ccattcaggc   14580
tgcgcaactg ttgggaaggg cgtttcggtg cgggcctctt cgctattacg ccagctggcg   14640
aaaggggat gtgctgcaag gcgattaagt tgggtaacgc cagggttttc ccagtcacac    14700
gcgtaatacg actcactata g                                            14721
```

<210> SEQ ID NO 12
<211> LENGTH: 14721
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12

-continued

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020 tctctttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctcccct tccatgaatt cgcctacgag agtctgagaa    2160
cacgaccagc cgctccttac caagtaccaa ccatagggt gtatgcgtg ccaggatcag    2220 gcaagtctgg catcattaaa agcgcagtca ccaaaaaaga tctagtggtg agcgccaaga    2280
aagaaaactg tgcagaaatt ataagggacg tcaagaaaat gaagggctg gacgtcaatg    2340
```

```
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttaac atgatgtgcc      2520 tgaaagtgca ttttaaccac gagatttgca cacaagtctt ccacaaaagc atctctcgcc    2580
gttgcactaa atctgtgact tcggtcgtct caaccttgtt ttacgacaaa aaatgagaa     2640 cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacgag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg ataactccc     3300 cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca gtttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag acaacctgg cggagggtg tgcggagcgc      4140 tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga atgggaaat gactctcaag gaagcagtgg     4500
ctaggagaga agcagtggag gagatatgca tatccgacga ctcttcagtg acagaacctg    4560
atgcagagct ggtgagggtg catccgaaga gttctttggc tggaaggaag gctacagcag   4620
caagcgatgg caaaacttc tcatatttgg aagggaccaa gttcaccag gcggccaagg     4680 atatagcaga aattaatgcc atgtggcccg ttgcaacgga ggccaatgag caggtatgca    4740
```

```
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggaggagct agcgtgacca    5340 gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccacccccgc    5520
caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaacttttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360 cggccttaa tgtggaatgc ttcaagaaat atgcgtgtaa taatgaatat gggaaacgt    6420 ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga gaacggcccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
```

```
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccctaaaa aggctgttta agcttggcaa acctctggca gcagacgatg     7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gctattccag aagtagtgag gaggcttttt tggaggccta ggcttttgca aaaagcttgt    7620
atatccattt tcggatctga tcaagagaca ggatgaggat cgtttcgcat gattgaataa    7680
gatggattgc acgtaggttc tccggccgct tgggtggaga ggctattcgg ctatgactgg    7740
gcacaactga caatcggctg ctctgatgcc gccgtgatcc ggttgtcagc gcaggggcgc    7800
ccggttcttt ttgtcaagac cgacctgtcc ggtgccctga atgaactgaa ggacgaggca    7860
gcgcggctat cgtggctggc cacgacgggc gttccttgcg cagtctagac tggcgcgcca    7920
aacctgcagg ttaaaacagc tgtgggttgt tcccacccac agggcccact gggcgctagc    7980
actctgattt tacgaaatcc ttgtgcgcct gttttatatc ccttccctaa ttcgaaacgt    8040
agaagcaatg cgcaccactg atcaatagta ggcgtaacgc gccagttacg tcatgatcaa    8100
gcatatctgt tcccccggac tgagtatcaa tagactgctt acgcggttga aggagaaaac    8160
gttcgttatc cggctaacta cttcgagaag cccagtaaca ccatggaagc tgcagggtgt    8220
ttcgctcagc acttcccccg tgtagatcag gtcgatgagc cactgcaatc cccacaggtg    8280
actgtggcag tggctgcgtt ggcggcctgc ctatggggag acccatagga cgctctaatg    8340
tggacatggt gcgaagagcc tattgagcta gttagtagtc ctccggcccc tgaatgcggc    8400
taatcctaac tgcggagcac atgccttcaa cccagagggt agtgtgtcgt aatgggcaac    8460
tctgcagcgg aaccgactac tttgggtgtc cgtgtttctt tttattctta tattggctgc    8520
ttatggtgac aattacagaa ttgttaccat atagctattg gattggccat ccggtgtgta    8580
atagagctgt tatataccta tttgttggct ttgtaccact aactttaaaa tctataacta    8640
ccctcaactt tatattaacc ctcaatacag ttgaacatgt gcagaaggcc cgactgcggc    8700
ttcagcttca gccctggacc cgtgatcctg ctgtggtgct gcctgctgct gcctatcgtg    8760
tcctctgccg ccgtgtctgt ggcccctaca gccgccgaga aggtgccagc cgagtgcccc    8820
gagctgacca gaagatgcct gctgggcgag gtgttcgagg gcgacaagta cgagagctgg    8880
ctgcggcccc tggtcaacgt gaccggcaga gatggccccc tgagccagct gatccggtac    8940
agacccgtga ccccgaggc cgccaatagc gtgctgctgg acgaggcctt cctggatacc    9000
ctggccctgc tgtacaacaa ccccgaccag ctgagagccc tgctgaccct gctgtccagc    9060
gacaccgccc ccagatggat gaccgtgatg cggggctaca gcgagtgtgg agatggcagc    9120
cctgccgtgt acacctgcgt ggacgacctg tgcagaggct acgacctgac cagactgagc    9180 tacgccggt ccatcttcac agagcacgtg ctgggcttcg agctggtgcc ccccagcctg    9240
ttcaacgtgg tggtggccat ccggaacgag gccaccagaa ccaacagagc cgtgcggctg    9300
cctgtgtcta cagccgctgc acctgagggc atcacactgt tctacggcct gtacaacgcc    9360
gtgaaagagt tctgcctccg gcaccagctg gatccccccc tgctgagaca cctggacaag    9420
tactacgccg gcctgccccc agagctgaag cagaccgagt gaacctgcc cgcccacagc    9480
```

```
agatatggcc ctcaggccgt ggacgccaga tgataacgcc ggcgccccc cctaacgtta     9540
ctggccgaag ccgcttggaa taaggccggt gtgcgtttgt ctatatgtta ttttccacca     9600
tattgccgtc ttttggcaat gtgagggccc ggaaacctgg ccctgtcttc ttgacgagca     9660
ttcctagggg tctttcccct ctcgccaaag gaatgcaagg tctgttgaat gtcgtgaagg     9720
aagcagttcc tctggaagct tcttgaagac aaacaacgtc tgtagcgacc ctttgcaggc     9780
agcggaaccc cccacctggc gacaggtgcc tctgcggcca aaagccacgt gtataagata     9840
cacctgcaaa ggcggcacaa ccccagtgcc acgttgtgag ttggatagtt gtggaaagag     9900
tcaaatggct ctcctcaagc gtattcaaca aggggctgaa ggatgcccag aaggtacccc     9960
attgtatggg atctgatctg gggcctcggt gcacatgctt tacatgtgtt tagtcgaggt    10020
taaaaaaacg tctaggcccc ccgaaccacg ggacgtggt tttcctttga aaaacacgat    10080
aataatatga ggcctggcct gccctcctac ctgatcatcc tggccgtgtg cctgttcagc    10140
cacctgctgt ccagcagata cggcgccgag gccgtgagcg agcccctgga caaggctttc    10200
cacctgctgc tgaacaccta cggcagaccc atccggtttc tgcgggagaa caccacccag    10260
tgcacctaca cagcagcct gcggaacagc accgtcgtga gagagaacgc catcagcttc    10320
aacttttttcc agagctacaa ccagtactac gtgttccaca tgcccagatg cctgtttgcc    10380
ggccctctgg ccgagcagtt cctgaaccag gtggacctga ccgagacact ggaaagatac    10440
cagcagcggc tgaataccta cgccctggtg tccaaggacc tggccagcta ccggtccttt    10500
agccagcagc tcaaggctca ggatagcctc ggcgagcagc ctaccaccgt gccccctccc    10560
atcgacctga gcatccccca cgtgtggatg cctccccaga ccaccctca cggctggacc    10620
gagagccaca ccacctccgg cctgcacaga ccccacttca accagacctg catcctgttc    10680
gacggccacg acctgctgtt tagcaccgtg accccctgcc tgcaccaggg cttctacctg    10740
atcgacgagc tgagatacgt gaagatcacc ctgaccgagg atttcttcgt ggtcaccgtg    10800
tccatcgacg acgacacccc catgctgctg atcttcggcc acctgccag agtgctgttc    10860
aaggcccct accagcggga caacttcatc ctgcggcaga ccgagaagca cgagctgctg    10920
gtgctggtca agaaggacca gctgaaccgg cactcctacc tgaaggaccc cgacttcctg    10980
gacgccgccc tggacttcaa ctacctggac ctgagcgccc tgctgagaaa cagcttccac    11040
agatacgccg tggacgtgct gaagtccgga cggtgccaga tgctcgatcg gcggaccgtg    11100
gagatggcct tcgcctatgc cctcgccctg ttcgccgctg ccagacagga agaggctggc    11160
gcccaggtgt cagtgcccag agccctggat agacaggccg ccctgctgca gatccaggaa    11220
ttcatgatca cctgcctgag ccagaccccc cctagaacca ccctgctgct gtaccccaca    11280
gccgtggatc tggccaagag ggccctgtgg acccccaacc agatcaccga catcacaagc    11340
ctcgtgcggc tcgtgtacat cctgagcaag cagaaccagc agcacctgat cccccagtgg    11400
gccctgagac agatcgccga cttcgccctg aagctgcaca agaccatct ggccagcttt    11460
ctgagcgcct tcgccaggca ggaactgtac ctgatgggca gcctggtcca cagcatgctg    11520
gtgcatacca ccgagcggcg ggagatcttc atcgtggaga caggcctgtg tagcctggcc    11580
gagctgtccc actttaccca gctgctggcc caccctcacc acgagtacct gagcgacctg    11640
tacacccct gcagcagcag cggcagacgg gaccacagcc tggaacggct gaccagactg    11700
ttccccgatg ccaccgtgcc tgctacagtg cctgccgccc tgtccatcct gtccaccatg    11760
cagcccagca ccctggaaac cttccccgac ctgttctgcc tgcccctggg cgagagcttt    11820
```

```
agcgccctga ccgtgtccga gcacgtgtcc tacatcgtga ccaatcagta cctgatcaag    11880
ggcatcagct accccgtgtc caccacagtc gtgggccaga gcctgatcat cacccagacc    11940
gacagccaga ccaagtgcga gctgacccgg aacatgcaca ccacacacag catcaccgtg    12000
gccctgaaca tcagcctgga aaactgcgct ttctgtcagt ctgccctgct ggaatacgac    12060
gatacccagg gcgtgatcaa catcatgtac atgcacgaca gcgacgacgt gctgttcgcc    12120
ctggacccct acaacgaggt ggtggtgtcc agccccgga cccactacct gatgctgctg    12180
aagaacggca ccgtgctgga agtgaccgac gtggtggtgg acgccaccga ctgataagcg    12240
gccgcataca gcagcaattg gcaagctgct tacatagaac tcgcggcgat tggcatgccg    12300
ccttaaaatt tttatttat ttttcttttc ttttccgaat cggattttgt ttttaatatt    12360
tcaaaaaaaa aaaaaaaaa aaaaaaaaa aaaaaagggg tcggcatggc atctccacct    12420
cctcgcggtc cgacctgggc atccgaagga ggacgcacgg ccactcggat ggctaaggga    12480
gagccacgtt taaacacgtg atatctggcc tcatgggcct tcctttcact gcccgctttc    12540
cagtcgggaa acctgtcgtg ccagctgcat taacatggtc atagctgttt ccttgcgtat    12600
tgggcgctct ccgcttcctc gctcactgac tcgctgcgct cggtcgttcg gtaaagcct    12660 ggggtgccta atgagcaaaa ggccagcaaa aggccaggaa ccgtaaaaag gccgcgttgc    12720
tggcgttttt ccataggctc cgcccccctg acgagcatca caaaaatcga cgctcaagtc    12780
agaggtggcg aaacccgaca ggactataaa gataccaggc gtttccccct ggaagctccc    12840
tcgtgcgctc tcctgttccg accctgccgc ttaccggata cctgtccgcc tttctccctt    12900
cgggaagcgt ggcgctttct catagctcac gctgtaggta tctcagttcg gtgtaggtcg    12960
ttcgctccaa gctgggctgt gtgcacgaac cccccgttca gcccgaccgc tgcgccttat    13020
ccggtaacta tcgtcttgag tccaacccgg taagacacga cttatcgcca ctggcagcag    13080
ccactggtaa caggattagc agagcgaggt atgtaggcgg tgctacagag ttcttgaagt    13140
ggtggcctaa ctacggctac actagaagaa cagtatttgg tatctgcgct ctgctgaagc    13200
cagttacctt cggaaaaaga gttggtagct cttgatccgg caaacaaacc accgctggta    13260
gcggtggttt ttttgtttgc aagcagcaga ttacgcgcag aaaaaaagga tctcaagaag    13320
atcctttgat cttttctacg gggtctgacg ctcagtggaa cgaaaactca cgttaaggga    13380
ttttggtcat gagattatca aaaaggatct caccctagat cctttttaaat taaaatgaa    13440 gttttaaatc aatctaaagt atatatgagt aaacttggtc tgacagttat tagaaaaatt    13500
catccagcag acgataaaac gcaatacgct ggctatccgg tgccgcaatg ccatacagca    13560
ccagaaaacg atccgcccat tcgccgccca gttcttccgc aatatcacgg gtggccagcg    13620
caatatcctg ataacgatcc gccacgccca gacggccgca atcaataaag ccgctaaaac    13680
ggccattttc caccataatg ttcggcaggc acgcatcacc atgggtcacc accagatctt    13740
cgccatccgg catgctcgct ttcagacgcg caaacagctc tgccggtgcc aggccctgat    13800
gttcttcatc cagatcatcc tgatccacca ggcccgcttc catacgggta cgcgcacgtt    13860
caatacgatg tttcgcctga tgatcaaacg gacaggtcgc cgggtccagg gtatgcagac    13920
gacgcatggc atccgccata atgctcactt tttctgccgg cgccagatgg ctagacagca    13980
gatcctgacc cggcacttcg cccagcagca gccaatcacg gccgcttcg gtcaccacat    14040 ccagcaccgc cgcacacgga acaccggtgg tggccagcca gctcagacgc gccgcttcat    14100
cctgcagctc gttcagcgca ccgctcagat cggttttcac aaacagcacc ggacgaccct    14160
gcgcgctcag acgaaacacc gccgcatcag agcagccaat ggtctgctgc gcccaatcat    14220
```

```
agccaaacag acgttccacc cacgctgccg ggctacccgc atgcaggcca tcctgttcaa    14280
tcatactctt cctttttcaa tattattgaa gcatttatca gggttattgt ctcatgagcg    14340
gatacatatt tgaatgtatt tagaaaaata acaaatagg  ggttccgcgc acatttcccc    14400
gaaaagtgcc acctaaattg taagcgttaa tattttgtta aaattcgcgt taaattttg     14460 ttaaatcagc tcatttttta accaataggc cgaaatcggc aaaatcccctt ataaatcaaa   14520 agaatagacc gagatagggt tgagtggccg ctacagggcg ctcccattcg ccattcaggc    14580
tgcgcaactg ttgggaaggg cgtttcggtg cgggcctctt cgctattacg ccagctggcg    14640
aaagggggat gtgctgcaag gcgattaagt tgggtaacgc cagggttttc ccagtcacac    14700
gcgtaatacg actcactata g                                              14721
```

<210> SEQ ID NO 13
<211> LENGTH: 15300
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agaggatgt      720 ccattcttag aaagaagtat ttgaaaccat ccaacaatgt tctattctct gttggctcga     780
ccatctacca cgaagagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca agtgacaga  cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg ataccaaac catcatcaaa gtgaacagcg    1380
atttccactc attcgtgctg cccaggatag gcagtaacac attggagatc gggctgagaa    1440
```

```
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccataggggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg tttttttaac atgatgtgcc    2520
tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgcataaata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
```

```
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg ccaccgaag   4080 gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt ccaccccgc   5520 caggcgtgaa tagggtgatc actagagagg agctcgaggc gcttacccg tcacgcactc   5580 ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag gcatttaca acaaaaatca gtaaggcaaa   5760
cggtgctatc cgaagtggtg ttggagagga ccgaattgga gatttcgtat gccccgcgcc   5820
tcgaccaaga aaagaagaa ttactacgca agaaattaca gttaaatccc acctgctgct   5880
acagaagcag ataccagtcc aggaaggtgg agaacatgaa agccataaca gctagacgta   5940
ttctgcaagg cctagggcat atttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
```

```
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta gcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgaggcct ggcctgccct cctacctgat catcctggcc gtgtgcctgt tcagccacct    7620
gctgtccagc agatacggcg ccgaggccgt gagcgagccc ctggacaagg ctttccacct    7680
gctgctgaac acctacggca gacccatccg gtttctgcgg gagaacacca cccagtgcac    7740
ctacaacagc agcctgcgga acagcaccgt cgtgagagag aacgccatca gcttcaactt    7800
tttccagagc tacaaccagt actacgtgtt ccacatgccc agatgcctgt ttgccggccc    7860
tctggccgag cagttcctga accaggtgga cctgaccgag acactggaaa gataccagca    7920
gcggctgaat acctacgccc tggtgtccaa ggacctggcc agctaccggt cctttagcca    7980
gcagctcaag gctcaggata gcctcggcga gcagcctacc accgtgcccc ctcccatcga    8040
cctgagcatc ccccacgtgt ggatgcctcc ccagaccacc cctcacggct ggaccgagag    8100
ccacaccacc tccggcctgc acagacccca cttcaaccag acctgcatcc tgttcgacgg    8160
ccacgacctg ctgtttagca ccgtgacccc ctgcctgcac agggcttct acctgatcga    8220 cgagctgaga tacgtgaaga tcaccctgac cgaggatttc ttcgtggtca ccgtgtccat    8280
cgacgacgac accccccatgc tgctgatctt cggccacctg cccagagtgc tgttcaaggc    8340
cccctaccag cgggacaact tcatcctgcg gcagaccgag aagcacgagc tgctggtgct    8400
ggtcaagaag gaccagctga accggcactc ctacctgaag gaccccgact tcctggacgc    8460
cgccctggac ttcaactacc tggacctgag cgccctgctg agaaacagct tccacagata    8520
cgccgtggac gtgctgaagt ccggacggtg ccagatgctc gatcggcgga ccgtggagat    8580
```

```
ggccttcgcc tatgccctcg ccctgttcgc cgctgccaga caggaagagg ctggcgccca   8640
ggtgtcagtg cccagagccc tggatagaca ggccgccctg ctgcagatcc aggaattcat   8700
gatcacctgc ctgagccaga ccccccctag aaccaccctg ctgctgtacc ccacagccgt   8760
ggatctggcc aagagggccc tgtggacccc caaccagatc accgacatca caagcctcgt   8820
gcggctcgtg tacatcctga gcaagcagaa ccagcagcac ctgatccccc agtgggccct   8880
gagacagatc gccgacttcg ccctgaagct gcacaagacc catctggcca gctttctgag   8940
cgccttcgcc aggcaggaac tgtacctgat gggcagcctg gtccacagca tgctggtgca   9000
taccaccgag cggcgggaga tcttcatcgt ggagacaggc ctgtgtagcc tggccgagct   9060
gtcccacttt acccagctgc tggcccaccc tcaccacgag tacctgagcg acctgtacac   9120
cccctgcagc agcagcggca gacgggacca cagcctggaa cggctgacca gactgttccc   9180
cgatgccacc gtgcctgcta cagtgcctgc cgccctgtcc atcctgtcca ccatgcagcc   9240
cagcaccctg gaaaccttcc ccgacctgtt ctgcctgccc ctgggcgaga gctttagcgc   9300
cctgaccgtg tccgagcacg tgtcctacat cgtgaccaat cagtacctga tcaagggcat   9360
cagctacccc gtgtccacca cagtcgtggg ccagagcctg atcatcaccc agaccgacag   9420
ccagaccaag tgcgagctga cccggaacat gcacaccaca cacagcatca ccgtggccct   9480
gaacatcagc ctggaaaaact gcgctttctg tcagtctgcc ctgctggaat acgacgatac   9540
ccagggcgtg atcaacatca tgtacatgca cgacagcgac gacgtgctgt cgccctgga   9600 cccctacaac gaggtggtgg tgtccagccc ccggacccac tacctgatgc tgctgaagaa   9660
cggcaccgtg ctggaagtga ccgacgtggt ggtggacgcc accgacagca gactgctgat   9720
gatgagcgtg tacgccctga cgccatcat cggcatctac ctgctgtacc ggatgctgaa   9780
aacctgctga taatctagag gccctataa ctctctacgg ctaacctgaa tggactacga   9840
catagtctag tccgccaaga tgtgcagaag gcccgactgc ggcttcagct tcagccctgg   9900
acccgtgatc ctgctgtggt gctgcctgct gctgcctatc gtgtcctctg ccgccgtgtc   9960
tgtggcccct acagccgccg agaaggtgcc agccgagtgc cccgagctga ccagaagatg  10020
cctgctgggc gaggtgttcg agggcgacaa gtacgagagc tggctgcggc ccctggtcaa  10080
cgtgaccggc agagatggcc ccctgagcca gctgatccgg tacagacccg tgaccccga  10140 ggccgccaat agcgtgctgc tggacgaggc cttcctggat accctggccc tgctgtacaa  10200 caacccgac cagctgagag ccctgctgac cctgctgtcc agcgacaccg ccccagatg  10260 gatgaccgtg atgcggggct acagcgagtg tggagatggc agccctgccg tgtacacctg  10320
cgtggacgac ctgtgcagag gctacgacct gaccagactg agctacggcc ggtccatctt  10380
cacagagcac gtgctgggct tcgagctggt gccccccagc ctgttcaacg tggtggtggc  10440
catccggaac gaggccacca gaaccaacag agccgtgcgg ctgcctgtgt ctacagccgc  10500
tgcacctgag gcatcacac tgttctacgg cctgtacaac gccgtgaaag agttctgcct  10560
ccggcaccag ctggatcccc cctgctgag acacctggac aagtactacg ccggcctgcc  10620
cccagagctg aagcagacca gagtgaacct gcccgcccac agcagatatg gccctcaggc  10680
cgtggacgcc agatgataac gccggcggcc cctataactc tctacggcta acctgaatgg  10740
actacgacat agtctagtcc gccaagatga gccccaagga cctgacccc ttcctgacaa  10800 ccctgtggct gctcctgggc catagcagag tgcctagagt gcgggccgag gaatgctgcg  10860
agttcatcaa cgtgaaccac ccccccgagc ggtgctacga cttcaagatg tgcaaccggt  10920
```

-continued

```
tcaccgtggc cctgagatgc cccgacggcg aagtgtgcta cagccccgag aaaaccgccg  10980
agatccgggg catcgtgacc accatgaccc acagcctgac ccggcaggtg gtgcacaaca  11040
agctgaccag ctgcaactac aaccccctgt acctggaagc cgacggccgg atcagatgcg  11100
gcaaagtgaa cgacaaggcc cagtacctgc tgggagccgc cggaagcgtg ccctaccggt  11160
ggatcaacct ggaatacgac aagatcaccc ggatcgtggg cctggaccag tacctggaaa  11220
gcgtgaagaa gcacaagcgg ctggacgtgt gcagagccaa gatgggctac atgctgcagt  11280
gataaggcgc gccgccccta taactctcta cggctaacct gaatggacta cgacatagtc  11340
tagtccgcca agatgctgcg gctgctgctg agacaccact ccactgcct gctgctgtgt  11400
gccgtgtggg ccaccccttg tctggccagc ccttggagca ccctgaccgc caaccagaac  11460
cctagccccc cttggtccaa gctgacctac agcaagcccc acgacgccgc caccttctac  11520
tgcccctttc tgtaccccag ccctcccaga agcccctgc agttcagcgg cttcagaga  11580
gtgtccaccg ccctgagtg ccggaacgag acactgtacc tgctgtacaa ccgggagggc  11640
cagacactgg tggagcggag cagcacctgg gtgaaaaaag tgatctggta tctgagcggc  11700
cggaaccaga ccatcctgca gcggatgccc agaaccgcca gcaagcccag cgacggcaac  11760
gtgcagatca gcgtggagga cgccaaaatc ttcggagccc acatggtgcc caagcagacc  11820
aagctgctga gattcgtggt caacgacggc accagatatc agatgtgcgt gatgaagctg  11880
gaaagctggg cccacgtgtt ccgggactac tccgtgagct ccaggtccg gctgaccttc  11940
accgaggcca caaccagac ctacaccttc tgcacccacc ccaacctgat cgtgtgataa  12000
gcggccgcgc ccctataact ctctacggct aacctgaatg gactacgaca tagtctagtc  12060
cgccaagatg cggctgtgca gagtgtggct gtccgtgtgc ctgtgtgccg tggtgctggg  12120
ccagtgccag agagagacag ccgagaagaa cgactactac cgggtgcccc actactggga  12180
tgcctgcagc agagccctgc ccgaccagac ccggtacaaa tacgtggagc agctcgtgga  12240
cctgaccctg aactaccact acgacgccag ccacggcctg acaacttcg acgtgctgaa  12300
gcggatcaac gtgaccgagg tgtccctgct gatcagcgac ttccggcggc agaacagaag  12360
aggcggcacc aacaagcgga ccaccttcaa cgccgctggc tctctggccc ctcacgccag  12420
atccctggaa ttcagcgtgc ggctgttcgc caactgataa cgttgcatcc tgcaggatac  12480
agcagcaatt ggcaagctgc ttacatagaa ctcgcggcga ttggcatgcc gccttaaaat  12540
ttttatttta tttttctttt cttttccgaa tcggattttg tttttaatat ttcaaaaaaa  12600
aaaaaaaaaa aaaaaaaaaa aaaaaaaagg gtcggcatgg catctccacc tcctcgcggt  12660
ccgacctggg catccgaagg aggacgcacg tccactcgga tggctaaggg agagccacgt  12720
ttaaacgcta gagcaagacg tttccgttg aatatggctc ataacacccc ttgtattact  12780
gtttatgtaa gcagacagtt ttattgttca tgatgatata tttttatctt gtgcaatgta  12840
acatcagaga ttttgagaca caacgtggct ttgttgaata atcgaactt ttgctgagtt  12900
gaaggatcag atcacgcatc ttcccgacaa cgcagaccgt tccgtggcaa agcaaaagtt  12960
caaaatcacc aactggtcca cctacaacaa agctctcatc aaccgtggct ccctcacttt  13020
ctggctggat gatggggcga ttcaggcctg gtatgagtca gcaacaccttc ttcacgagg  13080
cagacctcag cgctagcgga gtgtatactg gcttactatg ttggcactga tgagggtgtc  13140
agtgaagtgc ttcatgtggc aggagaaaaa aggctgcacc ggtgcgtcag cagaatatgt  13200
gatacaggat atattccgct tcctcgctca ctgactcgct acgctcggtc gttcgactgc  13260
ggcgagcgga aatggcttac gaacggggcg gagatttcct ggaagatgcc aggaagatac  13320
```

```
ttaacaggga agtgagaggg ccgcggcaaa gccgttttc cataggctcc gcccctga    13380
caagcatcac gaaatctgac gctcaaatca gtggtggcga aacccgacag gactataaag  13440
ataccaggcg tttcccctgg cggctccctc gtgcgctctc ctgttcctgc ctttcggttt  13500
accggtgtca ttccgctgtt atggccgcgt ttgtctcatt ccacgcctga cactcagttc  13560
cgggtaggca gttcgctcca agctggactg tatgcacgaa ccccccgttc agtccgaccg  13620
ctgcgcctta tccggtaact atcgtcttga gtccaacccg aaagacatg caaaagcacc    13680
actggcagca gccactggta attgatttag aggagttagt cttgaagtca tgcgccggtt  13740
aaggctaaac tgaaaggaca agttttggtg actgcgctcc tccaagccag ttacctcggt  13800
tcaaagagtt ggtagctcag agaaccttcg aaaaaccgcc ctgcaaggcg gttttttcgt  13860
tttcagagca agagattacg cgcagaccaa aacgatctca agaagatcat cttattaagg  13920
ggtctgacgc tcagtggaac gaaaactcac gttaagggat tttggtcatg agattatcaa  13980
aaaggatctt caccctagatc ctttaaatt aaaaatgaag ttttaaatca atctaaagta  14040
tatatgagta aacttggtct gacagttatt agaaaaattc atccagcaga cgataaaacg  14100
caatacgctg gctatccggt gccgcaatgc catacagcac cagaaaacga tccgcccatt  14160
cgccgcccag ttcttccgca atatcacggg tggccagcgc aatatcctga taacgatccg  14220
ccacgcccag acgccgcaa tcaataaagc cgctaaaacg gccatttcc accataatgt  14280
tcggcaggca cgcatcacca tgggtcacca ccagatcttc gccatccggc atgctcgctt  14340
tcagacgcgc aaacagctct gccggtgcca ggccctgatg ttcttcatcc agatcatcct  14400
gatccaccag gcccgcttcc atacgggtac gcgcacgttc aatacgatgt ttcgcctgat  14460
gatcaaacgg acaggtcgcc gggtccaggg tatgcagacg acgcatggca tccgccataa  14520
tgctcacttt ttctgccggc gccagatggc tagacagcag atcctgaccc ggcacttcgc  14580
ccagcagcag ccaatcacgg cccgcttcgg tcaccacatc cagcaccgcc gcacacggaa  14640
caccggtggt ggccagccag ctcagacgcg ccgcttcatc ctgcagctcg ttcagcgcac  14700
cgctcagatc ggttttcaca aacagcaccg gacgaccctg cgcgctcaga cgaaacaccg  14760
ccgcatcaga gcagccaatg gtctgctgcg cccaatcata gccaaacaga cgttccaccc  14820
acgctgccgg gctacccgca tgcaggccat cctgttcaat catactcttc cttttcaat  14880
attattgaag catttatcag ggttattgtc tcatgagcgg atacatattt gaatgtattt  14940
agaaaaataa acaaataggg gttccgcgca catttccccg aaagtgccac cctaaattgt   15000
aagcgttaat attttgttaa aattcgcgtt aaattttgt taaatcagct catttttaa     15060
ccaataggcc gaaatcggca aaatccctta taatcaaaa gaatagaccg atagggtt     15120
gagtggccgc tacagggcgc tcccattcgc cattcaggct gcgcaactgt tgggaagggc  15180
gtttcggtgc gggcctcttc gctattacgc cagctggcga aggggggatg tgctgcaagg  15240
cgattaagtt gggtaacgcc agggttttcc cagtcacacg cgtaatacga ctcactatag  15300
```

<210> SEQ ID NO 14
<211> LENGTH: 16324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg acaagaaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctctttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg aagccgatg     1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctcoct tccatgaatt cgcctacgag agtctgagaa    2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaagggctg acgtcaatg     2340
ccagaactgt ggactcagtg ctcttgaatg gatgcaaaca ccccgtagag accctgtata    2400
```

```
ttgacgaagc ttttgcttgt catgcaggta ctctcagagc gctcatagcc attataagac    2460
ctaaaaaggc agtgctctgc ggggatccca aacagtgcgg ttttttttaac atgatgtgcc    2520 tgaaagtgca ttttaaccac gagatttgca cacaagtctt ccacaaaagc atctctcgcc    2580
gttgcactaa atctgtgact tcggtcgtct caaccttgtt ttacgacaaa aaatgagaa    2640 cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct ggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggaccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacatta tacaggttcc agactccacg    4020
aagccggatg tgcaccctca tatcatgtgg tgcgagggga tattgccacg gccaccgaag    4080
gagtgattat aaatgctgct aacagcaaag acaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatga caaaactttc tcatatttgg aagggaccaa gttccaccag gcggccaagg    4680
atatagcaga aattaatgcc atgtggcccg ttgcaacgga ggccaatgag caggtatgca    4740
```

```
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta aacgcctga gccgatcatc atcgaagagg    5160
aagaaggaga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttacccg tcacgcactc     5580 ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gcttttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg aatgttcct cacactgttt gtgaacacag    7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
```

-continued

```
acaggtgcgc cacctggttg aatatggaag tcaagattat agatgctgtg gtgggcgaga      7200
aagcgcctta tttctgtgga gggtttattt tgtgtgactc cgtgaccggc acagcgtgcc      7260
gtgtggcaga cccctaaaa aggctgttta agcttggcaa acctctggca gcagacgatg       7320
aacatgatga tgacaggaga agggcattgc atgaagagtc aacacgctgg aaccgagtgg      7380
gtattctttc agagctgtgc aaggcagtag aatcaaggta tgaaaccgta ggaacttcca      7440
tcatagttat ggccatgact actctagcta gcagtgttaa atcattcagc tacctgagag      7500
gggcccctat aactctctac ggctaacctg aatggactac gacatagtct agtccgccaa      7560
gatgaggcct ggcctgccct cctacctgat catcctggcc gtgtgcctgt tcagccacct      7620
gctgtccagc agatacggcg ccgaggccgt gagcgagccc ctggacaagg ctttccacct      7680
gctgctgaac acctacggca gacccatccg gtttctgcgg gagaacacca cccagtgcac      7740
ctacaacagc agcctgcgga acagcaccgt cgtgagagag aacgccatca gcttcaactt      7800
tttccagagc tacaaccagt actacgtgtt ccacatgccc agatgcctgt ttgccggccc      7860
tctggccgag cagttcctga accaggtgga cctgaccgag acactggaaa gataccagca      7920
gcggctgaat acctacgccc tggtgtccaa ggacctggcc agctaccggt cctttagcca      7980
gcagctcaag gctcaggata gcctcggcga gcagcctacc accgtgcccc ctcccatcga      8040
cctgagcatc ccccacgtgt ggatgcctcc ccagaccacc cctcacggct ggaccgagag      8100
ccacaccacc tccggcctgc acagacccca cttcaaccag acctgcatcc tgttcgacgg      8160
ccacgacctg ctgtttagca ccgtgacccc ctgcctgcac cagggcttct acctgatcga      8220
cgagctgaga tacgtgaaga tcaccctgac cgaggatttc ttcgtggtca ccgtgtccat      8280
cgacgacgac accccccatgc tgctgatctt cggccacctg cccagagtgc tgttcaaggc      8340
cccctaccag cgggacaact tcatcctgcg gcagaccgag aagcacgagc tgctggtgct      8400
ggtcaagaag gaccagctga accggcactc ctacctgaag gaccccgact tcctggacgc      8460
cgccctggac ttcaactacc tggacctgag cgccctgctg agaaacagct ccacagata      8520 cgccgtggac gtgctgaagt ccggacggtg ccagatgctc gatcggcgga ccgtggagat      8580
ggccttcgcc tatgccctcg ccctgttcgc cgctgccaga caggaagagg ctggcgccca      8640
ggtgtcagtg cccagagccc tggatagaca ggccgccctg ctgcagatcc aggaattcat      8700
gatcacctgc ctgagccaga ccccccctag aaccaccctg ctgctgtacc ccacagccgt      8760
ggatctggcc aagagggccc tgtggacccc caaccagatc accgacatca agcctcgt       8820 gcggctcgtg tacatcctga gcaagcagaa ccagcagcac ctgatccccc agtgggccct      8880
gagacagatc gccgacttcg ccctgaagct gcacaagacc catctggcca gctttctgag      8940
cgccttcgcc aggcaggaac tgtacctgat gggcagcctg gtccacagca tgctggtgca      9000
taccaccgag cggcgggaga tcttcatcgt ggagacaggc ctgtgtagcc tggccgagct      9060
gtcccacttt acccagctgc tggcccaccc tcaccacgag tacctgagcg acctgtacac      9120
cccctgcagc agcagcggca gacgggacca cagcctggaa cggctgacca gactgttccc      9180
cgatgccacc gtgcctgcta cagtgcctgc cgccctgtcc atcctgtcca ccatgcagcc      9240
cagcaccctg gaaaccttcc ccgacctgtt ctgcctgccc ctgggcgaga gctttagcgc      9300
cctgaccgtg tccgagcacg tgtcctacat cgtgaccaat cagtacctga tcaagggcat      9360
cagctacccc gtgtccacca cagtcgtggg ccagagcctg atcatcaccc agaccgcacg      9420
ccagaccaag tgcgagctga cccggaacat gcacaccaca cacagcatca ccgtggccct      9480
```

```
gaacatcagc ctggaaaact gcgctttctg tcagtctgcc ctgctggaat acgacgatac    9540
ccagggcgtg atcaacatca tgtacatgca cgacagcgac gacgtgctgt tcgccctgga    9600
ccccctacaac gaggtggtgg tgtccagccc ccggacccac tacctgatgc tgctgaagaa   9660
cggcaccgtg ctggaagtga ccgacgtggt ggtggacgcc accgactgat aatctagagg    9720
cccctataac tctctacggc taacctgaat ggactacgac atagtctagt ccgccaagat    9780
gtgcagaagg cccgactgcg gcttcagctt cagccctgga cccgtgatcc tgctgtggtg    9840
ctgcctgctg ctgcctatcg tgtcctctgc cgccgtgtct gtggcccta cagccgccga     9900
gaaggtgcca gccgagtgcc ccgagctgac cagaagatgc ctgctgggcg aggtgttcga    9960
gggcgacaag tacgagagct ggctgcggcc cctggtcaac gtgaccggca gagatggccc   10020
cctgagccag ctgatccggt acagaccccgt gaccccccgag ccgccaata gcgtgctgct  10080
ggacgaggcc ttcctggata ccctggccct gctgtacaac aaccccgacc agctgagagc   10140
cctgctgacc ctgctgtcca cgacaccgc ccccagatgg atgaccgtga tgcgggcta     10200
cagcgagtgt ggagatggca gccctgccgt gtacacctgc gtggacgacc tgtgcagagg   10260
ctacgacctg accagactga gctacggccg gtccatcttc acagagcacg tgctgggctt   10320
cgagctggtg cccccccagcc tgttcaacgt ggtggtggcc atccggaacg aggccaccag  10380
aaccaacaga gccgtgcggc tgcctgtgtc tacagccgct gcacctgagg gcatcacact   10440
gttctacggc ctgtacaacg ccgtgaaaga gttctgcctc cggcaccagc tggatccccc   10500
cctgctgaga cacctggaca agtactacgc cggcctgccc ccagagctga agcagaccag   10560
agtgaacctg cccgcccaca gcagatatgg ccctcaggcc gtggacgcca gatgataacg   10620
ccggcggccc ctataactct ctacggctaa cctgaatgga ctacgacata gtctagtccg   10680
ccaagatgag ccccaaggac ctgaccccct tcctgacaac cctgtggctg ctcctgggcc   10740
atagcagagt gcctagagtg cgggccgagg aatgctgcga gttcatcaac gtgaaccacc   10800
cccccgagcg gtgctacgac ttcaagatgt gcaaccggtt caccgtggcc ctgagatgcc   10860
ccgacggcga agtgtgctac agccccgaga aaaccgccga gatccggggc atcgtgacca   10920
ccatgaccca cagcctgacc cggcaggtgg tgcacaacaa gctgaccagc tgcaactaca   10980
acccccctgta cctggaagcc gacggccgga tcagatgcgg caaagtgaac gacaaggccc  11040
agtacctgct gggagccgcc ggaagcgtgc cctaccggtg gatcaacctg gaatacgaca   11100
agatcacccg gatcgtgggc ctggaccagt acctggaaag cgtgaagaag cacaagcggc   11160
tggacgtgtg cagagccaag atgggctaca tgctgcagtg ataaggcgcg ccaacgttac   11220
tggccgaagc cgcttggaat aaggccggtg tgcgtttgtc tatatgttat tttccaccat   11280
attgccgtct tttggcaatg tgagggcccg gaaacctggc cctgtcttct tgacgagcat   11340
tcctaggggt cttttccctc tcgccaaagg aatgcaaggt ctgttgaatg tcgtgaagga   11400
agcagttcct ctggaagctt cttgaagaca acaacgtctg tagcgaccc tttgcaggca    11460
gcggaacccc ccacctggcg acaggtgcct ctgcggccaa aagccacgtg tataagatac   11520
acctgcaaag gcggcacaac cccagtgcca cgttgtgagt tggatagttg tggaaagagt   11580
caaatggctc tcctcaagcg tattcaacaa ggggctgaag gatgcccaga aggtacccca   11640
ttgtatggga tctgatctgg ggcctcggtg cacatgcttt acatgtgttt agtcgaggtt   11700
aaaaaaacgt ctaggccccc cgaaccacgg ggacgtggtt ttcctttgaa aaacacgata   11760
atatgctgcg gctgctgctg agacaccact tccactgcct gctgctgtgt gccgtgtggg   11820
ccaccccttg tctggccagc ccttggagca ccctgaccgc caaccagaac cctagccccc   11880
```

```
cttggtccaa gctgacctac agcaagcccc acgacgccgc caccttctac tgcccctttc    11940 tgtacccag ccctcccaga agccccctgc agttcagcgg cttccagaga gtgtccaccg     12000
gccctgagtg ccggaacgag acactgtacc tgctgtacaa ccgggagggc cagacactgg    12060
tggagcggag cagcacctgg gtgaaaaaag tgatctggta tctgagcggc cggaaccaga    12120
ccatcctgca gcggatgccc agaaccgcca gcaagcccag cgacggcaac gtgcagatca    12180
gcgtggagga cgccaaaatc ttcggagccc acatggtgcc caagcagacc aagctgctga    12240
gattcgtggt caacgacggc accagatatc agatgtgcgt gatgaagctg gaaagctggg    12300
cccacgtgtt ccgggactac tccgtgagct tccaggtccg gctgaccttc accgaggcca    12360
acaaccagac ctacaccttc tgcacccacc ccaacctgat cgtgtgataa gtacctttgt    12420
acgcctgttt tataccccct ccctgatttg caacttagaa gcaacgcaaa ccagatcaat    12480
agtaggtgtg acataccagt cgcatcttga tcaagcactt ctgtatcccc ggaccgagta    12540
tcaatagact gtgcacacgg ttgaaggaga aaacgtccgt tacccggcta actacttcga    12600
gaagcctagt aacgccattg aagttgcaga gtgtttcgct cagcactccc ccgtgtaga     12660 tcaggtcgat gagtcaccgc attccccacg ggcgaccgtg gcggtggctg cgttggcggc    12720
ctgcctatgg ggtaacccat aggacgctct aatacggaca tggcgtgaag agtctattga    12780
gctagttagt agtcctccgg cccctgaatg cggctaatcc taactgcgga gcacataccc    12840
ttaatccaaa gggcagtgtg tcgtaacggg caactctgca gcggaaccga ctactttggg    12900
tgtccgtgtt tcttttttatt cttgtattgg ctgcttatgg tgacaattaa agaattgtta   12960
ccatatagct attggattgg ccatccagtg tcaaacagag ctattgtata tctctttgtt    13020
ggattcacac ctctcactct tgaaacgtta cacaccctca attacattat actgctgaac    13080
acgaagcgca tatgcggctg tgcagagtgt ggctgtccgt gtgcctgtgt gccgtggtgc    13140
tgggccagtg ccagagagag acagccgaga agaacgacta ctaccgggtg ccccactact    13200
gggatgcctg cagcagagcc ctgcccgacc agacccggta caaatacgtg gagcagctcg    13260
tggacctgac cctgaactac cactacgacg ccagccacgg cctggacaac ttcgacgtgc    13320
tgaagcggat caacgtgacc gaggtgtccc tgctgatcag cgacttccgg cggcagaaca    13380
gaagaggcgg caccaacaag cggaccacct tcaacgccgc tggctctctg gcccctcacg    13440
ccagatccct ggaattcagc gtgcggctgt tcgccaactg ataacgttgc atcctgcagg    13500
atacagcagc aattggcaag ctgcttacat agaactcgcg gcgattggca tgccgcctta    13560 aaattttat tttatttttc ttttcttttc cgaatcggat tttgttttta atatttcaaa     13620 aaaaaaaaa aaaaaaaaa aaaaaaaaa aagggtcggc atggcatctc cacctcctcg      13680
cggtccgacc tgggcatccg aaggaggacg cacgtccact cggatggcta agggagagcc    13740
acgtttaaac gctagagcaa gacgtttccc gttgaatatg gctcataaca ccccttgtat    13800
tactgtttat gtaagcagac agtttttattg ttcatgatga tatatttta tcttgtgcaa   13860 tgtaacatca gagatttga gacacaacgt ggctttgttg aataaatcga acttttgctg     13920
agttgaagga tcagatcacg catcttcccg acaacgcaga ccgttccgtg gcaaagcaaa    13980
agttcaaaat caccaactgg tccacctaca acaaagctct catcaaccgt ggctccctca    14040
ctttctggct ggatgatggg gcgattcagg cctggtatga gtcagcaaca ccttcttcac    14100
gaggcagacc tcagcgctag cggagtgtat actggcttac tatgttggca ctgatgaggg    14160
tgtcagtgaa gtgcttcatg tggcaggaga aaaaaggctg caccggtgcg tcagcagaat    14220
```

```
atgtgataca ggatatattc cgcttcctcg ctcactgact cgctacgctc ggtcgttcga   14280
ctgcggcgag cggaaatggc ttacgaacgg ggcggagatt tcctggaaga tgccaggaag   14340
atacttaaca gggaagtgag agggccgcgg caaagccgtt tttccatagg ctccgccccc   14400
ctgacaagca tcacgaaatc tgacgctcaa atcagtggtg gcgaaacccg acaggactat   14460
aaagatacca ggcgtttccc ctggcggctc cctcgtgcgc tctcctgttc ctgcctttcg   14520
gtttaccggt gtcattccgc tgttatggcc gcgtttgtct cattccacgc ctgacactca   14580
gttccgggta ggcagttcgc tccaagctgg actgtatgca cgaaccccc gttcagtccg   14640
accgctgcgc cttatccggt aactatcgtc ttgagtccaa cccggaaaga catgcaaaag   14700
caccactggc agcagccact ggtaattgat ttagaggagt tagtcttgaa gtcatgcgcc   14760
ggttaaggct aaactgaaag acaagttttt ggtgactgcg ctcctccaag ccagttacct   14820
cggttcaaag agttggtagc tcagagaacc ttcgaaaaac cgccctgcaa ggcggttttt   14880
tcgttttcag agcaagagat tacgcgcaga ccaaaacgat ctcaagaaga tcatcttatt   14940
aaggggtctg acgctcagtg gaacgaaaac tcacgttaag ggattttggt catgagatta   15000
tcaaaaagga tcttcaccta gatccttta aattaaaaat gaagttttaa atcaatctaa   15060
agtatatatg agtaaacttg gtctgacagt tattagaaaa attcatccag cagacgataa   15120
aacgcaatac gctggctatc cggtgccgca atgccataca gcaccagaaa acgatccgcc   15180
cattcgccgc ccagttcttc cgcaatatca cgggtggcca cgcaatatc ctgataacga   15240
tccgccacgc ccagacggcc gcaatcaata aagccgctaa acggccatt ttccaccata   15300
atgttcggca ggcacgcatc accatgggtc accaccagat cttcgccatc cggcatgctc   15360
gctttcagac gcgcaaacag ctctgccggt gccaggccct gatgttcttc atccagatca   15420
tcctgatcca ccaggcccgc ttccatacgg gtacgcgcac gttcaatacg atgtttcgcc   15480
tgatgatcaa acggacaggt cgccgggtcc agggtatgca gacgacgcat ggcatccgcc   15540
ataatgctca cttttctgc cggcgccaga tggctagaca gcagatcctg acccggcact   15600
tcgcccagca gcagccaatc acggcccgct tcggtcacca catccagcac cgccgcacac   15660
ggaacaccgg tggtggccag ccagctcaga gcgccgctt catcctgcag ctcgttcagc   15720
gcaccgctca gatcggtttt cacaaacagc accggacgac cctgcgcgct cagacgaaac   15780
accgccgcat cagagcagcc aatggtctgc tgcgcccaat catagccaaa cagacgttcc   15840
acccacgctg ccgggctacc cgcatgcagg ccatcctgtt caatcatact cttccttttt   15900
caatattatt gaagcattta tcagggttat tgtctcatga gcggatacat atttgaatgt   15960
atttagaaaa ataaacaaat aggggttccg cgcacatttc cccgaaaagt gccacctaaa   16020
ttgtaagcgt taatattttg ttaaaattcg cgttaaattt ttgttaaatc agctcatttt   16080
ttaaccaata ggccgaaatc ggcaaaatcc cttataaatc aaaagaatag accgagatag   16140
ggttgagtgg ccgctacagg gcgctcccat tcgccattca ggctgcgcaa ctgttgggaa   16200
gggcgtttcg gtgcgggcct cttcgctatt acgccagctg gcgaaagggg gatgtgctgc   16260
aaggcgatta agttgggtaa cgccagggtt ttcccagtca cacgcgtaat acgactcact   16320
atag                                                                16324
```

<210> SEQ ID NO 15
<211> LENGTH: 16360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg acaagaaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg ataccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctcct tccatgaatt cgcctacgag agtctgagaa    2160
cacgaccagc cgctccttac caagtaccaa ccataggggt gtatggcgtg ccaggatcag    2220
```

-continued

```
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg     2340 ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca aacagtgcgg ttttttttaac atgatgtgcc   2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag tacctggga atttcactgc cacgatagag gagtggcaag     3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg ttgactggt     3600 tgtcagaccg gcctgaggct accttcagag ctcggctgga tttaggcatc ccaggtgatg    3660
tgcccaaata tgacataata tttgttaatg tgaggaccc  atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag acaacctgg cggaggggtg tgcggagcgc     4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
```

```
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccgc    5520
caggcgtgaa tagggtgatc actagagagg agctcgaggc gcttacccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gcttttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
```

```
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgaggcct ggcctgccct cctacctgat catcctggcc gtgtgcctgt tcagccacct    7620
gctgtccagc agatacggcg ccgaggccgt gagcgagccc ctggacaagg ctttccacct    7680
gctgctgaac acctacggca gacccatccg gtttctgcgg gagaacacca cccagtgcac    7740
ctacaacagc agcctgcgga acagcaccgt cgtgagagag aacgccatca gcttcaactt    7800
tttccagagc tacaaccagt actacgtgtt ccacatgccc agatgcctgt ttgccggccc    7860
tctggccgag cagttcctga accaggtgga cctgaccgag acactggaaa gataccagca    7920
gcggctgaat acctacgccc tggtgtccaa ggacctggcc agctaccggt cctttagcca    7980
gcagctcaag gctcaggata gcctcggcga gcagcctacc accgtgcccc ctcccatcga    8040
cctgagcatc ccccacgtgt ggatgcctcc ccagaccacc cctcacggct ggaccgagag    8100
ccacaccacc tccggcctgc acagacccca cttcaaccag acctgcatcc tgttcgacgg    8160
ccacgacctg ctgtttagca ccgtgacccc ctgcctgcac caggggcttct acctgatcga    8220
cgagctgaga tacgtgaaga tcaccctgac cgaggatttc ttcgtggtca ccgtgtccat    8280
cgacgacgac accccccatgc tgctgatctt cggccacctg cccagagtgc tgttcaaggc    8340
cccctaccag cgggacaact tcatcctgcg gcagaccgag aagcacgagc tgctggtgct    8400
ggtcaagaag gaccagctga accggcactc ctacctgaag gaccccgact tcctggacgc    8460
cgccctggac ttcaactacc tggacctgag cgccctgctg agaaacagct tccacagata    8520
cgccgtggac gtgctgaagt ccggacggtg ccagatgctc gatcggcgga ccgtggagat    8580
ggccttcgcc tatgccctcg ccctgttcgc cgctgccaga caggaagagg ctggcgccca    8640
ggtgtcagtg cccagagccc tggatagaca ggccgccctg ctgcagatcc aggaattcat    8700
gatcacctgc ctgagccaga cccccctag aaccaccctg ctgctgtacc ccacagccgt    8760
ggatctggcc aagagggccc tgtggacccc caaccagatc accgacatca caagcctcgt    8820
gcggctcgtg tacatcctga gcaagcagaa ccagcagcac ctgatccccc agtgggccct    8880
gagacagatc gccgacttcg ccctgaagct gcacaagacc catctggcca gctttctgag    8940
cgccttcgcc aggcaggaac tgtacctgat gggcagcctg gtccacagca tgctggtgca    9000
taccaccgag cggcgggaga tcttcatcgt ggagacaggc ctgtgtagcc tggccgagct    9060
gtcccacttt acccagctgc tggcccaccc tcaccgcgag tacctgagcg acctgtacac    9120
cccctgcagc agcagcggca acgggaccca cagcctggaa cggctgacca gactgttccc    9180
cgatgccacc gtgcctgcta cagtgcctgc cgccctgtcc atcctgtcca ccatgcagcc    9240
cagcaccctg gaaaccttcc ccgacctgtt ctgcctgccc ctgggcgaga gctttagcgc    9300
cctgaccgtg tccgagcacg tgtcctacat cgtgaccaat cagtacctga tcaagggcat    9360
```

```
cagctacccc gtgtccacca cagtcgtggg ccagagcctg atcatcaccc agaccgacag    9420
ccagaccaag tgcgagctga cccggaacat gcacaccaca cacagcatca ccgtggccct    9480
gaacatcagc ctggaaaact gcgctttctg tcagtctgcc ctgctggaat acgacgatac    9540
ccagggcgtg atcaacatca tgtacatgca cgacagcgac gacgtgctgt tcgccctgga    9600
cccctacaac gaggtggtgg tgtccagccc ccggacccac tacctgatgc tgctgaagaa    9660
cggcaccgtg ctgaagtgaa ccgacgtggt ggtggacgcc accgacggca gcggatctgg    9720
gtcccaccat caccatcacc attgataatc tagaggcccc tataactctc tacggctaac    9780
ctgaatggac tacgacatag tctagtccgc caagatgtgc agaaggcccg actgcggctt    9840
cagcttcagc cctggacccg tgatcctgct gtggtgctgc ctgctgctgc ctatcgtgtc    9900
ctctgccgcc gtgtctgtgg ccctacagc cgccgagaag gtgccagccg agtgccccga    9960
gctgaccaga agatgcctgc tgggcgaggt gttcgagggc gacaagtacg agagctggct   10020
gcggcccctg gtcaacgtga ccggcagaga tggcccctg agccagctga tccggtacag   10080
acccgtgacc cccgaggccg ccaatagcgt gctgctggac gaggccttcc tggatccct   10140
ggccctgctg tacaacaacc ccgaccagct gagagccctg ctgaccctgc tgtccagcga   10200
caccgccccc agatggatga ccgtgatgcg gggctacagc gagtgtggag atggcagccc   10260
tgccgtgtac acctgcgtgg acgacctgtg cagaggctac gacctgacca gactgagcta   10320
cggccggtcc atcttcacag agcacgtgct gggcttcgag ctggtgcccc cagcctgtt   10380
caacgtggtg gtggccatcc ggaacgaggc caccagaacc aacagagccg tgcggctgcc   10440
tgtgtctaca gccgctgcac ctgagggcat cacactgttc tacggcctgt acaacgccgt   10500
gaaagagttc tgcctccggc accagctgga tccccctg ctgagacacc tggacaagta   10560
ctacgccggc ctgcccccag agctgaagca gaccagagta acctgcccg cccacagcag   10620
atatggccct caggccgtgg acgccagatg ataacgccgg cggcccctat aactctctac   10680
ggctaacctg aatggactac gacatagtct agtccgccaa gatgagcccc aaggacctga   10740
ccccttcct gacaaccctg tggctgctcc tgggccatag cagagtgcct agagtgcggg   10800
ccgaggaatg ctgcgagttc atcaacgtga accacccccc cgagcggtgc tacgacttca   10860
agatgtgcaa ccggttcacc gtggccctga gatgccccga cggcgaagtg tgctacagcc   10920
ccgagaaaac cgccgagatc cggggcatcg tgaccaccat gacccacagc ctgacccggc   10980
aggtggtgca caacaagctg accagctgca actacaaccc cctgtacctg aagccgacg   11040
gccggatcag atgcggcaaa gtgaacgaca aggcccagta cctgctggga ccgccgaa   11100
gcgtgcccta ccggtggatc aacctggaat acgacaagat cacccggatc gtgggcctgg   11160
accagtacct ggaaagcgtg aagaagcaca agcggctgga cgtgtgcaga gccaagatgg   11220
gctacatgct gcagtgataa ggcgcgccaa cgttactggc cgaagccgct tggaataagg   11280
ccggtgtgcg tttgtctata tgttattttc caccatattg ccgtcttttg gcaatgtgag   11340
ggcccggaaa cctggccctg tcttcttgac gagcattcct aggggtcttt cccctctcgc   11400
caaaggaatg caaggtctgt tgaatgtcgt gaaggaagca gttcctctgg aagcttcttg   11460
aagacaaaca acgtctgtag cgaccctttg caggcagcgg aaccccccac ctggcgacag   11520
gtgcctctgc ggccaaaagc cacgtgtata agatacacct gcaaaggcgg cacaacccca   11580
gtgccacgtt gtgagttgga tagttgtgga aagagtcaaa tggctctcct caagcgtatt   11640
caacaagggg ctgaaggatg cccagaaggt accccattgt atgggatctg atctgggcc   11700
```

```
tcggtgcaca tgctttacat gtgtttagtc gaggttaaaa aaacgtctag gccccccgaa   11760
ccacggggac gtggttttcc tttgaaaaac acgataatat gctgcggctg ctgctgagac   11820
accacttcca ctgcctgctg ctgtgtgccg tgtgggccac cccttgtctg gccagccctt   11880
ggagcaccct gaccgccaac cagaacccta gcccccttg gtccaagctg acctacagca    11940
agccccacga cgccgccacc ttctactgcc cctttctgta ccccagccct cccagaagcc   12000
ccctgcagtt cagcggcttc cagagagtgt ccaccggccc tgagtgccgg aacgagacac   12060
tgtacctgct gtacaaccgg gagggccaga cactggtgga gcggagcagc acctgggtga   12120
aaaaagtgat ctggtatctg agcggccgga accagaccat cctgcagcgg atgcccagaa   12180
ccgccagcaa gcccagcgac ggcaacgtgc agatcagcgt ggaggacgcc aaaatcttcg   12240
gagcccacat ggtgcccaag cagaccaagc tgctgagatt cgtggtcaac gacggcacca   12300
gatatcagat gtgcgtgatg aagctggaaa gctgggccca cgtgttccgg gactactccg   12360
tgagcttcca ggtccggctg accttcaccg aggccaacaa ccagacctac accttctgca   12420
cccaccccaa cctgatcgtg tgataagtac ctttgtacgc ctgttttata cccctccct    12480 gatttgcaac ttagaagcaa cgcaaaccag atcaatagta ggtgtgacat accagtcgca   12540
tcttgatcaa gcacttctgt atccccggac cgagtatcaa tagactgtgc acacggttga   12600
aggagaaaac gtccgttacc cggctaacta cttcgagaag cctagtaacg ccattgaagt   12660
tgcagagtgt ttcgctcagc actcccccg tgtagatcag gtcgatgagt caccgcattc    12720
cccacgggcg accgtggcgg tggctgcgtt ggcggcctgc ctatggggta acccatagga   12780
cgctctaata cggacatggc gtgaagagtc tattgagcta gttagtagtc ctccggcccc   12840
tgaatgcggc taatcctaac tgcggagcac atacccttaa tccaaagggc agtgtgtcgt   12900
aacgggcaac tctgcagcgg aaccgactac tttgggtgtc cgtgtttctt tttattcttg   12960
tattggctgc ttatggtgac aattaaagaa ttgttaccat atagctattg gattggccat   13020
ccagtgtcaa acagagctat tgtatatctc tttgttggat tcacacctct cactcttgaa   13080
acgttacaca ccctcaatta cattatactg ctgaacacga agcgcatatg cggctgtgca   13140
gagtgtggct gtccgtgtgc ctgtgtgccg tggtgctggg ccagtgccag agagagacag   13200
ccgagaagaa cgactactac cgggtgcccc actactggga tgcctgcagc agagccctgc   13260
ccgaccagac ccgtacaaa tacgtggagc agctcgtgga cctgaccctg aactaccact    13320
acgacgccag ccacggcctg gacaacttcg acgtgctgaa gcggatcaac gtgaccgagg   13380
tgtccctgct gatcagcgac ttccggcgg agaacagaag aggcggcacc aacaagcgga    13440
ccaccttcaa cgccgctggc tctctggccc ctcacgccag atccctggaa ttcagcgtgc   13500
ggctgttcgc caactgataa cgttgcatcc tgcaggatac agcagcaatt ggcaagctgc   13560
ttacatagaa ctcgcggcga ttggcatgcc gccttaaaat ttttattta tttttctttt    13620 cttttccgaa tcggattttg ttttaatat tcaaaaaaa aaaaaaaaa aaaaaaaaa       13680 aaaaaaaagg gtcggcatgg catctccacc tcctcgcggt ccgacctggg catccgaagg   13740
aggacgcacg tccactcgga tggctaaggg agagccacgt ttaaacgcta gagcaagacg   13800
tttcccgttg aatatggctc ataacacccc ttgtattact gttatgtaa gcagacagtt    13860 ttattgttca tgatgatata ttttatctt gtgcaatgta acatcagaga ttttgagaca    13920
caacgtggct tgttgaata aatcgaactt ttgctgagtt gaaggatcag atcacgcatc    13980
ttcccgacaa cgcagaccgt tccgtggcaa agcaaaagtt caaatcacc aactggtcca    14040 cctacaacaa agctctcatc aaccgtggct ccctcacttt ctggctggat gatggggcga   14100
```

```
ttcaggcctg gtatgagtca gcaacacctt cttcacgagg cagacctcag cgctagcgga   14160
gtgtatactg gcttactatg ttggcactga tgagggtgtc agtgaagtgc ttcatgtggc   14220
aggagaaaaa aggctgcacc ggtgcgtcag cagaatatgt gatacaggat atattccgct   14280
tcctcgctca ctgactcgct acgctcggtc gttcgactgc ggcgagcgga aatggcttac   14340
gaacggggcg gagatttcct ggaagatgcc aggaagatac ttaacaggga agtgagaggg   14400
ccgcggcaaa gccgttttc cataggctcc gccccctga caagcatcac gaaatctgac    14460
gctcaaatca gtggtggcga aacccgacag gactataaag ataccaggcg tttccctgg    14520
cggctccctc gtgcgctctc ctgttcctgc ctttcggttt accggtgtca ttccgctgtt   14580
atggccgcgt ttgtctcatt ccacgcctga cactcagttc cgggtaggca gttcgctcca   14640
agctggactg tatgcacgaa ccccccgttc agtccgaccg ctgcgcctta tccggtaact   14700
atcgtcttga gtccaacccg gaaagacatg caaaagcacc actggcagca gccactggta   14760
attgatttag aggagttagt cttgaagtca tgcgccggtt aaggctaaac tgaaaggaca   14820
agttttggtg actgcgctcc tccaagccag ttacctcggt tcaaagagtt ggtagctcag   14880
agaaccttcg aaaaaccgcc ctgcaaggcg gttttttcgt tttcagagca agagattacg   14940
cgcagaccaa aacgatctca agaagatcat cttattaagg ggtctgacgc tcagtggaac   15000
gaaaactcac gttaagggat tttggtcatg agattatcaa aaaggatctt cacctagatc   15060
cttttaaatt aaaaatgaag ttttaaatca atctaaagta tatatgagta aacttggtct   15120
gacagttatt agaaaaattc atccagcaga cgataaaacg caatacgctg gctatccggt   15180
gccgcaatgc catacagcac cagaaaacga tccgcccatt cgccgcccag ttcttccgca   15240
atatcacggg tggccagcgc aatatcctga taacgatccg ccacgccag acggccgcaa   15300
tcaataaagc cgctaaaacg gccatttttcc accataatgt tcggcaggca cgcatcacca   15360
tgggtcacca ccagatcttc gccatccggc atgctcgctt tcagacgcgc aaacagctct   15420
gccggtgcca ggccctgatg ttcttcatcc agatcatcct gatccaccag gcccgcttcc   15480
atacgggtac gcgcacgttc aatacgatgt ttcgcctgat gatcaaacgg acaggtcgcc   15540
gggtccaggg tatgcagacg acgcatggca tccgccataa tgctcacttt ttctgccggc   15600
gccagatggc tagacagcag atcctgaccc ggcacttcgc ccagcagcag ccaatcacgg   15660
cccgcttcgg tcaccacatc cagcaccgcc gcacacggaa caccggtggt ggccagccag   15720
ctcagacgcg ccgcttcatc ctgcagctcg ttcagcgcac cgctcagatc ggttttcaca   15780
aacagcaccg gacgaccctg cgcgctcaga cgaaacaccg ccgcatcaga gcagccaatg   15840
gtctgctgcg cccaatcata gccaaacaga cgttccaccc acgctgccgg gctacccgca   15900
tgcaggccat cctgttcaat catactcttc ctttttcaat attattgaag catttatcag   15960
ggttattgtc tcatgagcgg atacatattt gaatgtattt agaaaaataa acaaataggg   16020
gttccgcgca catttccccg aaaagtgcca cctaaattgt aagcgttaat attttgttaa   16080
aattcgcgtt aaattttgt taaatcagct cattttttaa ccaataggcc gaaatcggca    16140
aaatccctta taaatcaaaa gaatagaccg agatagggtt gagtggccgc tacagggcgc   16200
tcccattcgc cattcaggct gcgcaactgt tgggaagggc gtttcggtgc gggcctcttc   16260
gctattacgc cagctggcga aagggggatg tgctgcaagg cgattaagtt gggtaacgcc   16320
agggttttcc cagtcacacg cgtaatacga ctcactatag                        16360
```

<210> SEQ ID NO 16

<211> LENGTH: 868
<212> TYPE: PRT
<213> ORGANISM: Varicella zoster virus

<400> SEQUENCE: 16

```
Met Phe Val Thr Ala Val Val Ser Val Ser Pro Ser Ser Phe Tyr Glu
1               5                   10                  15

Ser Leu Gln Val Glu Pro Thr Gln Ser Glu Asp Ile Thr Arg Ser Ala
            20                  25                  30

His Leu Gly Asp Gly Asp Glu Ile Arg Glu Ala Ile His Lys Ser Gln
        35                  40                  45

Asp Ala Glu Thr Lys Pro Thr Phe Tyr Val Cys Pro Pro Pro Thr Gly
    50                  55                  60

Ser Thr Ile Val Arg Leu Glu Pro Pro Arg Thr Cys Pro Asp Tyr His
65                  70                  75                  80

Leu Gly Lys Asn Phe Thr Glu Gly Ile Ala Val Val Tyr Lys Glu Asn
                85                  90                  95

Ile Ala Ala Tyr Lys Phe Lys Ala Thr Val Tyr Tyr Lys Asp Val Ile
            100                 105                 110

Val Ser Thr Ala Trp Ala Gly Ser Ser Tyr Thr Gln Ile Thr Asn Arg
        115                 120                 125

Tyr Ala Asp Arg Val Pro Ile Pro Val Ser Glu Ile Thr Asp Thr Ile
    130                 135                 140

Asp Lys Phe Gly Lys Cys Ser Ser Lys Ala Thr Tyr Val Arg Asn Asn
145                 150                 155                 160

His Lys Val Glu Ala Phe Asn Glu Asp Lys Asn Pro Gln Asp Met Pro
                165                 170                 175

Leu Ile Ala Ser Lys Tyr Asn Ser Val Gly Ser Lys Ala Trp His Thr
            180                 185                 190

Thr Asn Asp Thr Tyr Met Val Ala Gly Thr Pro Gly Thr Tyr Arg Thr
        195                 200                 205

Gly Thr Ser Val Asn Cys Ile Ile Glu Glu Val Glu Ala Arg Ser Ile
    210                 215                 220

Phe Pro Tyr Asp Ser Phe Gly Leu Ser Thr Gly Asp Ile Ile Tyr Met
225                 230                 235                 240

Ser Pro Phe Phe Gly Leu Arg Asp Gly Ala Tyr Arg Glu His Ser Asn
                245                 250                 255

Tyr Ala Met Asp Arg Phe His Gln Phe Glu Gly Tyr Arg Gln Arg Asp
            260                 265                 270

Leu Asp Thr Arg Ala Leu Leu Glu Pro Ala Ala Arg Asn Phe Leu Val
        275                 280                 285

Thr Pro His Leu Thr Val Gly Trp Asn Trp Lys Pro Lys Arg Thr Glu
    290                 295                 300

Val Cys Ser Leu Val Lys Trp Arg Glu Val Glu Asp Val Val Arg Asp
305                 310                 315                 320

Glu Tyr Ala His Asn Phe Arg Phe Thr Met Lys Thr Leu Ser Thr Thr
                325                 330                 335

Phe Ile Ser Glu Thr Asn Glu Phe Asn Leu Asn Gln Ile His Leu Ser
            340                 345                 350

Gln Cys Val Lys Glu Glu Ala Arg Ala Ile Ile Asn Arg Ile Tyr Thr
        355                 360                 365

Thr Arg Tyr Asn Ser Ser His Val Arg Thr Gly Asp Ile Gln Thr Tyr
    370                 375                 380

Leu Ala Arg Gly Gly Phe Val Val Val Phe Gln Pro Leu Leu Ser Asn
```

```
              385                 390                 395                 400
        Ser Leu Ala Arg Leu Tyr Leu Gln Glu Leu Val Arg Glu Asn Thr Asn
                        405                 410                 415

His Ser Pro Gln Lys His Pro Thr Arg Asn Thr Arg Ser Arg Arg Ser
                        420                 425                 430

Val Pro Val Glu Leu Arg Ala Asn Arg Thr Ile Thr Thr Ser Ser
                        435                 440                 445

Val Glu Phe Ala Met Leu Gln Phe Thr Tyr Asp His Ile Gln Glu His
        450                 455                 460

Val Asn Glu Met Leu Ala Arg Ile Ser Ser Trp Cys Gln Leu Gln
        465                 470                 475                 480

Asn Arg Glu Arg Ala Leu Trp Ser Gly Leu Phe Pro Ile Asn Pro Ser
                        485                 490                 495

Ala Leu Ala Ser Thr Ile Leu Asp Gln Arg Val Lys Ala Arg Ile Leu
                        500                 505                 510

Gly Asp Val Ile Ser Val Ser Asn Cys Pro Glu Leu Gly Ser Asp Thr
                        515                 520                 525

Arg Ile Ile Leu Gln Asn Ser Met Arg Val Ser Gly Ser Thr Thr Arg
                        530                 535                 540

Cys Tyr Ser Arg Pro Leu Ile Ser Ile Val Ser Leu Asn Gly Ser Gly
        545                 550                 555                 560

Thr Val Glu Gly Gln Leu Gly Thr Asp Asn Glu Leu Ile Met Ser Arg
                        565                 570                 575

Asp Leu Leu Glu Pro Cys Val Ala Asn His Lys Arg Tyr Phe Leu Phe
                        580                 585                 590

Gly His His Tyr Val Tyr Tyr Glu Asp Tyr Arg Tyr Val Arg Glu Ile
                        595                 600                 605

Ala Val His Asp Val Gly Met Ile Ser Thr Tyr Val Asp Leu Asn Leu
                        610                 615                 620

Thr Leu Leu Lys Asp Arg Glu Phe Met Pro Leu Gln Val Tyr Thr Arg
        625                 630                 635                 640

Asp Glu Leu Arg Asp Thr Gly Leu Leu Asp Tyr Ser Glu Ile Gln Arg
                        645                 650                 655

Arg Asn Gln Met His Ser Leu Arg Phe Tyr Asp Ile Asp Lys Val Val
                        660                 665                 670

Gln Tyr Asp Ser Gly Thr Ala Ile Met Gln Gly Met Ala Gln Phe Phe
                        675                 680                 685

Gln Gly Leu Gly Thr Ala Gly Gln Ala Val Gly His Val Val Leu Gly
                        690                 695                 700

Ala Thr Gly Ala Leu Leu Ser Thr Val His Gly Phe Thr Thr Phe Leu
        705                 710                 715                 720

Ser Asn Pro Phe Gly Ala Leu Ala Val Gly Leu Leu Val Leu Ala Gly
                        725                 730                 735

Leu Val Ala Ala Phe Phe Ala Tyr Arg Tyr Val Leu Lys Leu Lys Thr
                        740                 745                 750

Ser Pro Met Lys Ala Leu Tyr Pro Leu Thr Thr Lys Gly Leu Lys Gln
                        755                 760                 765

Leu Pro Glu Gly Met Asp Pro Phe Ala Glu Lys Pro Asn Ala Thr Asp
                        770                 775                 780

Thr Pro Ile Glu Glu Ile Gly Asp Ser Gln Asn Thr Glu Pro Ser Val
        785                 790                 795                 800

Asn Ser Gly Phe Asp Pro Asp Lys Phe Arg Glu Ala Gln Glu Met Ile
                        805                 810                 815
```

```
Lys Tyr Met Thr Leu Val Ser Ala Ala Glu Arg Gln Glu Ser Lys Ala
            820                 825                 830

Arg Lys Lys Asn Lys Thr Ser Ala Leu Leu Thr Ser Arg Leu Thr Gly
        835                 840                 845

Leu Ala Leu Arg Asn Arg Arg Gly Tyr Ser Arg Val Arg Thr Glu Asn
    850                 855                 860

Val Thr Gly Val
865

<210> SEQ ID NO 17
<211> LENGTH: 841
<212> TYPE: PRT
<213> ORGANISM: Varicella zoster virus

<400> SEQUENCE: 17

Met Phe Ala Leu Val Leu Ala Val Val Ile Leu Pro Leu Trp Thr Thr
1               5                   10                  15

Ala Asn Lys Ser Tyr Val Thr Pro Thr Pro Ala Thr Arg Ser Ile Gly
            20                  25                  30

His Met Ser Ala Leu Leu Arg Glu Tyr Ser Asp Arg Asn Met Ser Leu
        35                  40                  45

Lys Leu Glu Ala Phe Tyr Pro Thr Gly Phe Asp Glu Glu Leu Ile Lys
    50                  55                  60

Ser Leu His Trp Gly Asn Asp Arg Lys His Val Phe Leu Val Ile Val
65                  70                  75                  80

Lys Val Asn Pro Thr Thr His Glu Gly Asp Val Gly Leu Val Ile Phe
                85                  90                  95

Pro Lys Tyr Leu Leu Ser Pro Tyr His Phe Lys Ala Glu His Arg Ala
            100                 105                 110

Pro Phe Pro Ala Gly Arg Phe Gly Phe Leu Ser His Pro Val Thr Pro
        115                 120                 125

Asp Val Ser Phe Phe Asp Ser Ser Phe Ala Pro Tyr Leu Thr Thr Gln
    130                 135                 140

His Leu Val Ala Phe Thr Thr Phe Pro Pro Asn Pro Leu Val Trp His
145                 150                 155                 160

Leu Glu Arg Ala Glu Thr Ala Ala Thr Ala Glu Arg Pro Phe Gly Val
                165                 170                 175

Ser Leu Leu Pro Ala Arg Pro Thr Val Pro Lys Asn Thr Ile Leu Glu
            180                 185                 190

His Lys Ala His Phe Ala Thr Trp Asp Ala Leu Ala Arg His Thr Phe
        195                 200                 205

Phe Ser Ala Glu Ala Ile Ile Thr Asn Ser Thr Leu Arg Ile His Val
    210                 215                 220

Pro Leu Phe Gly Ser Val Trp Pro Ile Arg Tyr Trp Ala Thr Gly Ser
225                 230                 235                 240

Val Leu Leu Thr Ser Asp Ser Gly Arg Val Glu Val Asn Ile Gly Val
                245                 250                 255

Gly Phe Met Ser Ser Leu Ile Ser Leu Ser Ser Gly Leu Pro Ile Glu
            260                 265                 270

Leu Ile Val Val Pro His Thr Val Lys Leu Asn Ala Val Thr Ser Asp
        275                 280                 285

Thr Thr Trp Phe Gln Leu Asn Pro Pro Gly Pro Asp Pro Gly Pro Ser
    290                 295                 300

Tyr Arg Val Tyr Leu Leu Gly Arg Gly Leu Asp Met Asn Phe Ser Lys
```

```
             305                 310                 315                 320
        His Ala Thr Val Asp Ile Cys Ala Tyr Pro Glu Glu Ser Leu Asp Tyr
                        325                 330                 335
        Arg Tyr His Leu Ser Met Ala His Thr Glu Ala Leu Arg Met Thr Thr
                        340                 345                 350
        Lys Ala Asp Gln His Asp Ile Asn Glu Glu Ser Tyr Tyr His Ile Ala
                        355                 360                 365
        Ala Arg Ile Ala Thr Ser Ile Phe Ala Leu Ser Glu Met Gly Arg Thr
                        370                 375                 380
        Thr Glu Tyr Phe Leu Leu Asp Glu Ile Val Asp Val Gln Tyr Gln Leu
        385                 390                 395                 400
        Lys Phe Leu Asn Tyr Ile Leu Met Arg Ile Gly Ala Gly Ala His Pro
                        405                 410                 415
        Asn Thr Ile Ser Gly Thr Ser Asp Leu Ile Phe Ala Asp Pro Ser Gln
                        420                 425                 430
        Leu His Asp Glu Leu Ser Leu Leu Phe Gly Gln Val Lys Pro Ala Asn
                        435                 440                 445
        Val Asp Tyr Phe Ile Ser Tyr Asp Glu Ala Arg Asp Gln Leu Lys Thr
                        450                 455                 460
        Ala Tyr Ala Leu Ser Arg Gly Gln Asp His Val Asn Ala Leu Ser Leu
        465                 470                 475                 480
        Ala Arg Arg Val Ile Met Ser Ile Tyr Lys Gly Leu Leu Val Lys Gln
                        485                 490                 495
        Asn Leu Asn Ala Thr Glu Arg Gln Ala Leu Phe Phe Ala Ser Met Ile
                        500                 505                 510
        Leu Leu Asn Phe Arg Glu Gly Leu Glu Asn Ser Ser Arg Val Leu Asp
                        515                 520                 525
        Gly Arg Thr Thr Leu Leu Met Thr Ser Met Cys Thr Ala Ala His
                        530                 535                 540
        Ala Thr Gln Ala Ala Leu Asn Ile Gln Glu Gly Leu Ala Tyr Leu Asn
        545                 550                 555                 560
        Pro Ser Lys His Met Phe Thr Ile Pro Asn Val Tyr Ser Pro Cys Met
                        565                 570                 575
        Gly Ser Leu Arg Thr Asp Leu Thr Glu Glu Ile His Val Met Asn Leu
                        580                 585                 590
        Leu Ser Ala Ile Pro Thr Arg Pro Gly Leu Asn Glu Val Leu His Thr
                        595                 600                 605
        Gln Leu Asp Glu Ser Glu Ile Phe Asp Ala Ala Phe Lys Thr Met Met
                        610                 615                 620
        Ile Phe Thr Thr Trp Thr Ala Lys Asp Leu His Ile Leu His Thr His
        625                 630                 635                 640
        Val Pro Glu Val Phe Thr Cys Gln Asp Ala Ala Arg Asn Gly Glu
                        645                 650                 655
        Tyr Val Leu Ile Leu Pro Ala Val Gln Gly His Ser Tyr Val Ile Thr
                        660                 665                 670
        Arg Asn Lys Pro Gln Arg Gly Leu Val Tyr Ser Leu Ala Asp Val Asp
                        675                 680                 685
        Val Tyr Asn Pro Ile Ser Val Tyr Leu Ser Lys Asp Thr Cys Val
                        690                 695                 700
        Ser Glu His Gly Val Ile Glu Thr Val Ala Leu Pro His Pro Asp Asn
        705                 710                 715                 720
        Leu Lys Glu Cys Leu Tyr Cys Gly Ser Val Phe Leu Arg Tyr Leu Thr
                        725                 730                 735
```

```
Thr Gly Ala Ile Met Asp Ile Ile Ile Asp Ser Lys Asp Thr Glu
            740                 745                 750

Arg Gln Leu Ala Ala Met Gly Asn Ser Thr Ile Pro Pro Phe Asn Pro
        755                 760                 765

Asp Met His Gly Asp Ser Lys Ala Val Leu Leu Phe Pro Asn Gly
        770                 775                 780

Thr Val Val Thr Leu Leu Gly Phe Glu Arg Arg Gln Ala Ile Arg Met
785                 790                 795                 800

Ser Gly Gln Tyr Leu Gly Ala Ser Leu Gly Gly Ala Phe Leu Ala Val
                805                 810                 815

Val Gly Phe Gly Ile Ile Gly Trp Met Leu Cys Gly Asn Ser Arg Leu
                820                 825                 830

Arg Glu Tyr Asn Lys Ile Pro Leu Thr
            835                 840

<210> SEQ ID NO 18
<211> LENGTH: 160
<212> TYPE: PRT
<213> ORGANISM: Varicella zoster virus

<400> SEQUENCE: 18

Met Ala Ser His Lys Trp Leu Leu Gln Met Ile Val Phe Leu Lys Thr
1               5                   10                  15

Ile Thr Ile Ala Tyr Cys Leu His Leu Gln Asp Asp Thr Pro Leu Phe
                20                  25                  30

Phe Gly Ala Lys Pro Leu Ser Asp Val Ser Leu Ile Ile Thr Glu Pro
            35                  40                  45

Cys Val Ser Ser Val Tyr Glu Ala Trp Asp Tyr Ala Ala Pro Pro Val
        50                  55                  60

Ser Asn Leu Ser Glu Ala Leu Ser Gly Ile Val Val Lys Thr Lys Cys
65                  70                  75                  80

Pro Val Pro Glu Val Ile Leu Trp Phe Lys Asp Lys Gln Met Ala Tyr
                85                  90                  95

Trp Thr Asn Pro Tyr Val Thr Leu Lys Gly Leu Thr Gln Ser Val Gly
            100                 105                 110

Glu Glu His Lys Ser Gly Asp Ile Arg Asp Ala Leu Leu Asp Ala Leu
        115                 120                 125

Ser Gly Val Trp Val Asp Ser Thr Pro Ser Ser Thr Asn Ile Pro Glu
130                 135                 140

Asn Gly Cys Val Trp Gly Ala Asp Arg Leu Phe Gln Arg Val Cys Gln
145                 150                 155                 160

<210> SEQ ID NO 19
<211> LENGTH: 354
<212> TYPE: PRT
<213> ORGANISM: Varicella zoster virus

<400> SEQUENCE: 19

Met Phe Leu Ile Gln Cys Leu Ile Ser Ala Val Ile Phe Tyr Ile Gln
1               5                   10                  15

Val Thr Asn Ala Leu Ile Phe Lys Gly Asp His Val Ser Leu Gln Val
                20                  25                  30

Asn Ser Ser Leu Thr Ser Ile Leu Ile Pro Met Gln Asn Asp Asn Tyr
            35                  40                  45

Thr Glu Ile Lys Gly Gln Leu Val Phe Ile Gly Glu Gln Leu Pro Thr
        50                  55                  60
```

```
Gly Thr Asn Tyr Ser Gly Thr Leu Glu Leu Leu Tyr Ala Asp Thr Val
65                  70                  75                  80

Ala Phe Cys Phe Arg Ser Val Gln Val Ile Arg Tyr Asp Gly Cys Pro
                85                  90                  95

Arg Ile Arg Thr Ser Ala Phe Ile Ser Cys Arg Tyr Lys His Ser Trp
            100                 105                 110

His Tyr Gly Asn Ser Thr Asp Arg Ile Ser Thr Glu Pro Asp Ala Gly
        115                 120                 125

Val Met Leu Lys Ile Thr Lys Pro Gly Ile Asn Asp Ala Gly Val Tyr
    130                 135                 140

Val Leu Leu Val Arg Leu Asp His Ser Arg Ser Thr Asp Gly Phe Ile
145                 150                 155                 160

Leu Gly Val Asn Val Tyr Thr Ala Gly Ser His His Asn Ile His Gly
                165                 170                 175

Val Ile Tyr Thr Ser Pro Ser Leu Gln Asn Gly Tyr Ser Thr Arg Ala
            180                 185                 190

Leu Phe Gln Gln Ala Arg Leu Cys Asp Leu Pro Ala Thr Pro Lys Gly
        195                 200                 205

Ser Gly Thr Ser Leu Phe Gln His Met Leu Asp Leu Arg Ala Gly Lys
    210                 215                 220

Ser Leu Glu Asp Asn Pro Trp Leu His Glu Asp Val Val Thr Thr Glu
225                 230                 235                 240

Thr Lys Ser Val Val Lys Glu Gly Ile Glu Asn His Val Tyr Pro Thr
                245                 250                 255

Asp Met Ser Thr Leu Pro Glu Lys Ser Leu Asn Asp Pro Pro Glu Asn
            260                 265                 270

Leu Leu Ile Ile Ile Pro Ile Val Ala Ser Val Met Ile Leu Thr Ala
        275                 280                 285

Met Val Ile Val Ile Val Ile Ser Val Lys Arg Arg Arg Ile Lys Lys
    290                 295                 300

His Pro Ile Tyr Arg Pro Asn Thr Lys Thr Arg Arg Gly Ile Gln Asn
305                 310                 315                 320

Ala Thr Pro Glu Ser Asp Val Met Leu Glu Ala Ala Ile Ala Gln Leu
                325                 330                 335

Ala Thr Ile Arg Glu Glu Ser Pro Pro His Ser Val Val Asn Pro Phe
            340                 345                 350

Val Lys

<210> SEQ ID NO 20
<211> LENGTH: 623
<212> TYPE: PRT
<213> ORGANISM: Varicella zoster virus

<400> SEQUENCE: 20

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80
```

```
Tyr Ile Trp Pro Arg Asn Asp Tyr Asp Gly Phe Leu Glu Asn Ala His
                 85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Ser Thr
                485                 490                 495
```

```
Val Asp His Phe Val Asn Ala Ile Glu Arg Gly Phe Pro Pro Thr
            500                 505                 510
Ala Gly Gln Pro Pro Ala Thr Thr Lys Pro Lys Glu Ile Thr Pro Val
        515                 520                 525
Asn Pro Gly Thr Ser Pro Leu Leu Arg Tyr Ala Ala Trp Thr Gly Gly
    530                 535                 540
Leu Ala Ala Val Val Leu Leu Cys Leu Val Ile Phe Leu Ile Cys Thr
545                 550                 555                 560
Ala Lys Arg Met Arg Val Lys Ala Tyr Arg Val Asp Lys Ser Pro Tyr
                565                 570                 575
Asn Gln Ser Met Tyr Tyr Ala Gly Leu Pro Val Asp Asp Phe Glu Asp
            580                 585                 590
Ser Glu Ser Thr Asp Thr Glu Glu Phe Gly Asn Ala Ile Gly Gly
        595                 600                 605
Ser His Gly Gly Ser Ser Tyr Thr Val Tyr Ile Asp Lys Thr Arg
    610                 615                 620

<210> SEQ ID NO 21
<211> LENGTH: 13339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
ataggcggcg catgagagaa gcccagacca attacctacc caaaatggag aaagttcacg        60
ttgacatcga ggaagacagc ccattcctca gagctttgca gcggagcttc ccgcagtttg      120
aggtagaagc caagcaggtc actgataatg accatgctaa tgccagagcg ttttcgcatc      180
tggcttcaaa actgatcgaa acggaggtgg acccatccga cacgatcctt gacattggaa      240
gtgcgcccgc ccgcagaatg tattctaagc acaagtatca ttgtatctgt ccgatgagat      300
gtgcggaaga tccggacaga ttgtataagt atgcaactaa gctgaagaaa aactgtaagg      360
aaataactga taaggaattg acaagaaaaa tgaaggagct cgccgccgtc atgagcgacc      420
ctgacctgga aactgagact atgtgcctcc acgacgacga gtcgtgtcgc tacgaagggc      480
aagtcgctgt ttaccaggat gtatacgcgg ttgacggacc gacaagtctc tatcaccaag      540
ccaataaggg agttagagtc gcctactgga taggctttga caccacccct tttatgttta      600
agaacttggc tggagcatat ccatcatact ctaccaactg ggccgacgaa accgtgttaa      660
cggctcgtaa cataggccta tgcagctctg acgttatgga gcggtcacgt agagggatgt      720
ccattcttag aaagaagtat ttgaaaccat ccaacaatgt tctattctct gttggctcga      780
ccatctacca cgagaagagg gacttactga ggagctggca cctgccgtct gtatttcact      840
tacgtggcaa gcaaaattac acatgtcggt gtgagactat agttagttgc gacgggtacg      900
tcgttaaaag aatagctatc agtccaggcc tgtatgggaa gccttcaggc tatgctgcta      960
cgatgcaccg cgagggattc ttgtgctgca aagtgacaga cacattgaac ggggagaggg     1020 tctctttttcc cgtgtgcacg tatgtgccag ctacattgtg tgaccaaatg actggcatac     1080
tggcaacaga tgtcagtgcg gacgacgcgc aaaaactgct ggttgggctc aaccagcgta     1140
tagtcgtcaa cggtcgcacc cagagaaaca ccaataccat gaaaaattac ctttttgcccg     1200 tagtggccca ggcatttgct aggtgggcaa aggaatataa ggaagatcaa gaagatgaaa     1260
ggccactagg actacgagat agacagttag tcatggggtg ttgttgggct tttagaaggc     1320
```

```
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttaac atgatgtgcc    2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
```

```
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgc caaaactttc tcatatttgg aagggaccaa gtttcaccag gcggccaagg    4680
atatagcaga aattaatgcc atgtgggccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccgc    5520 caggcgtgaa tagggtgatc actagagagg agctcgaggc gcttacccc tcacgcactc    5580 ctagcaggtc ggtctcgaga accagcctgg tctccaaccc gccaggcgta aataggtga   5640 ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tccttttgtat tcatctagtg tgaaccgtgc cttttcaagc cccaaggtcg    6060
```

```
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg aatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgagtct    7560
agtcgacgcc accatgttcg tgaccgccgt ggtgtccgtg tccccagca gcttttacga    7620 gagcctgcag gtcgagccca cccagagcga ggacatcaca agatctgccc acctgggcga    7680
cggcgacgag atcagagagg ccatccacaa gagccaggac gccgagacaa agcccacctt    7740
ctacgtgtgc ccccaccta ccggctctac aattgtgcgg ctggaacccc ccagaacctg    7800
ccctgattac cacctgggca agaacttcac cgagggaatt gccgtggtgt acaaagagaa    7860
tatcgccgcc tacaagttca aggccaccgt gtactacaag gacgtgatcg tgtccaccgc    7920
ctgggccggc agcagctaca cccagatcac caacagatac gccgaccggg tgcccatccc    7980
cgtgtctgag atcaccgaca ccatcgacaa gttcggcaag tgcagcagca aggccaccta    8040
cgtgcggaac aaccacaagg tggaagcctt caacgaggac aagaaccccc aggacatgcc    8100
cctgatcgcc agcaagtaca acagcgtggg ctccaaggcc tggcacacca ccaacgacac    8160
ctacatggtg gccggcaccc ccggcacata cagaacagga ccagcgtga actgcatcat    8220 cgaggaagtg gaagcccggt ccatcttccc atacgacagc ttcggcctga gcaccggcga    8280
cattatctac atgagccctt tcttcggcct gcgggacggc gcctacagag agcacagcaa    8340
ctacgccatg gaccggttcc accagttcga gggctacaga cagcgggacc tggacacaag    8400
```

```
agccctgctg gaacctgccg ccagaaactt cctggtcacc cctcacctga ccgtgggctg   8460
gaactggaag cccaagcgga ccgaagtgtg cagcctggtc aagtggcgcg aggtggaaga   8520
tgtcgtgcgg gatgagtacg cccacaactt ccggttcacc atgaagaccc tgagcaccac   8580
cttcatcagc gagacaaacg agttcaacct gaaccagatc cacctgagcc agtgcgtgaa   8640
agaggaagcc agagccatca tcaaccggat ctacaccacc cggtacaaca gcagccacgt   8700
gcggaccggc gatatccaga cctatctggc tagaggcggc ttcgtggtgg tgtttcagcc   8760
cctgctgagc aacagcctgg ctagactgta cctgcaggaa ctcgtcagag agaacaccaa   8820
ccacagcccc cagaagcacc ccacccggaa taccagatcc agacgcagcg tgcccgtgga   8880
actgagagcc aaccggacca tcaccaccac cagcagcgtg gaattcgcca tgctgcagtt   8940
cacctacgac cacatccagg aacacgtgaa cgagatgctg gcccggatca gcagcagttg   9000
gtgccagctg cagaatcggg aaagggccct gtggtccggc ctgttcccca tcaatccaag   9060
cgccctggcc agcaccatcc tggaccagag agtgaaggcc agaatcctgg gggacgtgat   9120
cagcgtgtcc aactgtcctg agctgggcag cgacacccgg atcatcctgc agaacagcat   9180
gcgggtgtcc ggcagcacca ccagatgcta cagcagaccc ctgatcagca tcgtgtccct   9240
gaacggcagc ggcacagtgg aaggccagct gggcaccgat aacgagctga tcatgagccg   9300
ggacctgctc gaaccctgcg tggccaatca caagcggtac tttctgttcg gccaccacta   9360
cgtgtactat gaggactaca gatacgtgcg cgagatcgcc gtgcacgacg tgggcatgat   9420
cagcacctac gtggacctga acctgaccct gctgaaggac cgcgagttca tgccactgca   9480
ggtctacacc cgggacgagc tgagagatac cggcctgctg gactcagcg agatccagcg   9540
gcggaaccag atgcactccc tgcggttcta cgacatcgac aaggtggtgc agtacgacag   9600
cggcaccgcc atcatgcagg gcatggccca gttctttcag ggcctgggaa cagccggaca   9660
ggccgtggga catgtggtgc tgggagctac aggcgccctg ctgtctaccg tgcacggctt   9720
caccaccttt ctgagcaacc ccttcggagc cctggctgtg gactgctgg tcctggctgg   9780
actggtggcc gccttctttg cctaccgcta cgtgctgaag ctgaaaacca gccccatgaa   9840
ggccctgtac cccctgacca ccaagggcct gaagcagctg cctgagggca tggacccctt   9900
cgccgagaag cccaatgcca ccgacacccc catcgaggaa atcggcgaca gccagaacac   9960
cgagccctcc gtgaacagcg gcttcgaccc cgacaagttt cgcgaggccc aggaaatgat  10020
caagtacatg accctggtgt ctgctgccga gcggcaggaa agcaaggccc ggaagaagaa  10080
caagacctcc gccctgctga ccagcagact gacaggactg gccctgcgga acagacgggg  10140
ctatagcaga gtgcggaccg agaatgtgac cggcgtgtaa tctagacgcg gccgcataca  10200
gcagcaattg gcaagctgct tacatagaac tcgcggcgat tggcatgccg ccttaaaatt  10260
tttattttat ttttcttttc ttttccgaat cggattttgt tttaatatt tcaaaaaaaa  10320
aaaaaaaaaa aaaaaaaaaa aaaaaaggg tcggcatggc atctccacct cctcgcggtc  10380
cgacctgggc atccgaagga ggacgcacgt ccactcggat ggctaaggga gagccacgtt  10440
taaaccagct ccaattcgcc ctatagtgag tcgtattacg cgcgctcact ggccgtcgtt  10500
ttacaacgtc gtgactggga aaaccctggc gttacccaac ttaatcgcct tgcagcacat  10560
ccccctttcg ccagctggcg taatagcgaa gaggcccgca ccgatcgccc ttcccaacag  10620
ttgcgcagcc tgaatggcga atgggacgcg ccctgtagcg cgcattaag cgcggcgggt  10680
gtggtggtta cgcgcagcgt gaccgctaca cttgccagcg ccctagcgcc cgctcctttc  10740
gctttcttcc cttcctttct cgccacgttc gccggctttc cccgtcaagc tctaaatcgg  10800
```

```
gggctccctt tagggttccg atttagtgct ttacggcacc tcgacccaa aaaacttgat    10860 tagggtgatg gttcacgtag tgggccatcg ccctgataga cggttttcg ccctttgacg    10920 ttggagtcca cgttctttaa tagtggactc ttgttccaaa ctggaacaac actcaaccct    10980
atctcggtct attcttttga tttataaggg attttgccga tttcggccta ttggttaaaa    11040
aatgagctga tttaacaaaa atttaacgcg aattttaaca aaatattaac gcttacaatt    11100
taggtggcac ttttcgggga aatgtgcgcg gaaccccat ttgtttatt ttctaaatac      11160 attcaaatat gtatccgctc atgagacaat aaccctgata aatgcttcaa taatattgaa    11220
aaaggaagag tatgagtatt caacatttcc gtgtcgccct tattccctt tttgcggcat     11280 tttgccttcc tgtttttgct cacccagaaa cgctggtgaa agtaaaagat gctgaagatc    11340
agttgggtgc acgagtgggt tacatcgaac tggatctcaa cagcggtaag atccttgaga    11400
gttttcgccc cgaagaacgt tttccaatga tgagcacttt taaagttctg ctatgtggcg    11460
cggtattatc ccgtattgac gccgggcaag agcaactcgg tcgccgcata cactattctc    11520
agaatgactt ggttgagtac tcaccagtca cagaaaagca tcttacggat ggcatgacag    11580
taagagaatt atgcagtgct gccataacca tgagtgataa cactgcggcc aacttacttc    11640
tgacaacgat cggaggaccg aaggagctaa ccgctttttt gcacaacatg ggggatcatg    11700
taactcgcct tgatcgttgg gaaccggagc tgaatgaagc cataccaaac gacgagcgtg    11760
acaccacgat gcctgtagca atggcaacaa cgttgcgcaa actattaact ggcgaactac    11820
ttactctagc ttcccggcaa caattaatag actggatgga ggcggataaa gttgcaggac    11880
cacttctgcg ctcggccctt ccggctggct ggtttattgc tgataaatct ggagccggtg    11940
agcgtgggtc tcgcggtatc attgcagcac tggggccaga tggtaagccc tcccgtatcg    12000
tagttatcta cacgacgggg agtcaggcaa ctatggatga acgaaataga cagatcgctg    12060
agataggtgc ctcactgatt aagcattggt aactgtcaga ccaagtttac tcatatatac    12120
tttagattga tttaaaactt catttttaat ttaaaaggat ctaggtgaag atcctttttg    12180
ataatctcat gaccaaaatc ccttaacgtg agttttcgtt ccactgagcg tcagaccccg    12240
tagaaaagat caaaggatct tcttgagatc ctttttttct gcgcgtaatc tgctgcttgc    12300
aaacaaaaaa accaccgcta ccagcggtgg tttgtttgcc ggatcaagag ctaccaactc    12360
tttttccgaa ggtaactggc ttcagcagag cgcagatacc aaatactgtt cttctagtgt    12420
agccgtagtt aggccaccac ttcaagaact ctgtagcacc gcctacatac ctcgctctgc    12480
taatcctgtt accagtggct gctgccagtg gcgataagtc gtgtcttacc gggttggact    12540
caagacgata gttaccggat aaggcgcagc ggtcgggctg aacggggggt tcgtgcacac    12600
agcccagctt ggagcgaacg acctacaccg aactgagata cctacagcgt gagctatgag    12660
aaagcgccac gcttcccgaa gggagaaagg cggacaggta tccggtaagc ggcagggtcg    12720
gaacaggaga gcgcacgagg gagcttccag ggggaaacgc ctggtatctt tatagtcctg    12780
tcgggtttcg ccacctctga cttgagcgtc gatttttgtg atgctcgtca gggggggcgga    12840 gcctatggaa aaacgccagc aacgcggcct ttttacggtt cctggccttt tgctggcctt    12900
ttgctcacat gttctttcct gcgttatccc ctgattctgt ggataaccgt attaccgcct    12960
ttgagtgagc tgataccgct cgccgcagcc gaacgaccga gcgcagcgag tcagtgagcg    13020
aggaagcgga gagcgcccca atacgcaaac cgcctctccc cgcgcgttgg ccgattcatt    13080
aatgcagctg gcacgacagg tttcccgact ggaaagcggg cagtgagcgc aacgcaatta    13140
```

```
atgtgagtta gctcactcat taggcacccc aggctttaca ctttatgctc ccggctcgta    13200
tgttgtgtgg aattgtgagc ggataacaat tcacacagg  aaacagctat gaccatgatt    13260
acgccaagcg cgcaattaac cctcactaaa gggaacaaaa gctgggtacc gggcccacgc    13320
gtaatacgac tcactatag                                                 13339
```

<210> SEQ ID NO 22
<211> LENGTH: 13258
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg ataccccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctgggggcg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
```

| | |
|---|---|
| taacacactc tggccgaaaa gggcgttatg ccgtggaacc ataccatggt aaagtagtgg | 1860 |
| tgccagaggg acatgcaata cccgtccagg actttcaagc tctgagtgaa agtgccacca | 1920 |
| ttgtgtacaa cgaacgtgag ttcgtaaaca ggtacctgca ccatattgcc acacatggag | 1980 |
| gagcgctgaa cactgatgaa gaatattaca aaactgtcaa gcccagcgag cacgacggcg | 2040 |
| aatacctgta cgacatcgac aggaaacagt gcgtcaagaa agaactagtc actgggctag | 2100 |
| ggctcacagg cgagctggtg gatcctccct tccatgaatt cgcctacgag agtctgagaa | 2160 |
| cacgaccagc cgctccttac caagtaccaa ccatagggt gtatggcgtg ccaggatcag | 2220 |
| gcaagtctgg catcattaaa agcgcagtca ccaaaaaaga tctagtggtg agcgccaaga | 2280 |
| aagaaaactg tgcagaaatt ataagggacg tcaagaaaat gaagggctg acgtcaatg | 2340 |
| ccagaactgt ggactcagtg ctcttgaatg gatgcaaaca ccccgtagag accctgtata | 2400 |
| ttgacgaagc ttttgcttgt catgcaggta ctctcagagc gctcatagcc attataagac | 2460 |
| ctaaaaaggc agtgctctgc ggggatccca aacagtgcgg ttttttttaac atgatgtgcc | 2520 |
| tgaaagtgca ttttaaccac gagatttgca cacaagtctt ccacaaaagc atctctcgcc | 2580 |
| gttgcactaa atctgtgact tcggtcgtct caaccttgtt ttacgacaaa aaaatgagaa | 2640 |
| cgacgaatcc gaaagagact aagattgtga ttgacactac cggcagtacc aaacctaagc | 2700 |
| aggacgatct cattctcact tgtttcagag ggtgggtgaa gcagttgcaa atagattaca | 2760 |
| aaggcaacga ataatgacg gcagctgcct ctcaagggct gacccgtaaa ggtgtgtatg | 2820 |
| ccgttcggta caaggtgaat gaaaatcctc tgtacgcacc cacctcagaa catgtgaacg | 2880 |
| tcctactgac ccgcacggag gaccgcatcg tgtggaaaac actagccggc gacccatgga | 2940 |
| taaaaacact gactgccaag taccctggga atttcactgc cacgatagag gagtggcaag | 3000 |
| cagagcatga tgccatcatg aggcacatct ggagagacc ggaccctacc gacgtcttcc | 3060 |
| agaataaggc aaacgtgtgt gggccaagg cttagtgcc ggtgctgaag accgctggca | 3120 |
| tagacatgac cactgaacaa tggaacactg tggattattt tgaaacggac aaagctcact | 3180 |
| cagcagagat agtattgaac caactatgcg tgaggttctt tggactcgat ctggactccg | 3240 |
| gtctatttc tgcacccact gttccgttat ccattaggaa taatcactgg gataactccc | 3300 |
| cgtcgcctaa catgtacggg ctgaataaag aagtggtccg tcagctctct cgcaggtacc | 3360 |
| cacaactgcc tcgggcagtt gccactggaa gagtctatga catgaacact ggtacactgc | 3420 |
| gcaattatga tccgcgcata aacctagtac ctgtaaacag aagactgcct catgctttag | 3480 |
| tcctccacca taatgaacac ccacagagtg acttttcttc attcgtcagc aaattgaagg | 3540 |
| gcagaactgt cctggtggtc ggggaaaagt tgtccgtccc aggcaaaatg gttgactggt | 3600 |
| tgtcagaccg gcctgaggct accttcgag ctcggctgga tttaggcatc ccaggtgatg | 3660 |
| tgcccaaata tgacataata tttgttaatg tgaggacccc atataaatac catcactatc | 3720 |
| agcagtgtga agaccatgcc attaagctta gcatgttgac caagaaagct tgtctgcatc | 3780 |
| tgaatcccgg cggaacctgt gtcagcatag gttatggtta cgctgacagg gccagcgaaa | 3840 |
| gcatcattgg tgctatagcg cggcagttca agttttcccg ggtatgcaaa ccgaaatcct | 3900 |
| cacttgaaga gacggaagtt ctgtttgtat tcattgggta cgatcgcaag gcccgtacgc | 3960 |
| acaatcctta caagctttca tcaaccttga ccaacattta tacaggttcc agactccacg | 4020 |
| aagccggatg tgcaccctca tatcatgtgg tgcgagggga tattgccacg gccaccgaag | 4080 |
| gagtgattat aaatgctgct aacagcaaag gacaacctgg cggaggggtg tgcggagcgc | 4140 |

```
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccaccccgc    5520 caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tccttttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
```

-continued

```
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgagtct    7560
agtcgacgcc accatgttcg ccctggtgct ggccgtggtc atcctgcctc tgtggaccac    7620
cgccaacaag agctacgtga cccccacacc cgccaccaga tccatcggac acatgagcgc    7680
cctgctgaga gagtacagcg accggaacat gagcctgaag ctggaagcct tctaccccac    7740
cggcttcgac gaggaactga tcaagagcct gcactggggc aacgaccgga agcacgtgtt    7800
cctcgtgatc gtgaaagtga accccaccac ccacgagggc gacgtcggcc tggtcatctt    7860
ccccaagtac ctgctgagcc cctaccactt caaggccgag cacagagccc ccttccctgc    7920
tggccgcttt ggcttctgat gccaccctgt gaccccgac gtgtcattct tcgacagcag    7980
cttcgccccc tacctgacca cacagcacct ggtggcttc accaccttcc cccccaatcc    8040
tctcgtgtgg cacctggaaa gagccgagac agccgccacc gccgaaagac cttttggcgt    8100
gtccctgctg cccgccagac ctaccgtgcc caagaacacc atcctggaac acaaggccca    8160
cttcgccacc tgggatgccc tggccagaca caccttcttt agcgccgagg ccatcatcac    8220
caacagcacc ctgagaatcc acgtgcccct gttcggcagc gtgtggccca tcagatactg    8280
ggccacaggc agcgtgctgc tgaccagcga tagcggcaga gtggaagtga acatcggcgt    8340
gggcttcatg agcagcctga tcagcctgag cagcggcctg cccatcgagc tgattgtggt    8400
gccccacacc gtgaagctga acgccgtgac cagcgacacc acctggttcc agctgaaccc    8460
ccctggccct gatcctggcc ctagttacag agtgtacctg ctgggcagag cctggacat    8520
gaacttcagc aagcacgcca ccgtggacat ctgcgcctac cctgaggaaa gcctggacta    8580
cagataccac ctgagcatgg cccacaccga ggccctgaga atgaccacca aggccgacca    8640
gcacgacatc aacgaggaaa gctactacca cattgccgcc agaatcgcca ccagcatctt    8700
cgccctgagc gagatgggcc ggaccaccga gtactttctg ctggacgaga tcgtggacgt    8760
gcagtaccag ctgaagttcc tgaactacat cctgatgcgg atcggcgctg cgcccaccc    8820
taataccatc agcggcacca gcgacctgat cttcgccgat cctagccagc tgcacgacga    8880
```

```
gctgagcctg ctgttcggcc aggtcaaacc cgccaacgtg gactacttca tcagctacga    8940
cgaggcccgg gaccagctga aaacagccta cgccctgtcc agaggccagg atcatgtgaa    9000
cgccctgtcc ctggccaggc gcgtgatcat gagcatctac aagggcctgc tggtcaagca    9060
gaacctgaac gccaccgagc ggcaggccct gttcttcgcc agcatgatcc tgctgaactt    9120
cagagagggc ctggaaaaca gcagccgggt gctggatggc agaaccaccc tgctgctgat    9180
gaccagcatg tgcacagccg cccatgccac acaggccgcc ctgaatatcc aggaaggcct    9240
ggcttacctg aaccccagca agcacatgtt caccatcccc aacgtgtaca gccctgcat    9300
gggcagcctg agaaccgacc tgaccgaaga gatccacgtg atgaacctgc tgtccgccat    9360
ccccaccaga cccggactga atgaggtgct gcacacccag ctggacgagt ccgagatctt    9420
cgacgccgcc ttcaagacca tgatgatctt taccacctgg accgccaagg acctgcacat    9480
cctgcacaca cacgtgcccg aggtgttcac atgccaagat gccgccgctc ggaacggcga    9540
gtatgtgctg attctgcctg ccgtgcaggg ccacagctac gtgatcaccc ggaacaagcc    9600
ccagcggggc ctggtgtata gcctggctga cgtggacgtg tacaaccca tcagcgtggt    9660
gtacctgagc aaggatacct gcgtgtccga gcacggcgtg atcgaaacag tggccctgcc    9720
ccaccccgac aacctgaaag agtgcctgta ctgcggctcc gtgttcctgc ggtatctgac    9780
caccggcgcc atcatggaca tcatcatcat cgacagcaag gacaccgaga gacagctggc    9840
cgccatgggc aacagcacca tcccccctt caaccccgac atgcacggcg acgatagcaa    9900
ggccgtgctg ctgttccca acggcaccgt ggtcacactg ctgggcttcg agcggagaca    9960
ggccatcaga atgagcggcc agtacctggg cgcctctctg gtggtgcct ttctggccgt   10020
cgtgggcttt ggcatcatcg gctggatgct gtgcggcaac agcagactgc gcgagtacaa   10080
caagatcccc ctgacctaat ctagacgcgg ccgcatacag cagcaattgg caagctgctt   10140
acatagaact cgcggcgatt ggcatgccgc cttaaaattt ttattttatt tttcttttct   10200
tttccgaatc ggattttgtt tttaatattt caaaaaaaaa aaaaaaaaa aaaaaaaaa   10260
aaaaaagggt cggcatggca tctccacctc ctcgcggtcc gacctgggca tccgaaggag   10320
gacgcacgtc cactcggatg gctaagggag agccacgttt aaaccagctc caattcgccc   10380
tatagtgagt cgtattacgc gcgctcactg gccgtcgttt tacaacgtcg tgactgggaa   10440
aaccctggcg ttacccaact taatcgcctt gcagcacatc cccctttcgc cagctggcgt   10500
aatagcgaag aggcccgcac cgatcgccct tcccaacagt tgcgcagcct gaatggcgaa   10560
tgggacgcgc cctgtagcgg cgcattaagc gcggcgggtg tggtggttac gcgcagcgtg   10620
accgctacac ttgccagcgc cctagcgccc gctcctttcg ctttcttccc ttcctttctc   10680
gccacgttcg ccggctttcc ccgtcaagct ctaaatcggg gctccctttt agggttccga   10740
tttagtgctt tacggcacct cgaccccaaa aaacttgatt agggtgatgg ttcacgtagt   10800
gggccatcgc cctgatagac ggtttttcgc cctttgacgt tggagtccac gttctttaat   10860
agtggactct tgttccaaac tggaacaaca ctcaaccta tctcggtcta ttcttttgat   10920
ttataaggga ttttgccgat ttcggcctat tggttaaaaa atgagctgat ttaacaaaaa   10980
tttaacgcga attttaacaa aatattaacg cttacaattt aggtggcact tttcgggaa   11040
atgtgcgcgg aaccctatt tgtttatttt tctaaataca ttcaaatatg tatccgctca   11100
tgagacaata accctgataa atgcttcaat aatattgaaa aaggaagagt atgagtattc   11160
aacatttccg tgtcgccctt attcccttt ttgcggcatt ttgccttcct gttttgctc   11220
acccagaaac gctggtgaaa gtaaaagatg ctgaagatca gttgggtgca cgagtgggtt   11280
```

```
acatcgaact ggatctcaac agcggtaaga tccttgagag ttttcgcccc gaagaacgtt    11340
ttccaatgat gagcactttt aaagttctgc tatgtggcgc ggtattatcc cgtattgacg    11400
ccgggcaaga gcaactcggt cgccgcatac actattctca gaatgacttg gttgagtact    11460
caccagtcac agaaaagcat cttacggatg gcatgacagt aagagaatta tgcagtgctg    11520
ccataaccat gagtgataac actgcggcca acttacttct gacaacgatc ggaggaccga    11580
aggagctaac cgctttttg cacaacatgg gggatcatgt aactcgcctt gatcgttggg    11640
aaccggagct gaatgaagcc ataccaaacg acgagcgtga caccacgatg cctgtagcaa    11700
tggcaacaac gttgcgcaaa ctattaactg gcgaactact tactctagct tcccggcaac    11760
aattaataga ctggatggag gcggataaag ttgcaggacc acttctgcgc tcggcccttc    11820
cggctggctg gtttattgct gataaatctg gagccggtga gcgtgggtct cgcggtatca    11880
ttgcagcact ggggccagat ggtaagccct cccgtatcgt agttatctac acgacgggga    11940
gtcaggcaac tatggatgaa cgaaatagac agatcgctga ataggtgcc tcactgatta    12000 agcattggta actgtcagac caagtttact catatatact ttagattgat ttaaaacttc    12060
atttttaatt taaaaggatc taggtgaaga tcctttttga taatctcatg accaaaatcc    12120
cttaacgtga gttttcgttc cactgagcgt cagacccgt agaaaagatc aaaggatctt    12180
cttgagatcc ttttttctg cgcgtaatct gctgcttgca acaaaaaaa ccaccgctac    12240 cagcggtggt ttgtttgccg gatcaagagc taccaactct ttttccgaag gtaactggct    12300
tcagcagagc gcagatacca aatactgttc ttctagtgta gccgtagtta ggccaccact    12360
tcaagaactc tgtagcaccg cctacatacc tcgctctgct aatcctgtta ccagtggctg    12420
ctgccagtgg cgataagtcg tgtcttaccg ggttggactc aagacgatag ttaccggata    12480
aggcgcagcg gtcgggctga acggggggtt cgtgcacaca gcccagcttg gagcgaacga    12540
cctacaccga actgagatac ctacagcgtg agctatgaga aagcgccacg cttcccgaag    12600
ggagaaaggc ggacaggtat ccggtaagcg gcagggtcgg aacaggagag cgcacgaggg    12660
agcttccagg gggaaacgcc tggtatcttt atagtcctgt cgggtttcgc cacctctgac    12720
ttgagcgtcg attttgtga tgctcgtcag ggggcggag cctatggaaa aacgccagca    12780
acgcggcctt tttacggttc ctggccttt gctggccttt tgctcacatg ttctttcctg    12840
cgttatcccc tgattctgtg gataaccgta ttaccgcctt tgagtgagct gataccgctc    12900
gccgcagccg aacgaccgag cgcagcgagt cagtgagcga ggaagcggaa gagcgcccaa    12960
tacgcaaacc gcctctcccc gcgcgttggc cgattcatta atgcagctgg cacgacaggt    13020
ttcccgactg gaaagcgggc agtgagcgca acgcaattaa tgtgagttag ctcactcatt    13080
aggcacccca ggctttacac tttatgctcc cggctcgtat gttgtgtgga attgtgagcg    13140
gataacaatt tcacacagga aacagctatg accatgatta cgccaagcgc gcaattaacc    13200
ctcactaaag ggaacaaaag ctgggtaccg ggccacgcg taatacgact cactatag    13258
```

<210> SEQ ID NO 23
<211> LENGTH: 11215
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
ataggcggcg catgagagaa gcccagacca attacctacc caaaatggag aaagttcacg    60
ttgacatcga ggaagacagc ccattcctca gagctttgca gcggagcttc ccgcagtttg   120
aggtagaagc caagcaggtc actgataatg accatgctaa tgccagagcg ttttcgcatc   180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactaa gctgaagaaa aactgtaagg   360
aaataactga taaggaattg acaagaaaaa tgaaggagct cgccgccgtc atgagcgacc   420
ctgacctgga aactgagact atgtgcctcc acgacgacga gtcgtgtcgc tacgaagggc   480
aagtcgctgt ttaccaggat gtatacgcgg ttgacggacc gacaagtctc tatcaccaag   540
ccaataaggg agttagagtc gcctactgga taggctttga caccacccct tttatgttta   600
agaacttggc tggagcatat ccatcatact ctaccaactg ggccgacgaa accgtgttaa   660
cggctcgtaa cataggccta tgcagctctg acgttatgga gcggtcacgt agagggatgt   720
ccattcttag aaagaagtat ttgaaaccat ccaacaatgt tctattctct gttggctcga   780
ccatctacca cgagaagagg gacttactga ggagctggca cctgccgtct gtatttcact   840
tacgtggcaa gcaaaattac acatgtcggt gtgagactat agttagttgc gacgggtacg   900
tcgttaaaag aatagctatc agtccaggcc tgtatgggaa gccttcaggc tatgctgcta   960
cgatgcaccg cgagggattc ttgtgctgca aagtgacaga cacattgaac ggggagaggg  1020 tctctttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaagccgatg  1620
tagacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaggggctg gacgtcaatg  2340
ccagaactgt ggactcagtg ctccttgaatg gatgcaaaca ccccgtagag accctgtata  2400
```

```
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520 tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa    2640 cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct ggagagacc ggaccctacc gacgtcttcc    3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataaatac catcactatc    3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgttttgtat tcattgggta cgatcgcaag gcccgtacgc   3960
acaatcctta caagctttca tcaaccttga ccaacatttta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgc caaaacttc tcatatttgg aagggaccaa gttccaccag gcggccaagg    4680
atatagcaga aattaatgcc atgtggcccg ttgcaacgga ggccaatgag caggtatgca   4740
```

-continued

```
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccccgc   5520
caggcgtgaa tagggtgatc actagagagg agctcgaggc gcttacccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gcttttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
```

```
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccectaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgagtct    7560
agtcgacgcc accatggcca gccacaagtg gctgctgcag atgatcgtgt cctgaaaaac    7620
catcacaatc gcctactgcc tgcatctgca ggacgacacc cctctgttct cggcgccaa     7680
gcctctgagc gacgtgtccc tgatcatcac cgagccttgc gtgtccagcg tgtacgaggc    7740
ctgggattat gccgcccctc ccgtgtccaa tctgagcgaa gccctgagcg catcgtggt     7800
caagaccaag tgccccgtgc ccgaagtgat cctgtggttc aaggacaagc agatggccta    7860
ctggaccaac ccttacgtga ccctgaaggg cctgacccag agcgtgggcg aggaacacaa    7920
gagcggcgac atcagagatg ccctgctgga tgccctgtcc ggtgtctggg tggacagcac    7980
accctccagc accaacatcc ccgagaacgg ctgtgtgtgg ggagccgacc ggctgttcca    8040
gagagtgtgt cagtaatcta gacgcggccg catacagcag caattggcaa gctgcttaca    8100
tagaactcgc ggcgattggc atgccgcctt aaaatttta ttttattttt cttttctttt     8160
ccgaatcgga ttttgttttt aatatttcaa aaaaaaaaa aaaaaaaaa aaaaaaaaa       8220
aaagggtcgg catggcatct ccacctcctc gcggtccgac ctgggcatcc gaaggaggac    8280
gcacgtccac tcggatggct aagggagagc cacgtttaaa ccagctccaa ttcgccctat    8340
agtgagtcgt attacgcgcg ctcactggcc gtcgttttac aacgtcgtga ctgggaaaac    8400
cctggcgtta cccaacttaa tcgccttgca gcacatcccc ctttcgccag ctggcgtaat    8460
agcgaagagg cccgcaccga tcgcccttcc caacagttgc gcagcctgaa tggcgaatgg    8520
gacgcgccct gtagcggcgc attaagcgcg gcgggtgtgg tggttacgcg cagcgtgacc    8580
gctacacttg ccagcgccct agcgcccgct cctttcgctt tcttcccttc ctttctcgcc    8640
acgttcgccg gctttccccg tcaagctcta atcgggggc tccctttagg gttccgattt     8700
agtgctttac ggcacctcga ccccaaaaaa cttgattagg gtgatggttc acgtagtggg    8760
ccatcgccct gatagacggt ttttcgccct ttgacgttgg agtccacgtt ctttaatagt    8820
ggactcttgt tccaaactgg aacaacactc aaccctatct cggtctattc ttttgattta    8880
taagggattt tgccgatttc ggcctattgg ttaaaaaatg agctgattta acaaaaattt    8940
aacgcgaatt ttaacaaaat attaacgctt acaatttagg tggcacttt cggggaaatg    9000
tgcgcggaac ccctatttgt ttatttttct aaatacattc aaatatgtat ccgctcatga    9060
gacaataacc ctgataaatg cttcaataat attgaaaaag gaagagtatg agtattcaac    9120
atttccgtgt cgcccttatt cccttttttg cggcattttg ccttcctgtt tttgctcacc    9180
cagaaacgct ggtgaaagta aaagatgctg aagatcagtt gggtgcacga gtgggttaca    9240
tcgaactgga tctcaacagc ggtaagatcc ttgagagttt tcgccccgaa gaacgttttc    9300
caatgatgag cacttttaaa gttctgctat gtggcgcggt attatcccgt attgacgccg    9360
ggcaagagca actcggtcgc cgcatacact attctcagaa tgacttggtt gagtactcac    9420
cagtcacaga aaagcatctt acggatggca tgacagtaag agaattatgc agtgctgcca    9480
```

| | |
|---|---|
| taaccatgag tgataacact gcggccaact tacttctgac aacgatcgga ggaccgaagg | 9540 |
| agctaaccgc ttttttgcac aacatggggg atcatgtaac tcgccttgat cgttgggaac | 9600 |
| cggagctgaa tgaagccata ccaaacgacg agcgtgacac cacgatgcct gtagcaatgg | 9660 |
| caacaacgtt gcgcaaacta ttaactggcg aactacttac tctagcttcc cggcaacaat | 9720 |
| taatagactg gatggaggcg gataaagttg caggaccact tctgcgctcg gcccttccgg | 9780 |
| ctggctggtt tattgctgat aaatctggag ccggtgagcg tgggtctcgc ggtatcattg | 9840 |
| cagcactggg gccagatggt aagccctccc gtatcgtagt tatctacacg acggggagtc | 9900 |
| aggcaactat ggatgaacga atagacaga tcgctgagat aggtgcctca ctgattaagc | 9960 |
| attggtaact gtcagaccaa gtttactcat atatacttta gattgattta aaacttcatt | 10020 |
| tttaatttaa aaggatctag gtgaagatcc tttttgataa tctcatgacc aaaatccctt | 10080 |
| aacgtgagtt ttcgttccac tgagcgtcag accccgtaga aaagatcaaa ggatcttctt | 10140 |
| gagatccttt ttttctgcgc gtaatctgct gcttgcaaac aaaaaaacca ccgctaccag | 10200 |
| cggtggtttg tttgccggat caagagctac caactctttt tccgaaggta actggcttca | 10260 |
| gcagagcgca gataccaaat actgttcttc tagtgtagcc gtagttaggc caccacttca | 10320 |
| agaactctgt agcaccgcct acatacctcg ctctgctaat cctgttacca gtggctgctg | 10380 |
| ccagtggcga taagtcgtgt cttaccgggt tggactcaag acgatagtta ccggataagg | 10440 |
| cgcagcggtc gggctgaacg gggggttcgt gcacacagcc cagcttggag cgaacgacct | 10500 |
| acaccgaact gagataccta cagcgtgagc tatgagaaag cgccacgctt cccgaaggga | 10560 |
| gaaaggcgga caggtatccg gtaagcggca gggtcgaac aggagagcgc acgagggagc | 10620 |
| ttccaggggg aaacgcctgg tatctttata gtcctgtcgg gtttcgccac ctctgacttg | 10680 |
| agcgtcgatt tttgtgatgc tcgtcagggg ggcggagcct atggaaaaac gccagcaacg | 10740 |
| cggccttttt acggttcctg gccttttgct ggccttttgc tcacatgttc tttcctgcgt | 10800 |
| tatcccctga ttctgtggat aaccgtatta ccgcctttga gtgagctgat accgctcgcc | 10860 |
| gcagccgaac gaccgagcgc agcgagtcag tgagcgagga agcggaagag cgcccaatac | 10920 |
| gcaaaccgcc tctccccgcg cgttggccga ttcattaatg cagctggcac gacaggtttc | 10980 |
| ccgactggaa agcgggcagt gagcgcaacg caattaatgt gagttagctc actcattagg | 11040 |
| caccccaggc tttacacttt atgctcccgg ctcgtatgtt gtgtggaatt gtgagcggat | 11100 |
| aacaatttca cacaggaaac agctatgacc atgattacgc caagcgcgca attaaccctc | 11160 |
| actaaaggga caaaagctg ggtaccgggc ccacgcgtaa tacgactcac tatag | 11215 |

<210> SEQ ID NO 24
<211> LENGTH: 13827
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

| | |
|---|---|
| ataggcggcg catgagagaa gcccagacca attacctacc caaaatggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |

```
gtgcggaaga tccggacaga ttgtataagt atgcaactaa gctgaagaaa aactgtaagg      360
aaataactga taaggaattg gacaagaaaa tgaaggagct cgccgccgtc atgagcgacc      420
ctgacctgga aactgagact atgtgcctcc acgacgacga gtcgtgtcgc tacgaagggc      480
aagtcgctgt ttaccaggat gtatacgcgg ttgacggacc gacaagtctc tatcaccaag      540
ccaataaggg agttagagtc gcctactgga taggctttga caccacccct tttatgttta      600
agaacttggc tggagcatat ccatcatact ctaccaactg ggccgacgaa accgtgttaa      660
cggctcgtaa cataggccta tgcagctctg acgttatgga gcggtcacgt agagggatgt      720
ccattcttag aaagaagtat ttgaaaccat ccaacaatgt tctattctct gttggctcga      780
ccatctacca cgagaagagg gacttactga ggagctggca cctgccgtct gtatttcact      840
tacgtggcaa gcaaaattac acatgtcggt gtgagactat agttagttgc gacgggtacg      900
tcgttaaaag aatagctatc agtccaggcc tgtatgggaa gccttcaggc tatgctgcta      960
cgatgcaccg cgagggattc ttgtgctgca aagtgacaga cacattgaac ggggagaggg     1020
tctcttttcc cgtgtgcacg tatgtgccag ctacattgtg tgaccaaatg actggcatac     1080
tggcaacaga tgtcagtgcg gacgacgcgc aaaaactgct ggttgggctc aaccagcgta     1140
tagtcgtcaa cggtcgcacc cagagaaaca ccaataccat gaaaaattac cttttgcccg     1200
tagtggccca ggcatttgct aggtgggcaa aggaatataa ggaagatcaa gaagatgaaa     1260
ggccactagg actacgagat agacagttag tcatggggtg ttgttgggct tttagaaggc     1320
acaagataac atctatttat aagcgcccgg atacccaaac catcatcaaa gtgaacagcg     1380
atttccactc attcgtgctg cccaggatag gcagtaacac attggagatc gggctgagaa     1440
caagaatcag gaaaatgtta gaggagcaca aggagccgtc acctctcatt accgccgagg     1500
acgtacaaga agctaagtgc gcagccgatg aggctaagga ggtgcgtgaa gccgaggagt     1560
tgcgcgcagc tctaccacct ttggcagctg atgttgagga gcccactctg gaagccgatg     1620
tagacttgat gttacaagag gctggggccg gctcagtgga gacacctcgt ggcttgataa     1680
aggttaccag ctacgatggc gaggacaaga tcggctctta cgctgtgctt tctccgcagg     1740
ctgtactcaa gagtgaaaaa ttatcttgca tccaccctct cgctgaacaa gtcatagtga     1800
taacacactc tggccgaaaa gggcgttatg ccgtggaacc ataccatggt aaagtagtgg     1860
tgccagaggg acatgcaata cccgtccagg actttcaagc tctgagtgaa agtgccacca     1920
ttgtgtacaa cgaacgtgag ttcgtaaaca ggtacctgca ccatattgcc acacatggag     1980
gagcgctgaa cactgatgaa gaatattaca aaactgtcaa gcccagcgag cacgacggcg     2040
aatacctgta cgacatcgac aggaaacagt gcgtcaagaa agaactagtc actgggctag     2100
ggctcacagg cgagctggtg gatcctccct tccatgaatt cgcctacgag agtctgagaa     2160
cacgaccagc cgctccttac caagtaccaa ccataggggt gtatggcgtg ccaggatcag     2220
gcaagtctgg catcattaaa agcgcagtca ccaaaaaaga tctagtggtg agcgccaaga     2280
aagaaaactg tgcagaaatt ataagggacg tcaagaaaat gaagggctga cgtcaatg      2340 ccagaactgt ggactcagtg ctcttgaatg gatgcaaaca ccccgtagag accctgtata     2400
ttgacgaagc ttttgcttgt catgcaggta ctctcagagc gctcatagcc attataagac     2460
ctaaaaaggc agtgctctgc ggggatccca acagtgcgg tttttttaac atgatgtgcc      2520
tgaaagtgca ttttaaccac gagatttgca cacaagtctt ccacaaaagc atctctcgcc     2580
gttgcactaa atctgtgact tcggtcgtct caaccttgtt ttacgacaaa aaaatgagaa     2640
```

```
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240 gtctatttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactgaaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga gaccatgcc attaagctta gcatgttgac caagaaagct tgtctgcatc   3780
tgaatcccgg cggaacctgt gtcagcatag gttatggtta cgctgacagg gccagcgaaa   3840 gcatcattg tgctatagcg cggcagttca gttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaacttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tccttcccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
```

```
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc tgtaacgcc  atgttgaaag agaactttcc gactgtggct tcttactgta   6120
ttattccaga gtacgatgcc tatttggaca tggttgacgg agcttcatgc tgcttagaca   6180
ctgccagttt ttgccctgca agctgcgca  gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
```

```
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgagtct    7560
agtcgacgcc accatgttcg ccctggtgct ggccgtggtc atcctgcctc tgtggaccac    7620
cgccaacaag agctacgtga ccccccacacc cgccaccaga tccatcggac acatgagcgc    7680
cctgctgaga gagtacagcg accggaacat gagcctgaag ctggaagcct tctaccccac    7740
cggcttcgac gaggaactga tcaagagcct gcactggggc aacgaccgga agcacgtgtt    7800
cctcgtgatc gtgaaagtga accccaccac ccacgagggc gacgtcggcc tggtcatctt    7860
ccccaagtac ctgctgagcc cctaccactt caaggccgag cacagagccc ccttccctgc    7920
tggccgcttt ggcttctga gccacccctgt gaccccccgac gtgtcattct tcgacagcag    7980
cttcgccccc tacctgacca cacagcacct ggtggccttc accaccttcc ccccaatcc    8040 tctcgtgtgg cacctggaaa gagccgagac agccgccacc gccgaaagac ctttggcgt    8100 gtccctgctg cccgccagac ctaccgtgcc caagaacacc atcctggaac acaaggccca    8160
cttcgccacc tgggatgccc tggccagaca caccttcttt agcgccgagg ccatcatcac    8220
caacagcacc ctgagaatcc acgtgcccct gttcggcagc gtgtgcccca tcagatactg    8280
ggccacaggc agcgtgctgc tgaccagcga tagcggcaga gtggaagtga acatcggcgt    8340
gggcttcatg agcagcctga tcagcctgag cagcggcctg cccatcgagc tgattgtggt    8400
gccccacacc gtgaagctga acgccgtgac cagcgacacc acctggttcc agctgaaccc    8460
ccctggccct gatcctggcc ctagttacag agtgtacctg ctgggcagag gcctggacat    8520
gaacttcagc aagcacgcca ccgtggacat ctgcgcctac cctgaggaaa gcctggacta    8580
cagataccac ctgagcatgg cccacaccga ggccctgaga atgaccacca aggccgacca    8640
gcacgacatc aacgaggaaa gctactacca cattgccgcc agaatcgcca ccagcatctt    8700
cgccctgagc gagatgggcc ggaccaccga gtactttctg ctggacgaga tcgtggacgt    8760
gcagtaccag ctgaagttcc tgaactacat cctgatgcgg atcggcgctg cgcccaccc    8820 taataccatc agcggcacca gcgacctgat cttcgccgat cctagccagc tgcacgacga    8880
gctgagcctg ctgttcggcc aggtcaaacc cgccaacgtg gactacttca tcagctacga    8940
cgaggcccgg gaccagctga aaacagccta cgccctgtcc agaggccagg atcatgtgaa    9000
cgccctgtcc ctggccaggc gcgtgatcat gagcatctac aagggcctgc tggtcaagca    9060
gaacctgaac gccaccgagc ggcaggccct gttcttcgcc agcatgatcc tgctgaactt    9120
cagagagggc ctgaaaaaca gcagccgggt gctggatggc agaaccaccc tgctgctgat    9180
gaccagcatg tgcacagccg cccatgccac acaggccgcc ctgaatatcc aggaaggcct    9240
ggcttacctg aaccccagca agcacatgtt caccatcccc aacgtgtaca gcccctgcat    9300
gggcagcctg agaaccgacc tgaccgaaga gatccacgtg atgaacctgc tgtccgccat    9360
ccccaccaga cccggactga atgaggtgct gcacacccag ctggacagt ccgagatctt    9420 cgacgccgcc ttcaagacca tgatgatctt taccacctgg accgccaagg acctgcacat    9480
cctgcacaca cacgtgcccg aggtgttcac atgccaagat gccgccgctc ggaacggcga    9540
gtatgtgctg attctgcctg ccgtgcaggg ccacagctac gtgatcaccc ggaacaagcc    9600
ccagcggggc ctggtgtata gcctggctga cgtggacgtg tacaacccca tcagcgtggt    9660
gtacctgagc aaggatccct gcgtgtccga gcacggcgtg atcgaaacag tggccctgcc    9720
ccaccccgac aacctgaaag agtgcctgta ctgcggctcc gtgttcctgc ggtatctgac    9780
```

```
caccggcgcc atcatggaca tcatcatcat cgacagcaag gacaccgaga gacagctggc   9840
cgccatgggc aacagcacca tccccccctt caaccccgac atgcacggcg acgatagcaa   9900
ggccgtgctg ctgttcccca acggcaccgt ggtcacactg ctgggcttcg agcggagaca   9960
ggccatcaga atgagcggcc agtacctggg cgcctctctg ggtggtgcct ttctggccgt  10020
cgtgggcttt ggcatcatcg gctggatgct gtgcggcaac agcagactgc gcgagtacaa  10080
caagatcccc ctgacctaat ctagacgtcg cgaccaccca ggatccgcct ataactctct  10140
acggctaacc tgaatggact acgacatagt ctagtcgacg ccaccatggc cagccacaag  10200
tggctgctgc agatgatcgt gttcctgaaa accatcacaa tcgcctactg cctgcatctg  10260
caggacgaca cccctctgtt cttcggcgcc aagcctctga gcgacgtgtc cctgatcatc  10320
accgagcctt gcgtgtccag cgtgtacgag gcctgggatt atgccgcccc tcccgtgtcc  10380
aatctgagcg aagccctgag cggcatcgtg gtcaagacca agtgccccgt gcccgaagtg  10440
atcctgtggt tcaaggacaa gcagatggcc tactggacca cccttacgt gaccctgaag  10500
ggcctgaccc agagcgtggg cgaggaacac aagagcggcg acatcagaga tgccctgctg  10560
gatgccctgt ccggtgtctg ggtggacagc acaccctcca gcaccaacat ccccgagaac  10620
ggctgtgtgt ggggagccga ccggctgttc cagagagtgt gtcagtaatc tagacgcggc  10680
cgcatacagc agcaattggc aagctgctta catagaactc gcggcgattg gcatgccgcc  10740
ttaaaatttt tattttattt ttcttttctt ttccgaatcg gattttgttt ttaatatttc  10800
aaaaaaaaaa aaaaaaaaaa aaaaaaaaaa aaaagggtc ggcatggcat ctccacctcc  10860
tcgcggtccg acctgggcat ccgaaggagg acgcacgtcc actcggatgg ctaagggaga  10920
gccacgttta aaccagctcc aattcgccct atagtgagtc gtattacgcg cgctcactgg  10980
ccgtcgtttt acaacgtcgt gactgggaaa accctggcgt tacccaactt aatcgccttg  11040
cagcacatcc cccttttgcc agctggcgta atagcgaaga ggcccgcacc gatcgccctt  11100
cccaacagtt gcgcagcctg aatggcgaat gggacgcgcc ctgtagcggc gcattaagcg  11160
cggcgggtgt ggtggttacg cgcagcgtga ccgctacact tgccagcgcc ctagcgcccg  11220
ctcctttcgc tttcttccct tcctttctcg ccacgttcgc cggctttccc cgtcaagctc  11280
taaatcgggg gctcccttta gggttccgat ttagtgcttt acggcacctc gaccccaaaa  11340
aacttgatta gggtgatggt tcacgtagtg gccatcgcc ctgatagacg ttttttcgcc  11400
ctttgacgtt ggagtccacg ttctttaata gtggactctt gttccaaact ggaacaacac  11460
tcaaccctat ctcggtctat tcttttgatt tataagggat tttgccgatt tcggcctatt  11520
ggttaaaaaa tgagctgatt taacaaaaat ttaacgcgaa ttttaacaaa atattaacgc  11580
ttacaattta ggtggcactt ttcggggaaa tgtgcgcgga accctatttt gtttattttt  11640
ctaaatacat tcaaatatgt atccgctcat gagacaataa ccctgataaa tgcttcaata  11700
atattgaaaa aggaagagta tgagtattca acatttccgt gtcgccctta ttcccttttt  11760
tgcggcattt tgccttcctg ttttgctca cccagaaacg ctggtgaaag taaaagatgc  11820
tgaagatcag ttgggtgcac gagtgggtta catcgaactg gatctcaaca gcggtaagat  11880
ccttgagagt tttcgccccg aagaacgttt tccaatgatg agcactttta aagttctgct  11940
atgtggcgcg gtattatccc gtattgacgc cgggcaagag caactcggtc gccgcataca  12000
ctattctcag aatgacttgg ttgagtactc accagtcaca gaaaagcatc ttacggatgg  12060
catgacagta agagaattat gcagtgctgc cataaccatg agtgataaca ctgcggccaa  12120
```

```
cttacttctg acaacgatcg gaggaccgaa ggagctaacc gcttttttgc acaacatggg    12180
ggatcatgta actcgccttg atcgttggga accggagctg aatgaagcca taccaaacga    12240
cgagcgtgac accacgatgc ctgtagcaat ggcaacaacg ttgcgcaaac tattaactgg    12300
cgaactactt actctagctt cccggcaaca attaatagac tggatggagg cggataaagt    12360
tgcaggacca cttctgcgct cggcccttcc ggctggctgg tttattgctg ataaatctgg    12420
agccggtgag cgtgggtctc gcggtatcat tgcagcactg gggccagatg gtaagccctc    12480
ccgtatcgta gttatctaca cgacggggag tcaggcaact atggatgaac gaaatagaca    12540
gatcgctgag ataggtgcct cactgattaa gcattggtaa ctgtcagacc aagtttactc    12600
atatatactt tagattgatt taaaacttca tttttaattt aaaaggatct aggtgaagat    12660
cctttttgat aatctcatga ccaaaatccc ttaacgtgag ttttcgttcc actgagcgtc    12720
agaccccgta gaaaagatca aaggatcttc ttgagatcct ttttttctgc gcgtaatctg    12780
ctgcttgcaa acaaaaaaac caccgctacc agcggtggtt tgtttgccgg atcaagagct    12840
accaactctt tttccgaagg taactggctt cagcagagcg cagataccaa atactgttct    12900
tctagtgtag ccgtagttag gccaccactt caagaactct gtagcaccgc ctacatacct    12960
cgctctgcta atcctgttac cagtggctgc tgccagtggc gataagtcgt gtcttaccgg    13020
gttggactca agacgatagt taccggataa ggcgcagcgg tcgggctgaa cggggggttc    13080
gtgcacacag cccagcttgg agcgaacgac ctacaccgaa ctgagatacc tacagcgtga    13140
gctatgagaa agcgccacgc ttcccgaagg gagaaaggcg gacaggtatc cggtaagcgg    13200
cagggtcgga acaggagagc gcacgaggga gcttccaggg ggaaacgcct ggtatcttta    13260
tagtcctgtc gggtttcgcc acctctgact tgagcgtcga ttttttgtgat gctcgtcagg    13320 ggggcggagc ctatggaaaa acgccagcaa cgcggccttt ttacggttcc tggccttttg    13380
ctggcctttt gctcacatgt tctttcctgc gttatcccct gattctgtgg ataaccgtat    13440
taccgccttt gagtgagctg ataccgctcg ccgcagccga acgaccgagc gcagcgagtc    13500
agtgagcgag gaagcggaag agcgcccaat acgcaaaccg cctctccccg cgcgttggcc    13560
gattcattaa tgcagctggc acgacaggtt tcccgactgg aaagcgggca gtgagcgcaa    13620
cgcaattaat gtgagttagc tcactcatta ggcacccag gctttacact ttatgctccc    13680
ggctcgtatg ttgtgtggaa ttgtgagcgg ataacaattt cacacaggaa acagctatga    13740
ccatgattac gccaagcgcg caattaaccc tcactaaagg gaacaaaagc tgggtaccgg    13800 gccccacgcgt aatacgactc actatag                                        13827
```

<210> SEQ ID NO 25
<211> LENGTH: 12604
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25

```
ataggcggcg catgagagaa gcccagacca attacctacc caaaatggag aaagttcacg       60
ttgacatcga ggaagacagc ccattcctca gagctttgca gcggagcttc ccgcagtttg      120
aggtagaagc caagcaggtc actgataatg accatgctaa tgccagagcg ttttcgcatc      180
tggcttcaaa actgatcgaa acggaggtgg acccatccga cacgatcctt gacattggaa      240
gtgcgcccgc ccgcagaatg tattctaagc acaagtatca ttgtatctgt ccgatgagat      300
```

```
gtgcggaaga tccggacaga ttgtataagt atgcaactaa gctgaagaaa aactgtaagg      360
aaataactga taaggaattg gacaagaaaa tgaaggagct cgccgccgtc atgagcgacc      420
ctgacctgga aactgagact atgtgcctcc acgacgacga gtcgtgtcgc tacgaagggc      480
aagtcgctgt ttaccaggat gtatacgcgg ttgacggacc gacaagtctc tatcaccaag      540
ccaataaggg agttagagtc gcctactgga taggctttga caccacccct tttatgttta      600
agaacttggc tggagcatat ccatcatact ctaccaactg ggccgacgaa accgtgttaa      660
cggctcgtaa cataggccta tgcagctctg acgttatgga gcggtcacgt agagggatgt      720
ccattcttag aaagaagtat ttgaaaccat ccaacaatgt tctattctct gttggctcga      780
ccatctacca cgagaagagg gacttactga ggagctggca cctgccgtct gtatttcact      840
tacgtggcaa gcaaaattac acatgtcggt gtgagactat agttagttgc gacgggtacg      900
tcgttaaaag aatagctatc agtccaggcc tgtatgggaa gccttcaggc tatgctgcta      960
cgatgcaccg cgagggattc ttgtgctgca aagtgacaga cacattgaac ggggagaggg     1020
tctcttttcc cgtgtgcacg tatgtgccag ctacattgtg tgaccaaatg actggcatac     1080
tggcaacaga tgtcagtgcg gacgacgcgc aaaaactgct ggttgggctc aaccagcgta     1140
tagtcgtcaa cggtcgcacc cagagaaaca ccaataccat gaaaaattac cttttgcccg     1200
tagtggccca ggcatttgct aggtgggcaa aggaatataa ggaagatcaa gaagatgaaa     1260
ggccactagg actacgagat agacagttag tcatggggtg ttgttgggct tttagaaggc     1320
acaagataac atctatttat aagcgcccgg atacccaaac catcatcaaa gtgaacagcg     1380
atttccactc attcgtgctg cccaggatag gcagtaacac attggagatc gggctgagaa     1440
caagaatcag gaaaatgtta gaggagcaca aggagccgtc acctctcatt accgccgagg     1500
acgtacaaga agctaagtgc gcagccgatg aggctaagga ggtgcgtgaa gccgaggagt     1560
tgcgcgcagc tctaccacct ttggcagctg atgttgagga gcccactctg gaagccgatg     1620
tagacttgat gttacaagag gctggggccg gctcagtgga gacacctcgt ggcttgataa     1680
aggttaccag ctacgatggc gaggacaaga tcggctctta cgctgtgctt tctccgcagg     1740
ctgtactcaa gagtgaaaaa ttatcttgca tccaccctct cgctgaacaa gtcatagtga     1800
taacacactc tggccgaaaa gggcgttatg ccgtggaacc ataccatggt aaagtagtgg     1860
tgccagaggg acatgcaata cccgtccagg actttcaagc tctgagtgaa agtgccacca     1920
ttgtgtacaa cgaacgtgag ttcgtaaaca ggtacctgca ccatattgcc acacatggag     1980
gagcgctgaa cactgatgaa gaatattaca aaactgtcaa gcccagcgag cacgacggcg     2040
aataccgtta cgacatcgac aggaaacagt gcgtcaagaa agaactagtc actgggctag     2100
ggctcacagg cgagctggtg gatcctccct tccatgaatt cgcctacgag agtctgagaa     2160
cacgaccagc cgctccttac caagtaccaa ccatagggt gtatggcgtg ccaggatcag     2220
gcaagtctgg catcattaaa agcgcagtca ccaaaaaaga tctagtggtg agcgccaaga     2280
aagaaaactg tgcagaaatt ataagggacg tcaagaaaat gaaagggctg gacgtcaatg     2340
ccagaactgt ggactcagtg ctcttgaatg gatgcaaaca ccccgtagag accctgtata     2400
ttgacgaagc ttttgcttgt catgcaggta ctctcagagc gctcatagcc attataagac     2460
ctaaaaaggc agtgctctgc ggggatccca acagtgcgg ttttttttaac atgatgtgcc     2520 tgaaagtgca tttaaccac gagatttgca cacaagtctt ccacaaaagc atctctcgcc     2580
gttgcactaa atctgtgact tcggtcgtct caaccttgtt ttacgacaaa aaaatgagaa     2640
```

```
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactgaaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccccc atataaatac catcactatc   3720
agcagtgtga gaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggtg tgcggagcgc   4140 tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaaccccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag gctacagcag   4620
caagcgatgg caaaacttc tcatatttgg aagggaccaa gtttcaccag gcggccaagg   4680
atatagcaga aattaatgcc atgtggccccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tccttttcat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
```

| | |
|---|---|
| acgagactcc ggagccatcg gcagagaacc aatccacaga ggggacacct gaacaaccac | 5100 |
| cacttataac cgaggatgag accaggacta gaacgcctga gccgatcatc atcgaagagg | 5160 |
| aagaagagga tagcataagt ttgctgtcag atggcccgac ccaccaggtg ctgcaagtcg | 5220 |
| aggcagacat tcacgggccg ccctctgtat ctagctcatc ctggtccatt cctcatgcat | 5280 |
| ccgactttga tgtggacagt ttatccatac ttgacaccct ggagggagct agcgtgacca | 5340 |
| gcggggcaac gtcagccgag actaactctt acttcgcaaa gagtatggag tttctggcgc | 5400 |
| gaccggtgcc tgcgcctcga acagtattca ggaaccctcc acatcccgct ccgcgcacaa | 5460 |
| gaacaccgtc acttgcaccc agcagggcct gctcgagaac cagcctagtt tccaccccgc | 5520 |
| caggcgtgaa tagggtgatc actagagagg agctcgaggc gcttaccccg tcacgcactc | 5580 |
| ctagcaggtc ggtctcgaga accagcctgg tctccaaccc gccaggcgta aatagggtga | 5640 |
| ttacaagaga ggagtttgag gcgttcgtag cacaacaaca atgacggttt gatgcgggtg | 5700 |
| catacatctt ttcctccgac accggtcaag ggcatttaca acaaaaatca gtaaggcaaa | 5760 |
| cggtgctatc cgaagtggtg ttggagagga ccgaattgga gatttcgtat gccccgcgcc | 5820 |
| tcgaccaaga aaaagaagaa ttactacgca agaaattaca gttaaatccc acacctgcta | 5880 |
| acagaagcag ataccagtcc aggaaggtgg agaacatgaa agccataaca gctagacgta | 5940 |
| ttctgcaagg cctagggcat tatttgaagg cagaaggaaa agtggagtgc taccgaaccc | 6000 |
| tgcatcctgt tcctttgtat tcatctagtg tgaaccgtgc cttttcaagc cccaaggtcg | 6060 |
| cagtggaagc ctgtaacgcc atgttgaaag agaactttcc gactgtggct tcttactgta | 6120 |
| ttattccaga gtacgatgcc tatttggaca tggttgacgg agcttcatgc tgcttagaca | 6180 |
| ctgccagttt ttgccctgca aagctgcgca gctttccaaa gaaacactcc tatttggaac | 6240 |
| ccacaatacg atcggcagtg ccttcagcga tccagaacac gctccagaac gtcctggcag | 6300 |
| ctgccacaaa aagaaattgc aatgtcacgc aaatgagaga attgcccgta ttggattcgg | 6360 |
| cggcctttaa tgtggaatgc ttcaagaaat atgcgtgtaa taatgaatat tgggaaacgt | 6420 |
| ttaaagaaaa ccccatcagg cttactgaag aaaacgtggt aaattacatt accaaattaa | 6480 |
| aaggaccaaa agctgctgct cttttttgcga agacacataa tttgaatatg ttgcaggaca | 6540 |
| taccaatgga caggtttgta atggacttaa agagagacgt gaaagtgact ccaggaacaa | 6600 |
| aacatactga agaacggccc aaggtacagg tgatccaggc tgccgatccg ctagcaacag | 6660 |
| cgtatctgtg cggaatccac cgagagctgg ttaggagatt aaatgcggtc ctgcttccga | 6720 |
| acattcatac actgtttgat atgtcggctg aagactttga cgctattata gccgagcact | 6780 |
| tccagcctgg ggattgtgtt ctggaaactg acatcgcgtc gtttgataaa agtgaggacg | 6840 |
| acgccatggc tctgaccgcg ttaatgattc tggaagactt aggtgtggac gcagagctgt | 6900 |
| tgacgctgat tgaggcggct ttcggcgaaa tttcatcaat acatttgccc actaaaacta | 6960 |
| aatttaaatt cggagccatg atgaaatctg aatgttcct cacactgttt gtgaacacag | 7020 |
| tcattaacat tgtaatcgca agcagagtgt tgagagaacg gctaaccgga tcaccatgtg | 7080 |
| cagcattcat tggagatgac aatatcgtga aaggagtcaa atcggacaaa ttaatggcag | 7140 |
| acaggtgcgc cacctggttg aatatggaag tcaagattat agatgctgtg gtgggcgaga | 7200 |
| aagcgcctta tttctgtgga gggtttattt tgtgtgactc cgtgaccggc acagcgtgcc | 7260 |
| gtgtggcaga ccccctaaaa aggctgttta agcttggcaa acctctggca gcagacgatg | 7320 |
| aacatgatga tgacaggaga agggcattgc atgaagagtc aacacgctgg aaccgagtgg | 7380 |

-continued

```
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgagtct    7560
agtcgacgcc accatgggca ccgtgaacaa gcctgtcgtg ggcgtgctga tgggcttcgg    7620
catcatcacc ggcaccctga gaatcaccaa ccctgtgcgg gccagcgtgc tgagatacga    7680
cgacttccac atcgacgagg acaagctgga caccaacagc gtgtacgagc cctactacca    7740
cagcgaccac gccgagagca gctgggtcaa cagaggcgag agcagccgga aggcctacga    7800
ccacaacagc ccctacatct ggccccggaa cgactacgac ggcttcctgg aaaacgccca    7860
cgagcaccac ggcgtgtaca atcagggcag aggcatcgac agcggcgaga gactgatgca    7920
gcccacacag atgagcgccc aggaagatct gggcgacgac acaggcatcc acgtgatccc    7980
cacccctgaac ggcgacgacc ggcacaagat cgtgaacgtg gaccagcggc agtacggcga    8040
cgtgttcaag ggcgacctga accctaagcc ccagggccag agactgatcg aggtgtccgt    8100
ggaagagaac cacccttca ccctgagagc ccccatccga agaatctacg gcgtgcggta    8160
taccgagact tggagcttcc tgcccagcct gacctgtaca ggcgacgccg ctcctgccat    8220
ccagcacatc tgcctgaagc acaccacctg tttccaggac gtggtggtgg acgtggactg    8280
cgccgagaac accaaagagg accagctggc cgagatcagc taccggttcc agggcaagaa    8340
agaggccgac cagccctgga tcgtggtcaa taccagcacc ctgttcgacg agctggaact    8400
ggaccccccc gagattgaac ccggcgtgct gaaggtgctg cggaccgaga agcagtacct    8460
gggcgtgtac atctggaaca tgcggggctc cgacggcacc tctacctacg ccaccttcct    8520
ggtcacatgg aagggcgacg agaaaacccg gaaccctacc cctgccgtga cccctcagcc    8580
tagaggcgcc gagttccata tgtggaatta ccactcccac gtgttcagcg tgggcgacac    8640
cttcagcctg gccatgcatc tgcagtacaa gatccacgag gcccccttcg acctgctgct    8700
ggaatggctg tacgtgccca tcgacccctac ctgccagccc atgcggctgt acagcacctg    8760
tctgtaccac cccaacgccc ctcagtgcct gagccacatg aacagcggct gcaccttcac    8820
cagccctcac ctggctcaga gggtggccag caccgtgtac cagaattgcg agcacgccga    8880
caactacacc gcctactgcc tgggcatcag ccacatggaa cccagcttcg gcctgatcct    8940
gcacgatggc ggcaccaccc tgaagttcgt ggacacaccc gagagcctga gcggcctgta    9000
cgtgttcgtg gtgtacttca acggccacgt ggaagccgtg gcctacaccg tggtgtccac    9060
cgtgaccac ttcgtgaacg ccatcgagga aagaggcttc ccacccacag ccggacagcc    9120
tccagccacc accaagccca agaaatcac ccccgtgaac cccggcacca gcccctgct    9180
gagatatgct gcttggacag gcggactggc cgctgtggtg ctgctgtgcc tggtcatctt    9240
cctgatctgc accgccaagc ggatgagagt gaaggcctac cgggtggaca gtcccccta    9300
caaccagagc atgtactacg ccggcctgcc cgtggacgat ttcgaggata gcgagagcac    9360
cgacaccgag gaagagttcg gcaacgccat cggcggatct caccggcgca gcagctacac    9420
cgtgtacatc gacaagacca gataatctag acgcggccgc atacagcagc aattggcaag    9480
ctgcttacat agaactcgcg gcgattggca tgccgcctta aaattttat tttatttttc    9540
ttttctttc cgaatcggat tttgtttta atatttcaaa aaaaaaaaa aaaaaaaaa    9600
aaaaaaaaaa aagggtcggc atggcatctc cacctcctcg cggtccgacc tgggcatccg    9660
aaggaggacg cacgtccact cggatggcta agggagagcc acgtttaaac cagctccaat    9720
tcgccctata gtgagtcgta ttacgcgcgc tcactggccg tcgttttaca acgtcgtgac    9780
```

```
tgggaaaacc ctggcgttac ccaacttaat cgccttgcag cacatccccc tttcgccagc   9840
tggcgtaata gcgaagaggc ccgcaccgat cgcccttccc aacagttgcg cagcctgaat   9900
ggcgaatggg acgcgccctg tagcggcgca ttaagcgcgg cgggtgtggt ggttacgcgc   9960
agcgtgaccg ctacacttgc cagcgcccta gcgcccgctc ctttcgcttt cttcccttcc  10020
tttctcgcca cgttcgccgg ctttccccgt caagctctaa atcggggggct cccctttaggg  10080 ttccgattta gtgctttacg gcacctcgac cccaaaaaac ttgattaggg tgatggttca  10140
cgtagtgggc catcgccctg atagacggtt tttcgcccctt tgacgttgga gtccacgttc  10200
tttaatagtg gactcttgtt ccaaactgga acaacactca accctatctc ggtctattct  10260
tttgatttat aagggatttt gccgatttcg gcctattggt taaaaaatga gctgatttaa  10320
caaaaattta acgcgaattt taacaaaata ttaacgctta caatttaggt ggcacttttc  10380
ggggaaatgt gcgcggaacc cctatttgtt tatttttcta aatacattca aatatgtatc  10440
cgctcatgag acaataaccc tgataaatgc ttcaataata ttgaaaaagg aagagtatga  10500
gtattcaaca tttccgtgtc gcccttattc ccttttttgc ggcattttgc cttcctgttt  10560
ttgctcaccc agaaacgctg gtgaaagtaa aagatgctga agatcagttg ggtgcacgag  10620
tgggttacat cgaactggat ctcaacagcg gtaagatcct tgagagtttt cgccccgaag  10680
aacgttttcc aatgatgagc acttttaaag ttctgctatg tggcgcggta ttatcccgta  10740
ttgacgccgg gcaagagcaa ctcggtcgcc gcatacacta ttctcagaat gacttggttg  10800
agtactcacc agtcacagaa aagcatctta cggatggcat gacagtaaga gaattatgca  10860
gtgctgccat aaccatgagt gataacactg cggccaactt acttctgaca acgatcggag  10920
gaccgaagga gctaaccgct tttttgcaca acatggggga tcatgtaact cgccttgatc  10980
gttgggaacc ggagctgaat gaagccatac caaacgacga gcgtgacacc acgatgcctg  11040
tagcaatggc aacaacgttg cgcaaactat taactggcga actacttact ctagcttccc  11100
ggcaacaatt aatagactgg atggaggcgg ataaagttgc aggaccactt ctgcgctcgg  11160
cccttccggc tggctggttt attgctgata aatctggagc cggtgagcgt gggtctcgcg  11220
gtatcattgc agcactgggg ccagatggta agccctcccg tatcgtagtt atctacacga  11280
cggggagtca ggcaactatg gatgaacgaa atagacagat cgctgagata ggtgcctcac  11340
tgattaagca ttggtaactg tcagaccaag tttactcata tatactttag attgatttaa  11400
aacttcattt ttaatttaaa aggatctagg tgaagatcct tttgataat ctcatgacca  11460 aaatccctta acgtgagttt tcgttccact gagcgtcaga ccccgtagaa aagatcaaag  11520
gatcttcttg agatcctttt tttctgcgcg taatctgctg cttgcaaaca aaaaaaccac  11580
cgctaccagc ggtggtttgt ttgccggatc aagagctacc aactcttttt ccgaaggtaa  11640
ctggcttcag cagagcgcag ataccaaata ctgttcttct agtgtagccg tagttaggcc  11700
accacttcaa gaactctgta gcaccgccta catacctcgc tctgctaatc ctgttaccag  11760
tggctgctgc cagtggcgat aagtcgtgtc ttaccgggtt ggactcaaga cgatagttac  11820
cggataaggc gcagcggtcg ggctgaacgg ggggttcgtg cacacagccc agcttggagc  11880
gaacgaccta caccgaactg agatacctac agcgtgagct atgagaaagc gccacgcttc  11940
ccgaagggag aaaggcggac aggtatccgg taagcggcag ggtcggaaca ggagagcgca  12000
cgagggagct tccaggggga aacgcctggt atctttatag tcctgtcggg tttcgccacc  12060
tctgacttga gcgtcgattt ttgtgatgct cgtcaggggg gcggagccta tggaaaaacg  12120
```

| | |
|---|---:|
| ccagcaacgc ggccttttta cggttcctgg ccttttgctg gccttttgct cacatgttct | 12180 |
| ttcctgcgtt atcccctgat tctgtggata accgtattac cgccttttgag tgagctgata | 12240 |
| ccgctcgccg cagccgaacg accgagcgca gcgagtcagt gagcgaggaa gcggaagagc | 12300 |
| gcccaatacg caaaccgcct ctccccgcgc gttggccgat tcattaatgc agctggcacg | 12360 |
| acaggtttcc cgactggaaa gcgggcagtg agcgcaacgc aattaatgtg agttagctca | 12420 |
| ctcattaggc accccaggct ttacacttta tgctcccggc tcgtatgttg tgtggaattg | 12480 |
| tgagcggata caatttcac acaggaaaca gctatgacca tgattacgcc aagcgcgcaa | 12540 |
| ttaaccctca ctaaagggaa caaaagctgg gtaccgggcc cacgcgtaat acgactcact | 12600 |
| atag | 12604 |

<210> SEQ ID NO 26
<211> LENGTH: 11797
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

| | |
|---|---:|
| ataggcggcg catgagagaa gcccagacca attacctacc caaaatggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |
| gtgcggaaga tccggacaga ttgtataagt atgcaactaa gctgaagaaa aactgtaagg | 360 |
| aaataactga taaggaattg gacaagaaaa tgaaggagct cgccgccgtc atgagcgacc | 420 |
| ctgacctgga aactgagact atgtgcctcc acgacgacga gtcgtgtcgc tacgaagggc | 480 |
| aagtcgctgt ttaccaggat gtatacgcgg ttgacggacc gacaagtctc tatcaccaag | 540 |
| ccaataaggg agttagagtc gcctactgga taggctttga caccacccct tttatgttta | 600 |
| agaacttggc tggagcatat ccatcatact ctaccaactg ggccgacgaa accgtgttaa | 660 |
| cggctcgtaa cataggccta tgcagctctg acgttatgga gcggtcacgt agagggatgt | 720 |
| ccattcttag aaagaagtat ttgaaaccat ccaacaatgt tctattctct gttggctcga | 780 |
| ccatctacca cgagaagagg gacttactga ggagctggca cctgccgtct gtatttcact | 840 |
| tacgtggcaa gcaaaattac acatgtcggt gtgagactat agttagttgc gacgggtacg | 900 |
| tcgttaaaag aatagctatc agtccaggcc tgtatgggaa gccttcaggc tatgctgcta | 960 |
| cgatgcaccg cgagggattc ttgtgctgca aagtgacaga cacattgaac ggggagaggg | 1020 |
| tctcttttcc cgtgtgcacg tatgtgccag ctacattgtg tgaccaaatg actggcatac | 1080 |
| tggcaacaga tgtcagtgcg gacgacgcgc aaaaactgct ggttgggctc aaccagcgta | 1140 |
| tagtcgtcaa cggtcgcacc cagagaaaca ccaataccat gaaaaattac cttttgcccg | 1200 |
| tagtggccca ggcatttgct aggtgggcaa aggaatataa ggaagatcaa gaagatgaaa | 1260 |
| ggccactagg actacgagat agacagttag tcatggggtg ttgttgggct tttagaaggc | 1320 |
| acaagataac atctatttat aagcgcccgg atacccaaac catcatcaaa gtgaacagcg | 1380 |
| atttccactc attcgtgctg cccaggatag gcagtaacac attggagatc gggctgagaa | 1440 |
| caagaatcag gaaaatgtta gaggagcaca aggagccgtc acctctcatt accgccgagg | 1500 |

-continued

```
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg    2340 ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttttaac atgatgtgcc    2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga aataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggaccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
```

```
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggaggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt ccacccccgc   5520
caggcgtgaa tagggtgatc actagagagg agctcgaggc gcttacccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag gcatttaca acaaaaatca gtaaggcaaa   5760
cggtgctatc cgaagtggtg ttggagagga ccgaattgga gatttcgtat gccccgcgcc   5820
tcgaccaaga aaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tccttgtat tcatctagtg tgaaccgtgc cttttcaagc cccaaggtcg   6060
cagtggaagc ctgtaacgcc atgttgaaag agactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
```

```
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgtttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgagtct    7560
agtcgacgcc accatgtttc tgatccagtg cctgatcagc gccgtgatct tctatattca    7620
agtcacaaac gccctgatct ttaagggcga ccacgtgtca ctgcaggtca acagcagcct    7680
gaccagcatc ctgatcccca tgcagaacga caattcaccc gagatcaagg gccagctggt    7740
gttcatcggc gagcagctgc ccaccggcac caattacagc ggcaccctgg aactgctgta    7800
cgccgatacc gtggccttct gcttcagaag cgtgcaggtc atcagatacg acggctgccc    7860
ccggatcaga accagcgcct tcatcagctg ccggtacaag cacagctggc actacggcaa    7920
cagcaccgac cggatcagca ccgaacctga tgccggcgtg atgctgaaga tcaccaagcc    7980
cggcatcaac gacgccggcg tgtacgtgct gctcgtgcgg ctggatcaca gcagaagcac    8040
cgacggcttc atcctgggcg tgaacgtgta caccgccggc agccaccaca catccacgg    8100 cgtgatctac accagcccca gcctgcagaa cggctacagc accagagccc tgttccagca    8160
ggccagactg tgcgatctgc ccgccacacc taagggcagc ggcacaagcc tgtttcagca    8220
catgctggac ctgagagccg gcaagagcct ggaagataac ccctggctgc acgaggacgt    8280
ggtcaccacc gagacaaaga gcgtggtcaa agagggcatc gagaaccacg tgtacccac    8340 cgacatgagc accctgcccg agaagtccct gaacgacccc cctgagaacc tgctgatcat    8400
catccccatc gtggccagcg tgatgatcct gaccgccatg gtcatcgtga tcgtgatcag    8460
cgtgaagcgg cggagaatca agaagcaccc catctaccgg cccaacacca agaccagacg    8520
gggcatccag aacgccaccc ctgagtccga cgtgatgctg gaagccgcca ttgcccagct    8580
```

```
ggccaccatc agagaggaaa gccccccctca cagcgtcgtg aaccccttcg tgaagtaatc    8640
tagacgcggc cgcatacagc agcaattggc aagctgctta catagaactc gcggcgattg    8700
gcatgccgcc ttaaaatttt tattttattt ttcttttctt ttccgaatcg gattttgttt    8760
ttaatatttc aaaaaaaaaa aaaaaaaaaa aaaaaaaaaa aaaaagggtc ggcatggcat    8820
ctccacctcc tcgcggtccg acctgggcat ccgaaggagg acgcacgtcc actcggatgg    8880
ctaagggaga gccacgttta aaccagctcc aattcgccct atagtgagtc gtattacgcg    8940
cgctcactgg ccgtcgtttt acaacgtcgt gactgggaaa accctggcgt tacccaactt    9000
aatcgccttg cagcacatcc ccctttcgcc agctggcgta atagcgaaga ggcccgcacc    9060
gatcgccctt cccaacagtt gcgcagcctg aatggcgaat gggacgcgcc ctgtagcggc    9120
gcattaagcg cggcgggtgt ggtggttacg cgcagcgtga ccgctacact tgccagcgcc    9180
ctagcgcccg ctcctttcgc tttcttccct tcctttctcg ccacgttcgc cggctttccc    9240
cgtcaagctc taaatcgggg gctcccttta gggttccgat ttagtgcttt acggcacctc    9300
gaccccaaaa aacttgatta gggtgatggt tcacgtagtg ggccatcgcc ctgatagacg    9360
gtttttcgcc ctttgacgtt ggagtccacg ttctttaata gtggactctt gttccaaact    9420
ggaacaacac tcaaccctat ctcggtctat tcttttgatt tataagggat tttgccgatt    9480
tcggcctatt ggttaaaaaa tgagctgatt taacaaaaat ttaacgcgaa ttttaacaaa    9540
atattaacgc ttacaattta ggtggcactt ttcggggaaa tgtgcgcgga acccctattt    9600
gtttattttt ctaaatacat tcaaatatgt atccgctcat gagacaataa ccctgataaa    9660
tgcttcaata atattgaaaa aggaagagta tgagtattca acatttccgt gtcgccctta    9720
ttccctttt  tgcggcattt tgccttcctg tttttgctca cccagaaacg ctggtgaaag    9780
taaaagatgc tgaagatcag ttgggtgcac gagtgggtta catcgaactg gatctcaaca    9840
gcggtaagat ccttgagagt tttcgccccg aagaacgttt tccaatgatg agcactttta    9900
aagttctgct atgtggcgcg gtattatccc gtattgacgc cgggcaagag caactcggtc    9960
gccgcataca ctattctcag aatgacttgg ttgagtactc accagtcaca gaaaagcatc   10020
ttacggatgg catgacagta agagaattat gcagtgctgc cataaccatg agtgataaca   10080
ctgcggccaa cttacttctg acaacgatcg gaggaccgaa ggagctaacc gcttttttgc   10140
acaacatggg ggatcatgta actcgcctg atcgttggga accggagctg aatgaagcca   10200
taccaaacga cgagcgtgac accacgatgc ctgtagcaat ggcaacaacg ttgcgcaaac   10260
tattaactgg cgaactactt actctagctt cccggcaaca attaatagac tggatggagg   10320
cggataaagt tgcaggacca cttctgcgct cggcccttcc ggctggctgg tttattgctg   10380
ataaatctgg agccggtgag cgtgggtctc gcggtatcat tgcagcactg gggccagatg   10440
gtaagccctc ccgtatcgta gttatctaca cgacggggag tcaggcaact atggatgaac   10500
gaaatagaca gatcgctgag ataggtgcct cactgattaa gcattggtaa ctgtcagacc   10560
aagtttactc atatatactt tagattgatt taaaacttca ttttaatttt aaaaggatct   10620
aggtgaagat cctttttgat aatctcatga ccaaaatccc ttaacgtgag ttttcgttcc   10680
actgagcgtc agaccccgta gaaaagatca aaggatcttc ttgagatcct ttttttctgc   10740
gcgtaatctg ctgcttgcaa acaaaaaaac caccgctacc agcggtggtt tgtttgccgg   10800
atcaagagct accaactctt tttccgaagg taactggctt cagcagagcg cagataccaa   10860
atactgttct tctagtgtag ccgtagttag gccaccactt caagaactct gtagcaccgc   10920
ctacatacct cgctctgcta atcctgttac cagtggctgc tgccagtggc gataagtcgt   10980
```

```
gtcttaccgg gttggactca agacgatagt taccggataa ggcgcagcgg tcgggctgaa    11040 cgggggggttc gtgcacacag cccagcttgg agcgaacgac ctacaccgaa ctgagatacc    11100
tacagcgtga gctatgagaa agcgccacgc ttcccgaagg gagaaaggcg acaggtatc     11160 cggtaagcgg cagggtcgga acaggagagc gcacgaggga gcttccaggg ggaaacgcct    11220
ggtatcttta tagtcctgtc gggtttcgcc acctctgact tgagcgtcga tttttgtgat    11280
gctcgtcagg ggggcggagc ctatggaaaa acgccagcaa cgcggccttt ttacggttcc    11340
tggccttttg ctggcctttt gctcacatgt tctttcctgc gttatcccct gattctgtgg    11400
ataaccgtat taccgccttt gagtgagctg ataccgctcg ccgcagccga acgaccgagc    11460
gcagcgagtc agtgagcgag gaagcggaag agcgcccaat acgcaaaccg cctctccccg    11520
cgcgttggcc gattcattaa tgcagctggc acgacaggtt cccgactgg aaagcgggca    11580 gtgagcgcaa cgcaattaat gtgagttagc tcactcatta ggcaccccag ctttacact     11640 ttatgctccc ggctcgtatg ttgtgtggaa ttgtgagcgg ataacaattt cacacaggaa    11700
acagctatga ccatgattac gccaagcgcg caattaaccc tcactaaagg gaacaaaagc    11760
tgggtaccgg gccacgcgt aatacgactc actatag                              11797
```

<210> SEQ ID NO 27
<211> LENGTH: 13755
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccaccccct tttatgttta     600 agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
```

-continued

```
tagtcgtcaa cggtcgcacc cagagaaaca ccaataccat gaaaaattac cttttgcccg      1200
tagtggccca ggcatttgct aggtgggcaa aggaatataa ggaagatcaa gaagatgaaa      1260
ggccactagg actacgagat agacagttag tcatggggtg ttgttgggct tttagaaggc      1320
acaagataac atctatttat aagcgcccgg atacccaaac catcatcaaa gtgaacagcg      1380
atttccactc attcgtgctg cccaggatag gcagtaacac attggagatc gggctgagaa      1440
caagaatcag gaaaatgtta gaggagcaca aggagccgtc acctctcatt accgccgagg      1500
acgtacaaga agctaagtgc gcagccgatg aggctaagga ggtgcgtgaa gccgaggagt      1560
tgcgcgcagc tctaccacct ttggcagctg atgttgagga gcccactctg gaagccgatg      1620
tagacttgat gttacaagag gctggggccg gctcagtgga gacacctcgt ggcttgataa      1680
aggttaccag ctacgatggc gaggacaaga tcggctctta cgctgtgctt tctccgcagg      1740
ctgtactcaa gagtgaaaaa ttatcttgca tccaccctct cgctgaacaa gtcatagtga      1800
taacacactc tggccgaaaa gggcgttatg ccgtggaacc ataccatggt aaagtagtgg      1860
tgccagaggg acatgcaata cccgtccagg actttcaagc tctgagtgaa agtgccacca      1920
ttgtgtacaa cgaacgtgag ttcgtaaaca ggtacctgca ccatattgcc acacatggag      1980
gagcgctgaa cactgatgaa gaatattaca aaactgtcaa gcccagcgag cacgacggcg      2040
aatacctgta cgacatcgac aggaaacagt gcgtcaagaa agaactagtc actgggctag      2100
ggctcacagg cgagctggtg gatcctccct tccatgaatt cgcctacgag agtctgagaa      2160
cacgaccagc cgctccttac caagtaccaa ccatagggt gtatggcgtg ccaggatcag      2220
gcaagtctgg catcattaaa agcgcagtca ccaaaaaaga tctagtggtg agcgccaaga      2280
aagaaaactg tgcagaaatt ataagggacg tcaagaaaat gaaagggctg gacgtcaatg      2340
ccagaactgt ggactcagtg ctcttgaatg gatgcaaaca ccccgtagag accctgtata      2400
ttgacgaagc ttttgcttgt catgcaggta ctctcagagc gctcatagcc attataagac      2460
ctaaaaaggc agtgctctgc ggggatccca aacagtgcgg ttttttttaac atgatgtgcc      2520
tgaaagtgca ttttaaccac gagatttgca cacaagtctt ccacaaaagc atctctcgcc      2580
gttgcactaa atctgtgact tcggtcgtct caaccttgtt ttacgacaaa aaaatgagaa      2640
cgacgaatcc gaaagagact aagattgtga ttgacactac cggcagtacc aaacctaagc      2700
aggacgatct cattctcact tgtttcagag ggtgggtgaa gcagttgcaa atagattaca      2760
aaggcaacga ataatgacg gcagctgcct ctcaagggct gacccgtaaa ggtgtgtatg      2820
ccgttcggta caaggtgaat gaaaatcctc tgtacgcacc cacctcagaa catgtgaacg      2880
tcctactgac ccgcacggag gaccgcatcg tgtggaaaac actagccggc gacccatgga      2940
taaaaacact gactgccaag tacccgggga atttcactgc cacgatagag gagtggcaag      3000
cagagcatga tgccatcatg aggcacatct ggagagacc ggaccctacc gacgtcttcc      3060
agaataaggc aaacgtgtgt tgggccaagg ctttagtgcc ggtgctgaag accgctggca      3120
tagacatgac cactgaacaa tggaacactg tggattattt tgaaacggac aaagctcact      3180
cagcagagat agtattgaac caactatgcg tgaggttctt tggactcgat ctggactccg      3240
gtctattttc tgcacccact gttccgttat ccattaggaa taatcactgg gataactccc      3300
cgtcgcctaa catgtacggg ctgaataaag aagtggtccg tcagctctct cgcaggtacc      3360
cacaactgcc tcgggcagtt gccactggaa gagtctatga catgaacact ggtacactgc      3420
gcaattatga tccgcgcata aacctagtac ctgtaaacag aagactgcct catgctttag      3480
tcctccacca taatgaacac ccacagagtg acttttcttc attcgtcagc aaattgaagg      3540
```

```
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag acaacctggg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga ccgatcatc atcgaagagg    5160 aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340 gcgggcaac gtcagccgag actaactctt acttcgcaaa gagtatggag tttctggcgc    5400
gaccggtgcc tgcgcctcga acagtattca ggaaccctcc acatccgct ccgcgcacaa    5460 gaacaccgtc acttgcaccc agcagggcct gctcagaac cagcctagtt tccaccccgc    5520
caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag gcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
```

```
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc tgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatgcag    7140 acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgagtct    7560
agtcgacgcc accatgggca ccgtgaacaa gcctgtcgtg ggcgtgctga tgggcttcgg    7620
catcatcacc ggcacccctga gaatcaccaa ccctgtgcgg gccagcgtgc tgagatacga    7680
cgacttccac atcgacgagg acaagctgga caccaacagc gtgtacgagc ctactacca    7740 cagcgaccac gccgagagca gctgggtcaa cagaggcgag agcagccgga aggcctacga    7800
ccacaacagc ccctacatct ggccccggaa cgactacgac ggcttcctgg aaaacgccca    7860
cgagcaccac ggcgtgtaca atcagggcag aggcatcgac agcggcgaga gactgatgca    7920
gcccacacag atgagcgccc aggaagatct gggcgacgac acaggcatcc acgtgatccc    7980
caccctgaac ggcgacgacc ggcacaagat cgtgaacgtg gaccagcggc agtacgcga    8040 cgtgttcaag ggcgacctga accctaagcc ccagggccag agactgatcg aggtgtccgt    8100
ggaagagaac caccccttca ccctgagagc cccatccag agaatctacg gcgtgcggta    8160
taccgagact tggagcttcc tgcccagcct gacctgtaca ggcgacgccg ctcctgccat    8220
ccagcacatc tgcctgaagc acaccacctg tttccaggac gtggtggtgg acgtggactg    8280
```

```
cgccgagaac accaaagagg accagctggc cgagatcagc taccggttcc agggcaagaa    8340
agaggccgac cagccctgga tcgtggtcaa taccagcacc ctgttcgacg agctggaact    8400
ggacccccc  gagattgaac ccggcgtgct gaaggtgctg cggaccgaga agcagtacct    8460
gggcgtgtac atctggaaca tgcgggctc  cgacggcacc tctacctacg ccaccttcct    8520
ggtcacatgg aagggcgacg agaaaaccg  gaaccctacc cctgccgtga ccctcagcc     8580
tagaggcgcc gagttccata tgtggaatta ccactccac  gtgttcagcg tgggcgacac    8640
cttcagcctg gccatgcatc tgcagtacaa gatccacgag gcccccttcg acctgctgct    8700
ggaatggctg tacgtgccca tcgaccctac ctgccagccc atgcggctgt acagcacctg    8760
tctgtaccac cccaacgccc ctcagtgcct gagccacatg aacagcggct gcaccttcac    8820
cagccctcac ctggctcaga gggtggccag caccgtgtac cagaattgcg agcacgccga    8880
caactacacc gcctactgcc tgggcatcag ccacatggaa cccagcttcg gcctgatcct    8940
gcacgatggc ggcaccaccc tgaagttcgt ggacacaccc gagagcctga gcggcctgta    9000
cgtgttcgtg gtgtacttca acggccacgt ggaagccgtg gcctacaccg tggtgtccac    9060
cgtggaccac ttcgtgaacg ccatcgagga aagaggcttc ccacccacag ccggacagcc    9120
tccagccacc accaagccca agaaatcac  ccccgtgaac cccggcacca gccccctgct    9180
gagatatgct gcttggacag gcggactggc cgctgtggtg ctgctgtgcc tggtcatctt    9240
cctgatctgc accgccaagc ggatgagagt gaaggcctac cgggtggaca gtcccccta    9300
caaccagagc atgtactacg ccggcctgcc cgtggacgat ttcgaggata gcagagcac    9360
cgacaccgag gaagagttcg gcaacgccat cggcggatct cacggcggca gcagctacac    9420
cgtgtacatc gacaagacca gataatctag acgtcgcgac cacccaggat ccgcctataa    9480
ctctctacgg ctaacctgaa tggactacga catagtctag tcgacgccac catgtttctg    9540
atccagtgcc tgatcagcgc cgtgatcttc tatattcaag tcacaaacgc cctgatcttt    9600
aagggcgacc acgtgtcact gcaggtcaac agcagcctga ccagcatcct gatccccatg    9660
cagaacgaca attacaccga gatcaagggc cagctggtgt tcatcggcga gcagctgccc    9720
accggcacca attacagcgg caccctggaa ctgctgtacg ccgataccgt ggccttctgc    9780
ttcagaagcg tgcaggtcat cagatacgac ggctgccccc ggatcagaac cagcgccttc    9840
atcagctgcc ggtacaagca cagctggcac tacggcaaca gcaccgaccg gatcagcacc    9900
gaacctgatg ccggcgtgat gctgaagatc accaagcccg gcatcaacga cgccggcgtg    9960
tacgtgctgc tcgtgcggct ggatcacagc agaagcaccg acggcttcat cctgggcgtg   10020
aacgtgtaca ccgccggcag ccaccacaac atccacggcg tgatctacac cagccccagc   10080
ctgcagaacg gctacagcac cagagccctg ttccagcagg ccagactgtg cgatctgccc   10140
gccacaccta agggcagcgg cacaagcctg tttcagcaca tgctggacct gagagccggc   10200
aagagcctgg aagataaccc ctggctgcac gaggacgtgg tcaccaccga acaaagagc    10260
gtggtcaaag agggcatcga gaaccacgtg tacccaccg  acatgagcac cctgcccgag   10320
aagtccctga cgaccccccc tgagaacctg ctgatcatca tccccatcgt ggccagcgtg   10380
atgatcctga ccgccatggt catcgtgatc gtgatcagct gaagcggcg  gagaatcaag   10440
aagcacccca tctaccggcc caacaccaag accagacggg gcatccagaa cgccacccct   10500
gagtccgacg tgatgctgga agccgccatt gcccagctgg ccaccatcag agaggaaagc   10560
cccccctcaca gcgtcgtgaa ccccttcgtg aagtaatcta gacgcggccg catacagcag   10620
```

```
caattggcaa gctgcttaca tagaactcgc ggcgattggc atgccgcctt aaaatttta   10680
ttttatttt cttttctttt ccgaatcgga ttttgttttt aatatttcaa aaaaaaaaa   10740
aaaaaaaaa aaaaaaaaa aaagggtcgg catggcatct ccacctcctc gcggtccgac   10800
ctgggcatcc gaaggaggac gcacgtccac tcggatggct aagggagagc cacgtttaaa   10860
ccagctccaa ttcgccctat agtgagtcgt attacgcgcg ctcactggcc gtcgttttac   10920
aacgtcgtga ctgggaaaac cctggcgtta cccaacttaa tcgccttgca gcacatcccc   10980
ctttcgccag ctggcgtaat agcgaagagg cccgcaccga tcgcccttcc caacagttgc   11040
gcagcctgaa tggcgaatgg gacgcgccct gtagcggcgc attaagcgcg gcgggtgtgg   11100
tggttacgcg cagcgtgacc gctacacttg ccagcgccct agcgcccgct cctttcgctt   11160
tcttcccttc ctttctcgcc acgttcgccg gctttccccg tcaagctcta atcgggggc   11220
tcccctttagg gttccgattt agtgcttac ggcacctcga ccccaaaaaa cttgattagg   11280
gtgatggttc acgtagtggg ccatcgccct gatagacggt ttttcgccct ttgacgttgg   11340
agtccacgtt ctttaatagt ggactcttgt tccaaactgg aacaacactc aaccctatct   11400
cggtctattc ttttgattta agggattt tgccgatttc ggcctattgg ttaaaaaatg   11460
agctgattta acaaaaattt aacgcgaatt ttaacaaaat attaacgctt acaatttagg   11520
tggcactttt cggggaaatg tgcgcggaac ccctatttgt ttattttct aaatacattc   11580
aaatatgtat ccgctcatga caataaacc ctgataaatg cttcaataat attgaaaaag   11640
gaagagtatg agtattcaac atttccgtgt cgcccttatt cccttttttg cggcattttg   11700
ccttcctgtt tttgctcacc cagaaacgct ggtgaaagta aaagatgctg aagatcagtt   11760
gggtgcacga gtgggttaca tcgaactgga tctcaacagc ggtaagatcc ttgagagttt   11820
tcgccccgaa gaacgttttc caatgatgag cacttttaaa gttctgctat gtggcgcggt   11880
attatcccgt attgacgccg ggcaagagca actcggtcgc cgcatacact attctcagaa   11940
tgacttggtt gagtactcac cagtcacaga aaagcatctt acggatggca tgacagtaag   12000
agaattatgc agtgctgcca taaccatgag tgataacact gcggccaact tacttctgac   12060
aacgatcgga ggaccgaagg agctaaccgc ttttttgcac aacatgggggg atcatgtaac   12120
tcgccttgat cgttgggaac cggagctgaa tgaagccata ccaaacgacg agcgtgacac   12180
cacgatgcct gtagcaatgg caacaacgtt gcgcaaacta ttaactggcg aactacttac   12240
tctagcttcc cggcaacaat taatagactg gatggaggcg gataaagttg caggaccact   12300
tctgcgctcg gcccttccgg ctggctggtt tattgctgat aaatctggag ccggtgagcg   12360
tgggtctcgc ggtatcattg cagcactggg gccagatggt aagccctccc gtatcgtagt   12420
tatctacacg acggggagtc aggcaactat ggatgaacga aatagacaga tcgctgagat   12480
aggtgcctca ctgattaagc attggtaact gtcagaccaa gtttactcat atatactta   12540
gattgattta aaacttcatt tttaatttaa aaggatctag gtgaagatcc ttttgataa   12600
tctcatgacc aaaatccctt aacgtgagtt ttcgttccac tgagcgtcag accccgtaga   12660
aaagatcaaa ggatcttctt gagatccttt ttttctgcgc gtaatctgct gcttgcaaac   12720
aaaaaaacca ccgctaccag cggtggtttg tttgccggat caagagctac caactctttt   12780
tccgaaggta actggcttca gcagagcgca gataccaaat actgttcttc tagtgtagcc   12840
gtagttaggc caccacttca agaactctgt agcaccgcct acatacctcg ctctgctaat   12900
cctgttacca gtggctgctg ccagtggcga taagtcgtgt cttaccgggt tggactcaag   12960
acgatagtta ccggataagg cgcagcggtc gggctgaacg gggggttcgt gcacacagcc   13020
```

-continued

```
cagcttggag cgaacgacct acaccgaact gagataccta cagcgtgagc tatgagaaag    13080
cgccacgctt cccgaaggga gaaaggcgga caggtatccg gtaagcggca gggtcggaac    13140
aggagagcgc acgagggagc ttccaggggg aaacgcctgg tatctttata gtcctgtcgg    13200
gtttcgccac ctctgacttg agcgtcgatt tttgtgatgc tcgtcagggg ggcggagcct    13260
atggaaaaac gccagcaacg cggccttttt acggttcctg gccttttgct ggccttttgc    13320
tcacatgttc tttcctgcgt tatcccctga ttctgtggat aaccgtatta ccgcctttga    13380
gtgagctgat accgctcgcc gcagccgaac gaccgagcgc agcgagtcag tgagcgagga    13440
agcggaagag cgcccaatac gcaaaccgcc tctccccgcg cgttggccga ttcattaatg    13500
cagctggcac gacaggtttc ccgactggaa agcgggcagt gagcgcaacg caattaatgt    13560
gagttagctc actcattagg caccccaggc tttacacttt atgctcccgg ctcgtatgtt    13620
gtgtggaatt gtgagcggat aacaatttca cacaggaaac agctatgacc atgattacgc    13680
caagcgcgca attaaccctc actaaaggga acaaaagctg ggtaccgggc ccacgcgtaa    13740
tacgactcac tatag                                                    13755
```

```
<210> SEQ ID NO 28
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
aaaaaaaaaa aaaaaaaaaa aaaaaaaaaa                                    30
```

US 9,636,410 B2

CATIONIC OIL-IN-WATER EMULSIONS

RELATED APPLICATIONS

This application is the U.S. National Phase of International Application No. PCT/US2012/045845, filed Jul. 6, 2012 and published in English, which claims the benefit of U.S. Provisional Application No. 61/505,109, filed Jul. 6, 2011, U.S. Provisional Application No. 61/545,936, filed Oct. 11, 2011, and U.S. Provisional Application No. 61/585,641, filed Jan. 11, 2012; the entire contents of each of the foregoing patent applications is incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 3, 2014, is named PAT54691.txt and is 424,331 bytes in size.

BACKGROUND OF THE INVENTION

Nucleic acid therapeutics have promise for treating diseases ranging from inherited disorders to acquired conditions such as cancer, infectious disorders (AIDS), heart disease, arthritis, and neurodegenerative disorders (e.g., Parkinson's and Alzheimer's). Not only can functional genes be delivered to repair a genetic deficiency or induce expression of exogenous gene products, but nucleic acid can also be delivered to inhibit endogenous gene expression to provide a therapeutic effect. Inhibition of gene expression can be mediated by, e.g., antisense oligonucleotides, double-stranded RNAs (e.g., siRNAs, miRNAs), or ribozymes.

A key step for such therapy is to deliver nucleic acid molecules into cells in vivo. However, in vivo delivery of nucleic acid molecules, in particular RNA molecules, faces a number of technical hurdles. First, due to cellular and serum nucleases, the half life of RNA injected in vivo is only about 70 seconds (see, e.g., Kurreck, Eur. J. Bioch. 270: 1628-44 (2003)). Efforts have been made to increase stability of injected RNA by the use of chemical modifications; however, there are several instances where chemical alterations led to increased cytotoxic effects or loss of or decreased function. In one specific example, cells were intolerant to doses of an RNAi duplex in which every second phosphate was replaced by phosphorothioate (Harborth, et al, Antisense Nucleic Acid Drug Rev. 13(2): 83-105 (2003)). As such, there is a need to develop delivery systems that can deliver sufficient amounts of nucleic acid molecules (in particular RNA molecules) in vivo to elicit a therapeutic response, but that are not toxic to the host.

Nucleic acid based vaccines are an attractive approach to vaccination. For example, intramuscular (IM) immunization of plasmid DNA encoding for antigen can induce cellular and humoral immune responses and protect against challenge. DNA vaccines offer certain advantages over traditional vaccines using protein antigens, or attenuated pathogens. For example, as compared to protein vaccines, DNA vaccines can be more effective in producing a properly folded antigen in its native conformation, and in generating a cellular immune response. DNA vaccines also do not have some of the safety problems associated with killed or attenuated pathogens. For example, a killed viral preparation may contain residual live viruses, and an attenuated virus may mutate and revert to a pathogenic phenotype.

One limitation of nucleic acid based vaccines is that large doses of nucleic acid are generally required to obtain potent immune responses in non-human primates and humans. Therefore, delivery systems and adjuvants are required to enhance the potency of nucleic acid based vaccines. Various methods have been developed for introducing nucleic acid molecules into cells, such as calcium phosphate transfection, polyprene transfection, protoplast fusion, electroporation, microinjection and lipofection.

Cationic lipids have been formulated as liposomes to deliver genes into cells. In addition, cationic lipid emulsions have been developed to deliver DNA molecules into cells. See, e.g., Kim, et al., International Journal of Pharmaceutics, 295, 35-45 (2005).

Ott et al. (Journal of Controlled Release, volume 79, pages 1-5, 2002) describes an approach involving a cationic sub-micron emulsion as a delivery system/adjuvant for DNA. The sub-micron emulsion approach is based on MF59, a potent squalene in water adjuvant that is a component of commercially approved product Fluad®. 1,2-dioleoyl-3-trimethylammonium-propane (DOTAP) was used to facilitate intracellular delivery of plasmid DNA.

Yi et al. (Pharmaceutical Research, 17, 314-320 (2000)) discloses cationic oil-in-water emulsions that used soybean oil and DOTAP as the cationic lipid. Cholesterol, DOPE, and polymeric lipids were also included in some of the emulsions. The emulsions were shown to enhance the efficiency of in vitro transfection of DNA in the presence of up to 90% serum. The average size of the emulsion particles ranged from 181 nm to 344 nm, and the particle size increased after the emulsions were diluted in PBS buffer.

Kim et al. (Pharmaceutical Research, vol. 18, pages 54-60, 2001) and Chung et al. (Journal of Controlled Release, volume 71, pages 339-350, 2001) disclose various oil-in-water emulsions that were used to enhance in vitro and in vivo transfection efficiency of DNA molecules. Among the cationic lipids tested, DOTAP formed the most stable and efficient emulsion for DNA delivery. Among the oils tested, squalene, light mineral oil, and jojoba bean oil formed stable emulsions with small particles. The efficiencies of in vitro transfection were shown to correlate to the stability of the emulsions (e.g., the emulsion formulated by squalene at 100 mg/mL and DOTAP at 24 mg/mL showed high in vitro transfection efficiency). The emulsions were prepared by first mixing the cationic lipid with water to form a liposome suspension (by sonication). Liposomes were then added to the oil (such as squalene) and the mixture was sonicated to form an oil-in-water emulsion.

RNA molecules encoding an antigen or a derivative thereof may also be used as vaccines. RNA vaccines offer certain advantages as compared to DNA vaccines. However, compared with DNA-based vaccines, relatively minor attention has been given to RNA-based vaccines. RNAs are highly susceptible to degradation by nucleases when administered as a therapeutic or vaccine. Additionally, RNAs are not actively transported into cells. See, e.g., Vajdy, M., et al., *Mucosal adjuvants and delivery systems for protein-, DNA- and RNA-based vaccines*, Immunol Cell Biol, 2004. 82(6): p. 617-27.

Therefore, there is a need to provide delivery systems for nucleic acid molecules or other negatively charged molecules. The delivery systems are useful for nucleic acid-based vaccines, in particular RNA-based vaccines.

SUMMARY OF THE INVENTION

The invention relates to cationic oil-in-water emulsions that contain high concentrations of cationic lipids and have a defined oil:lipid ratio. The oil and cationic lipid are separate components of the emulsions, and preferably the oil is not ionic. The cationic lipid can interact with the negatively charged molecule thereby anchoring the molecule to the emulsion particles. The cationic emulsions described herein are useful for delivering negatively charged molecules, such as nucleic acid molecules (e.g., an RNA molecule encoding an antigen), to cells, and for formulating nucleic acid-based vaccines.

In one aspect, the invention provides an oil-in-water emulsion comprising particles that are dispersed in an aqueous continuous phase, wherein the emulsion is characterized by: (a) the average diameter of said particles is from about 80 nm to 180 nm in diameter; (b) the emulsion comprises an oil and a cationic lipid, wherein (i) the ratio of oil:cationic lipid (mole:mole) is at least about 8:1 (mole:mole), (ii) the concentration of cationic lipid in said emulsion is at least about 2.5 mM, and (iii) with the proviso that the cationic lipid is not DC-Cholesterol. Preferably, the oil-in-water emulsion is stable. In some embodiments, the ratio of oil:lipid (mole:mole) is from about 10:1 (mole:mole) to about 43:1 (mole:mole). The oil in water emulsion can contain from about 0.2% to about 8% (w/v) oil. In some embodiments, the oil is squalene or squalane.

In another aspect, the invention provides an oil-in-water emulsion comprising particles that are dispersed in an aqueous continuous phase, wherein the emulsion is characterized by: (a) the average diameter of said particles is from about 80 nm to 180 nm in diameter; (b) the emulsion comprises an oil and a cationic lipid, wherein (i) the ratio of oil:cationic lipid (mole:mole) is at least about 4:1 (mole:mole), (ii) the concentration of cationic lipid in said emulsion is at least about 2.5 mM, (iii) the oil is present from about 0.2% to about 8% (w/v); and (iv) with the proviso that the cationic lipid is not DC-Cholesterol. Preferably, the oil-in-water emulsion is stable. In some embodiments, the ratio of oil:lipid (mole:mole) is from about 4:1 (mole:mole) to about 43:1 (mole:mole). In some embodiments, the oil is squalene or squalane. In some embodiments, the oil is present from 0.6% to 4% (w/v). In some embodiments, the oil is present from about 1% to about 3.2% (w/v).

The oil-in-water emulsion of this aspect can further comprise a surfactant, such as a nonionic surfactant. Preferably, the surfactant is not a Polyethylene Glycol (PEG)-lipid. The surfactant can be present in an amount from about 0.01% to about 2.5% (w/v). In some embodiments, the surfactant is SPAN85 (Sorbtian Trioleate), Tween 80 (polysorbate 80), or a combination thereof. In some embodiments, the oil-in-water emulsion contains equal amounts of SPAN85 (Sorbtian Trioleate) and Tween 80 (polysorbate 80), for example 0.5% (w/v) of each.

Preferably the head group of the cationic lipid comprises a quaternary amine. For example, in some embodiments the cationic lipid is selected from the group consisting of: 1,2-dioleoyloxy-3-(trimethylammonio)propane (DOTAP), 1,2-dioleoyl-sn-glycero-3-ethylphosphocholine (DOEPC), N,N-dioleoyl-N,N-dimethylammonium chloride (DODAC), and N-[1-(2,3-dioleyloxy)propyl]-N,N,N-trimethylammonium chloride (DOTMA).

In some embodiments, the emulsion is characterized by: (a) the average diameter of the emulsion particles is from about 80 nm to 180 nm in diameter; (b) the emulsion comprises an oil and DOTAP, wherein (i) the ratio of oil:DOTAP (mole:mole) is at least about 8:1 (mole:mole), and (ii) the concentration of DOTAP in said emulsion is at least about 2.58 mM (1.8 mg/mL), or from about 2.58 mM (1.8 mg/mL) to about 7.16 mM (5 mg/mL). The oil can be squalene or squalane.

In some embodiments, the emulsion is characterized by: (a) the average diameter of the emulsion particles is from about 80 nm to 180 nm in diameter; (b) the emulsion comprises an oil and DOTAP, wherein (i) the ratio of oil:DOTAP (mole:mole) is at least about 4:1 (mole:mole), (ii) the concentration of DOTAP in said emulsion is at least about 2.58 mM (1.8 mg/mL), and (iii) the oil is present from about 0.2% to about 8% (w/v). In some embodiments, the oil is squalene or squalane. In some embodiments, the concentration of DOTAP from about 2.58 mM (1.8 mg/mL) to about 7.16 mM (5 mg/mL). In some embodiments, the oil is present from 0.6% to 4% (w/v). In some embodiments, the oil is present from about 1% to about 3.2% (w/v).

The invention also provides a method for preparing an oil-in-water emulsion comprising particles that are dispersed in an aqueous continuous phase, wherein the emulsion is characterized by: (a) the average diameter of said particles is from about 80 nm to 180 nm in diameter; (b) the emulsion comprises an oil and a cationic lipid, wherein (i) the ratio of oil:cationic lipid (mole:mole) is at least about 8:1 (mole:mole), (ii) the concentration of cationic lipid in said emulsion is at least about 2.5 mM, and (iii) with the proviso that the cationic lipid is not DC-Cholesterol, the method comprises (a) directly dissolving the cationic lipid in the oil to form an oil phase; (b) providing an aqueous phase of the emulsion; and (c) dispersing the oil phase in the aqueous phase by homogenization. The oil can be heated to a temperature between about 30° C. to about 65° C. to facilitate dissolution of the cationic lipid in the oil. Higher temperatures may also be used, as long as there is no significant degradation of oil or the cationic lipid.

The invention also provides a method for preparing an oil-in-water emulsion comprising particles that are dispersed in an aqueous continuous phase, wherein the emulsion is characterized by: (a) the average diameter of said particles is from about 80 nm to 180 nm in diameter; (b) the emulsion comprises an oil and a cationic lipid, wherein (i) the ratio of oil:cationic lipid (mole:mole) is at least about 4:1 (mole:mole), (ii) the concentration of cationic lipid in said emulsion is at least about 2.5 mM, (iii) the oil is present from about 0.2% to about 8% (w/v); and (iv) with the proviso that the cationic lipid is not DC-Cholesterol, the method comprises (a) directly dissolving the cationic lipid in the oil to form an oil phase; (b) providing an aqueous phase of the emulsion; and (c) dispersing the oil phase in the aqueous phase by homogenization. The oil can be heated to a temperature between about 30° C. to about 65° C. to facilitate dissolution of the cationic lipid in the oil. Higher temperatures may also be used, as long as there is no significant degradation of oil or the cationic lipid.

In another aspect, the invention provides a composition comprising a nucleic acid molecule (preferably an RNA molecule) complexed with a particle of a cationic oil-in-water emulsion, wherein the particle comprises an oil that is in liquid phase at 25° C., and a cationic lipid; and (i) the ratio of oil:lipid (mole:mole) is at least about 8:1 (mole:mole); (ii) the concentration of cationic lipid in said composition is at least about 1.25 mM; and (iii) with the proviso that the cationic lipid is not DC-Cholesterol. Preferably, the average diameter of the emulsion particles is from about 80 nm to 180 nm, or about 80 nm to 150 nm, or about 80 nm to about 130 nm, and the N/P ratio of the composition is at least about 4:1, or from about 4:1 to about 20:1, or from about 4:1 to about 15:1. In certain embodiments, the ratio of oil:lipid (mole:mole) is from about 10:1 (mole:mole) to about 43:1 (mole:mole). The oil in water emulsion can contain from about 0.1% to about 5% (w/v) oil. In some embodiments, the oil is squalene or squalane.

In another aspect, the invention provides a composition comprising a nucleic acid molecule (preferably an RNA molecule) complexed with a particle of a cationic oil-in-water emulsion, wherein the particle comprises an oil that is in liquid phase at 25° C., and a cationic lipid; and (i) the ratio of oil:lipid (mole:mole) is at least about 4:1 (mole:mole); (ii) the concentration of cationic lipid in said composition is at least about 1.25 mM; (iii) the oil is present from about 0.1% to about 4% (w/v); and (iv) with the proviso that the cationic lipid is not DC-Cholesterol. Preferably, the average diameter of the emulsion particles is from about 80 nm to 180 nm, or about 80 nm to 150 nm, or about 80 nm to about 130 nm, and the N/P ratio of the composition is at least about 4:1, or from about 4:1 to about 20:1, or from about 4:1 to about 15:1. In certain embodiments, the ratio of oil:lipid (mole:mole) is from about 4:1 (mole:mole) to about 43:1 (mole:mole). In some embodiments, the oil is squalene or squalane. In some embodiments, the oil is present from 0.6% to 4% (w/v). In some embodiments, the oil is present from about 1% to about 3.2% (w/v).

The oil-in-water emulsion of this aspect can further comprise a surfactant, such as a nonionic surfactant. Preferably, surfactant is not a Polyethylene Glycol (PEG)-lipid. The surfactant can be present in an amount from about 0.005% to about 1.25% (w/v). In some embodiments, the surfactant is SPAN85 (Sorbtian Trioleate), Tween 80 (polysorbate 80), or a combination thereof. In some embodiments, the oil-in-water emulsion contains equal amounts of SPAN85 (Sorbtian Trioleate) and Tween 80 (polysorbate 80), for example 0.25% or 0.5% (w/v) of each.

Preferably the head group of the cationic lipid comprises a quaternary amine. For example, in some embodiments the cationic lipid is selected from the group consisting of: 1,2-dioleoyloxy-3-(trimethylammonio)propane (DOTAP), 1,2-dioleoyl-sn-glycero-3-ethylphosphocholine (DOEPC), N,N-dioleoyl-N,N-dimethylammonium chloride (DODAC), and N-[1-(2,3-dioleyloxy)propyl]-N,N,N-trimethylammonium chloride (DOTMA).

In some embodiments, the invention provides a composition comprising a nucleic acid molecule (preferably an RNA molecule) complexed with a particle of a cationic oil-in-water emulsion, wherein the particle comprises an oil that is in liquid phase at 25° C. and DOTAP; and (i) the ratio of oil:DOTAP (mole:mole) is at least about 8:1 (mole:mole); (ii) the concentration of DOTAP in said composition is at least about 1.29 mM, or from about 1.29 mM (0.9 mg/mL) to about 3.58 mM (2.5 mg/mL). The oil can be squalene or squalane. Optionally, the N/P ratio is at least 4:1.

In preferred embodiments, the composition is buffered (e.g., with a citrate buffer, succinate buffer, acetate buffer) and has a pH of about 6.0 to about 8.0, preferably about 6.2 to about 6.8. The composition can further comprise an inorganic salt, and the concentration of inorganic salt is preferably no greater than 30 mM. Optionally, the composition can further comprise a nonionic tonicifying agent, and preferably is isotonic.

The invention also provides a method for preparing a composition comprising a nucleic acid molecule (preferably an RNA molecule) complexed with a particle of a cationic oil-in-water emulsion, comprising: (i) providing an oil-in-water emulsion as described herein; (ii) providing an aqueous solution comprising the RNA molecule; and (iii) combining the oil-in-water emulsion of (i) and the aqueous solution of (ii), thereby preparing the composition. In some embodiments, the cationic oil-in-water emulsion and RNA solution are combined at about 1:1 (v/v) ratio. The aqueous solution comprising the RNA molecule is preferably buffered (e.g., with a citrate buffer, succinate buffer, acetate buffer), can contain a inorganic salt (e.g. NaCl), which is preferably present at about 20 mM or less. In one embodiment, the aqueous solution comprising the RNA molecule contains 2 mM citrate buffer and 20 mM NaCl. Optionally, the aqueous solution comprising the RNA molecule further comprises an nonionic tonicifying agent, and is isotonic. In one embodiment, the aqueous solution further comprises about 560 mM sucrose. Optionally, the aqueous solution comprising the RNA molecule further comprises a polymer or nonionic surfactant, such as Pluronic® F127, at from about 0.05% to about 20% (w/v).

In another aspect, the invention provides an oil-in-water emulsion comprising particles that are dispersed in an aqueous continuous phase, wherein the emulsion comprises an oil and a cationic lipid, the average diameter of said particles is from about 80 nm to 180 nm, the oil is present from 0.6% to 4% (w/v); and the concentration of cationic lipid in said emulsion is at least about 1.25 mM. Preferably, the oil-in-water emulsion is stable. In some embodiments, the concentration of cationic lipid in said emulsion is at least about 2.5 mM. In some embodiments, the oil is squalene or squalane.

The oil-in-water emulsion of this aspect can further comprise a surfactant, such as a nonionic surfactant. Preferably, surfactant is not a Polyethylene Glycol (PEG)-lipid. The surfactant can be present in an amount from about 0.01% to about 2.5% (w/v). In some embodiments, the surfactant is SPAN85 (Sorbtian Trioleate), Tween 80 (polysorbate 80), or a combination thereof. In some embodiments, the oil-in-water emulsion contains equal amounts of SPAN85 (Sorbtian Trioleate) and Tween 80 (polysorbate 80), for example 0.25% or 0.5% (w/v) of each.

Preferably the head group of the cationic lipid comprises a quaternary amine. For example, in some embodiments the cationic lipid is selected from the group consisting of: 1,2-dioleoyloxy-3-(trimethylammonio)propane (DOTAP), 1,2-dioleoyl-sn-glycero-3-ethylphosphocholine (DOEPC), N,N-dioleoyl-N,N-dimethylammonium chloride (DODAC), and N-[1-(2,3-dioleyloxy)propyl]-N,N,N-trimethylammonium chloride (DOTMA).

The invention provides a composition comprising a nucleic acid molecule (preferably an RNA molecule) complexed with a particle of an oil-in-water emulsion that contains particles that are dispersed in an aqueous continuous phase, wherein the emulsion comprises an oil and a cationic lipid, the average diameter of said particles is from about 80 nm to 180 nm, the oil is present from 0.6% to 4% (w/v); and the concentration of cationic lipid in said emulsion is at least about 1.25 mM. Preferably, the oil-in-water emulsion is stable. In some embodiments, the concentration of cationic lipid in said emulsion is at least about 2.5 mM. In some embodiments, the oil s squalene or squalane. Preferably, the N/P ratio of the composition is at least about 4:1.

In preferred embodiments, the composition is buffered (e.g., with a citrate buffer, succinate buffer, acetate buffer) and has a pH of about 6.0 to about 8.0, preferably about 6.2 to about 6.8. The composition can further comprise an inorganic salt, and the concentration of inorganic salt is preferably no greater than 30 mM. Optionally, the composition can further comprise a nonionic tonicifying agent, and preferably is isotonic.

The invention also relates to a method of generating an immune response in a subject, comprising administering to a subject in need thereof the composition as described herein. Preferably the amount of the cationic lipid administered to the subject (as a component of the composition) in a single administration is no more than about 30 mg. In particular embodiments, the cationic lipid is DOTAP and the total amount of DOTAP administered to the subject in a single administration is no more than about 24 mg, or no more than about 4 mg.

DETAILED DESCRIPTION OF THE INVENTION

1. Overview

Figure 1:
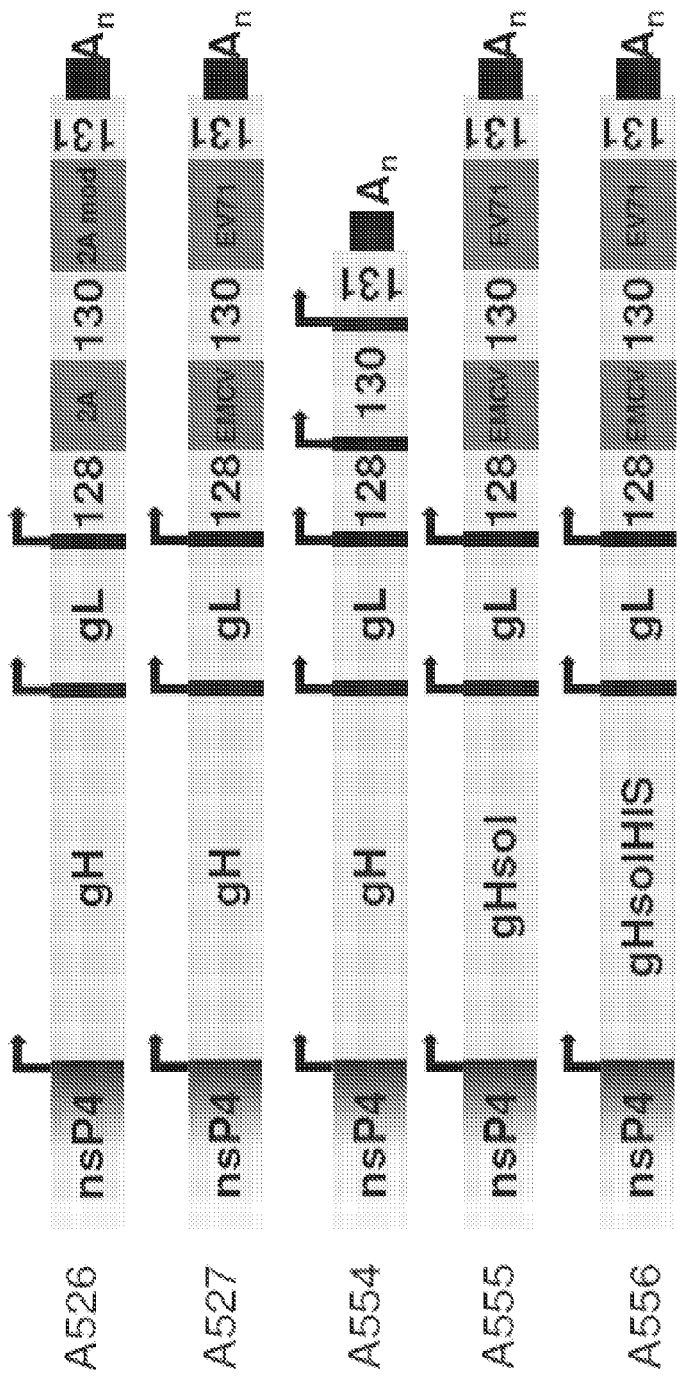
FIG. 1 is a schematic of pentacistronic RNA replicons, A526, A527, A554, A555 and A556, that encode five CMV proteins. Subgenomic promoters are shown by arrows, other control elements are labeled.

This invention generally relates to cationic oil-in-water emulsions that contain high concentrations of cationic lipids and have a defined oil:cationic lipid ratio. The oil and cationic lipid are separate components of the emulsions, and preferably the oil is not ionic. The cationic lipid can interact with a negatively charged molecule, such as a nucleic acid, thereby anchoring the negatively charged molecule to the emulsion particles. The cationic emulsions described herein are useful for delivering negatively charged molecules, such as nucleic acid molecules (e.g., an RNA molecule encoding a protein or peptide, small interfering RNA, self-replicating RNA, and the like), to cells in vivo, and for formulating nucleic acid-based vaccines.

In particular, the present invention is based on the discovery that stable cationic oil-in-water emulsions that contain high concentrations of cationic lipids and have a defined oil:cationic lipid ratio can be successfully made. Emulsions that contain high concentrations of cationic lipids allow more negatively charged molecules (such as RNA molecules) to be formulated with emulsion particles, thereby increasing the efficiency of delivery. In particular, for many therapeutics such as vaccines small volumes (e.g., 0.5 mL per dose) are preferred for administration. Emulsions that contain high concentrations of cationic lipids and have a defined oil:cationic lipid ratio, as described herein, will allow for the delivery of a higher dose of RNA within a specified volume.

In preferred embodiments, an RNA molecule is complexed with a particle of the oil-in-water emulsion. The complexed RNA molecule is stabilized and protected from RNase-mediated degradation, and is more efficiently taken up by cells relative to free ("naked") RNA.

In addition, when the RNA is delivered to induce expression of an encoded protein, such as in the context of an RNA vaccine, emulsions that contain high concentrations of cationic lipids can increase the amount of RNA molecules that are complexed with emulsion particles. As more RNA molecules are delivered to host cells, higher amount of the encoded protein antigen is produced, which in turn enhances the potency and immunogenicity of the RNA vaccine. Finally, the immunogenicity of the encoded protein can be enhanced due to adjuvant effects of the emulsion. Therefore, in addition to more efficient delivery of a negatively charged molecule (e.g., an RNA molecule that encodes an antigen), the cationic emulsions can also enhance the immune response through adjuvant activity. For example, as described and exemplified herein, formulations in which RNA molecules (encoding respiratory syncytial virus (RSV) F protein) were complexed with high-DOTAP emulsions generated higher immune responses in a mouse model and a cotton rat model of RSV, as compared to RNA molecules complexed with low-DOTAP emulsions.

Accordingly, in one aspect, the invention provides an oil-in-water emulsion comprising particles that are dispersed in an aqueous continuous phase, wherein the emulsion is characterized by: (a) the average diameter of said particles is from about 80 nm to 180 nm; (b) the emulsion comprises an oil and a cationic lipid, wherein (i) the ratio of oil:cationic lipid (mole:mole) is at least about 8:1 (mole:mole), (ii) the concentration of cationic lipid in said emulsion is at least about 2.5 mM, and (iii) the cationic lipid is not DC-Cholesterol.

In another aspect, the invention provides an oil-in-water emulsion comprising particles that are dispersed in an aqueous continuous phase, wherein the emulsion is characterized by: (a) the average diameter of said particles is from about 80 nm to 180 nm; (b) the emulsion comprises an oil and a cationic lipid, wherein (i) the ratio of oil:cationic lipid (mole:mole) is at least about 4:1 (mole:mole), (ii) the concentration of cationic lipid in said emulsion is at least about 2.5 mM, (iii) the oil is present from about 0.2% to about 8% (w/v); and (iv) with the proviso that the cationic lipid is not DC-Cholesterol.

The cationic emulsion may further comprise a surfactant (e.g., Tween 80, SPAN85, or a combination thereof).

In another aspect, the invention also provides several specific formulations of cationic oil-in-water emulsions that contain high concentrations of cationic lipids and can be used to deliver negatively charged molecules.

In another aspect, the invention provides a method of preparing an oil-in-water emulsion, comprising: (1) directly dissolving a cationic lipid in an oil to form an oil phase; (2) providing an aqueous phase of the emulsion; and (3) dispersing the oil phase in the aqueous phase (e.g., by homogenization). If desired, the oil may be heated to a temperature between about 30° C. to about 65° C. to facilitate the dissolving of the lipid in the oil. Preferably, the ratio of oil:cationic lipid (mole:mole) in the oil phase is at least about 8:1 (mole:mole), and alternatively or in addition, the average diameter of said particles is from about 80 nm to 180 nm, and/or the concentration of cationic lipid in the oil phase is at least about 5 mM.

In another aspect, the invention provides a method of preparing a composition that comprises a negatively charged molecule (such as an RNA molecule) complexed with a particle of a cationic oil-in-water emulsion, comprising: (i) providing an oil-in-water emulsion as described herein; (ii) providing an aqueous solution comprising the RNA molecule; and (iii) combining the aqueous solution of (ii) and the oil-in-water emulsion of (i), thereby preparing the composition. If desired, the aqueous solution comprising the RNA molecule may comprise a salt (e.g., NaCl), a buffer (e.g., a citrate buffer), a nonionic tonicifying agent (e.g., sucrose, trehalose, sorbitol, or dextrose), a polymer (e.g., Pluronic® F127), or any combination thereof.

The cationic emulsions of the invention can be used to deliver a negatively charge molecule, such as a nucleic acid (e.g., RNA). The compositions may be administered to a subject in need thereof to generate or potentiate an immune response. The compositions can also be co-delivered with another immunogenic molecule, immunogenic composition or vaccine to enhance the effectiveness of the induced immune response.

2. Definitions

The term "about", as used here, refers to +/−5% of a value.

An "antigen" refers to a molecule containing one or more epitopes (either linear, conformational or both).

A "buffer" refers to an aqueous solution that resists changes in the pH of the solution.

As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)).

As used herein, an emulsion "particle" refers to a oil droplet suspended in the aqueous (continuous) phase of an oil-in-water emulsion. The particle further comprises a cationic liquid, and optionally additional components, such as a surfactant.

The term "polymer" refers to a molecule consisting of individual chemical moieties, which may be the same or different, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure. Exemplary polymers include, e.g., poloxamers. Poloxamers are nonionic triblock copolymers having a central hydrophobic chain of polyoxypropylene (poly(propylene oxide)) flanked by two hydrophilic chains of polyoxyethylene (poly(ethylene oxide)).

As use herein, "saccharide" encompasses monosaccharides, oligosaccharides, or polysaccharides in straight chain or ring forms, or a combination thereof to form a saccharide chain. Oligosaccharides are saccharides having two or more monosaccharide residues. Examples of saccharides include glucose, maltose, maltotriose, maltotetraose, sucrose and trehalose.

An emulsion is "stable" when the emulsion particles remain separated without significant agglomeration or coalescence for at least one month, preferably at least two months, at 4° C. The average particle diameter (average number diameter) of a stable emulsion does not change by more than 10% when the emulsion is stored at 4° C. for one month, or preferably two months.

The term "surfactant" is a term of art and generally refers to any molecule having both a hydrophilic group (e.g., a polar group), which energetically prefers solvation by water, and a hydrophobic group which is not well solvated by water. The term "nonionic surfactant" is a known term in the art and generally refers to a surfactant molecule whose hydrophilic group (e.g., polar group) is not electrostatically charged.

The "Zeta potential" of an emulsion is determined by the electrophoretic mobility of the emulsion particles. The velocity of a particle in a unit electric field is referred to as its electrophoretic mobility. Zeta potential is related to the electrophoretic mobility by the Henry equation:

$$U_E = \frac{2\varepsilon z f(ka)}{3\eta}$$

where $U_E$=electrophoretic mobility, $z$=zeta potential, $\varepsilon$=dielectric constant, $\eta$=viscosity and $f(ka)$=Henry's function. Zeta potential is typically measured using an electrophoretic mobility apparatus, such as a Zetasizer Nano Z (Malvern Instruments Ltd, United Kingdom).

3. Cationic Oil-in-Water Emulsions

The cationic oil-in-water emulsions disclosed herein are generally described in the manner that is conventional in the art, by concentrations of components that are used to prepare the emulsions. It is understood in the art that during the process of producing emulsions, including sterilization and other downstream processes, small amounts of oil (e.g., squalene), cationic lipid (e.g., DOTAP), or other components may be lost, and the actual concentrations of these components in the final product (e.g., a packaged, sterilized emulsion that is ready for administration) might be slightly lower than starting amounts, sometimes by up to about 10%, by up to about 20%, by up to about 25%, or by up to about 35%.

This invention generally relates to cationic oil-in-water emulsions that contain high concentrations of cationic lipids and a defined oil:cationic lipid ratio. The emulsions are particularly suitable for delivering negatively charged molecules, such as an RNA molecule, to a cell. The cationic lipid can interact with the negatively charged molecule, for example through electrostatic forces and hydrophobic/hydrophilic interactions, thereby anchoring the molecule to the emulsion particles. The cationic emulsions described herein are useful for delivering a negatively charged molecule, such as an RNA molecule encoding an antigen or small interfering RNA to cells in vivo. For example, the cationic emulsions described herein provide advantages for delivering RNA molecules that encode one or more antigens, including self-replicating RNAs, as vaccines.

The discrete phase (or dispersed phase) of the emulsion comprises an oil and a cationic lipid, wherein the cationic lipid facilitates dispersing the oil in the aqueous (continuous) phase. One or more optional components may be present in the emulsion, such as surfactants (e.g., nonionic surfactants) as described below.

The particles of the oil-in-water emulsions have an average diameter (i.e., average number diameter) of 1 micrometer or less. It is particularly desirable that the average particle diameter of the cationic emulsions is about 180 nm or less, about 170 nm or less, about 160 nm or less, about 150 nm or less, about 140 nm or less, about 130 nm or less, about 120 nm or less, about 110 nm or less, or about 100 nm or less; for example, from about 80 nm to 180 nm, from about 80 nm to 170 nm, from about 80 nm to 160 nm, from about 80 nm to 150 nm, from about 80 nm to 140 nm, from about 80 nm to 130 nm, from about 80 nm to 120 nm; from about 80 nm to 110 nm, or from about 80 nm to 100 nm. Particularly preferred average particle diameter is about 100 nm, or from about 100 nm to about 130 nm.

The size (average diameter) of the emulsion particles can be varied by changing the ratio of surfactant to oil (increasing the ratio decreases particle size), operating pressure of homogenization (increasing operating pressure of homogenization typically reduces particle size), temperature (increasing temperature decreases particle size), changing the type of oil, inclusion of certain types of buffers in the aqueous phase, and other process parameters, as described in detail below. In some cases, the size of the emulsion particles may affect the immunogenicity of the RNA-emulsion complex, as exemplified herein.

The oil-in-water emulsions described herein are stable.

The particles of the emulsions described herein can be complexed with a negatively charged molecule. Prior to complexation with the negatively charged molecule, the overall net charge of the particles (typically measured as zeta-potential) should be positive (cationic). The overall net charge of the particles may vary, depending on the type of the cationic lipid and the amount of the cationic lipid in the emulsion, the amount of oil in the emulsion (e.g., higher percentage of oil typically results in less charge on the surface of the particles), and may also be affected by any additional component (e.g., surfactant(s)) that is present in the emulsion. Preferably, the zeta-potential of the pre-complexation particles are no more than about 50 mV, no more than about 45 mV, no more than about 40 mV, no more than about 35 mV, no more than about 30 mV, no more than about 25 mV, no more than about 20 mV; from about 5 mV to about 50 mV, from about 10 mV to about 50 mV, from about 10 mV to about 45 mV, from about 10 mV to about 40 mV, from about 10 mV to about 35 mV, from about 10 mV to about 30 mV, from about 10 mV to about 25 mV, or from about 10 mV to about 20 mV. Zeta potential can be affected by (i) pH of the emulsion, (ii) conductivity of the emulsion (e.g., salinity), and (iii) the concentration of the various components of the emulsion (polymer, non-ionic surfactants etc.). The Zeta potential of the cationic oil-in-water emulsions is measured using a Malvern Nanoseries Zetasizer (Westborough, Mass.). The sample is diluted 1:100 in water (viscosity: 0.8872 cp, RI: 1.330, Dielectric constant: 78.5) and is added to a polystyrene latex capillary cell (Malvern, Westborough, Mass.). Zeta potential is measured at 25° C. with a 2 minute equilibration time and analyzed using the Smoluchowski model (F(Ka) value=1.5). Data is reported in mV.

An exemplary cationic emulsion of the invention is referred herein as "CMF32." The oil of CMF32 is squalene (at 4.3% w/v) and the cationic lipid is DOTAP (at 3.2 mg/mL). CMF32 also includes the surfactants SPAN85 (sorbitan trioleate at 0.5% v/v) and Tween 80 (polysorbate 80; polyoxyethuylenesorbitan monooleate; at 0.5% v/v). Thus, emulsion particles of CMF32 comprise squalene, SPAN85, Tween80, and DOTAP. RNA molecules were shown to complex with CMF32 particles efficiently at 4:1, 6:1, 8:1, 10:1, 12:1, and 14:1 N/P ratios. Other exemplary cationic emulsions include, e.g., the emulsions referred to herein as "CMF34" (4.3% w/v squalene, 0.5% Tween 80, 0.5% SPAN85, and 4.4 mg/mL DOTAP), "CMF35" (4.3% w/v squalene, 0.5% Tween 80, 0.5% SPAN85, 5.0 mg/mL DOTAP), and other emulsions described herein.

Certain exemplary cationic oil-in-water emulsions of the invention comprise DOTAP and squalene at concentrations of 2.1 mg/ml to 2.84 mg/ml (preferably 2.23 mg/ml to 2.71 mg/ml), and 30.92 mg/ml to 41.92 mg/ml (preferably 32.82 mg/ml to about 40.02 mg/ml), respectively, and further comprise equal amounts of SPAN85 and Tween80 (e.g., about 0.5% each). Other exemplary cationic oil-in-water emulsions of the invention comprise DOTAP and squalene at concentrations of 2.78 mg/ml to 3.76 mg/ml (preferably 2.94 mg/ml to 3.6 mg/ml), and 18.6 mg/ml to 25.16 mg/ml (preferably 19.69 mg/ml to about 24.07 mg/ml), respectively, and further comprise equal amounts of SPAN85 and Tween80 (e.g., about 0.5% each). Preferably, the particles of these emulsions have an average diameter from 80 nm to 180 nm.

The individual components of the oil-in-water emulsions of the present invention are known in the art, although such compositions have not been combined in the manner described herein. Accordingly, the individual components, although described below both generally and in some-detail for preferred embodiments, are well known in the art, and the terms used herein, such as oil, surfactant, etc., are sufficiently well known to one skilled in the art without further description. In addition, while preferred ranges of the amount of the individual components of the emulsions are provided, the actual ratios of the components of a particular emulsion may need to be adjusted so that emulsion particles of desired size and physical property are properly formed. For example, if a particular amount of oil is used (e.g. 5% v/v oil), then, the amount of surfactant should be at level that is sufficient to disperse the oil particle into the aqueous phase to form a stable emulsion. The actual amount of surfactant required to disperse the oil into the aqueous phase depends on the type of surfactant and the type of oil used for the emulsion; and the amount of oil may also vary according to the desired particle size (as this changes the surface area between the two phases). The actual amounts and the relative proportions of the components of a desired emulsion can be readily determined by a skilled artisan.

A. Oil

The particles of the cationic oil-in-water emulsions comprise an oil.

The oil preferably is in the liquid phase at 1° C. or above, and is immiscible to water.

Preferably, the oil is a metabolizable, non-toxic oil; more preferably one of about 6 to about 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil that can be metabolized by the body of the subject to which the emulsion will be administered, and is not toxic to the subject. The subject may be an animal, typically a mammal, and preferably a human.

In certain embodiments, the oil is in liquid phase at 25° C. The oil is in liquid phase at 25° C., when it displays the properties of a fluid (as distinguished from solid and gas; and having a definite volume but no definite shape) when stored at 25° C. The emulsion, however, may be stored and used at any suitable temperature. Preferably, the oil is in liquid phase at 4° C.

The oil may be any long chain alkane, alkene or alkyne, or an acid or alcohol derivative thereof either as the free acid, its salt or an ester such as a mono-, or di- or triester, such as the triglycerides and esters of 1,2-propanediol or similar poly-hydroxy alcohols. Alcohols may be acylated employing a mono- or poly-functional acid, for example acetic acid, propanoic acid, citric acid or the like. Ethers derived from long chain alcohols which are oils and meet the other criteria set forth herein may also be used.

The individual alkane, alkene or alkyne moiety and its acid or alcohol derivatives will generally have from about 6 to about 30 carbon atoms. The moiety may have a straight or branched chain structure. It may be fully saturated or have one or more double or triple bonds. Where mono or poly ester- or ether-based oils are employed, the limitation of about 6 to about 30 carbons applies to the individual fatty acid or fatty alcohol moieties, not the total carbon count.

Any suitable oils from an animal, fish or vegetable source may be used. Sources for vegetable oils include nuts, seeds and grains, and suitable oils peanut oil, soybean oil, coconut oil, and olive oil and the like. Other suitable seed oils include safflower oil, cottonseed oil, sunflower seed oil, sesame seed oil and the like. In the grain group, corn oil, and the oil of other cereal grains such as wheat, oats, rye, rice, teff, triticale and the like may also be used. The technology for obtaining vegetable oils is well developed and well known. The compositions of these and other similar oils may be found in, for example, the Merck Index, and source materials on foods, nutrition and food technology.

About six to about ten carbon fatty acid esters of glycerol and 1,2-propanediol, while not occurring naturally in seed oils, may be prepared by hydrolysis, separation and esterification of the appropriate materials starting from the nut and seed oils. These products are commercially available under the name NEOBEES from PVO International, Inc., Chemical Specialties Division, 416 Division Street, Boongon, N.J. and others.

Animal oils and fats are often in solid phase at physiological temperatures due to the fact that they exist as triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and may therefore be used in the practice of this invention. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalene (2,6,10,15,19,23-hexamethyl-2,6,10,14,18,22-tetracosahexaene), a branched, unsaturated terpenoid, is particularly preferred herein. A major source of squalene is shark liver oil, although plant oils (primarily vegetable oils), including amaranth seed, rice bran, wheat germ, and olive oils, are also suitable sources. Squalene can also be obtained from yeast or other suitable microbes. In some embodiments, Squalene is preferably obtained from non-animal sources, such as from olives, olive oil or yeast. Squalane, the saturated analog to squalene, is also preferred. Fish oils, including squalene and squalane, are readily available from commercial sources or may be obtained by methods known in the art.

In certain embodiments, the oil comprises an oil that is selected from the group consisting of: Castor oil, Coconut oil, Corn oil, Cottonseed oil, Evening primrose oil, Fish oil, Jojoba oil, Lard oil, Linseed oil, Olive oil, Peanut oil, Safflower oil, Sesame oil, Soybean oil, Squalene, Squalane, Sunflower oil and Wheatgerm oil. In exemplary embodiments, the oil comprises Squalene or Squalane.

The oil component of the emulsion may be present in an amount from about 0.2% to about 10% (v/v). For example, the cationic oil-in-water emulsion may comprise from about 0.2% to about 10% (v/v) oil, from about 0.2% to about 9% (v/v) oil, from about 0.2% to about 8% (v/v) oil, from about 0.2% to about 7% (v/v) oil, from about 0.2% to about 6% (v/v) oil, from about 0.2% to about 5% (v/v) oil, from about 0.3% to about 10% (v/v) oil, from about 0.4% to about 10% (v/v) oil, from about 0.5% to about 10% (v/v) oil, from about 1% to about 10% (v/v) oil, from about 2% to about 10% (v/v) oil, from about 3% to about 10% (v/v) oil, from about 4% to about 10% (v/v) oil, from about 5% to about 10% (v/v) oil, from about 0.2% to about 10% (w/v) oil, from about 0.2% to about 9% (w/v) oil, from about 0.2% to about 8% (w/v) oil, from about 0.2% to about 7% (w/v) oil, from about 0.2% to about 6% (w/v) oil, from about 0.2% to about 5% (w/v) oil, from about 0.2% to about 4.3% (w/v) oil, from about 0.6% to about 4% (w/v) oil, from about 0.7% to about 4% (w/v) oil, from about 0.8% to about 4% (w/v) oil, from about 0.9% to about 4% (w/v) oil, from about 1.0% to about 4% (w/v) oil, from about 0.6% to about 3.5% (w/v) oil, from about 0.6% to about 3% (w/v) oil, about 0.5% (v/v) oil, about 0.6% (v/v) oil, about 0.7% (v/v) oil, about 0.8% (v/v) oil, about 0.9% (v/v) oil, about 1% (v/v) oil, about 1.5% (v/v) oil, about 2% (v/v) oil, about 2.5% (v/v) oil, about 3% (v/v) oil, about 3.5% (v/v) oil, about 4% (v/v) oil, about 5% (v/v) oil, about 10% (v/v) oil, about 0.5% (w/v) oil, about 1% (w/v) oil, about 1.5% (w/v) oil, about 2% (w/v) oil, about 2.5% (w/v) oil, about 3% (w/v) oil, about 3.5% (w/v) oil, about 4% (w/v) oil, about 4.3% (w/v) oil, about 5% (w/v) oil, about 5.5% (w/v) oil, about 6% (w/v) oil, about 6.5% (w/v) oil, about 7% (w/v) oil, about 7.5% (w/v) oil, or about 8% (w/v) oil.

The cationic oil-in-water emulsion may also comprise from about 0.2% to about 8% (v/v) oil, for example, from 0.6% (w/v) to 4% (w/v), from about 1% (w/v) to about 3.2% (w/v), about 1% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2.0% (w/v), about 2.1% (w/v), about 2.15% (w/v), about 2.2% (w/v), about 2.3% (w/v), about 2.4% (w/v), about 2.5% (w/v), about 2.6% (w/v), about 2.7% (w/v), about 2.8% (w/v), about 2.9% (w/v), 3.0% (w/v), about 3.1% (w/v), about 3.2% (w/v), about 3.3% (w/v), about 3.4% (w/v), about 3.5% (w/v), about 3.6% (w/v), about 3.7% (w/v), about 3.8% (w/v), about 3.9% (w/v), or about 4.0% (w/v) oil.

In an exemplary embodiment, the cationic oil-in-water emulsion comprises about 5% (v/v) oil. In another exemplary embodiment, the cationic oil-in-water emulsion comprises about 4.3% (w/v) squalene. In other exemplary embodiments, the cationic oil-in-water emulsion comprises from 0.6% (w/v) to 4% (w/v) squalene, for example, from about 1% (w/v) to about 3.2% (w/v) squalene, such as 1.08% (w/v), 2.15% (w/v), or 3.23% (w/v) squalene, as shown in the Examples.

As noted above, the percentage of oil described above is determined based on the initial amount of the oil that is used to prepare the emulsions. It is understood in the art that the actual concentration of the oil in the final product (e.g., a packaged, sterilized emulsion that is ready for administration) might be slightly lower, sometimes by up to about 10%, by up to about 20%, by up to about 25%, or by up to about 35%.

B. Cationic Lipids

The emulsion particles described herein comprise a cationic lipid, which can interact with the negatively charged molecule thereby anchoring the molecule to the emulsion particles.

Any suitable cationic lipid may be used. Generally, the cationic lipid contains a nitrogen atom that is positively charged under physiological conditions. The head group of the cationic lipid can comprise a tertiary amine or, preferably, a quaternary amine. Certain suitable cationic lipids comprise two saturated or unsaturated fatty acid chains (e.g., side chains having from about 10 to about 30 carbon atoms).

The cationic lipid can have a positive charge at about 12 pH, about 11 pH, about 10 pH, about 9 pH, about 8 pH, about 7 pH, or about 6 pH.

Suitable cationic lipids include, benzalkonium chloride (BAK), benzethonium chloride, cetrimide (which contains tetradecyltrimethylammonium bromide and possibly small amounts of dodecyltrimethylammonium bromide and hexadecyltrimethyl ammonium bromide), cetylpyridinium chloride (CPC), cetyl trimethylammonium chloride (CTAC), primary amines, secondary amines, tertiary amines, including but not limited to N,N',N'-polyoxyethylene (10)-N-tallow-1,3-diaminopropane, other quaternary amine salts, including but not limited to dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimethylammonium salts, [1-(2,3-dioleyloxy)-propyl]-N,N,N,trimethylammonium chloride, 1,2-diacyl-3-(trimethylammonio) propane (acyl group=dimyristoyl, dipalmitoyl, distearoyl, dioleoyl), 1,2-diacyl-3 (dimethylammonio)propane (acyl group=dimyristoyl, dipalmitoyl, distearoyl, dioleoyl), 1,2-dioleoyl-3-(4'-trimethyl-ammonio)butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkylglycetylphosphoryl-choline, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group ($C_{12}GluPhC_nN^+$), ditetradecyl glutamate ester with pendant amino group ($C_{14}GluC_nN^+$), cationic derivatives of cholesterol, including but not limited to cholesteryl-3β-oxysuccinamidoethylenetrimethylammonium salt, cholesteryl-3β-oxysuccinamidoethylenedimethylamine, cholesteryl-3β-carboxyamidoethylenetrimethylammonium salt, cholesteryl-3β-carboxyamidoethylenedimethylamine, and 3γ-[N—(N',N-dimethylaminoetanecarbomoyl]cholesterol) (DC-Cholesterol), 1,2-dioleoyloxy-3-(trimethylammonio) propane (DOTAP), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethyl-phosphocholine (DOEPC), 1,2-dioleoyl-3-dimethylammonium-propane (DODAP), 1,2-dilinoleyloxy-3-dimethylaminopropane (DLinDMA), and combination thereof.

In preferred embodiments, the cationic lipid is selected from the group consisting of 1,2-dioleoyloxy-3-(trimethylammonio)propane (DOTAP), 1,2-dioleoyl-sn-glycero-3-ethylphosphocholine (DOEPC), N,N-dioleoyl-N,N-dimethylammonium chloride (DODAC), and N-[1-(2,3-dioleyloxy)propyl]-N,N,N-trimethylammonium chloride (DOTMA). In certain embodiments, the cationic lipid is not DC-Cholesterol.

Preferably, the cationic lipid selected for the emulsion is soluble in the oil that is selected for the emulsion. This permits high cationic lipid concentrations to be achieved in the emulsion, by directly dissolving the lipid in the oil prior to dispersion in the mobile phase. It is within the knowledge in the art to determine whether a particular lipid is soluble in the oil and choose an appropriate oil and lipid combination accordingly. For example, solubility can be predicted based on the structures of the lipid and oil (e.g., the solubility of a lipid may be determined by the structure of its tail). For example, lipids having one or two unsaturated fatty acid chains (e.g., oleoyl tails, or linolyl tails), such as DOTAP, DOEPC, DODAC, DOTMA, are soluble in squalene or squalane. Alternatively, solubility can be determined according to the quantity of the lipid that dissolves in a given quantity of the oil to form a saturated solution. Such methods are known in the art. The solubility of exemplary saturated or unsaturated fatty acids in squalene is also provided in the Examples. Preferably, the saturation concentration of the lipid in the oil is at least about 1 mg/ml, at least about 5 mg/ml, at least about 10 mg/ml, at least about 25 mg/ml, at least about 50 mg/ml or at least about 100 mg/ml.

Preferably, the concentration of cationic lipid in the emulsion before the negatively charged molecule is complexed is at least about 1.25 mM, at least about 1.5 mM, at least about 1.75 mM, at least about 2.0 mM, at least about 2.25 mM, at least about 2.5 mM, at least about 2.75 mM, at least about 3.0 mM, at least about 3.25 mM, at least about 3.5 mM, at least about 3.75 mM, at least about 4.0 mM, at least about 4.25 mM, at least about 4.5 mM, at least about 4.75 mM, at least about 5.0 mM, at least about 5.25 mM, at least about 5.5 mM, at least about 5.75 mM, at least about 6 mM, at least about 6.25 mM, at least about 6.5 mM, at least about 6.75 mM, at least about 7 mM, at least about 7.25 mM, at least about 7.5 mM, at least about 7.75 mM, at least about 8 mM, at least about 8.25 mM, at least about 8.5 mM, at least about 8.75 mM, at least about 9 mM, at least about 9.25 mM, at least about 9.5 mM, at least about 9.75 mM, or at least about 10 mM.

In certain embodiments, the cationic lipid is DOTAP. The cationic oil-in-water emulsion may comprise from about 0.8 mg/ml to about 10 mg/ml DOTAP. For example, the cationic oil-in-water emulsion may comprise DOTAP at from about 1.7 mg/ml to about 10 mg/ml, from about 1.8 mg/ml to about 10 mg/ml, from about 2.0 mg/ml to about 10 mg/ml, from about 2.2 mg/ml to about 10 mg/ml, from about 2.4 mg/ml to about 10 mg/ml, from about 2.6 mg/ml to about 10 mg/ml, from about 2.8 mg/ml to about 10 mg/ml, from about 3.0 mg/ml to about 10 mg/ml, from about 3.2 mg/ml to about 10 mg/ml, from about 3.4 mg/ml to about 10 mg/ml, from about 3.6 mg/ml to about 10 mg/ml, from about 4.0 mg/ml to about 10 mg/ml, from about 4.4 mg/ml to about 10 mg/ml, from about 4.8 mg/ml to about 10 mg/ml, from about 5 mg/ml to about 10 mg/ml, from about 1.7 mg/ml to about 5 mg/ml, from about 1.8 mg/ml to about 5 mg/ml, from about 1.8 mg/ml to about 6 mg/ml, from about 1.8 mg/ml to about 7 mg/ml, from about 1.8 mg/ml to about 8 mg/ml, from about 1.8 mg/ml to about 9 mg/ml, about 1.7 mg/ml, about 1.8 mg/ml, about 2.0 mg/ml, about 2.2 mg/ml, about 2.4 mg/ml, about 2.6 mg/ml, about 2.8 mg/ml, about 3.0 mg/ml, about 3.2 mg/ml, about 3.4 mg/ml, about 3.6 mg/ml, about 3.8 mg/ml, about 4.0 mg/ml, about 4.2 mg/ml, about 4.4 mg/ml, about 4.6 mg/ml, about 4.8 mg/ml, about 5.0 mg/ml, about 5.2 mg/ml, about 5.5 mg/ml, about 6.0 mg/ml, at least about 0.8 mg/ml, at least about 0.85 mg/ml, at least about 0.9 mg/ml, at least about 1.0 mg/ml, at least about 1.1 mg/ml, at least about 1.2 mg/ml, at least about 1.3 mg/ml, at least about 1.4 mg/ml, at least about 1.5 mg/ml, at least about 1.6 mg/ml, at least about 1.7 mg/ml, etc.

In an exemplary embodiment, the cationic oil-in-water emulsion comprises from about 1.8 mg/ml to about 5.0 mg/ml DOTAP.

In certain embodiments, the cationic lipid is DOEPC. The cationic oil-in-water emulsion may comprise from about 0.8 mg/ml to about 10 mg/ml DOEPC. For example, the cationic oil-in-water emulsion may comprise DOEPC at from about 1.7 mg/ml to about 10 mg/ml, from about 1.8 mg/ml to about 10 mg/ml, from about 2.0 mg/ml to about 10 mg/ml, from about 2.2 mg/ml to about 10 mg/ml, from about 2.4 mg/ml to about 10 mg/ml, from about 2.6 mg/ml to about 10 mg/ml, from about 2.8 mg/ml to about 10 mg/ml, from about 3.0 mg/ml to about 10 mg/ml, from about 3.2 mg/ml to about 10 mg/ml, from about 3.4 mg/ml to about 10 mg/ml, from about 3.6 mg/ml to about 10 mg/ml, from about 4.0 mg/ml to about 10 mg/ml, from about 4.4 mg/ml to about 10 mg/ml, from about 4.8 mg/ml to about 10 mg/ml, from about 5 mg/ml to about 10 mg/ml, from about 1.7 mg/ml to about 5 mg/ml, from about 1.8 mg/ml to about 5 mg/ml, from about 1.8 mg/ml to about 6 mg/ml, from about 1.8 mg/ml to about 7 mg/ml, from about 1.8 mg/ml to about 8 mg/ml, from about 1.8 mg/ml to about 9 mg/ml, about 1.7 mg/ml, about 1.8 mg/ml, about 2.0 mg/ml, about 2.2 mg/ml, about 2.4 mg/ml, about 2.6 mg/ml, about 2.8 mg/ml, about 3.0 mg/ml, about 3.2 mg/ml, about 3.4 mg/ml, about 3.6 mg/ml, about 3.8 mg/ml, about 4.0 mg/ml, about 4.2 mg/ml, about 4.4 mg/ml, about 4.6 mg/ml, about 4.8 mg/ml, about 5.0 mg/ml, about 5.2 mg/ml, about 5.5 mg/ml, about 6.0 mg/ml, at least about 0.8 mg/ml, at least about 0.85 mg/ml, at least about 0.9 mg/ml, at least about 1.0 mg/ml, at least about 1.1 mg/ml, at least about 1.2 mg/ml, at least about 1.3 mg/ml, at least about 1.4 mg/ml, at least about 1.5 mg/ml, at least about 1.6 mg/ml, at least about 1.7 mg/ml, etc.

In certain embodiments, the cationic lipid is DODAC. The cationic oil-in-water emulsion may comprise from about 0.8 mg/ml to about 10 mg/ml DODAC. For example, the cationic oil-in-water emulsion may comprise DODAC at from about 1.7 mg/ml to about 10 mg/ml, from about 1.8 mg/ml to about 10 mg/ml, from about 2.0 mg/ml to about 10 mg/ml, from about 2.2 mg/ml to about 10 mg/ml, from about 2.4 mg/ml to about 10 mg/ml, from about 2.6 mg/ml to about 10 mg/ml, from about 2.8 mg/ml to about 10 mg/ml, from about 3.0 mg/ml to about 10 mg/ml, from about 3.2 mg/ml to about 10 mg/ml, from about 3.4 mg/ml to about 10 mg/ml, from about 3.6 mg/ml to about 10 mg/ml, from about 4.0 mg/ml to about 10 mg/ml, from about 4.4 mg/ml to about 10 mg/ml, from about 4.8 mg/ml to about 10 mg/ml, from about 5 mg/ml to about 10 mg/ml, from about 1.7 mg/ml to about 5 mg/ml, from about 1.8 mg/ml to about 5 mg/ml, from about 1.8 mg/ml to about 6 mg/ml, from about 1.8 mg/ml to about 7 mg/ml, from about 1.8 mg/ml to about 8 mg/ml, from about 1.8 mg/ml to about 9 mg/ml, about 1.7 mg/ml, about 1.8 mg/ml, about 2.0 mg/ml, about 2.2 mg/ml, about 2.4 mg/ml, about 2.6 mg/ml, about 2.8 mg/ml, about 3.0 mg/ml, about 3.2 mg/ml, about 3.4 mg/ml, about 3.6 mg/ml, about 3.8 mg/ml, about 4.0 mg/ml, about 4.2 mg/ml, about 4.4 mg/ml, about 4.6 mg/ml, about 4.8 mg/ml, about 5.0 mg/ml, about 5.2 mg/ml, about 5.5 mg/ml, about 6.0 mg/ml, at least about 0.8 mg/ml, at least about 0.85 mg/ml, at least about 0.9 mg/ml, at least about 1.0 mg/ml, at least about 1.1 mg/ml, at least about 1.2 mg/ml, at least about 1.3 mg/ml, at least about 1.4 mg/ml, at least about 1.5 mg/ml, at least about 1.6 mg/ml, at least about 1.7 mg/ml, etc.

In certain embodiments, the cationic lipid is DOTMA. The cationic oil-in-water emulsion may comprise from about 0.8 mg/ml to about 10 mg/ml DOTMA. For example, the cationic oil-in-water emulsion may comprise DOTMA at from about 1.7 mg/ml to about 10 mg/ml, from about 1.8 mg/ml to about 10 mg/ml, from about 2.0 mg/ml to about 10 mg/ml, from about 2.2 mg/ml to about 10 mg/ml, from about 2.4 mg/ml to about 10 mg/ml, from about 2.6 mg/ml to about 10 mg/ml, from about 2.8 mg/ml to about 10 mg/ml, from about 3.0 mg/ml to about 10 mg/ml, from about 3.2 mg/ml to about 10 mg/ml, from about 3.4 mg/ml to about 10 mg/ml, from about 3.6 mg/ml to about 10 mg/ml, from about 4.0 mg/ml to about 10 mg/ml, from about 4.4 mg/ml to about 10 mg/ml, from about 4.8 mg/ml to about 10 mg/ml, from about 5 mg/ml to about 10 mg/ml, from about 1.7 mg/ml to about 5 mg/ml, from about 1.8 mg/ml to about 5 mg/ml, from about 1.8 mg/ml to about 6 mg/ml, from about 1.8 mg/ml to about 7 mg/ml, from about 1.8 mg/ml to about 8 mg/ml, from about 1.8 mg/ml to about 9 mg/ml, about 1.7 mg/ml, about 1.8 mg/ml, about 2.0 mg/ml, about 2.2 mg/ml, about 2.4 mg/ml, about 2.6 mg/ml, about 2.8 mg/ml, about 3.0 mg/ml, about 3.2 mg/ml, about 3.4 mg/ml, about 3.6 mg/ml, about 3.8 mg/ml, about 4.0 mg/ml, about 4.2 mg/ml, about 4.4 mg/ml, about 4.6 mg/ml, about 4.8 mg/ml, about 5.0 mg/ml, about 5.2 mg/ml, about 5.5 mg/ml, about 6.0 mg/ml, at least about 0.8 mg/ml, at least about 0.85 mg/ml, at least about 0.9 mg/ml, at least about 1.0 mg/ml, at least about 1.1 mg/ml, at least about 1.2 mg/ml, at least about 1.3 mg/ml, at least about 1.4 mg/ml, at least about 1.5 mg/ml, at least about 1.6 mg/ml, at least about 1.7 mg/ml, etc.

As noted above, the concentration of a lipid described above is determined based on the initial amount of the lipid that is used to prepare the emulsions. It is understood in the art that the actual concentration of the oil in the final product (e.g., a packaged, sterilized emulsion that is ready for administration) might be slightly lower, sometimes by up to about 10%, by up to about 20%, by up to about 25%, or by up to about 35%.

C. Oil to Lipid Ratio

The cationic oil-in-water emulsions of the invention have a defined oil:lipid ratio. For example, the ratio of oil:lipid (mole:mole) of the emulsion may be at least about 8:1 (mole:mole), at least about 8.5:1 (mole:mole), at least about 9:1 (mole:mole), at least about 9.5:1 (mole:mole), at least about 10:1 (mole:mole), at least about 10.5:1 (mole:mole), at least about 11:1 (mole:mole), at least about 11.5:1 (mole:mole), at least about 12:1 (mole:mole), at least about 12.5:1 (mole:mole), at least about 13:1 (mole:mole), at least about 13.5:1 (mole:mole), at least about 14:1 (mole:mole), at least about 14.5:1 (mole:mole), at least about 15:1 (mole:mole), at least about 15.5:1 (mole:mole), at least about 16:1 (mole:mole), at least about 16.5:1 (mole:mole), at least about 17:1

(mole:mole), from about 8:1 (mole:mole) to about 50:1 (mole:mole), from about 9:1 (mole:mole) to about 50:1 (mole:mole), from about 10:1 (mole:mole) to about 50:1 (mole:mole), from about 8:1 (mole:mole) to about 49:1 (mole:mole), from about 8:1 (mole:mole) to about 48:1 (mole:mole), from about 8:1 (mole:mole) to about 47:1 (mole:mole), from about 8:1 (mole:mole) to about 46:1 (mole:mole), from about 8:1 (mole:mole) to about 45:1 (mole:mole), from about 8:1 (mole:mole) to about 44:1 (mole:mole), from about 8:1 (mole:mole) to about 43:1 (mole:mole), from about 8:1 (mole:mole) to about 42:1 (mole:mole), from about 8:1 (mole:mole) to about 41:1 (mole:mole), from about 9:1 (mole:mole) to about 43:1 (mole:mole), from about 10:1 (mole:mole) to about 43:1 (mole:mole), from about 11:1 (mole:mole) to about 43:1 (mole:mole), from about 12:1 (mole:mole) to about 43:1 (mole:mole), from about 13:1 (mole:mole) to about 43:1 (mole:mole), from about 14:1 (mole:mole) to about 43:1 (mole:mole), from about 15:1 (mole:mole) to about 43:1 (mole:mole), from about 16:1 (mole:mole) to about 43:1 (mole:mole), from about 17:1 (mole:mole) to about 43:1 (mole:mole), etc.

If desired, the ratio of oil:lipid (mole:mole) of the emulsion may be at least about 4:1 (mole:mole), at least about 4.2:1 (mole:mole), at least about 4.5:1 (mole:mole), at least about 5:1 (mole:mole), at least about 5.5:1 (mole:mole), at least about 6:1 (mole:mole), at least about 6.5:1 (mole:mole), 7:1 (mole:mole), at least about 7.5:1 (mole:mole), from about 4:1 (mole:mole) to about 50:1 (mole:mole), from about 5:1 (mole:mole) to about 50:1 (mole:mole), from about 6:1 (mole:mole) to about 50:1 (mole:mole), from about 7:1 (mole:mole) to about 50:1 (mole:mole), from about 4:1 (mole:mole) to about 49:1 (mole:mole), from about 4:1 (mole:mole) to about 48:1 (mole:mole), from about 4:1 (mole:mole) to about 47:1 (mole:mole), from about 4:1 (mole:mole) to about 46:1 (mole:mole), from about 4:1 (mole:mole) to about 45:1 (mole:mole), from about 4:1 (mole:mole) to about 44:1 (mole:mole), from about 4:1 (mole:mole) to about 43:1 (mole:mole), from about 4:1 (mole:mole) to about 42:1 (mole:mole), from about 4:1 (mole:mole) to about 41:1 (mole:mole), from about 5:1 (mole:mole) to about 43:1 (mole:mole), from about 6:1 (mole:mole) to about 43:1 (mole:mole), from about 7:1 (mole:mole) to about 43:1 (mole:mole), etc.

Sometimes, there may be a need to strike a balance between the desire to increase the concentration of a cationic lipid (thereby increasing the amount of nucleic acid molecules loaded to the emulsion particle), and toxicity or tolerability of the lipid when administered in vivo. For example, it has been reported that high doses of DOTAP can have toxic effects. See, e.g., Lappalainen et al., Pharm. Res., vol. 11(8):1127-31 (1994). The optimal range of lipid dose in a particular emulsion can be determined in accordance with the knowledge of a skilled clinician.

If the oil comprises a mixture of molecules, the molar concentration of the oil can be calculated based on the average molecular weight of the oil. For example, the average molecular weight of soybean oil (292.2) can be calculated according to the average fatty acid distribution (12% weight percentage of palmitic acid; 52% weight percentage of linolenic acid; etc), and the molecular weight of each component.

C. Additional Components

The cationic oil-in-water emulsions described herein may further comprise additional components. For example, the emulsions may comprise components that can promote particle formation, improve the complexation between the negatively charge molecules and the cationic particles, or increase the stability of the negatively charge molecule (e.g., to prevent degradation of an RNA molecule). If desired, the cationic oil-in-water emulsion can contain an antioxidant, such as citrate, ascorbate or salts thereof.

Surfactants

In certain embodiments, the cationic oil-in-water emulsion as described herein further comprises a surfactant.

A substantial number of surfactants have been used in the pharmaceutical sciences. These include naturally derived materials such as gums from trees, vegetable protein, sugar-based polymers such as alginates, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Ionic or nonionic detergents and long chain fatty-acid-derived compounds can also be used in this invention.

Specific examples of suitable surfactants include the following:

1. Water-soluble soaps, such as the sodium, potassium, ammonium and alkanol-ammonium salts of higher fatty acids ($C_{10}$-$C_{22}$), in particular sodium and potassium tallow and coconut soaps.

2. Anionic synthetic non-soap surfactants, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid esters of the reaction product of one mole of a higher fatty alcohol and about 1 to 6 moles of ethylene oxide; sodium or potassium alkyl phenol ethylene oxide ether sulfonates, with 1 to 10 units of ethylene oxide per molecule and in which the alkyl radicals contain from 8 to 12 carbon atoms; the reaction product of fatty acids esterified with isethionic acid and neutralized with sodium hydroxide; sodium or potassium salts of fatty acid amide of a methyl tauride; and sodium and potassium salts of $SO_3$-sulfonated $C_{10}$-$C_{24}$ α-olefins.

3. Nonionic synthetic surfactants made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids.

4. Nonionic surfactants, such as amine oxides, phosphine oxides and sulfoxides, having semipolar characteristics. Specific examples of long chain tertiary amine oxides include dimethyldodecylamine oxide and bis-(2-hydroxyethyl) dodecylamine. Specific examples of phosphine oxides are found in U.S. Pat. No. 3,304,263, issued Feb. 14, 1967, and include dimethyldodecylphosphine oxide and dimethyl-(2hydroxydodecyl) phosphine oxide.

5. Long chain sulfoxides, including those corresponding to the formula $R^1$—SO—$R^2$ wherein $R^1$ and $R^2$ are substituted or unsubstituted alkyl radicals, the former containing from about 10 to about 28 carbon atoms, whereas $R^2$ contains from 1 to 3 carbon atoms. Specific examples of these sulfoxides include dodecyl methyl sulfoxide and 3-hydroxy tridecyl methyl sulfoxide.

6. Ampholytic synthetic surfactants, such as sodium 3-dodecylaminopropionate and sodium 3-dodecylaminopropane sulfonate.

7. Zwitterionic synthetic surfactants, such as 3-(N,N-dimethyl-N-hexadecylammonio)propane-1-sulfonate and 3-(N,N-dimethyl-N-hexadecylammonio)-2-hydroxy propane-1-sulfonate.

Additionally, all of the following types of surfactants can be used in a composition of the present invention: (a) soaps (i.e., alkali salts) of fatty acids, rosin acids, and tall oil; (b) alkyl arene sulfonates; (c) alkyl sulfates, including surfactants with both branched-chain and straight-chain hydrophobic groups, as well as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; and (h) fatty acyl diethanol amides. Since surfactants can be classified in more than one manner, a number of classes of surfactants set forth in this paragraph overlap with previously described surfactant classes.

There are a number of surfactants specifically designed for and commonly used in biological situations. Such surfactants are divided into four basic types: anionic, cationic, zwitterionic (amphoteric), and nonionic. Exemplary anionic surfactants include, e.g., perfluorooctanoate (PFOA or PFO), perfluorooctanesulfonate (PFOS), alkyl sulfate salts such as sodium dodecyl sulfate (SDS) or ammonium lauryl sulfate, sodium laureth sulfate (also known as sodium lauryl ether sulfate, SLES), alkyl benzene sulfonate, and fatty acid salts. Exemplary cationic surfactants include, e.g., alkyltrimethylammonium salts such as cetyl trimethylammonium bromide (CTAB, or hexadecyl trimethyl ammonium bromide), cetylpyridinium chloride (CPC), polyethoxylated tallow amine (POEA), benzalkonium chloride (BAC), benzethonium chloride (BZT). Exemplary zwitterionic (amphoteric) surfactants include, e.g., dodecyl betaine, cocamidopropyl betaine, and coco ampho glycinate. Exemplary nonionic surfactants include, e.g., alkyl poly(ethylene oxide), alkylphenol poly(ethylene oxide), copolymers of poly(ethylene oxide) and poly(propylene oxide) (commercially called poloxamers or poloxamines), Aayl polyglucosides (e.g., octyl glucoside or decyl maltoside), fatty alcohols (e.g., cetyl alcohol or oleyl alcohol), cocamide MEA, cocamide DEA, Pluronic® F-68 (polyoxyethylene-polyoxypropylene block copolymer), and polysorbates, such as Tween 20 (polysorbate 20), Tween 80 (polysorbate 80; polyoxyethuylenesorbitan monooleate), dodecyl dimethylamine oxide, and vitamin E tocopherol propylene glycol succinate (Vitamin E TPGS).

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid-substituted moiety may be further reacted with ethylene oxide to give a second group of surfactants.

The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. These surfactants are commercially available under the name SPAN® or ARLACEL®, usually with a letter or number designation which distinguishes between the various mono, di- and triester substituted sorbitans.

SPAN® and ARLACEL® surfactants are hydrophilic and are generally soluble or dispersible in oil. They are also soluble in most organic solvents. In water they are generally insoluble but dispersible. Generally these surfactants will have a hydrophilic-lipophilic balance (HLB) number between 1.8 to 8.6. Such surfactants can be readily made by means known in the art or are commercially available.

A related group of surfactants comprises olyoxyethylene sorbitan monoesters and olyoxyethylene sorbitan triesters. These materials are prepared by addition of ethylene oxide to a 1,4-sorbitan monester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark TWEEN®, are useful for preparing oil-in-water emulsions and dispersions, or for the solubilization of oils and making anhydrous ointments water-soluble or washable. The TWEEN® surfactants may be combined with a related sorbitan monester or triester surfactants to promote emulsion stability. TWEEN® surfactants generally have a HLB value falling between 9.6 to 16.7. TWEEN® surfactants are commercially available.

A third group of non-ionic surfactants which could be used alone or in conjunction with SPANS, ARLACEL® and TWEEN® surfactants are the polyoxyethylene fatty acids made by the reaction of ethylene oxide with a long-chain fatty acid. The most commonly available surfactant of this type is solid under the name MYRJ® and is a polyoxyethylene derivative of stearic acid. MYRJ® surfactants are hydrophilic and soluble or dispersible in water like TWEEN® surfactants. The MYRJ® surfactants may be blended with TWEEN® surfactants or with TWEEN®/SPAN® or ARLACEL® surfactant mixtures for use in forming emulsions. MYRJ® surfactants can be made by methods known in the art or are available commercially.

A fourth group of polyoxyethylene based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from commercial sources.

Other non-ionic surfactants which could potentially be used are, for example, polyoxyethylene, polyol fatty acid esters, polyoxyethylene ether, polyoxypropylene fatty ethers, bee's wax derivatives containing polyoxyethylene, polyoxyethylene lanolin derivative, polyoxyethylene fatty glycerides, glycerol fatty acid esters or other polyoxyethylene acid alcohol or ether derivatives of long-chain fatty acids of 12-22 carbon atoms.

As the emulsions and formulations of the invention are intended to be multi-phase systems, it is preferable to choose an emulsion-forming non-ionic surfactant which has an HLB value in the range of about 7 to 16. This value may be obtained through the use of a single non-ionic surfactant such as a TWEEN® surfactant or may be achieved by the use of a blend of surfactants such as with a sorbitan mono, di- or triester based surfactant; a sorbitan ester polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

In certain embodiments, the emulsion comprises a single non-ionic surfactant, most particularly a TWEEN® surfactant, as the emulsion stabilizing non-ionic surfactant. In an exemplary embodiment, the emulsion comprises TWEEN® 80, otherwise known as polysorbate 80 or polyoxyethylene 20 sorbitan monooleate. In other embodiments, the emulsion comprises two or more non-ionic surfactants, in particular a TWEEN® surfactant and a SPAN® surfactant. In an exemplary embodiment, the emulsion comprises TWEEN® 80 and SPAN®85.

The oil-in-water emulsions can contain from about 0.01% to about 2.5% surfactant (w/v), about 0.01% to about 2% surfactant, 0.01% to about 1.5% surfactant, 0.01% to about 1% surfactant, 0.01% to about 0.5% surfactant, 0.05% to about 0.5% surfactant, 0.08% to about 0.5% surfactant, about 0.08% surfactant, about 0.1% surfactant, about 0.2% surfactant, about 0.3% surfactant, about 0.4% surfactant, about 0.5% surfactant, about 0.6% surfactant, about 0.7% surfactant, about 0.8% surfactant, about 0.9% surfactant, or about 1% surfactant.

Alternatively or in addition, the oil-in-water emulsions can contain 0.05% to about 1%, 0.05% to about 0.9%, 0.05% to about 0.8%, 0.05% to about 0.7%, 0.05% to about 0.6%, 0.05% to about 0.5%, about 0.08%, about 0.1%, about 0.2%, about 0.3%, about 0.4%, about 0.5%, about 0.6%, about 0.7%, about 0.8%, about 0.9%, or about 1% (w/v) Tween 80 (polysorbate 80; polyoxyethuylenesorbitan monooleate).

In an exemplary embodiment, the oil-in-water emulsion contains 0.08% (w/v) Tween 80 (polysorbate 80; polyoxyethuylenesorbitan monooleate).

Alternatively or in addition, the oil-in-water emulsions can contain 0.05% to about 1%, 0.05% to about 0.9%, 0.05% to about 0.8%, 0.05% to about 0.7%, 0.05% to about 0.6%, 0.05% to about 0.5%, about 0.08%, about 0.1%, about 0.2%, about 0.3%, about 0.4%, about 0.5%, about 0.6%, about 0.7%, about 0.8%, about 0.9%, or about 1% (w/v) SPAN85 (sorbitan trioleate).

The oil-in-water emulsions can contain a combination of surfactants described herein. For example, a combination of Tween 80 (polysorbate 80; polyoxyethuylenesorbitan monooleate) and SPAN85 (sorbitan trioleate) may be used. The emulsions may contain various amounts of Tween 80 and SPAN85 (e.g., those exemplified above) or equal amounts. For example, the oil-in-water emulsions can contain (w/v) about 0.05% Tween 80 and about 0.05% SPAN85, about 0.1% Tween 80 and about 0.1% SPAN85, about 0.2% Tween 80 and about 0.2% SPAN85, about 0.3% Tween 80 and about 0.3% SPAN85, about 0.4% Tween 80 and about 0.4% SPAN85, about 0.5% Tween 80 and about 0.5% SPAN85, about 0.6% Tween 80 and about 0.6% SPAN85, about 0.7% Tween 80 and about 0.7% SPAN85, about 0.8% Tween 80 and about 0.8% SPAN85, about 0.9% Tween 80 and about 0.9% SPAN85, or about 1% Tween 80 and about 1.0% SPAN85.

In certain embodiments, the surfactant is a Polyethylene Glycol (PEG)-lipid. In other embodiments, the emulsion does not comprise a PEG-lipid. PEG-lipids, such as PEG coupled to dialkyloxypropyls (PEG-DAA), PEG coupled to diacylglycerol (PEG-DAG), PEG coupled to phosphatidylethanolamine (PE) (PEG-PE) or some other phospholipids (PEG-phospholipids), PEG conjugated to ceramides (PEG-Cer), or a combination thereof, may also be used as surfactants (see, e.g., U.S. Pat. No. 5,885,613; U.S. patent application publication Nos. 2003/0077829, 2005/0175682 and 2006/0025366). Other suitable PEG-lipids include, e.g., PEG-dialkyloxypropyl (DAA) lipids or PEG-diacylglycerol (DAG) lipids. Exemplary PEG-DAG lipids include, e.g., PEG-dilauroylglycerol ($C_{12}$) lipids, PEG-dimyristoylglycerol ($C_{14}$) lipids, PEG-dipalmitoylglycerol ($C_{16}$) lipids, or PEG-distearoylglycerol ($C_{18}$) lipids. Exemplary PEG-DAA lipids include, e.g., PEG-dilauryloxypropyl ($C_{12}$) lipids, PEG-dimyristyloxypropyl ($C_{14}$) lipids, PEG-dipalmityloxypropyl ($C_{16}$) lipids, or PEG-distearyloxypropyl ($C_{18}$) lipids.

PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. as well as other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH), is particularly useful for preparing the PEG-lipid conjugates including, e.g., PEG-DAA conjugates.

D. Aqueous Phase (Continuous Phase)

The aqueous phase (continuous phase) of the oil-in-water emulsions is water, or an aqueous solution that can contain a salt (e.g., NaCl), a buffer (e.g., a citrate buffer), a nonionic tonicifying agent (e.g., a saccharide), a polymer, a surfactant, or any combination thereof. The aqueous phase of the pre-complexed emulsions (oil-in-water emulsions before the addition of the negatively charged molecules) can differ from the aqueous phase of the post-complexed emulsions (oil-in-water emulsions in which the negatively charged molecules are complexed with the emulsion particles). In general, the pre-complexed emulsions are prepared in an aqueous solvent that promotes the formation of particles with desired properties (e.g., average diameter, and the like). The pre-complexed emulsions are diluted with an aqueous solution that contains the negatively charged molecule, and other desired components, to produce the final cationic oil-in-water emulsion, which contains the final aqueous phase with desired osmolarity and tonicity. The aqueous phase can contain an antioxidant, such as citrate, ascorbate or salts thereof.

When the emulsions are formulated for in vivo administration, it is preferable to make up the final solution so that the tonicity and osmolarity of the emulsion are substantially the same as normal physiological fluids in order to prevent undesired post-administration consequences, such as swelling or rapid absorption of the composition. It is also preferable to buffer the aqueous phase in order to maintain a pH compatible with normal physiological conditions. Also, in certain instances, it may be desirable to maintain the pH at a particular level in order to insure the stability of certain components of the emulsion. For example, it may be desirable to prepare an emulsion that is isotonic and isosmotic. To control tonicity, the emulsion may comprise a physiological salt, such as a sodium salt. Sodium chloride (NaCl), for example, may be used at about 0.9% (w/v) (physiological saline). Other salts that may be present include potassium chloride, potassium dihydrogen phosphate, disodium phosphate, magnesium chloride, calcium chloride, etc. Non-ionic tonicifying agents can also be used to control tonicity. A number of non-ionic tonicity modifying agents ordinarily known to those in the art. These are typically carbohydrates of various classifications (see, for example, Voet and Voet (1990) Biochemistry (John Wiley & Sons, New York). Monosaccharides classified as aldoses such as glucose, mannose, arabinose, and ribose, as well as those classified as ketoses such as fructose, sorbose, and xylulose can be used as non-ionic tonicifying agents in the present invention. Disaccharides such a sucrose, maltose, trehalose, and lactose can also be used. In addition, alditols (acyclic polyhydroxy alcohols, also referred to as sugar alcohols) such as glycerol, mannitol, xylitol, and sorbitol are non-ionic tonicifying agents useful in the present invention. Non-ionic tonicity modifying agents can be present at a concentration of from about 0.1% to about 10% or about 1% to about 10%, depending upon the agent that is used.

The aqueous phase may be buffered. Any physiologically acceptable buffer may be used herein, such as water, citrate buffers, phosphate buffers, acetate buffers, tris buffers, bicarbonate buffers, carbonate buffers, succinate buffer, or the like. The pH of the aqueous component will preferably be between 6.0-8.0, more preferable about 6.2 to about 6.8. In an exemplary embodiment, the buffer is 10 mM citrate buffer with a pH at 6.5. In another exemplary embodiment, the aqueous phase is, or the buffer prepared using, RNase-free water or DEPC treated water. In some cases, high salt in the buffer might interfere with complexation of negatively charged molecule to the emulsion particle therefore is avoided. In other cases, certain amount of salt in the buffer may be included.

In an exemplary embodiment, the buffer is 10 mM citrate buffer with a pH at 6.5. If desired the aqueous phase is, or the buffer is prepared using, RNase-free water or DEPC treated water.

The aqueous phase may also comprise additional components such as molecules that change the osmolarity of the aqueous phase or molecules that stabilizes the negatively charged molecule after complexation. Preferably, the osmolarity of the aqueous phase is adjusted using a non-ionic tonicifying agent, such as a sugar (e.g., trehalose, sucrose, dextrose, fructose, reduced palatinose, etc.), a sugar alcohol (such as mannitol, sorbitol, xylitol, erythritol, lactitol, maltitol, glycerol, etc.). If desired a nonionic polymer polymer (e.g., a poly(alkyl glycol) such as polyethylene glycol, polypropylene glycol, or polybutlyene glycol) or nonionic surfactant can be used.

In certain embodiments, the aqueous phase of the cationic oil-in-water emulsion may comprise a polymer or a surfactant, or a combination thereof. In an exemplary embodiment, the oil-in-water emulsion contains a poloxamer. Poloxamers are nonionic triblock copolymers having a central hydrophobic chain of polyoxypropylene (poly(propylene oxide)) flanked by two hydrophilic chains of polyoxyethylene (poly(ethylene oxide)). Poloxamers are also known by the trade name Pluronic® polymers. Poloxamer polymers may lead to greater stability and increased RNase resistance of the RNA molecule after RNA complexation.

Alternatively or in addition, the cationic oil-in-water emulsion may comprise from about 0.1% to about 20% (w/v) polymer, or from about 0.05% to about 10% (w/v) polymer. For example, the cationic oil-in-water emulsion may comprise a polymer (e.g., a poloxamer such as Pluronic® F127 ((Ethylene Oxide/Propylene Oxide Block Copolymer: $H(OCH_2CH_2)_x(OCH_3CH(CH_3))_y(OCH_2CH_2)_zOH$)) at from about 0.1% to about 20% (w/v), from about 0.1% to about 10% (w/v), from about 0.05% to about 10% (w/v), or from about 0.05% to about 5% (w/v).

In an exemplary embodiment, the oil-in-water emulsion comprises about 4% (w/v), or about 8% (w/v) Pluronic® F127.

The quantity of the aqueous component employed in these compositions will be that amount necessary to bring the value of the composition to unity. That is, a quantity of aqueous component sufficient to make 100% will be mixed, with the other components listed above in order to bring the compositions to volume.

4. Negatively Charged Molecules

When a negatively charged molecule is to be delivered, it can be complexed with the particles of the cationic oil-in-water emulsions. The negatively charged molecule is complexed with the emulsion particles by, for example, interactions between the negatively charged molecule and the cationic lipid on the surface of the particles, as well as hydrophobic/hydrophilic interactions between the negatively charged molecule and the surface of the particles. Although not wishing to be bound by any particular theory, it is believed that the negatively charged molecules interact with the cationic lipid through non-covalent, ionic charge interactions (electrostatic forces), and the strength of the complex as well as the amount of negatively charged compound that can be complexed to a particle are related to the amount of cationic lipid in the particle. Additionally, hydrophobic/hydrophilic interactions between the negatively charged molecule and the surface of the particles may also play a role.

Examples of negatively charged molecules include negatively charged peptides, polypeptides or proteins, nucleic acid molecules (e.g., single or double stranded RNA or DNA), small molecules (e.g., small molecule immune potentiators (SMIPs), phosphonate, fluorophosphonate, etc.) and the like. In preferred aspects, the negatively charged molecule is an RNA molecule, such as an RNA that encodes a peptide, polypeptide or protein, including self-replicating RNA molecules, or a small interfering RNA.

The complex can be formed by using techniques known in the art, examples of which are described herein. For example, a nucleic acid-particle complex can be formed by mixing a cationic emulsion with the nucleic acid molecule, for example by vortexing. The amount of the negatively charged molecule and cationic lipid in the emulsions may be adjusted or optimized to provide desired strength of binding and binding capacity. For example, as described and exampled herein, exemplary RNA-particle complexes were produced by varying the RNA:cationic lipid ratios (as measured by the "N/P ratio"). The term N/P ratio refers to the amount (moles) of protonatable nitrogen atoms in the cationic lipid divided by the amount (moles) of phosphates on the RNA.

Preferred N/P ratios are from about 1:1 to about 20:1, from about 2:1 to about 18:1, from about 3:1 to 16:1, from about 4:1 to about 14:1, from about 6:1 to about 12:1, about 3:1, about 4:1, about 5:1, about 6:1, about 7:1, about 8:1, about 9:1, about 10:1, about 11:1, about 12:1, about 13:1, about 14:1, about 15:1, or about 16:1. Alternatively, preferred N/P ratios are at least about 3:1, at least about 4:1, at least about 5:1, at least about 6:1, at least about 7:1, at least about 8:1, at least about 9:1, at least about 10:1, at least about 11:1, at least about 12:1, at least about 13:1, at least about 14:1, at least about 15:1, or at least about 16:1. A more preferred N/P ratio is about 4:1 or higher.

Each emulsion may have its own optimal or preferred N/P ratio to produce desired effects (e.g., desired level of expression of the complexed RNA), which can be determined experimentally (e.g., using the assays as described herein or other techniques known in the art, such as measuring expression level of a protein that is encoded by the RNA, or measuring the percentage of the RNA molecules being released from the complex in the presence of heparin). Generally, the N/P ratio should be at a value that at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the RNA molecules are released from the RNA-particle complexes when the RNA-particle complexes are taken up by cells. In some embodiments, the N/P ratio is a value that provides for release of at least 0.5% or at least 1% of the RNA molecules are released from the RNA-particle complexes when the RNA-particle complexes are taken up by cells.

The expression level of an antigen encoded by the RNA molecule may not necessarily correlate with the immunogenicity of the antigen. In such cases, optimal or preferred N/P ratio fore immunogenicity may be determined by, e.g., measuring specific antibody titers.

The cationic oil-in-water emulsions described herein are particularly suitable for formulating nucleic acid-based vaccines (e.g., DNA vaccines, RNA vaccines). The formation of a nucleic acid-emulsion particle complex facilitates the uptake of the nucleic acid into host cells, and protects the nucleic acid molecule from nuclease degradation. Transfected cells can then express the antigen encoded by the nucleic acid molecule, which can produce an immune response to the antigen. Like live or attenuated viruses, nucleic acid-based vaccines can effectively engage both MHC-I and MHC-II pathways allowing for the induction of $CD8^+$ and $CD4^+$ T cell responses, whereas antigen present in soluble form, such as recombinant protein, generally induces only antibody responses.

In certain embodiments, the negatively charged molecule described herein is an RNA molecule. In certain embodiments, the RNA molecule encodes an antigen (peptide, polypeptide or protein) and the cationic oil in water emulsion is suitable for use as an RNA-based vaccine. The composition can contain more than one species of RNA molecule encoding an antigen, e.g., two, three, five, or ten different species of RNA molecules that are complexed to the emulsion particles. That is, the composition can contain one or more different species of RNA molecules, each encoding a different antigen. Alternatively or in addition, one RNA molecule may also encode more than one antigen, e.g., a bicistronic, or tricistronic RNA molecule that encodes different or identical antigens. Accordingly, the cationic oil in water emulsion is suitable for use as an RNA-based vaccine, that is monovalent or multivalent. If desired, the RNA molecule can be polycistronic.

The sequence of the RNA molecule may be codon optimized or deoptimized for expression in a desired host, such as a human cell.

The sequence of the RNA molecule may be modified if desired, for example to increase the efficacy of expression or replication of the RNA, or to provide additional stability or resistance to degradation. For example, the RNA sequence can be modified with respect to its codon usage, for example, to increase translation efficacy and half-life of the RNA. A poly A tail (e.g., of about 30 adenosine residues or more) (SEQ ID NO: 28) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methylransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O]N), which may further increases translation efficacy.

If desired, the RNA molecule can comprise one or more modified nucleotides in addition to any 5' cap structure. There are more than 96 naturally occurring nucleoside modifications found on mammalian RNA. See, e.g., Limbach et al., *Nucleic Acids Research,* 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated by reference in their entirety herein, and many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2 m6A (2-methylthio-N6-methyladenosine); i6A (N6-isopentenyladenosine); ms2i6A (2-methylthio-N6 isopentenyladenosine); io6A (N6-(cis-hydroxyisopentenyl) adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C(N4-acetylcytidine); f5C (5-formylcytidine); m5Cm (5,2-O-dimethyl cytidine); ac4 Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6, N6-dimethyladenosine); Tm (2'-β-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6 Am (N6,T-O-dimethyladenosine); rn62 Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6) alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Many of these modified nucleobases and their corresponding ribonucleosides are available from commercial suppliers. See, e.g., WO 2011/005799 which is incorporated herein by reference.

If desired, the RNA molecule can contain phosphoramidate, phosphorothioate, and/or methylphosphonate linkages.

In some embodiments, the RNA molecule does not include modified nucleotides, e.g., does not include modified nucleobases, and all of the nucleotides in the RNA molecule are conventional standard ribonucleotides A, U, G and C, with the exception of an optional 5' cap that may include, for example, 7-methylguanosine. In other embodiments, the RNA may include a 5' cap comprising a 7'-methylguanosine, and the first 1, 2 or 3 5' ribonucleotides may be methylated at the 2' position of the ribose.

A. Self-Replicating RNA

In some aspects, the cationic oil in water emulsion contains a self-replicating RNA molecule. In certain embodiments, the self-replicating RNA molecule is derived from or based on an alphavirus.

Self-replicating RNA molecules are well known in the art and can be produced by using replication elements derived from, e.g., alphaviruses, and substituting the structural viral proteins with a nucleotide sequence encoding a protein of interest. Cells transfected with self-replicating RNA briefly produce antigen before undergoing apoptotic death. This death is a likely result of requisite double-stranded (ds) RNA intermediates, which also have been shown to super-activate Dendritic Cells. Thus, the enhanced immunogenicity of self-replicating RNA may be a result of the production of pro-inflammatory dsRNA, which mimics an RNA-virus infection of host cells.

Advantageously, the cell's machinery is used by self-replicating RNA molecules to generate an exponential increase of encoded gene products, such as proteins or antigens, which can accumulate in the cells or be secreted from the cells. Overexpression of proteins or antigens by self-replicating RNA molecules takes advantage of the immunostimulatory adjuvant effects, including stimulation of toll-like receptors (TLR) 3, 7 and 8 and non TLR pathways (e.g, RIG-1, MD-5) by the products of RNA replication and amplification, and translation which induces apoptosis of the transfected cell.

The self-replicating RNA generally contains at least one or more genes selected from the group consisting of viral replicases, viral proteases, viral helicases and other non-structural viral proteins, and also comprise 5'- and 3'-end cis-active replication sequences, and if desired, a heterologous sequences that encode a desired amino acid sequences (e.g., an antigen of interest). A subgenomic promoter that directs expression of the heterologous sequence can be included in the self-replicating RNA. If desired, the heterologous sequence (e.g., an antigen of interest) may be fused in frame to other coding regions in the self-replicating RNA and/or may be under the control of an internal ribosome entry site (IRES).

In certain embodiments, the self-replicating RNA molecule is not encapsulated in a virus-like particle. Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinebis virus (SIN), Semliki forest virus and Venezuelan equine encephalitis virus (VEE), one or more genes encoding viral structural proteins, such as capsid and/or envelope glycoproteins, can be omitted.

If desired, self-replicating RNA molecules of the invention can also be designed to induce production of infectious viral particles that are attenuated or virulent, or to produce viral particles that are capable of a single round of subsequent infection.

When delivered to a vertebrate cell, a self-replicating RNA molecule can lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus the delivered RNA leads to the production of multiple daughter RNAs. These transcripts are antisense relative to the delivered RNA and may be translated themselves to provide in situ expression of a gene product, or may be transcribed to provide further transcripts with the same sense as the delivered RNA which are translated to provide in situ expression of the gene product.

One suitable system for achieving self-replication is to use an alphavirus-based RNA replicon. Alphaviruses comprise a set of genetically, structurally, and serologically related arthropod-borne viruses of the Togaviridae family. Twenty-six known viruses and virus subtypes have been classified within the alphavirus genus, including, Sindbis virus, Semliki Forest virus, Ross River virus, and Venezuelan equine encephalitis virus. As such, the self-replicating RNA of the invention may incorporate a RNA replicase derived from semliki forest virus (SFV), sindbis virus (SIN), Venezuelan equine encephalitis virus (VEE), Ross-River virus (RRV), or other viruses belonging to the alphavirus family.

An alphavirus-based "replicon" expression vectors can be used in the invention. Replicon vectors may be utilized in several formats, including DNA, RNA, and recombinant replicon particles. Such replicon vectors have been derived from alphaviruses that include, for example, Sindbis virus (Xiong et al. (1989) Science 243:1188-1191; Dubensky et al., (1996) J. Virol. 70:508-519; Hariharan et al. (1998) J. Virol. 72:950-958; Polo et al. (1999) PNAS 96:4598-4603), Semliki Forest virus (Liljestrom (1991) Bio/Technology 9:1356-1361; Berglund et al. (1998) Nat. Biotech. 16:562-565), and Venezuelan equine encephalitis virus (Pushko et al. (1997) Virology 239:389-401). Alphaviruses-derived replicons are generally quite similar in overall characteristics (e.g., structure, replication), individual alphaviruses may exhibit some particular property (e.g., receptor binding, interferon sensitivity, and disease profile) that is unique. Therefore, chimeric alphavirus replicons made from divergent virus families may also be useful.

Alphavirus-based replicons are (+)-stranded replicons that can be translated after delivery to a cell to give of a replicase (or replicase-transcriptase). The replicase is translated as a polyprotein which auto-cleaves to provide a replication complex which creates genomic (−)-strand copies of the +-strand delivered RNA. These (−)-strand transcripts can themselves be transcribed to give further copies of the (+)-stranded parent RNA and also to give a subgenomic transcript which encodes the desired gene product. Translation of the subgenomic transcript thus leads to in situ expression of the desired gene product by the infected cell. Suitable alphavirus replicons can use a replicase from a sindbis virus, a semliki forest virus, an eastern equine encephalitis virus, a venezuelan equine encephalitis virus, etc.

A preferred self-replicating RNA molecule thus encodes (i) a RNA-dependent RNA polymerase which can transcribe RNA from the self-replicating RNA molecule and (ii) a polypeptide antigen. The polymerase can be an alphavirus replicase e.g. comprising alphavirus protein nsP4.

Whereas natural alphavirus genomes encode structural virion proteins in addition to the non-structural replicase, it is preferred that an alphavirus based self-replicating RNA molecule of the invention does not encode alphavirus structural proteins. Thus the self-replicating RNA can lead to the production of genomic RNA copies of itself in a cell, but not to the production of RNA-containing alphavirus virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the desired gene product, such that the subgenomic transcript encodes the desired gene product rather than the structural alphavirus virion proteins.

Thus a self-replicating RNA molecule useful with the invention may have two open reading frames. The first (5') open reading frame encodes a replicase; the second (3') open reading frame encodes a polypeptide antigen. In some embodiments the RNA may have additional (downstream) open reading frames e.g. that encode another desired gene products. A self-replicating RNA molecule can have a 5' sequence which is compatible with the encoded replicase.

In other aspects, the self-replicating RNA molecule is derived from or based on a virus other than an alphavirus, preferably, a positive-stranded RNA virus, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA molecules of the invention are larger than other types of RNA (e.g. mRNA). Typically, the self-replicating RNA molecules of the invention contain at least about 4 kb. For example, the self-replicating RNA can contain at least about 5 kb, at least about 6 kb, at least about 7 kb, at least about 8 kb, at least about 9 kb, at least about 10 kb, at least about 11 kb, at least about 12 kb or more than 12 kb. In certain examples, the self-replicating RNA is about 4 kb to about 12 kb, about 5 kb to about 12 kb, about 6 kb to about 12 kb, about 7 kb to about 12 kb, about 8 kb to about 12 kb, about 9 kb to about 12 kb, about 10 kb to about 12 kb, about 11 kb to about 12 kb, about 5 kb to about 11 kb, about 5 kb to about 10 kb, about 5 kb to about 9 kb, about 5 kb to about 8 kb, about 5 kb to about 7 kb, about 5 kb to about 6 kb, about 6 kb to about 12 kb, about 6 kb to about 11 kb, about 6 kb to about 10 kb, about 6 kb to about 9 kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb.

The self-replicating RNA molecules of the invention may comprise one or more modified nucleotides (e.g., pseudouridine, N6-methyladenosine, 5-methylcytidine, 5-methyluridine).

The self-replicating RNA molecule may encode a single polypeptide antigen or, optionally, two or more of polypeptide antigens linked together in a way that each of the sequences retains its identity (e.g., linked in series) when expressed as an amino acid sequence. The polypeptides generated from the self-replicating RNA may then be produced as a fusion polypeptide or engineered in such a manner to result in separate polypeptide or peptide sequences.

The self-replicating RNA of the invention may encode one or more polypeptide antigens that contain a range of epitopes. Preferably epitopes capable of eliciting either a helper T-cell response or a cytotoxic T-cell response or both.

The self-replicating RNA molecules described herein may be engineered to express multiple nucleotide sequences, from two or more open reading frames, thereby allowing co-expression of proteins, such as a two or more antigens together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

The self-replicating RNA molecules of the invention can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

Suitable synthetic methods can be used alone, or in combination with one or more other methods (e.g., recombinant DNA or RNA technology), to produce a self-replicating RNA molecule of the invention. Suitable methods for de novo synthesis are well-known in the art and can be adapted for particular applications. Exemplary methods include, for example, chemical synthesis using suitable protecting groups such as CEM (Masuda et al., (2007) *Nucleic Acids Symposium Series* 51:3-4), the β-cyanoethyl phosphoramidite method (Beaucage S L et al. (1981) *Tetrahedron Lett* 22:1859); nucleoside H-phosphonate method (Garegg P et al. (1986) *Tetrahedron Lett* 27:4051-4; Froehler B C et al. (1986) *Nucl Acid Res* 14:5399-407; Garegg P et al. (1986) *Tetrahedron Lett* 27:4055-8; Gaffney B L et al. (1988) *Tetrahedron Lett* 29:2619-22). These chemistries can be performed or adapted for use with automated nucleic acid synthesizers that are commercially available. Additional suitable synthetic methods are disclosed in Uhlmann et al. (1990) *Chem Rev* 90:544-84, and Goodchild J (1990) *Bioconjugate Chem* 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast *Saccharomyces*, Eds. Strathern et al., Cold Spring Harbor Press, Vols. I and II, 1982; and Sambrook et al., Molecular Cloning: A Laboratory Manual, Cold Spring Harbor Press, 1989.)

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC (e.g., usings a YMC Pack ODS-AQ column (5 micron, 4.6×250 mm) and elute using a gradient, 30% B (0-5 min) to 100% B (5-13 min) and at 100% B (13-40) min, flow Rate (0.7 ml/min), UV detection (wavelength: 260 nm), column temperature (30° C.). Buffer A (20 mM acetic acid-ammonium acetate pH 3.5), buffer B (20 mM acetic acid-ammonium acetate pH 3.5/methanol [90/10])).

Optionally, the self-replicating RNA molecules of the invention may include one or more modified nucleotides so that the self-replicating RNA molecule will have less immunomodulatory activity upon introduction or entry into a host cell (e.g., a human cell) in comparison to the corresponding self-replicating RNA molecule that does not contain modified nucleotides.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self replicating RNA molecule that encodes a polypeptide antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode a polypeptide antigen can also be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays that can be used to characterize the self-replicating RNA molecules of the invention can involve detecting expression of the encoded antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

B. Antigens

In certain embodiments, the negatively charged molecule described herein is a nucleic acid molecule (e.g., an RNA molecule) that encodes an antigen. Suitable antigens include, but are not limited to, a bacterial antigen, a viral antigen, a fungal antigen, a protazoan antigen, a plant antigen, a cancer antigen, or a combination thereof.

Suitable antigens include proteins and peptides from a pathogen such as a virus, bacteria, fungus, protozoan, plant or from a tumor. Viral antigens and immunogens that can be encoded by the self-replicating RNA molecule include, but are not limited to, proteins and peptides from a Orthomyxoviruses, such as Influenza A, B and C; Paramyxoviridae viruses, such as Pneumoviruses (RSV), Paramyxoviruses (PIV), Metapneumovirus and Morbilliviruses (e.g., measles); Pneumoviruses, such as Respiratory syncytial virus (RSV), Bovine respiratory syncytial virus, Pneumonia virus of mice, and Turkey rhinotracheitis virus; Paramyxoviruses, such as Parainfluenza virus types 1-4 (PIV), Mumps virus, Sendai viruses, Simian virus 5, Bovine parainfluenza virus, Nipahvirus, Henipavirus and Newcastle disease virus; Poxyiridae, including a Orthopoxvirus such as Variola vera (including but not limited to, Variola major and Variola minor); Metapneumoviruses, such as human metapneumovirus (hMPV) and avian metapneumoviruses (aMPV); Morbilliviruses, such as Measles; Picornaviruses, such as Enteroviruses, Rhinoviruses, Heparnavirus, Parechovirus, Cardioviruses and Aphthoviruses; Enteroviruses, such as Poliovirus types 1, 2 or 3, Coxsackie A virus types 1 to 22 and 24, Coxsackie B virus types 1 to 6, Echovirus (ECHO) virus types 1 to 9, 11 to 27 and 29 to 34 and Enterovirus 68 to 71, Bunyaviruses, including a Orthobunyavirus such as California encephalitis virus; a Phlebovirus, such as Rift Valley Fever virus; a Nairovirus, such as Crimean-Congo hemorrhagic fever virus; Heparnaviruses, such as, Hepatitis A virus (HAV); Togaviruses (Rubella), such as a Rubivirus, an Alphavirus, or an Arterivirus; Flaviviruses, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus; Pestiviruses, such as Bovine viral diarrhea (BVDV), Classical swine fever (CSFV) or Border disease (BDV); Hepadnaviruses, such as Hepatitis B virus, Hepatitis C virus; Rhabdoviruses, such as a Lyssavirus (Rabies virus) and Vesiculovirus (VSV), Caliciviridae, such as Norwalk virus, and Norwalk-like Viruses, such as Hawaii Virus and Snow Mountain Virus; Coronaviruses, such as SARS, Human respiratory coronavirus, Avian infectious bronchitis (IBV), Mouse hepatitis virus (MHV), and Porcine transmissible gastroenteritis virus (TGEV); Retroviruses such as an Oncovirus, a Lentivirus or a Spumavirus; Reoviruses, as an Orthoreovirus, a Rotavirus, an Orbivirus, or a Coltivirus; Parvoviruses, such as Parvovirus B19; Delta hepatitis virus (HDV); Hepatitis E virus (HEV); Hepatitis G virus (HGV); Human Herpesviruses, such as, by way Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8); Papovaviruses, such as Papillomaviruses and Polyomaviruses, Adenoviruess and Arenaviruses.

In some embodiments, the antigen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), land-locked salmon virus (LSV), atlantic salmon rotavirus (ASR), trout strawberry disease virus (TSD), coho salmon tumor virus (CSTV), or viral hemorrhagic septicemia virus (VHSV).

In some embodiments the antigen elicits an immune response against a parasite from the *Plasmodium* genus, such as *P. falciparum, P. vivax, P. malariae* or *P. ovale*. Thus the invention may be used for immunizing against malaria. In some embodiments the antigen elicits an immune response against a parasite from the Caligidae family, particularly those from the Lepeophtheirus and *Caligus* genera e.g. sea lice such as *Lepeophtheirus salmonis* or *Caligus rogercresseyi*.

Bacterial antigens and immunogens that can be encoded by the self-replicating RNA molecule include, but are not limited to, proteins and peptides from *Neisseria meningitides, Streptococcus pneumoniae, Streptococcus pyogenes, Moraxella catarrhalis, Bordetella pertussis, Burkholderia* sp. (e.g., *Burkholderia mallei, Burkholderia pseudomallei* and *Burkholderia cepacia*), *Staphylococcus aureus, Staphylococcus epidermis, Haemophilus influenzae, Clostridium tetani* (Tetanus), *Clostridium perfringens, Clostridium botulinums* (Botulism), *Cornynebacterium diphtheriae* (Diphtheria), *Pseudomonas aeruginosa, Legionella pneumophila, Coxiella burnetii, Brucella* sp. (e.g., *B. abortus, B. canis, B. melitensis, B. neotomae, B. ovis, B. suis* and *B. pinnipediae*), *Francisella* sp. (e.g., *F. novicida, F. philomiragia* and *F. tularensis*), *Streptococcus agalactiae, Neiserria gonorrhoeae, Chlamydia trachomatis, Treponema pallidum* (Syphilis), *Haemophilus ducreyi, Enterococcus faecalis, Enterococcus faecium, Helicobacter pylori, Staphylococcus saprophyticus, Yersinia enterocolitica, E. coli* (such as enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC; such as uropathogenic *E. coli* (UPEC) and meningitis/sepsis-associated *E. coli* (MNEC)), and/or enterohemorrhagic *E. coli* (EHEC), *Bacillus anthracis* (anthrax), *Yersinia pestis* (plague), *Mycobacterium tuberculosis, Rickettsia, Listeria monocytogenes, Chlamydia pneumoniae, Vibrio cholerae, Salmonella typhi* (typhoid fever), *Borrelia burgdorfer, Porphyromonas gingivalis, Klebsiella, Mycoplasma pneumoniae*, etc.

Fungal antigens and immunogens that can be encoded by the self-replicating RNA molecule include, but are not limited to, proteins and peptides from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae,*

*Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Protazoan antigens and immunogens that can be encoded by the self-replicating RNA molecule include, but are not limited to, proteins and peptides from *Entamoeba histolytica, Giardia lambli, Cryptosporidium parvum, Cyclospora cayatanensis* and *Toxoplasma.*

Plant antigens and immunogens that can be encoded by the self-replicating RNA molecule include, but are not limited to, proteins and peptides from *Ricinus communis.*

Suitable antigens include proteins and peptides from a virus such as, for example, human immunodeficiency virus (HIV), hepatitis A virus (HAV), hepatitis B virus (HBV), hepatitis C virus (HCV), herpes simplex virus (HSV), cytomegalovirus (CMV), influenza virus (flu), respiratory syncytial virus (RSV), parvovorus, norovirus, human papilloma virus (HPV), rhinovirus, yellow fever virus, rabies virus, Dengue fever virus, measles virus, mumps virus, rubella virus, varicella zoster virus, enterovirus (e.g., enterovirus 71), ebola virus, and bovine diarrhea virus. Preferably, the antigenic substance is selected from the group consisting of HSV glycoprotein gD, HIV glycoprotein gp120, HIV glycoprotein gp 40, HIV p55 gag, and polypeptides from the pol and tat regions. In other preferred embodiments of the invention, the antigen is a protein or peptide derived from a bacterium such as, for example, *Helicobacter pylori, Haemophilus influenza, Vibrio cholerae* (cholera), *C. diphtheriae* (diphtheria), *C. tetani* (tetanus), *Neisseria meningitidis, B. pertussis, Mycobacterium tuberculosis*, and the like.

HIV antigens that can be encoded by the self-replicating RNA molecules of the invention are described in U.S. application Ser. No. 490,858, filed Mar. 9, 1990, and published European application number 181150 (May 14, 1986), as well as U.S. application Ser. Nos. 60/168,471; 09/475,515; 09/475,504; and 09/610,313, the disclosures of which are incorporated herein by reference in their entirety.

Cytomegalovirus antigens that can be encoded by the self-replicating RNA molecules of the invention are described in U.S. Pat. No. 4,689,225, U.S. application Ser. No. 367,363, filed Jun. 16, 1989 and PCT Publication WO 89/07143, the disclosures of which are incorporated herein by reference in their entirety.

Hepatitis C antigens that can be encoded by the self-replicating RNA molecules of the invention are described in PCT/US88/04125, published European application number 318216 (May 31, 1989), published Japanese application number 1-500565 filed Nov. 18, 1988, Canadian application 583,561, and EPO 388,232, disclosures of which are incorporated herein by reference in their entirety. A different set of HCV antigens is described in European patent application 90/302866.0, filed Mar. 16, 1990, and U.S. application Ser. No. 456,637, filed Dec. 21, 1989, and PCT/US90/01348, the disclosures of which are incorporated herein by reference in their entirety.

In some embodiments, the antigen is derived from an allergen, such as pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (*Apidae*), wasps (*Vespidea*), and ants (*Formicoidae*).

In certain embodiments, a tumor immunogen or antigen, or cancer immunogen or antigen, can be encoded by the self-replicating RNA molecule. In certain embodiments, the tumor immunogens and antigens are peptide-containing tumor antigens, such as a polypeptide tumor antigen or glycoprotein tumor antigens.

Tumor immunogens and antigens appropriate for the use herein encompass a wide variety of molecules, such as (a) polypeptide-containing tumor antigens, including polypeptides (which can range, for example, from 8-20 amino acids in length, although lengths outside this range are also common), lipopolypeptides and glycoproteins.

In certain embodiments, tumor immunogens are, for example, (a) full length molecules associated with cancer cells, (b) homologs and modified forms of the same, including molecules with deleted, added and/or substituted portions, and (c) fragments of the same. Tumor immunogens include, for example, class I-restricted antigens recognized by CD8+ lymphocytes or class II-restricted antigens recognized by CD4+ lymphocytes.

In certain embodiments, tumor immunogens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example).

In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

C. Formulations for the Negatively Charged Molecule

The negatively charged molecule (such as RNA) is generally provided in the form of an aqueous solution, or a form that can be readily dissolved in an aqueous solution (e.g., lyophilized). The aqueous solution can be water, or an aqueous solution that comprises a salt (e.g., NaCl), a buffer (e.g., a citrate buffer), a nonionic tonicifying agent (e.g., a saccharide), a polymer, a surfactant, or a combination thereof. If the formulation is intended for in vivo administration, it is preferable that the aqueous solution is a physiologically acceptable buffer that maintains a pH that is compatible with normal physiological conditions. Also, in certain instances, it may be desirable to maintain the pH at a particular level in order to insure the stability of certain components of the formulation.

For example, it may be desirable to prepare an aqueous solution that is isotonic and/or isosmotic. Hypertonic and hypotonic solutions sometimes could cause complications and undesirable effects when injected, such as post-administration swelling or rapid absorption of the composition because of differential ion concentrations between the composition and physiological fluids. To control tonicity, the emulsion may comprise a physiological salt, such as a sodium salt. Sodium chloride (NaCl), for example, may be used at about 0.9% (w/v) (physiological saline). Other salts that may be present include potassium chloride, potassium dihydrogen phosphate, disodium phosphate dehydrate, magnesium chloride, calcium chloride, etc. In an exemplary embodiment, the aqueous solution comprises 10 mM NaCl and other salts or non-ionic tonicifying agents. As described herein, non-ionic tonicifying agents can also be used to control tonicity.

The aqueous solution may be buffered. Any physiologically acceptable buffer may be used herein, such as citrate buffers, phosphate buffers, acetate buffers, succinate buffer, tris buffers, bicarbonate buffers, carbonate buffers, or the like. The pH of the aqueous solution will preferably be between 6.0-8.0, more preferably about 6.2 to about 6.8. In some cases, certain amount of salt may be included in the buffer. In other cases, salt in the buffer might interfere with complexation of negatively charged molecule to the emulsion particle, and therefore is avoided.

The aqueous solution may also comprise additional components such as molecules that change the osmolarity of the aqueous solution or molecules that stabilizes the negatively charged molecule after complexation. For example, the osmolality can be adjusted using a non-ionic tonicifying agent, which are generally carbohydrates but can also be polymers. (See, e.g., Voet and Voet (1990) Biochemistry (John Wiley & Sons, New York.) Examples of suitable non-ionic tonicifying agents include sugars (e.g., a monosaccharide, a disaccharide, or a polysaccharide, such as trehalose, sucrose, dextrose, fructose), sugar alcohols (e.g., mannitol, sorbitol, xylitol, erythritol, lactitol, maltitol, glycerol, reduced palatinose), and combinations thereof. If desired, a nonionic polymer (e.g., a poly(alkyl glycol)), such as polyethylene glycol, polypropylene glycol, or polybutylene glycol), or nonionic surfactant can be used. These types of agents, in particular sugar and sugar alcohols, are also cryoprotectants that can protect RNA, and other negatively charged molecules, when lyophilized. In exemplary embodiments, the buffer comprises from about 560 nM to 600 mM of trehalose, sucrose, sorbitol, or dextrose. In other exemplary embodiments, the buffer comprises from about 500 nM to 600 mM of trehalose, sucrose, sorbitol, or dextrose.

In some case, it may be preferable to prepare an aqueous solution comprising the negatively charged molecule as a hypertonic solution, and to prepare the cationic emulsion using unadulterated water or a hypotonic buffer. When the emulsion and the negatively charged molecule are combined, the mixture becomes isotonic. For example, an aqueous solution comprising RNA can be a 2× hypertonic solution, and the cationic emulsion can be prepared using 10 mM Citrate buffer. When the RNA solution and the emulsion are mixed at 1:1 (v/v) ratio, the composition becomes isotonic. Based on desired relative amounts of the emulsion to the aqueous solution that comprises the negatively charged molecule (e.g., 1:1 (v/v) mix, 2:1 (v/v) mix, 1:2 (v/v) mix, etc.), one can readily determine the tonicity of the aqueous solution that is required in order to achieve an isotonic mixture.

Similarly, compositions that have physiological osmolality may be desirable for in vivo administration. Physiological osmolality is from about 255 mOsm/kg water to about 315 mOsm/kg water. Sometimes, it may be preferable to prepare an aqueous solution comprising the negatively charged molecule as a hyperosmolar solution, and to prepare the cationic emulsion using unadulterated water or a hypoosmolar buffer. When the emulsion and the negatively charged molecule are combined, physiological osmolality is achieved. Based on desired relative amounts of the emulsion to the aqueous solution that comprises the negatively charged molecule (e.g., 1:1 (v/v) mix, 2:1 (v/v) mix, 1:2 (v/v) mix, etc.), one can readily determine the osmolality of the aqueous solution that is required in order to achieve an iso-osmolar mixture.

In certain embodiments, the aqueous solution comprising the negatively charged molecule may further comprise a polymer or a surfactant, or a combination thereof. In an exemplary embodiment, the oil-in-water emulsion contains a poloxamer. In particular, the inventors have observed that adding Pluronic® F127 to the RNA aqueous solution prior to complexation to cationic emulsion particles led to greater stability and increased RNase resistance of the RNA molecule. Addition of pluronic F127 to RNA aqueous solution was also found to decrease the particle size of the RNA/CNE complex. Poloxamer polymers may also facilitate appropriate decomplexation/release of the RNA molecule, prevent aggregation of the emulsion particles, and have immune modulatory effect. Other polymers that may be used include, e.g., Pluronic® F68 or PEG300.

Alternatively or in addition, the aqueous solution comprising the negatively charged molecule may comprise from about 0.05% to about 20% (w/v) polymer. For example, the cationic oil-in-water emulsion may comprise a polymer (e.g., a poloxamer such as Pluronic® F127, Pluronic® F68, or PEG300) at from about 0.05% to about 10% (w/v), such as 0.05%, 0.5%, 1%, or 5%.

The buffer system may comprise any combination of two or more molecules described above (salt, buffer, saccharide, polymer, etc). In an preferred embodiment, the buffer comprises 560 mM sucrose, 20 mM NaCl, and 2 mM Citrate, which can be mixed with a cationic oil in water emulsion described herein to produce a final aqueous phase that comprises 280 mM sucrose, 10 mM NaCl and 1 mM citrate.

5. Methods of Preparation

In another aspect, the invention provides a method of preparing the oil-in-water emulsions as described herein, comprising: (1) combining the oil and the cationic lipid to form the oil phase of the emulsion; (2) providing an aqueous solution to form the aqueous phase of the emulsion; and (3) dispersing the oil phase in the aqueous phase, for example, by homogenization. Homogenization may be achieved in any suitable way, for example, using a commercial homogenizer (e.g., IKA T25 homogenizer, available at VWR International (West Chester, Pa.).

In certain embodiments, the oil-in-water emulsions are prepared by (1) directly dissolving the cationic lipid in the oil to form an oil phase; (2) providing the aqueous phase of the emulsion; and (3) dispersing the oil phase in the aqueous phase by homogenization. The method does not use an organic solvent (such as chloroform ($CHCl_3$), dichloromethane (DCM), ethanol, acetone, Tetrahydrofuran (THF), 2,2,2 trifluoroethanol, acetonitrile, ethyl acetate, hexane, Dimethylformamide (DMF), Dimethyl sulfoxide (DMSO), etc.) to solubilize the cationic lipid first before adding the lipid to the oil.

It may be desirable to heat the oil to a temperature between about 37° C. to about 65° C. to facilitate the dissolving of the lipid. Desired amount of the cationic lipid (e.g., DOTAP) can be measured and added directly to the oil to reach a desired final concentration.

If the emulsion comprises one or more surfactants, the surfactant(s) may be included in the oil phase or the aqueous phase according to the conventional practice in the art. For example, SPAN85 can be dissolved in the oil phase (e.g., squalene), and Tween 80 may be dissolved in the aqueous phase (e.g., in a citrate buffer).

In another aspect, the invention provides a method of preparing a composition that comprises a negatively charged molecule (such as RNA) complexed with a particle of a cationic oil-in-water emulsion, comprising: (i) providing a cationic oil-in-water emulsion as described herein; (ii) providing a aqueous solution comprising the negatively charged molecule (such as RNA); and (iii) combining the oil-in-water emulsion of (i) and the aqueous solution of (iii), so that the negatively charged molecule complexes with the particle of the emulsion.

For example, a cationic oil-in-water emulsion may be combined with an aqueous RNA solution in any desired relative amounts, e.g., about 1:1 (v/v), about 1.5:1 (v/v), about 2:1 (v/v), about 2.5:1 (v/v), about 3:1 (v/v), about 3.5:1 (v/v), about 4:1 (v/v), about 5:1 (v/v), about 10:1 (v/v), about 1:1.5 (v/v), about 1:2 (v/v), about 1:2.5 (v/v), about 1:3 (v/v), about 1:3.5 (v/v), about 1:4 (v/v), about 1:1.5 (v/v), or about 1:1.10 (v/v), etc.

Additional optional steps to promote particle formation, to improve the complexation between the negatively charge molecules and the cationic particles, to increase the stability of the negatively charge molecule (e.g., to prevent degradation of an RNA molecule), to facilitate appropriate decomplexation/release of the negatively charged molecules (such as an RNA molecule), or to prevent aggregation of the emulsion particles may be included. For example, a polymer (e.g., Pluronic® F127) or a surfactant may be added to the aqueous solution that comprises the negatively charged molecule (such as RNA).

The size of the emulsion particles can be varied by changing the ratio of surfactant to oil (increasing the ratio decreases particle size), operating pressure (increasing operating pressure reduces particle size), temperature (increasing temperature decreases particle size), and other process parameters. Actual particle size will also vary with the particular surfactant, oil, and cationic lipid used, and with the particular operating conditions selected. Emulsion particle size can be verified by use of sizing instruments, such as the commercial Sub-Micron Particle Analyzer (Model N4MD) manufactured by the Coulter Corporation, and the parameters can be varied using the guidelines set forth above until the average diameter of the particles is less than less than about 200 nm, less than about 150 nm, or less than about 100 nm. Preferably, the particles have an average diameter of about 180 nm or less, about 150 nm or less, about 140 nm or less, or about 130 nm or less, about 120 nm or less, or about 100 nm or less, from about 50 nm to 200 nm, from about 80 nm to 200 nm, from about 50 nm to 180 nm, from about 60 nm to 180 nm, from about 70 to 180 nm, or from about 80 nm to 180 nm, from about 80 nm to about 170 nm, from about 80 nm to about 160 nm, from about 80 nm to about 150 nm, from about 80 nm to about 140 nm, from about 80 nm to about 130 nm, from about 80 nm to about 120 nm, from about 80 nm to about 110 nm, or from about 80 nm to about 100 nm. Emulsions wherein the mean particle size is about 200 nm or less allow for sterile filtration.

Optional processes for preparing the cationic oil-in-water emulsion (pre-complexation emulsion), or the negatively charged molecule-emulsion complex, include, e.g., sterilization, particle size selection (e.g., removing large particles), filling, packaging, and labeling, etc. For example, if the pre-complexation emulsion, or the negatively charged molecule-emulsion complex, is formulated for in vivo administration, it may be sterilized. For example, the formulation can be sterilized by filtering through a sterilizing grade filter (e.g., through a 0.22 micron filter). Other sterilization techniques include a thermal process, or a radiation sterilization process, or using pulsed light to produce a sterile composition.

The cationic oil-in-water emulsion described herein can be used to manufacture vaccines. Sterile and/or clinical grade cationic oil-in-water emulsions can be prepared using similar methods as described for MF59. See, e.g., Ott et al., Methods in Molecular Medicine, 2000, Volume 42, 211-228, in VACCINE ADJUVANTS (O'Hagan ed.), Humana Press. For example, similar to the manufacturing process of MF59, the oil phase and the aqueous phase of the emulsion can be combined and processed in a rotor stator homogenizer, or an inline homogenizer, to yield a coarse emulsion. The coarse emulsion can then be fed into a microfluidizer, where it can be further processed to obtain a stable submicron emulsion. The coarse emulsion can be passed through the interaction chamber of the microfluidizer repeatedly until the desired particle size is obtained. The bulk emulsion can then be filtered (e.g., though a 0.22-μm filter under nitrogen) to remove large particles, yielding emulsion bulk that can be filled into suitable containers (e.g., glass bottles). For vaccine antigens that have demonstrated long-term stability in the presence of oil-in-water emulsion for self storage, the antigen and emulsion may be combined and sterile-filtered (e.g., though a 0.22-μm filter membrane). The combined single vial vaccine can be filled into single-dose containers. For vaccine antigens where long-term stability has not been demonstrated, the emulsion can be supplied as a separate vial. In such cases, the emulsion bulk can be filtered-sterilized (e.g., though a 0.22-μm filter membrane), filled, and packaged in final single-dose vials.

Quality control may be optionally performed on a small sample of the emulsion bulk or admixed vaccine, and the bulk or admixed vaccine will be packaged into doses only if the sample passes the quality control test.

6. Kits, Pharmaceutical Compositions and Administration

In another aspect, the invention provides a pharmaceutical composition comprising a negatively charged molecule (such as RNA) complexed with a particle of a cationic oil-in-water emulsion, as described herein, and may further comprise one or more pharmaceutically acceptable carriers, diluents, or excipients. In preferred embodiments, the pharmaceutical composition is an immunogenic composition, which can be used as a vaccine.

Alternatively, the compositions described herein may be used to deliver a negatively charged molecule to cells. For example, nucleic acid molecules (e.g., DNA or RNA) can be delivered to cells for a variety of purposes, such as to induce production of a desired gene product (e.g., protein), to regulate expression of a gene, for gene therapy and the like. The compositions described herein may also be used to deliver a nucleic acid molecule (e.g., DNA or RNA) to cells for therapeutic purposes, such as to treat a disease such as cancers or proliferative disorders, metabolic diseases, cardiovascular diseases, infections, allergies, to induce an immune response and the like. For example, nucleic acid molecules may be delivered to cells to inhibit the expression of a target gene. Such nucleic acid molecules include, e.g., antisense oligonucleotides, double-stranded RNAs, such as small interfering RNAs and the like. Double-stranded RNA molecules, such as small interfering RNAs, can trigger RNA interference, which specifically silences the corresponding target gene (gene knock down). Antisense oligonucleotides are single strands of DNA or RNA that are complementary to a chosen sequence. Generally, antisense RNA can prevent protein translation of certain messenger RNA strands by binding to them. Antisense DNA can be used to target a specific, complementary (coding or non-coding) RNA. Therefore, the cationic emulsions described herein are useful for delivering antisense oligonucleotides or double-stranded RNAs for treatment of, for example, cancer by inhibiting production of an oncology target.

The invention also provides kits, wherein the negatively charged molecule (such as RNA) and the cationic oil-in-water emulsion are in separate containers. For example, the kit can contain a first container comprising a composition comprising the negatively charged molecule (such as RNA), and a second container comprising cationic oil-in-water emulsion. The two components may be mixed prior to administration, e.g., within about 72 hours, about 48 hours, about 24 hours, about 12 hours, about 10 hours, about 9 hours, about 8 hours, about 7 hours, about 6 hours, about 5 hours, about 4 hours, about 3 hours, about 2 hours, about 1 hour, about 45 minutes, about 30 minutes, about 15 minutes, about 10 minutes, about 5 minutes prior to administration. The two components may also be mixed about 1 minute or immediately prior to administration.

The negatively charged molecule (e.g., RNA) may be in liquid form or can be in solid form (e.g., lyophilized). If in solid form, the kit may comprise a third container comprising a suitable aqueous solution to rehydrate the negatively charged molecule. Suitable aqueous solutions include pharmaceutically-acceptable buffers such as phosphate-buffered saline, Ringer's solution, dextrose solution, or any one of the aqueous solutions described above. In certain embodiments, sterile water may be used as the aqueous solution for rehydration, in particular in cases where additional components, such as tonicifying agents and/or osmolality adjusting agents are lyophilized along with the negatively charged molecule (e.g., RNA). Alternatively, the lyophilized negatively charged molecule (e.g., RNA) may be mixed directly with the cationic emulsion.

If the composition (e.g., a vaccine) comprises a negatively charged molecule (e.g., RNA) and an additional component, such as a protein immunogen, both components can be frozen and lyophilized (either separately, or as a mixture), and reconstituted and mixed with the cationic emulsion prior to administration.

The kit can further comprise other materials useful to the end-user, including other pharmaceutically acceptable formulating solutions such as buffers, diluents, filters, needles, and syringes or other delivery device. For example, the kit may include a dual chamber syringe that contain water or the emulsion in one chamber, and the negatively charged molecule (e.g., RNA) is provided in solid (e.g. lyophilized) form in the other chamber.

The kit may further include another container comprising an adjuvant (such as an aluminum containing adjuvant or MF59). In general, aluminum containing adjuvants are not preferred because they may interfere with the complexation of the negatively charged molecule with the cationic emulsion.

Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle). Dual-chamber syringe may also be used, wherein the negatively charged molecule (e.g., RNA) is lyophilized, and either reconstituted with water in the syringe, or reconstituted directly with a cationic emulsion described herein.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the compositions described above.

The pharmaceutical compositions provided herein may be administered singly or in combination with one or more additional therapeutic agents. The method of administration include, but are not limited to, oral administration, rectal administration, parenteral administration, subcutaneous administration, intravenous administration, intravitreal administration, intramuscular administration, inhalation, intranasal administration, topical administration, ophthalmic administration, or otic administration.

A therapeutically effective amount of the compositions described herein will vary depending on, among others, the disease indicated, the severity of the disease, the age and relative health of the subject, the potency of the compound administered, the mode of administration and the treatment desired.

In other embodiments, the pharmaceutical compositions described herein can be administered in combination with one or more additional therapeutic agents. The additional therapeutic agents may include, but are not limited to antibiotics or antibacterial agents, antiemetic agents, antifungal agents, anti-inflammatory agents, antiviral agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferons, ribavirin, hormones, and other toll-like receptor modulators, immunoglobulins (Igs), and antibodies modulating Ig function (such as anti-IgE (omalizumab)).

In certain embodiments, the pharmaceutical compositions provided herein are used in the treatment of infectious diseases including, but not limited to, disease cased by the pathogens disclosed herein, including viral diseases such as genital warts, common warts, plantar warts, rabies, respiratory syncytial virus (RSV), hepatitis B, hepatitis C, Dengue virus, yellow fever, herpes simplex virus (by way of example only, HSV-I, HSV-II, CMV, or VZV), molluscum contagiosum, vaccinia, variola, lentivirus, human immunodeficiency virus (HIV), human papilloma virus (HPV), hepatitis virus (hepatitis C virus, hepatitis B virus, hepatitis A virus), cytomegalovirus (CMV), varicella zoster virus (VZV), rhinovirus, enterovirus (e.g. EV71), adenovirus, coronavirus (e.g., SARS), influenza, para-influenza, mumps virus, measles virus, rubella virus, papovavirus, hepadnavirus, flavivirus, retrovirus, arenavirus (by way of example only, LCM, Junin virus, Machupo virus, Guanarito virus and Lassa Fever) and Filovirus (by way of example only, ebola virus or marburg virus).

In certain embodiments, the pharmaceutical compositions provided herein are used in the treatment of bacterial, fungal, and protozoal infections including, but not limited to, malaria, tuberculosis and *mycobacterium avium*, leprosy; *pneumocystis carnii*, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus,* and *Chlamydia,* and fungal infections such as candidiasis, aspergillosis, histoplasmosis, and cryptococcal meningitis.

In certain embodiments, the pharmaceutical compositions provided herein are used in the treatment of respiratory diseases and/or disorders, dermatological disorders, ocular diseases and/or disorders, genitourinary diseases and/or disorders including, allograft rejection, auto-immune and allergic, cancer, or damaged or ageing skin such as scarring and wrinkles.

In another aspect, the invention provides a method for generating or potentiating an immune response in a subject in need thereof, such as a mammal, comprising administering an effective amount of a composition as disclosed herein. The immune response is preferably protective and preferably involves antibodies and/or cell-mediated immunity. The method may be used to induce a primary immune response and/or to boost an immune response.

In certain embodiments, the compositions disclosed herein may be used as a medicament, e.g., for use in raising or enhancing an immune response in a subject in need thereof, such as a mammal.

In certain embodiments, the compositions disclosed herein may be used in the manufacture of a medicament for generating or potentiating an immune response in a subject in need thereof, such as a mammal.

The mammal is preferably a human, but may be, e.g., a cow, a pig, a chicken, a cat or a dog, as the pathogens covered herein may be problematic across a wide range of species. Where the vaccine is for prophylactic use, the human is preferably a child (e.g., a toddler or infant), a teenager, or an adult; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the compositions or vaccines disclosed herein. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

Another way of assessing the immunogenicity of the compositions or vaccines disclosed herein where the nucleic acid molecule (e.g., the RNA) encodes a protein antigen is to express the protein antigen recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the compositions can also be determined in vivo by challenging appropriate animal models of the pathogen of interest infection.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

In certain embodiments, the total amount of cationic lipid, such as DOTAP, that is administered to the subject in a single administration is no more than about 30 mg, or no more than about 24 mg.

In certain embodiments, the total amount of cationic lipid, such as DOTAP, that is administered to the subject in a single administration is no more than 4 mg.

The compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving the compositions are the elderly (e.g., >50 years old, >60 years old, and preferably >65 years), the young (e.g., <5 years old), hospitalized patients, healthcare workers, armed service and military personnel, pregnant women, the chronically ill, or immunodeficient patients. The compositions are not suitable solely for these groups, however, and may be used more generally in a population.

The compositions disclosed herein that include one or more antigens or are used in conjunction with one or more antigens may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

In certain embodiments, the compositions provided herein include or optionally include one or more immunoregulatory agents such as adjuvants. Exemplary adjuvants include, but are not limited to, a TH1 adjuvant and/or a TH2 adjuvant, further discussed below. In certain embodiments, the adjuvants used in the immunogenic compositions provide herein include, but are not limited to:
1. Mineral-Containing Compositions;
2. Oil Emulsions;
3. Saponin Formulations;
4. Virosomes and Virus-Like Particles;
5. Bacterial or Microbial Derivatives;
6. Bioadhesives and Mucoadhesives;
7. Liposomes;
8. Polyoxyethylene Ether and Polyoxyethylene Ester Formulations;
9. Polyphosphazene (PCPP);
10. Muramyl Peptides;
11. Imidazoquinolone Compounds;
12. Thiosemicarbazone Compounds;
13. Tryptanthrin Compounds;
14. Human Immunomodulators;
15. Lipopeptides;
16. Benzonaphthyridines;
17. Microparticles
18. Immunostimulatory polynucleotide (such as RNA or DNA; e.g., CpG-containing oligonucleotides)

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

Development of Cationic Oil-in-Water Emulsions

In this Example, cationic nanoemulsions (referred herein as "CNEs") that contain high concentrations of cationic lipid (DOTAP) were developed for the delivery of self replicating RNA.

The CNE formulations are summarized in Table 1 below, and were modified based on CNE01. CNE01, CMF40, CNE16, CNE02, and CNE17 were used as reference samples for comparative studies.

TABLE 1

| | CNE | Cationic Lipid mg/mL | Surfactant | Squalene | oil:Lipid ratio (mole:mole) | Aqueous phase |
|---|---|---|---|---|---|---|
| Ref. 1 | CNE01 | DOTAP (in CHCl$_3$) 0.8 | 0.5% SPAN 85 0.5% Tween 80 | 4.3% | 91.7:1 | 10 mM citrate buffer pH 6.5 |
| Ref. 2 | CMF40 | DOTAP (no organic solvent) 1.0 | 0.5% SPAN 85 0.5% Tween 80 | 4.3% | 73.3:1 | 10 mM citrate buffer pH 6.5 |
| Ref. 3 | CNE16 | DOTAP (no organic solvent) 1.2 | 0.5% SPAN 85 0.5% Tween 80 | 4.3% | 61.1:1 | 10 mM citrate buffer pH 6.5 |
| Ref. 4 | CNE02 | DOTAP (no organic solvent) 1.6 | 0.5% SPAN 85 0.5% Tween 80 | 4.3% | 45.8:1 | 10 mM citrate buffer pH 6.5 |
| Ref. 5 | CNE17 | DOTAP (in DCM) 1.4 | 0.5% SPAN 85 0.5% Tween 80 | 4.3% | 52.4:1 | 10 mM citrate buffer pH 6.5 |
| Example 1 | CMF41 | DOTAP (no organic solvent) 1.8 | 0.5% SPAN 85 0.5% Tween 80 | 4.3% | 40.7:1 | 10 mM citrate buffer pH 6.5 |

TABLE 1-continued

| | CNE | Cationic Lipid mg/mL | Surfactant | Squalene | oil:Lipid ratio (mole:mole) | Aqueous phase |
|---|---|---|---|---|---|---|
| Example 2 | CMF30 | DOTAP (no organic solvent) 2.0 | 0.5% SPAN 85 0.5% Tween 80 | 4.3% | 36.7:1 | 10 mM citrate buffer pH 6.5 |
| Example 3 | CMF31 | DOTAP (no organic solvent) 2.6 | 0.5% SPAN 85 0.5% Tween 80 | 4.3% | 28.2:1 | 10 mM citrate buffer pH 6.5 |
| Example 4 | CMF32 | DOTAP (no organic solvent) 3.2 | 0.5% SPAN 85 0.5% Tween 80 | 4.3% | 22.9:1 | 10 mM citrate buffer pH 6.5 |
| Example 5 | CMF33 | DOTAP (no organic solvent) 3.8 | 0.5% SPAN 85 0.5% Tween 80 | 4.3% | 19.3:1 | 10mM citrate buffer pH 6.5 |
| Example 6 | CMF34 | DOTAP (no organic solvent) 4.4 | 0.5% SPAN 85 0.5% Tween 80 | 4.3% | 16.7:1 | 10mM citrate buffer pH 6.5 |
| Example 7 | CMF35 | DOTAP (no organic solvent) 5.0 | 0.5% SPAN 85 0.5% Tween 80 | 4.3% | 14.7:1 | 10mM citrate buffer pH 6.5 |
| Example 8 | CMF44 | DOTAP (no organic solvent) 4.4 | 0.5% SPAN 85 0.5% Tween 80 | 3.23% | 12.5:1 | 10mM citrate buffer pH 6.5 |
| Example 9 | CMF45 | DOTAP (no organic solvent) 4.4 | 0.5% SPAN 85 0.5% Tween 80 | 2.15% | 8.4:1 | 10mM citrate buffer pH 6.5 |
| Example 10 | CMF46 | DOTAP (no organic solvent) 4.4 | 0.5% SPAN 85 0.5% Tween 80 | 1.08% | 4.2:1 | 10mM citrate buffer pH 6.5 |

CNEs were prepared similar to charged MF59 as previously described (Ott et al., Journal of Controlled Release, volume 79, pages 1-5, 2002), with one major modification. DOTAP was dissolved in the squalene directly, and no organic solvent was used. It was discovered that inclusion of a solvent in emulsions that contained greater than 1.6 mg/ml DOTAP produced a foamy feedstock that could not be microfluidized to produce an emulsion. Heating squalene to 37° C. allowed DOTAP to be directly dissolved in squalene, and then the oil phase could be successfully dispersed in the aqueous phase (e.g., by homogenization) to produce an emulsion. DOTAP is soluble in squalene and higher concentrations of DOTAP in squalene than those listed in Table 1 may be achieved. However, it has been reported that high dose of DOTAP can have toxic effects. See, e.g., Lappalainen et al., Pharm. Res., vol. 11(8):1127-31 (1994).

Briefly, squalene was heated to 37° C., and DOTAP was dissolved directly in squalene in the presence of SPAN 85. The resulting oil phase was then combined with the aqueous phase (Tween 80 in citrate buffer) and immediately homogenized for 2 min using an IKA T25 homogenizer at 24K RPM to produce a homogeneous feedstock (primary emulsions). The primary emulsions were passed three to five times through a M-110S Microfluidizer or a M-110P Microfluidizer (Microfluidics, Newton, Mass.) with an ice bath cooling coil at a homogenization pressure of approximately 15K-20K PSI. The 20 ml batch samples were removed from the unit and stored at 4° C.

It should be noted that the concentrations of the components of the CNEs, as describes in Table 1, are concentrations calculated according the initial amounts of these components that were used to prepare the emulsions. It is understood that during the process of producing emulsions, or during the filter sterilization process, small amounts of squalene, DOTAP, or other components may be lost, and the actual concentrations of these components in the final product (e.g., a packaged, sterilized emulsion that is ready for administration) might be slightly lower, typically by up to about 20%, sometimes by up to about 25%, or up to about 35%. However, the conventional practice in the art is to describe the concentration of a particular component based on the initial amount that is used to prepare the emulsion, instead of the actual concentration in the final product.

Table 2 below shows the difference between the "theoretical" concentrations of squalene and DOTAP (calculated according the initial amounts of squalene and DOTAP that were used to prepare the emulsions), and the actual concentrations of squalene and DOTAP as measured in the final product.

TABLE 2

| CNE | Theoretical DOTAP (mg/mL) | Actual DOTAP (mg/mL) | % of Theoretical DOTAP Yield | Theoretical Squalene (mg/mL) | Actual Squalene (mg/mL) | % of Theoretical Squalene Yield |
|---|---|---|---|---|---|---|
| CMF32 Batch 1 | 3.2 | 2.20 | 68.76 | 43 | 19.33 | 44.95 |
| CMF32 Batch 2 | 3.2 | 2.57 | 80.32 | 43 | 34.45 | 80.12 |
| CMF32 Batch 3 | 3.2 | 2.37 | 73.95 | 43 | 38.38 | 89.25 |
| CMF34 Batch 1 | 4.4 | 2.75 | 62.44 | 43 | 30.46 | 70.84 |
| CMF34 Batch 2 | 4.4 | 3.21 | 73.00 | 43 | 33.98 | 79.02 |
| CMF34 Batch 3 | 4.4 | 3.08 | 70.08 | 43 | 32.71 | 76.07 |
| CMF34 Batch 4 | 4.4 | 3.52 | 79.93 | 43 | 28.95 | 67.34 |

EXAMPLE 2

Preparation RNA-Particle Complexes

1. RNA Synthesis

Plasmid DNA encoding an alphavirus replicon (self-replicating RNA) was used as a template for synthesis of RNA in vitro. Each replicon contains the genetic elements required for RNA replication but lacks sequences encoding gene products that are necessary for particle assembly. The structural genes of the alphavirus genome were replaced by sequences encoding a heterologous protein (whose expression is driven by the alphavirus subgenomic promoter). Upon delivery of the replicons to eukaryotic cells, the positive-stranded RNA is translated to produce four non-structural proteins, which together replicate the genomic RNA and transcribe abundant subgenomic mRNAs encoding the heterologous protein. Due to the lack of expression of the alphavirus structural proteins, replicons are incapable of generating infectious particles. A bacteriophage T7 promoter is located upstream of the alphavirus cDNA to facilitate the synthesis of the replicon RNA in vitro, and the hepatitis delta virus (HDV) ribozyme located immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) final concentration of each of the nucleoside triphosphates (ATP, CTP, GTP and UTP) following the instructions provided by the manufacturer (Ambion, Austin, Tex.). Following transcription, the template DNA was digested with TURBO DNase (Ambion, Austin, Tex.). The replicon RNA was precipitated with LiCl and reconstituted in nuclease-free water. Uncapped RNA was capped post-transcriptionally with Vaccinia Capping Enzyme (VCE) using the ScriptCap $m^7G$ Capping System (Epicentre Biotechnologies, Madison, Wis.) as outlined in the user manual. Post-transcriptionally capped RNA was precipitated with LiCl and reconstituted in nuclease-free water. Alternatively, replicons may be capped by supplementing the transcription reactions with 6 mM (for T7 RNA polymerase) or 4 mM (for SP6 RNA polymerase) $m^7G(5')ppp(5')G$, a non-reversible cap structure analog (New England Biolabs, Beverly, Mass.) and lowering the concentration of guanosine triphosphate to 1.5 mM (for T7 RNA polymerase) or 1 mM (for SP6 RNA polymerase). The transcripts may be then purified by TURBO DNase (Ambion, Austin, Tex.) digestion followed by LiCL precipitation and a wash in 75% ethanol.

The concentration of the RNA samples was determined by measuring the optical density at 260 nm. Integrity of the in vitro transcripts was confirmed by denaturing agarose gel electrophoresis for the presence of the full length construct.

2. RNA Complexation

The term N/P ratio refers to the amount of nitrogen in the cationic lipid in relation to the amount of phosphates on the RNA. The nitrogen is the charge bearing element within the cationic lipids tested. The phosphate can be found on the RNA backbone. An N/P charge ratio of 10/1 indicates that there are 10 positively charged nitrogen from the cationic lipid present for each negatively charged phosphate on the RNA.

The number of nitrogens in solution was calculated from the cationic lipid concentration, DOTAP for example has one nitrogen that can be protonated per molecule. The RNA concentration was used to calculate the amount of phosphate in solution using an estimate of 3 nmols of phosphate per microgram of RNA. By varying the amount of RNA:Lipid, the N/P ratio can be modified. RNA was complexed to the CNEs in a range of nitrogen/phosphate ratios (N/P). Calculation of the N/P ratio was done by calculating the number of moles of protonatable nitrogens in the emulsion per milliliter. To calculate the number of phosphates, a constant of 3 nmols of phosphate per microgram of RNA was used. After the values were determined, the appropriate ratio of the emulsion was added to the RNA. Using these values, the RNA was diluted to the appropriate concentration and added directly into an equal volume of emulsion while vortexing lightly. The solution was allowed to sit at room temperature for approximately 2 hours. Once complexed the resulting solution was diluted to the appropriate concentration and used within 1 hour.

3. Particle Size Assay

Particle size of the emulsion was measured using a Zetasizer Nano ZS (Malvern Instruments, Worcestershire, UK) according to the manufacturer's instructions. Particle sizes are reported as the Z-Average (ZAve) with the polydispersity index (pdi). All samples were diluted in water prior to measurements. Additionally, particle size of the emulsion was measured using Horiba LA-930 particle sizer (Horiba Scientific, USA). Samples were diluted in water prior to measurements. Zeta potential was measured using Zetasizer Nano ZS using diluted samples according to the manufacturer's instructions.

4. Viral Replicon Particles (VRP)

To compare RNA vaccines to traditional RNA-vectored approaches for achieving in vivo expression of reporter genes or antigens, we utilized viral replicon particles (VRPs) produced in BHK cells by the methods described by Perri et al., J. Virol, 77:10394-10403 (2003). In this system, the antigen (or reporter gene) replicons consisted of alphavirus chimeric replicons (VCR) derived from the genome of Venezuelan equine encephalitis virus (VEEV) engineered to contain the 3' terminal sequences (3' UTR) of Sindbis virus and a Sindbis virus packaging signal (PS) (see FIG. 2 of Perri S., et al., J Virol 77: 10394-10403 (2003)). These replicons were packaged into VRPs by co-electroporating them into baby hamster kidney (BHK) cells along with defective helper RNAs encoding the Sindbis virus capsid and glycoprotein genes (see FIG. 2 of Perri et al). The VRPs were then harvested and titrated by standard methods and inoculated into animals in culture fluid or other isotonic buffers.

EXAMPLE 3

The Effect of DOTAP Concentration on Immunogenicity

This Example shows that cationic oil-in-water emulsions made with high concentrations of DOTAP increased the immunogenicity of an RNA replicon that encodes the RSV-F antigen in a mouse model.

1. Materials and Methods
Heparin Binding Assay

RNA was complexed as described above. The RNA/CNE complex was incubated with various concentrations of heparin sulfate (Alfa Aesar, Ward Hill Mass.) for 30 minutes at Room Temperature. The resulting solutions were then placed on an Airfuge high speed centrifuge (Beckman Coulter, Brea, Calif.) for 15 minutes. The centrifuge tubes were punctured with a tuberculin syringe and the subnatant was removed. The solution was then assayed for RNA concentration using the Ribogreen assay (Invitrogen, Carlsbad Calif.) according to the manufactures directions. The samples were analyzed on a Biotek Synergy 4 (Winooski, Vt.) fluorescent plate reader. Free RNA values were calculated using a standard curve.

2. The Effect of DOTAP Concentration on RNA-Particle Interactions

Table 3 shows the effect of DOTAP concentration on RNA-particle interactions (as determined by Heparin binding assay, which measured the tightness of the RNA-particle interactions) and immunogenicity.

TABLE 3

| | | Heparin Binding Assay | |
| CNE | DOTAP concentration (mg/mL) | N/P ratio | % of RNA release in 8X heparin Sulfate |
| --- | --- | --- | --- |
| CNE01 | 0.8 | 2:1 | nt |
| | | 4:1 | nt |
| | | 6:1 | 62.82 |
| | | 8:1 | 54.18 |
| | | 10:1 | nt |
| | | 12:1 | 116.6 |
| | | 14:1 | 62.79 |
| CMF41 | 1.0 | 2:1 | nt |
| | | 4:1 | 4.61 |
| | | 6:1 | 33.41 |
| | | 8:1 | 70.68 |
| | | 10:1 | 54.92 |
| | | 12:1 | 52.93 |
| CNE16 | 1.2 | 2:1 | nt |
| | | 4:1 | 1.83 |
| | | 6:1 | nt |
| | | 8:1 | 33.79 |
| | | 10:1 | 58.86 |
| | | 12:1 | 68.02 |
| | | 14:1 | 55.07 |
| CNE17 | 1.4 | 2:1 | nt |
| | | 4:1 | nt |
| | | 6:1 | 3.91 |
| | | 8:1 | 44.00 |
| | | 10:1 | 69.65 |
| | | 12:1 | 61.53 |
| | | 14:1 | 57.26 |
| CNE02 | 1.6 | 2:1 | nt |
| | | 4:1 | nt |
| | | 6:1 | 2.01 |
| | | 8:1 | 2.87 |
| | | 10:1 | 7.38 |
| | | 12:1 | 19.37 |
| | | 14:1 | 21.44 |
| CMF41 | 1.8 | 2:1 | nt |
| | | 4:1 | 0.76 |
| | | 6:1 | 1.33 |
| | | 8:1 | 1.10 |
| | | 10:1 | 2.69 |
| | | 12:1 | 2.59 |
| | | 14:1 | 3.67 |
| CMF30 | 2.0 | 2:1 | nt |
| | | 4:1 | 0.7 |
| | | 6:1 | 0.81 |
| | | 8:1 | 1.17 |
| | | 10:1 | 2.35 |
| | | 12:1 | 5.15 |
| | | 14:1 | 9.44 |
| CMF30 | 2.6 | 2:1 | nt |
| | | 4:1 | nt |
| | | 6:1 | 0.83 |
| | | 8:1 | 1.18 |
| | | 10:1 | 1.00 |
| | | 12:1 | 0.96 |
| | | 14:1 | 1.10 | nt = not tested.

As shown in Table 3, RNA molecules bound strongly to emulsion particles that were made with high concentrations of DOTAP (1.8 mg/mL or higher).

3. The Effect of DOTAP Concentration on RNA Loading

Table 4 shows the effect of DOTAP concentration on RNA loading. Increasing the concentration of DOTAP resulted in higher amount of RNA molecules being formulated into RNA-particle complexes.

TABLE 4

| | CNE | | | | | | | |
|---|---|---|---|---|---|---|---|---|
| | CNE17 | CMF41 | CMF30 | CMF31 | CMF32 | CMF33 | CMF34 | CMF35 |
| | DOTAP (in 0.5 ml emulsion) | | | | | | | |
| N/P ratio | 0.35 mg | 0.45 mg | 0.5 mg | 0.65 mg | 0.8 mg | 0.95 mg | 1.1 mg | 1.25 mg |
| | Amount of RNA (µg) | | | | | | | |
| 4 to 1 | 41.8 | 53.7 | 59.6 | 77.5 | 95.4 | 113.3 | 131.2 | 149.1 |
| 6 to 1 | 27.8 | 35.8 | 39.8 | 51.7 | 63.6 | 75.6 | 87.5 | 99.4 |
| 8 to 1 | 20.9 | 26.8 | 29.8 | 38.8 | 47.7 | 56.7 | 65.6 | 74.6 |
| 10 to 1 | 16.7 | 21.5 | 23.9 | 31 | 38.2 | 45.3 | 52.5 | 59.6 |
| 12 to 1 | 13.9 | 17.9 | 19.9 | 25.8 | 31.8 | 37.8 | 43.7 | 49.7 |
| 14 to 1 | 11.9 | 15.3 | 17 | 22.2 | 27.3 | 32.4 | 37.5 | 42.6 |

4. The Effect of DOTAP Concentration on Immunogenicity

Table 5 shows the effect of DOTAP concentration on the immunogenicity of the RSV F antigen in an in vivo mouse model.

The vA317 replicon that expresses the surface fusion glycoprotein of RSV (RSV-F) was used for this study. BALB/c mice, aged 8-10 weeks and weighing about 20 g, 10 animals per group, were given bilateral intramuscular vaccinations. All animals were injected in the quadriceps in the two hind legs each getting an equivalent volume (50 µL per leg) on days 0 and 21 with naked self-replicating RNA expressing RSV-F (vA317, 1 µg), 1 µg of A317 formulated in a liposome that contained 40% DlinDMA, 10% DSPC, 48% Chol, 2% PEG DMG 2000 (RV01(15)), or self-replicating RNA formulated in the indicated CNEs (1 µg vA317). For each administration, the formulations were freshly prepared. Serum was collected for antibody analysis on days 14 (2wp1) and 35 (2wp2).

TABLE 5

| CNE ([ ] DOTAP) | RNA (µg/ 0.5 mL) | N/P ratio | DOTAP (mg/0.5 mL) | 2wp1 GMT (Pooled) | 2wp2 GMT | 2wp2/2wp1 ratio |
|---|---|---|---|---|---|---|
| 1 µg vA317 | — | — | — | 764 | 344 | 0.5 |
| 1 µg RV01(15) | — | — | — | 3898 | 66348 | 17.0 |
| CNE01 (0.8 mg/mL) | 9.55 | 10:1 | 0.20 | 163 | 993 | 6.1 |
| CMF40 (1.0 mg/mL) | 11.93 | 10:1 | 0.25 | 505 | 3350 | 6.6 |
| CNE16 (1.2 mg/mL) | 14.32 | 10:1 | 0.30 | 465 | 3851 | 8.3 |
| CNE17 (1.4 mg/mL) | 16.70 | 10:1 | 0.35 | 843 | 3638 | 4.3 |
| CNE02 (1.6 mg/mL) | 19.09 | 10:1 | 0.40 | 1253 | 5507 | 4.4 |
| CMF41 (1.8 mg/mL) | 21.48 | 10:1 | 0.45 | 961 | 5132 | 5.3 |
| CMF30 (2.0 mg/mL) | 23.86 | 10:1 | 0.50 | 2021 | 10068 | 5.0 |
| CMF31 (2.6 mg/mL) | 31.02 | 10:1 | 0.65 | 1557 | 11940 | 7.7 |
| CMF32 (3.2 mg/mL) | 38.18 | 10:1 | 0.80 | 1124 | 6941 | 6.2 |

As shown in Table 5, increasing DOTAP concentration resulted in higher amount of RNA being loaded to the emulsion particles, which in turn increased the host immune response. A 3-fold increase in antibody titer (at 2wp2) for CMF31 was observed as compared to CNE17. In this model, a plateau in immunogenicity was observed at 2.6 mg/mL DOTAP(CMF31).

When the amounts of RNA and DOTAP administered to each mouse were held constant (meaning for emulsions with higher concentrations of DOTAP, smaller volumes of emulsion were used to prepare the RNA/emulsion complex; then, prior to immunization, the RNA/emulsion formulations were diluted such that the volumes of the RNA/emulsion formulations injected to the mice were the same), F-specific total IgG titers were comparable with different CNE formulations (Table 6). vA317 replicon was used for all CNE formulations. RNAs were made with Ambion kit. The GMT data reflect the geometric mean titer of individual mice in each group (8 mice/group). The result shows that smaller amount of the formulations were needed for emulsions with higher concentrations of DOTAP.

TABLE 6

| Formulation | RNA (μg/dose) | N/P ratio | DOTAP (μg/dose) | Squalene (mg/dose) | 2wp1 GMT | 2wp2 GMT | 2wp2/2wp1 (boost) | % of max geo mean titer, 2wp2 |
|---|---|---|---|---|---|---|---|---|
| Naked RNA | 1 | — | — | — | 764 | 334 | 0 | 0 |
| RV01 particles | 1 | — | — | — | 3898 | 66348 | 17 | — |
| CNE17 | 1 | 10:1 | 21 | 0.65 | 673 | 5314 | 8 | 41 |
| CMF41 | 1 | 10:1 | 21 | 0.50 | 784 | 7083 | 9 | 55 |
| CMF30 | 1 | 10:1 | 21 | 0.45 | 492 | 8543 | 17 | 66 |
| CMF31 | 1 | 10:1 | 21 | 0.35 | 1123 | 6972 | 6 | 54 |
| CMF32 | 1 | 10:1 | 21 | 0.28 | 1665 | 10498 | 6 | 82 |
| CMF33 | 1 | 10:1 | 21 | 0.24 | 1351 | 12279 | 9 | 96 |
| CMF34 | 1 | 10:1 | 21 | 0.20 | 936 | 12851 | 14 | 100 |
| CMF35 | 1 | 10:1 | 21 | 0.18 | 628 | 7766 | 12 | 60 |

Titers from pre-immunization serum contained undetectable titers.

When the amount of squalene and N/P ratio (DOTAP:RNA) administered to each mouse were held constant, F-specific total IgG titers increased as the amount of RNA and DOTAP in the formulations increased (Table 7). The vA317 replicon was used for all CNE formulations. RNAs were made with Ambion kit. The GMT data reflect the geometric mean titer of individual mice in each group (8 mice/group). The result shows that increasing DOTAP concentration resulted in higher amount of RNA being loaded to the emulsion particles, which in turn increased the host immune response.

TABLE 7

| Formulation | RNA (μg/dose) | N/P ratio | DOTAP (μg/dose) | Squalene (mg/dose) | 2wp1 GMT | 2wp2 GMT | 2wp2/2wp1 (boost) | % of max geo mean titer, 2wp2 |
|---|---|---|---|---|---|---|---|---|
| Naked | 11.9 | — | — | — | 14 | 682 | 49 | 2 |
| RV01 particles | 3.3 | — | — | — | 3767 | 64889 | 17 | — |
| RV01 particles | 11.9 | — | — | — | 6562 | 102359 | 16 | — |
| CNE17 | 0 | — | 70 | 2.15 | 5 | 5 | 1 | 1 |
| CMF35 | 0 | — | 250 | 2.15 | 10 | 5 | 1 | 1 |
| CNE17 | 3.3 | 10:1 | 70 | 2.15 | 223 | 8567 | 38 | 25 |
| CMF41 | 4.3 | 10:1 | 90 | 2.15 | 974 | 7020 | 7 | 21 |
| CMF30 | 4.8 | 10:1 | 100 | 2.15 | 1212 | 10999 | 9 | 33 |
| CMF31 | 6.2 | 10:1 | 130 | 2.15 | 874 | 15142 | 17 | 45 |
| CMF32 | 7.6 | 10:1 | 160 | 2.15 | 1816 | 22239 | 12 | 66 |
| CMF33 | 9.1 | 10:1 | 190 | 2.15 | 1862 | 17445 | 9 | 52 |
| CMF34 | 10.5 | 10:1 | 220 | 2.15 | 1302 | 33634 | 26 | 100 |
| CMF35 | 11.9 | 10:1 | 250 | 2.15 | 1554 | 24971 | 16 | 74 |
| Naïve | — | — | — | — | 5 | 5 | 1 | 0 |

CMF32 and CMF34 were further studied using different N/P ratios. Table 8 shows the F-specific total IgG titers of the formulations. Theoretical N/P ratios reflect the N/P ratios calculated according to the initial amounts of DOTAP and RNA that were used to prepare the formulations. Actual N/P ratios were slightly lower than theoretical N/P ratios because small amounts of DOTAP were lost during preparation of the emulsions. The vA317 was used for all CNE and CMF formulations. The GMT data reflect the mean $\log_{10}$ titer of individual mice in each group (8 mice/group). All formulations were adjusted to 300 mOsm/kg with sucrose. There were no obvious tolerability issues observed (e.g., body weight, early serum cytokines) with either CMF32 or CMF34 formulations.

Actual N/P ratios were determined by quantifying DOTAP content in CNE or CMF batches using HPLC with a charged aerosol detector (Corona Ultra, Chelmsford, Mass.). The CNE and CMF samples were diluted in isopropanol and injected onto a XTera C18 4.6×150 mm 3.5 um column (Waters, Milford, Mass.). The area under the curve was taken from the DOTAP peak in the chromatogram and the concentration was interpolated off a DOTAP standard curve. Using the actual DOTAP concentration, an actual N/P ratio was be calculated.

TABLE 8

| Formulation | RNA (µg/dose) | Theoretical N/P ratio | Actual N/P ratio | 2wp1 GMT | 2wp1 GMT | 2wp2/2wp1 (boost) |
|---|---|---|---|---|---|---|
| Naked | 1 | — | — | 68 | 1019 | 15 |
| RV01 | 1 | — | — | 9883 | 68116 | 7 |
| CNE17 | 1 | 10:1 | — | 1496 | 6422 | 4 |
| CMF32 | 1 | 12:1 | 9.4:1 | 2617 | 14246 | 5 |
|  | 1 | 10:1 (batch 1) | 6.0:1 | 1537 | 10575 | 7 |
|  | 1 | 10:1 (batch 2) | 8.0:1 | 2047 | 16244 | 8 |
|  | 1 | 8:1 | 6.3:1 | 2669 | 7656 | 3 |
|  | 1 | 6:1 | 4.7:1 | 1713 | 4715 | 3 |
|  | 1 | 4:1 | 3.1:1 | 872 | 3773 | 4 |
| CMF34 | 1 | 12:1 | 7.4:1 | 3141 | 10134 | 3 |
|  | 1 | 10:1 (batch 1) | 6.1:1 | 1906 | 11081 | 6 |
|  | 1 | 10:1 (batch 2) | 7.0:1 | 2388 | 9857 | 4 |
|  | 1 | 8:1 | 5:1 | 1913 | 8180 | 4 |
|  | 1 | 6:1 | 3.7:1 | 1764 | 6209 | 4 |
|  | 1 | 4:1 | 2.5:1 | 1148 | 4936 | 4 |

EXAMPLE 4

The Effect of DOTAP Concentration on Immunogenicity

This Example shows that cationic oil-in-water emulsions made with high concentrations of DOTAP increased the immunogenicity of an RNA replicon that encodes the RSV-F antigen in a cotton rat model.

1. Materials and Methods
RNA Replicon.
The sequence of the RNA replicon, vA142 RSV-F-delFP-full ribozyme Vaccination of Cotton Rats.
Female cotton rats (*Sigmodon hispidis*) were obtained from Harlan Laboratories. All studies were approved and performed according to Novartis Animal Care and Use Committee. Groups of animals were immunized intramuscularly (i.m., 100 µl) with the indicated vaccines on day 0. Serum samples were collected 3 weeks after each immunization. Immunized or unvaccinated control animals were challenged intranasally (i.n.) with $1 \times 10^5$ PFU RSV 4 weeks after the final immunization.

RSV-F Trimer Subunit Vaccine.
The RSV F trimer is a recombinant protein comprising the ectodomain of RSV F with a deletion of the fusion peptide region preventing association with other trimers. The resulting construct forms a homogeneous trimer, as observed by size exclusion chromatography, and has an expected phenotype consistent with a postfusion F conformation as observed by electron microscopy. The protein was expressed in insect cells or CHO cells and purified by virtue of a HIS-tagged in fusion with the construct's C-terminus followed by size exclusion chromatography using conventional techniques. The resulting protein sample exhibits greater than 95% purity. For the in vivo evaluation of the F-subunit vaccine, 100 µg/mL trimer protein was adsorbed on 2 mg/mL alum using 10 mM Histidine buffer, pH 6.3 and isotonicity adjusted with sodium chloride to 150 mM. F-subunit protein was adsorbed on alum overnight with gentle stirring at 2-8° C.

RSV F-Specific ELISA.
Individual serum samples were assayed for the presence of RSV F-specific IgG by enzyme-linked immunosorbent assay (ELISA). ELISA plates (MaxiSorp 96-well, Nunc) were coated overnight at 4° C. with 1 µg/ml purified RSV F (delp23-furdel-trunc uncleaved) in PBS. After washing (PBS with 0.1% Tween-20), plates were blocked with Superblock Blocking Buffer in PBS (Thermo Scientific) for at least 1.5 hr at 37° C. The plates were then washed, serial dilutions of serum in assay diluent (PBS with 0.1% Tween-20 and 5% goat serum) from experimental or control cotton rats were added, and plates were incubated for 2 hr at 37° C. After washing, plates were incubated with horse radish peroxidase (HRP)-conjugated chicken anti-cotton rat IgG (Immunology Consultants Laboratory, Inc, diluted 1:5,000 in assay diluent) for 1 hr at 37° C. Finally, plates were washed and 100 µl of TMB peroxidase substrate solution (Kirkegaard & Perry Laboratories, Inc) was added to each well. Reactions were stopped by addition of 100 µl of 1M $H_3PO_4$, and absorbance was read at 450 nm using a plate reader. For each serum sample, a plot of optical density (OD) versus logarithm of the reciprocal serum dilution was generated by nonlinear regression (GraphPad Prism). Titers were defined as the reciprocal serum dilution at an OD of approximately 0.5 (normalized to a standard, pooled sera from RSV-infected cotton rats with a defined titer of 1:2500, that was included on every plate).

Micro Neutralization Assay.
Serum samples were tested for the presence of neutralizing antibodies by a plaque reduction neutralization test (PRNT). Two-fold serial dilutions of HI-serum (in PBS with 5% HI-FBS) were added to an equal volume of RSV Long previously titered to give approximately 115 PFU/25 µl. Serum/virus mixtures were incubated for 2 hours at 37° C. and 5% CO2, to allow virus neutralization to occur, and then 25 µl of this mixture (containing approximately 115 PFU) was inoculated on duplicate wells of HEp-2 cells in 96 well plates. After 2 hr at 37° C. and 5% CO2, the cells were overlayed with 0.75% Methyl Cellulose/EMEM 5% HI-FBS and incubated for 42 hours. The number of infectious virus particles was determined by detection of syncytia formation by immunostaining followed by automated counting. The neutralization titer is defined as the reciprocal of the serum dilution producing at least a 60% reduction in number of synctia per well, relative to controls (no serum).

2. The Effect of DOTAP Concentration on Immunogenicity

Table 9 shows the effect of DOTAP concentration on the immunogenicity of the RSV F antigen in an in vivo cotton rat model. The first two vaccination used the RNA/CNE formulations as shown in Table 9. For the third vaccination, 3 µg of RSV F subunit protein (in alum) were used for all animals except the naïve group.

TABLE 9

| Formulation | RNA (μg/dose) | 3wp1 F-specific total IgG titers | 3wp2 F-specific total IgG titers | 3wp3 F-specific total IgG titers | 3wp1 F-specific Neutralizing IgG titers | 3wp2 F-specific Neutralizing IgG titers | 3wp3 F-specific Neutralizing IgG titers |
|---|---|---|---|---|---|---|---|
| 6ug F-trimer + Alum | — | 16,373 | 64,928 | 84,133 | 327 | 3,565 | 3979 |
| 1E6 IU/200ul VRP | — | 2819 | 2,478 | 15,473 | 135 | 299 | 1791 |
| CNE17 (Ambion MegaScript RNA) | 0.01 | 112 | 771 | 23,939 | 28 | 66 | 689 |
| | 0.1 | 351 | 1,505 | 19,495 | 41 | 173 | 1060 |
| | 1 | 722 | 2,379 | 22,075 | 82 | 249 | 2550 |
| CMF31 (Ambion MegaScript RNA) | 0.01 | 184 | 1,015 | 31,082 | 31 | 67 | 1301 |
| | 0.1 | 375 | 1,250 | 16,597 | 51 | 99 | 2393 |
| | 1 | 1013 | 2,736 | 20,861 | 199 | 341 | 2783 |
| | 10 | 4556 | 6,867 | 27,299 | 253 | 672 | 3593 |
| CMF34 (Ambion MegaScript RNA) | 0.01 | 214 | 690 | 25,470 | 35 | 38 | 1440 |
| | 0.1 | 411 | 1,574 | 19,030 | 45 | 129 | 1835 |
| | 1 | 953 | 2,248 | 18,894 | 75 | 353 | 3224 |
| | 10 | 4,804 | 5,122 | 16,566 | 282 | 521 | 3738 |
| CNE17 (In house synthesized RNA) | 1 | 1,042 | 2,944 | 23,097 | 128 | 288 | 2086 |
| Naïve | 5 | 5 | 5 | 5 | 0 | 10 | 10 |

Ambion MegaScript RNA and in house synthesized RNA were prepared using different processes.

Data from Table 9 show that all CNE-RNA formulations induced dose-dependent immune responses in the hosts (total IgG titers as well as neutralizing antibody titers). Administering CMF31-RNA and CMF34-RNA formulations produced similar F-specific total IgG titers, and each was greater than that of CNE17 at each of the indicated RNA dose. In addition, all CNE-RNA formulations induced good neutralizing antibody titers at 10 μg RNA. Neutralizing antibody titers for the CMF31-RNA, CMF34-RNA, and CNE17-RNA groups were similar, except for surprisingly high titer for the 1 μg RNA/CMF31 group.

EXAMPLE 5

Assessing the Effects of Buffer Compositions on Immunogenicity

In this example, various emulsions based on CMF34 but with different buffer components were prepared.

Table 10 summarizes the results of murine immunogenicity studies when CMF34-formulated RNAs were prepared using different buffer systems.

TABLE 10

| Group # | RNA | Description Emulsion | N/P ratio | 2wp1 | 2wp2 | 2wp2/2wp1 ratio |
|---|---|---|---|---|---|---|
| 1 | 1 μg RSV-F* | PBS | — | 100 | 2269 | 23 |
| 2 | RV01 (15) | PBS | — | 8388 | 105949 | 13 |
| 3 | 1 μg RSV-F* | CNE17 with 280 mM Sucrose | 10:1 | 898 | 9384 | 10 |
| 4 | | CMF34 with 280 mM Sucrose | 10:1 | 1835 | 10853 | 6 |
| 5 | | CMF34 with 280 mM Sucrose and 1 mM citrate | 10:1 | 1751 | 15589 | 9 |
| 6 | | CMF34 with 280 mM Sucrose and 10 mM citrate | 10:1 | 1699 | 17078 | 10 |
| 7 | | CMF34 with 280 mM Sucrose, 1 mM citrate, and 2 mM NaCl | 10:1 | 1342 | 16400 | 12 |
| 8 | | CMF34 with 280 mM Sucrose, 10 mM citrate, and 2 mM NaCl | 10:1 | 1318 | 10467 | 8 |
| 9 | | CMF34 with 280 mM Sucrose, 1 mM citrate, and 10 mM NaCl | 10:1 | 1735 | 12457 | 7 |
| 10 | | CMF34 with 280 mM Sucrose, 10 mM citrate, and 10 mM NaCl | 10:1 | 1365 | 14414 | 11 |

*vA375 replicon.

EXAMPLE 6

Stability of the Emulsions

Stability of CMF34 was assessed by measuring the average diameter of the emulsion particles and polydispersity after the emulsion was produced (T=0) and after 1 month at 4° C. (T=1 month) and after 2 months at 4° C. (T=1 month). Stability was also assessed after 3, 6 and 12 months at 4° C. The results presented in Table 11 show that the emulsion was stabile for at least 12 months.

TABLE 11

|  | T = 0 | T = 1 month | T = 2 months | T = 3 months | T = 6 months | T = 12 months |
| --- | --- | --- | --- | --- | --- | --- |
| NanoZS (nm) | 101.4 | 100.6 | 99.76 | 99.23 | 101.0 | 101.0 |
| Polydispersity | 0.109 | 0.102 | 0.096 | 0.103 | 0.080 | 0.094 |

EXAMPLE 7

Immunogenicity of Replicons Encoding Herpes Virus Proteins

A. CMV Proteins

Figure 2:
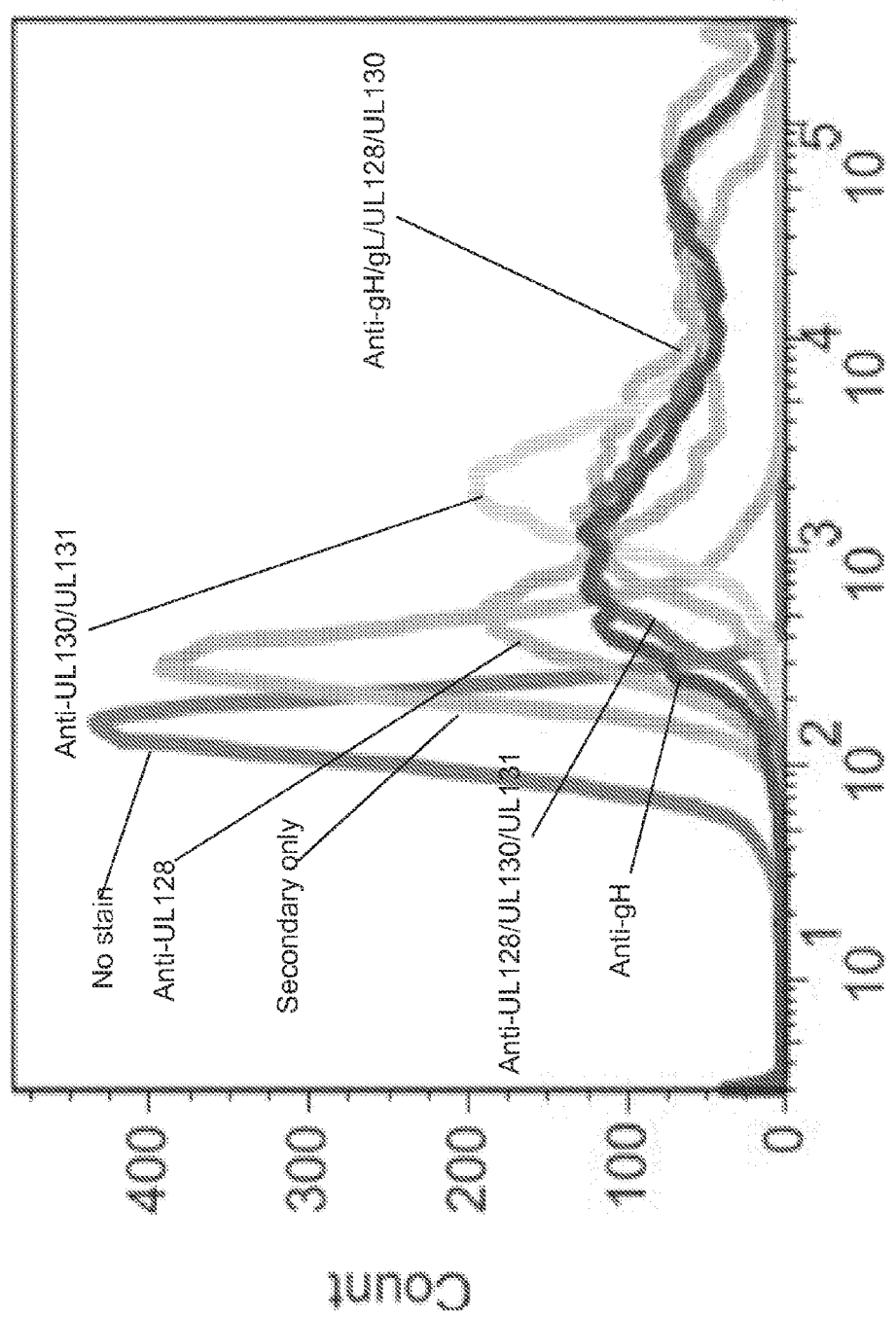
FIG. 2 is a fluorescence histogram showing that BHKV cells transfected with the A527 RNA replicon express the gH/gL/UL128/UL130/UL131 pentameric complex. Cell stain was performed using an antibody that binds a conformational epitope present on the pentameric complex.
Figure 3:
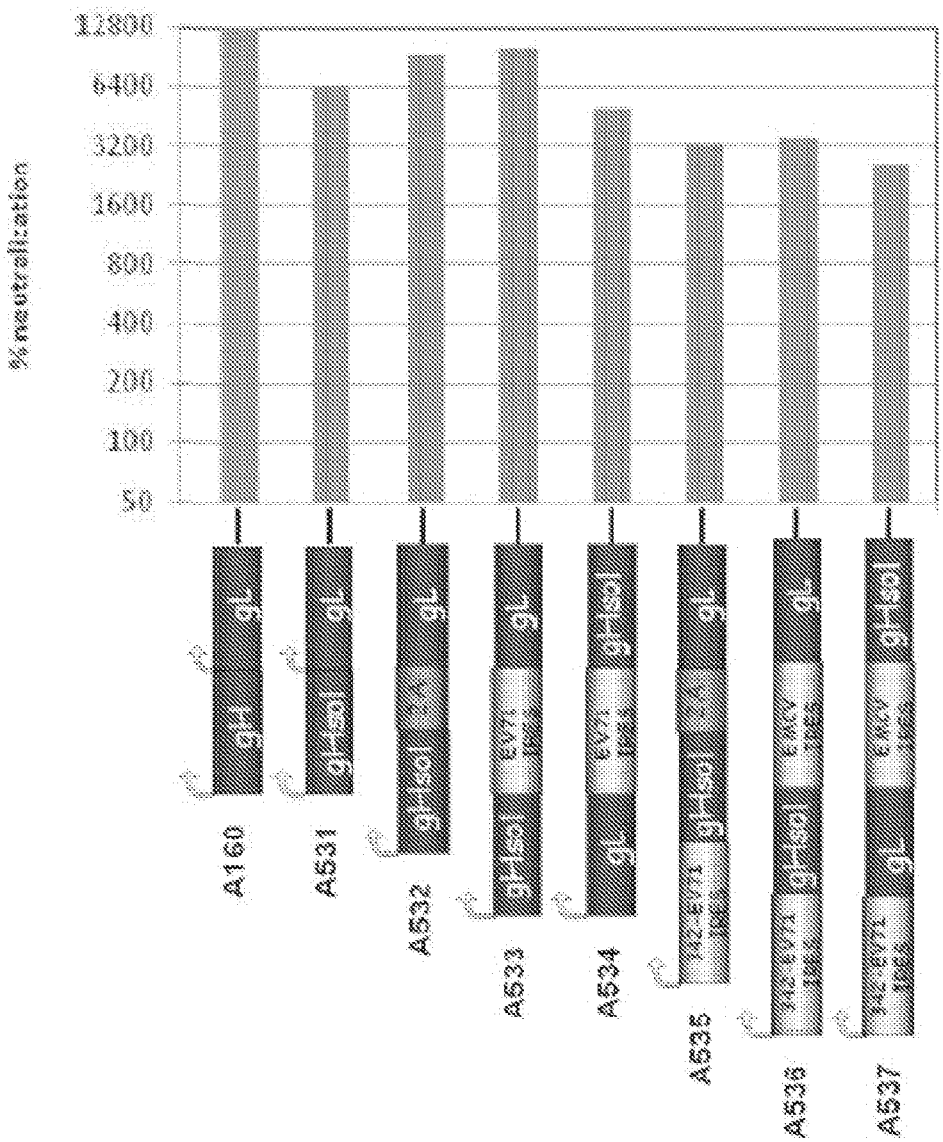
FIG. 3 is a schematic and graph. The schematic shows bicistronic RNA replicons, A160 and A531-A537, that encode CMV gH and gL. The graph shows neutralizing activity of immune sera from mice immunized with VRPs that contained the replicons.

Bicistronic and pentacistronic alphavirus replicons that express glycoprotein complexes from human cytomegalovirus (HCMV) were prepared, and are shown schematically in FIGS. 1 and 3. The alphavirus replicons were based on venezuelan equine encephalitis virus (VEE). The replicons were packaged into viral replicon particles (VRPs), encapsulated in lipid nanoparticles (LNP), or formulated with CMF34. Expression of the encoded HCMV proteins and protein complexes from each of the replicons was confirmed by immunoblot, co-immunoprecipitation, and flow cytometry. Flow cytometry was used to verify expression of the pentameric gH/gL/UL128/UL130/UL131 complex from pentameric replicons encoding the protein components of the complex, using human monoclonal antibodies specific to conformational epitopes present on the pentameric complex (Macagno et al (2010), J. Virol. 84(2):1005-13). FIG. 2 shows that these antibodies bind to BHKV cells transfected with replicon RNA expressing the HCMV gH/gL/UL128/UL130/UL131 pentameric complex (A527). Similar results were obtained when cells were infected with VRPs made from the same replicon construct. This shows that replicons designed to express the pentameric complex do indeed express the desired antigen and not the potential byproduct gH/gL.

The VRPs, RNA encapsulated in LNPs, and RNA formulated with CMF34 were used to immunize Balb/c mice by intramuscular injections in the rear quadriceps. The mice were immunized three times, three weeks apart, and serum samples were collected prior to each immunization as well as three weeks after the third and final immunization. The sera were evaluated in microneutralization assays and to measure the potency of the neutralizing antibody response that was elicited by the vaccinations. The titers are expressed as 50% neutralizing titer.

The immunogenicity of a number of different configurations of a bicistronic expression cassette for a soluble HCMV gH/gL complex in VRPs was assessed. FIG. 3 shows that VRPs expressing the membrane-anchored, full-length gH/gL complex elicited potent neutralizing antibodies at slightly higher titers than the soluble complex (gHsol/gL) expressed from a similar bicistronic expression cassette. Changing the order of the genes encoding gHsol and gL or replacing one of the subgenomic promoters with an IRES or an FMDV 2A site did not substantially improve immunogenicity.

To see if bicistronic and pentacistronic replicons expressing the gH/gL and pentameric complexes would elicit neutralizing antibodies in different formulations, cotton rats were immunized with bicistronic or pentacistronic replicons mixed with CMF34. Table 12 shows that replicons in CMF34 elicited comparable neutralizing antibody titers to the same replicons encapsulated in LNPs.

TABLE 12

Neutralizing antibody titers.
The sera were collected three weeks after the second immunization.

| Replicon | 50% Neutralizing Titer |
| --- | --- |
| A160 gH FL/gL VRP $10^6$ IU | 594 |
| A160 gH FL/gL 1 µg LNP | 141 |
| A527 Pentameric IRES 1 µg LNP | 4,416 |
| A160 gH FL/gL 1 µg CMF34 | 413 |
| A527 Pentameric IRES 1 µg CMF34 | 4,411 |

B. VZV Proteins

Nucleic acids encoding VZV proteins were cloned into a VEE replicon vector to produce monocystronic replicons that encode gB, gH, gL, gE, and gI, and to produce bicistronic replicons that encode gH/gL or gE/gI. In the bicistronic replicons, expression of each VZV open reading frame was driven by a separate subgenomic promoter.

To prepare replicon RNA, plasmid encoding the replicon was linearized by digestion with PmeI, and the linearized plasmid was extracted with phenol/chloroform/isoamylalchohol, precipitated in sodium acetate/ethanol and resuspended in 20 µl of RNase-free water.

RNA was prepared by In vitro transcription of 1 µg of linearized DNA using the MEGAscript T7 kit (AMBION #AM1333). A 20 µl reaction was set up according to the manufacturer's instruction without cap analog and incubated for 2 hours at 32° C. TURBO DNase (1 µl) was added and the mixture was incubate for 30 min. at 32° C. RNase-free water (30 µl) and ammonium acetate solution (30 µl) were added. The solution was mixed and chilled for at least 30 min at −20° C. Then the solution was centrifuged at maximum speed for 25 min. at 4° C. The supernatant was discarded, and the pellet was rinsed with 70% ethanol, and again centrifuged at maximum speed for 10 min. at 4° C. The pellet was air dried and resuspended in 50 µl of RNase-free water. The concentration of RNA was measured and quality was check on a denaturing gel.

The RNA was capped using the ScriptCap m7G Capping System (Epicentre #SCCE0625). The reaction was scaled by combining the RNA and RNase-free water. The RNA was then denatured for 5-10 min. at 65° C. The denatured RNA was transferred quickly to ice and the following reagents were added in the following order: ScriptCap Capping Buffer, 10 mM GTP, 2 mM SAM fresh prepared, ScriptGuard RNase inhibitor, and ScriptCap Capping Enzyme. The mixture was incubated for 60 min. at 37° C. The reaction was stopped by adding RNase-free water and 7.5 M LiCl, mixing well and storing the mixture for at least 30 min at −20° C. Then, the mixture was centrifuged at maximum speed for 25 min. at 4° C., the pellet was rinsed with 70% ethanol, again centrifuged at maximum speed for 10 min. at 4° C. and the pellet was air dried. The pellet was resuspended in RNase-free water. The concentration of RNA was measured and quality was checked on a denaturing gel.

RNA Transfection

Cells (BHK-V cells) were seeded on 6-well plates brought to 90-95% confluence at the time of transfection. For each transfection 3 μg of RNA was diluted in 50 mL OPTIMEM media in a first tube. Lipofectamine 2000 was added to a second tube contained 50 mL OPTIMEM media. The first and second tubes were combined and kept for 20 min. at room temperature. The culture media in the 6-well plates were replaced with fresh media, and the RNA-Lipofectamine complex was placed onto the cells, and mixed by gently rocking the plate. The plates were incubated for 24 hours at 37° C. in a $CO_2$ incubator.

For immunofluorescence, transfected cells were harvested and seeded in 96 well plate, and intracellular staining was performed using commercially available mouse mAbs (dilution range 1:100 1:400). Cell pellets were fixed and permeabilized with Citofix-Citoperm solutions. A secondary reagent, Alexa488 labelled goat anti-mouse F(ab')$_2$ (1:400 final dilution), was used.

Expression of VZV proteins gE and gI was detected in cells transfected with monocistronic constructs (gE or gI), and expression of both gE and gI was detected in cells transfected with a bicistronic gE/gI construct in western blots using commercially available mouse antibodies, 13B1 for gE and 8C4 for gI. Expression of VZV protein gB was detected in cells transfected with a monocistronic construct encoding gB, by immunofluorescence using commercially available antibody 10G6. Expression of the VZV protein complex gH/gL, was detected by immunofluorescence in cells transfected with monocistronic gH and monocistronic gL, or with a bicistronic gH/gL construct. The gH/gL complex was detected using commercially available antibody SG3.

Murine Immunogenicity Studies

Groups of 8 female BALB/c mice aged 6-8 weeks and weighing about 20 g were immunized intramuscularly with 7.0 or 1.0 ng of replicon RNA formulated with CMF32 or LNP(RV01) at day 0, 21 and 42. Blood samples were taken from the immunized animals 3 weeks after the 2nd immunization and 3 weeks after the 3rd immunization. The groups are shown in Table 13.

TABLE 13

| Group | Antigen | Dose (micrograms) | Formulation |
| --- | --- | --- | --- |
| 1 | YFP | 7 | CMF32 |
| 2 | YFP | 1 | CMF32 |
| 3 | gB | 7 | CMF32 |
| 4 | gB | 1 | CMF32 |
| 5 | gE | 7 | CMF32 |
| 6 | gE | 1 | CMF32 |
| 7 | gH | 7 | CMF32 |

TABLE 13-continued

| Group | Antigen | Dose (micrograms) | Formulation |
| --- | --- | --- | --- |
| 8 | gH | 1 | CMF32 |
| 9 | gI | 7 | CMF32 |
| 10 | gI | 1 | CMF32 |
| 11 | gL | 7 | CMF32 |
| 12 | gL | 1 | CMF32 |
| 13 | gE/gI | 7 | CMF32 |
| 14 | gE/gI | 1 | CMF32 |
| 15 | gH/gL | 7 | CMF32 |
| 16 | gH/gL | 1 | CMF32 |

Immune response to VZV antigens

Serum samples were tested for the presence of antibodies to gB, by intracellular staining of VZV-replicon transfected MRC-5 cells. MRC-5 cells were maintained in Dulbecco Modified Eagle's Medium with 10% fetal bovine serum. VZV Oka strain inoculum (obtained from ATCC) was used to infect MRC-5 cell culture and infected whole cells were used for subpassage of virus. The ratio between infected and un-infected cells was 1:10. 30 hrs post infection cells were trypsin-dispersed for seeding in a 96 well plate to perform an intracellular staining with pools of mice sera (dilution range 1:200 to 1:800) obtained after immunization. Commercial mAbs were used as controls to quantify the infection level. Cell pellets ware fixed and permeabilized with Citofix-Citoperm solutions. A secondary reagent, Alexa488 labelled goat anti-mouse F(ab')$_2$ was used (1:400 final dilution).

Figure 4:
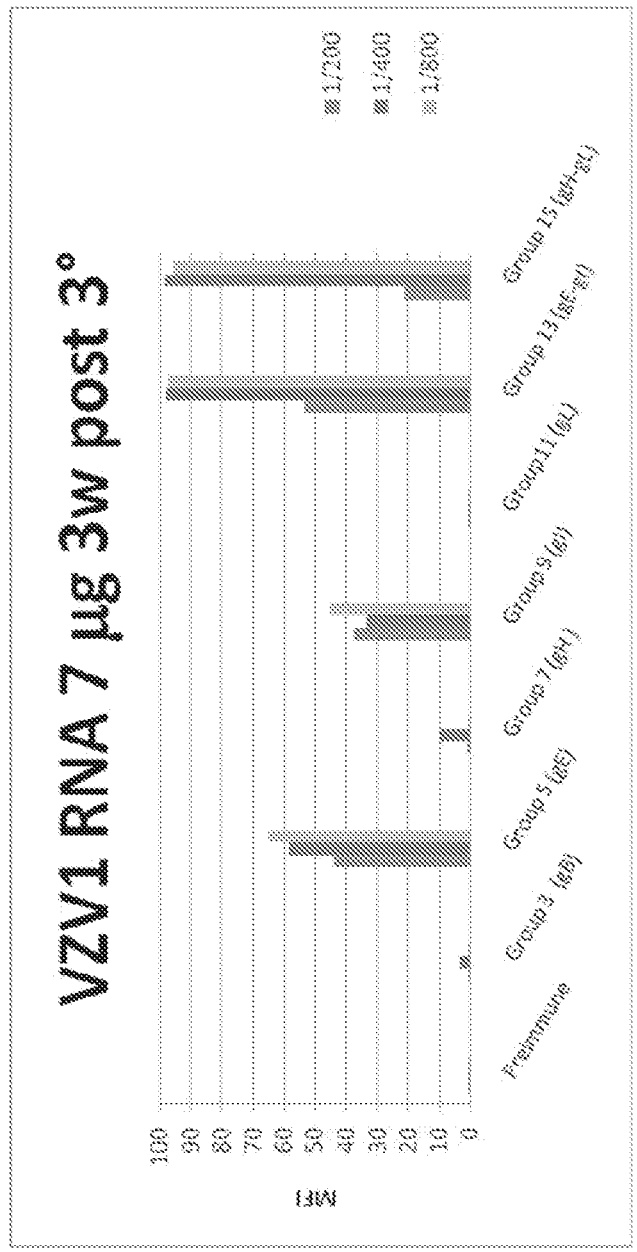
FIG. 4 is a graph showing anti-VZV protein antibody response in immune sera from mice immunized with monocistronic RNA replicons that encoded VZV proteins or bicistronic RNA replicons that encoded VZV gE and gI, or gH and gL. The mice were immunized with 7 μg RNA formulated with CMF32.

Commercial antibodies to gB (10G6), gH(SG3), and gE (13B1 (SBA) and 8612 (Millipore)) were used as positive controls, and each intracellularly stained infected MRC-5 cells Immune sera obtained 3 weeks after the third immunization with either 1 or 7 lag of RNA formulated with CMF32 were diluted 1/200, 1/400 and 1/800 and used to intracellularly stain infected MRC-5 cells. The results are shown in FIG. 4 (Study 1, groups 1, 5, 7, 9, 11, 13 and 15, CMF32 formulation).

Neutralizing Assay

Each immunized mouse serum was serially diluted by two fold increments starting at 1:20 in standard culture medium, and added to the equal volume of VZV suspension in the presence of guinea pig complement. After incubation for 1 hour at 37° C., the human epithelial cell line A549, was added. Infected cells can be measured after one week of culture by counting plaques formed in the culture under microscope. From the plaque number the % inhibition at each serum dilution was calculated. A chart for each serum sample was made by plotting the value of % inhibition against the logarithmic scale the dilution factor. Subsequently an approximate line of relationship between dilution factor and % inhibition was drawn. Then the 50% neutralization titer was determined as the dilution factor where the line crossed at the value of 50% inhibition.

Table 14 shows that sera obtained from mice immunized with monocistronic gE, bicistrnic gE/gI, and bicistronic gH/gL contained robust neutralizing antibody titers.

TABLE 14

Neutralization titers of pooled sera from mice immunized with 7 μg RNA in CMF32

| Mouse ID | Control (YFP) | gB | gE | gI | gE/gI | gH | gL | gH/gL |
| --- | --- | --- | --- | --- | --- | --- | --- | --- |
| 1 | <20 | <20 | 1111 | <20 | 440 | <20 | <20 | 1070 |
| 2 | <20 | <20 | 413 | 51 | >2560 | <20 | <20 | >2560 |
| 3 | <20 | <20 | >2560 | <20 | 1031 | <20 | <20 | >2560 |
| 4 | <20 | 20 | 2128 | <20 | 1538 | <20 | <20 | >2560 |
| 5 | <20 | 20 | 861 | <20 | 636 | 20 | <20 | >2560 |
| 6 | <20 | <20 | 1390 | <20 | 2339 | <20 | <20 | >2560 |

TABLE 14-continued

Neutralization titers of pooled sera from mice immunized with 7 µg RNA in CMF32

| Mouse ID | Control (YFP) | gB | gE | gI | gE/gI | gH | gL | gH/gL |
|---|---|---|---|---|---|---|---|---|
| 7 | <20 | <20 | 969 | <20 | 1903 | <20 | <20 | 900 |
| 8 | <20 | <20 | 1011 | 20 | 1969 | 20 | <20 | >2560 |
| 9 | <20* | <20* | <20* | <20* | <20* | <20* | <20* | <20* |

*pre-immune pooled sera

EXAMPLE 8

The Solubility of Fatty Acids in Squalene

In this Example, the solubility of various fatty acids in squalene was examined, and shown in Table 15. Fatty acids at indicated amounts (40, 20, 10, or 5 mg/mL,) were mixed with squalene at 60° C. In Table 15, (√) means that the fatty acid was soluble in squalene at the specified concentration; "x" means that the fatty acid was not soluble in squalene at the specified concentration; and "−" means that the solubility of the fatty acid at the specified concentration was not tested (because the fatty acid was soluble at a higher concentration). After the fatty acids were dissolved in squalene, the solutions were left at 4° C. overnight. The column labeled 4° C. overnight shows the solubility of the solutions in which each fatty acid was at its top concentration. For example oleic acid was soluble in squalene at 40 mg/ml and remained soluble in squalene at 4° C. overnight.

TABLE 15

| | Fatty acid | 40 mg/mL | 20 mg/mL | 10 mg/mL | 5 mg/mL | 4° C. (overnight) |
|---|---|---|---|---|---|---|
| Saturated Fatty Acids (Odd Carbon Chains) | Undecanoic Acid | ✓ | — | — | — | ✓ |
| | Tridecanoic Acid | ✓ | — | — | — | x |
| | Pentadecanoic Acid | ✓ | — | — | — | x |
| | Heptadecanoic Acid | x | x | x | ✓ | x |
| | Nonadecanoic Acid | x | x | x | x | x |
| | Heneicosanoic Acid | x | x | x | x | x |
| | Tricosanoic Acid | x | x | x | x | x |
| Saturated Fatty Acids (Even Carbon Chains) | Capric acid (10:0) | ✓ | — | — | — | ✓ |
| | Lauric acid (12:0) | ✓ | — | — | — | x |
| | Myristic Acid (14:0) | x | ✓ | — | — | x |
| | Palmitic Acid (16:0) | x | x | x | ✓ | x |
| | Stearic Acid (18:0) | x | x | x | ✓ | x |
| | Arachidic Acid (20:0) | x | x | x | ✓ | x |
| | Behenic Acid (22:0) | x | x | x | x | x |
| | Lignoceric Acid (24:0) | x | x | x | x | x |
| Unsaturated fatty acids | Docosahexaenoic Acid (22:6) | ✓ | — | — | — | ✓ |
| | Elaidic Acid (18:1)-trans | ✓ | — | — | — | x |
| | Erucic Acid (22:1) | ✓ | — | — | — | ✓ |
| | Linoleic Acid (18:2) | ✓ | — | — | — | ✓ |
| | Linolenic Acid (18:3) | ✓ | — | — | — | ✓ |
| | Nervonic Acid (24:1) | ✓ | — | — | — | x |
| | Oleic Acid (18:1)-cis | ✓ | — | — | — | ✓ |
| | Palmitoleic Acid (16:1) | ✓ | — | — | — | ✓ |
| | Petroselinic Acid (18:1) | ✓ | — | — | — | ✓ |

SEQUENCES

The nucleotide sequence of a DNA encoding the vA317 RNA, which encodes the RSV-F antigen (SEQ ID NO: 1).

The nucleotide sequence of a DNA encoding the vA142 RNA (SEQ ID NO: 2).

The nucleotide sequence of a DNA encoding the vA375 RNA (SEQ ID NO: 3).

A526 Vector: SGP-gH-SGP-gL-SGP-UL128-2A-UL130-2Amod-UL131 (SEQ ID NO: 4).

A527 Vector: SGP-gH-SGP-gL-SGP-UL128-EMCV-UL130-EV71-UL131 (SEQ ID NO: 5).

A531 Vector: SGP-gHsol-SGP-gL (SEQ ID NO: 6).

A532 Vector: SGP-gHsol-2A-gL (SEQ ID NO: 7).

A533 Vector: SGP-gHsol-EV71-gL (SEQ ID NO: 8).

A534 Vector: SGP-gL-EV71-gH (SEQ ID NO: 9).

A535 Vector: SGP-342-EV71-gHsol-2A-gL (SEQ ID NO: 10).

A536 Vector: SGP-342-EV71-gHsol-EMCV-gL (SEQ ID NO: 11).

A537 Vector: SGP-342-EV71-gL-EMCV-gHsol (SEQ ID NO: 12).

A554 Vector: SGP-gH-SGP-gL-SGP-UL128-SGP-UL130-SGP-UL131 (SEQ ID NO: 13).

A555 Vector: SGP-gHsol-SGP-gL-SGP-UL128-SGP-UL130-SGP-UL131 (SEQ ID NO: 14).

A556 Vector: SGP-gHsol6His-SGP-gL-SGP-UL128-SGP-UL130-SGP-UL131 (SEQ ID NO: 15).

VZV gB (SEQ ID NO: 16).

VZV gH (SEQ ID NO: 17).

VZV gL (SEQ ID NO: 18).

VZV gI (SEQ ID NO: 19).

VZV gE (SEQ ID NO: 20).

VZV VEERep.SGPgB (SEQ ID NO: 21).

VZV VEERep.SGPgH (SEQ ID NO: 22).

VZV VEERep.SGPgL (SEQ ID NO: 23).

VZV VEERep.SGPgH-SGPgL (SEQ ID NO: 24).

VZV VEERep.SGPgE (SEQ ID NO: 25).

VZV VEERep.SGPgI (SEQ ID NO: 26).

VZV VEErep.SGPgE-SGPgI (SEQ ID NO: 27).

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

---

The invention claimed is:

1. A stable oil-in-water emulsion comprising particles that are dispersed in an aqueous continuous phase, wherein the average diameter of said particles is from about 80 nm to 150 nm, wherein the average diameter does not change by more than 10% when the emulsion is stored at 4° C. for one month; and wherein the emulsion comprises an oil and a cationic lipid, wherein the head group of the cationic lipid comprises a quaternary amine, and
wherein:
  (i) the ratio of oil:lipid (mole:mole) is at least about 8:1 (mole:mole);
  (ii) the concentration of cationic lipid in said emulsion is at least about 2.5 mM; and
  (iii) the cationic lipid is not DC-Cholesterol.

2. The oil-in-water emulsion of claim 1, wherein the average diameter of said particles is from about 80 nm to about 130 nm.

3. The oil-in-water emulsion of claim 1, wherein the ratio of oil:lipid (mole:mole) is from about 10:1 (mole:mole) to about 43:1 (mole:mole).

4. The oil-in-water emulsion of claim 1, wherein said oil-in-water emulsion comprises from about 0.2% to about 8% (w/v) oil.

5. The oil-in-water emulsion of claim 4, wherein said oil is squalene or squalane.

6. The oil-in-water emulsion of claim 1, wherein the oil-in-water emulsion further comprises from about 0.01% to about 2.5% (v/v) surfactant.

7. The oil-in-water emulsion of claim 6, wherein said surfactant is SPAN85 (SorbitanTrioleate), Tween 80 (polysorbate 80), or a combination thereof.

8. The oil-in-water emulsion of claim 7, wherein the oil-in-water emulsion comprises about 0.5% (v/v) Tween 80 and about 0.5% (v/v) SPAN85.

9. The oil-in-water emulsion of claim 1, wherein the cationic lipid is selected from the group consisting of: 1,2-dioleoyloxy-3-(trimethylammonio)propane (DOTAP), 1,2-dioleoyl-sn-glycero-3-ethylphosphocholine (DOEPC), N,N-dioleoyl-N,N-dimethylammonium chloride (DODAC), and N-[1-(2, 3-dioleyloxy)propyl]-N,N,N-trimethylammonium chloride (DOTMA).

10. The oil-in-water emulsion of claim 9, wherein the cationic lipid is DOTAP and the concentration of DOTAP in said emulsion is from about 2.58 mM (1.8 mg/mL) to about 7.16 mM (5 mg/mL).

11. A method for preparing the oil-in-water emulsion of claim 1, comprising: (a) directly dissolving the cationic lipid in the oil to form an oil phase; (b) providing an aqueous phase of the emulsion; and (c) dispersing the oil phase in the aqueous phase by homogenization.

12. The method of claim 11, wherein step (a) further comprises heating the oil to a temperature between about 30° C. to about 65° C.

13. The oil-in-water emulsion of claim 1 further comprising an antioxidant.

* * * * *